(12) United States Patent
Viswanathan et al.

(10) Patent No.: US 11,020,179 B2
(45) Date of Patent: Jun. 1, 2021

(54) SYSTEMS, DEVICES, AND METHODS FOR FOCAL ABLATION

(71) Applicant: Farapulse, Inc., Menlo Park, CA (US)

(72) Inventors: Raju Viswanathan, Mountain View, CA (US); Allan Zingeler, Menlo Park, CA (US); Gary Long, Cincinnati, OH (US); Jean-Luc Pageard, Montreal (CA); Brittney Hachey, Dorval (CA)

(73) Assignee: Farapulse, Inc., Menlo Park, CA (US)

( * ) Notice: Subject to any disclaimer, the term of this patent is extended or adjusted under 35 U.S.C. 154(b) by 0 days.

(21) Appl. No.: 16/886,514

(22) Filed: May 28, 2020

(65) Prior Publication Data

US 2020/0289197 A1   Sep. 17, 2020

Related U.S. Application Data

(63) Continuation of application No. PCT/US2020/026682, filed on Apr. 3, 2020, which is
(Continued)

(51) Int. Cl.
*A61B 18/14* (2006.01)
*A61N 1/05* (2006.01)
(Continued)

(52) U.S. Cl.
CPC .......... *A61B 18/1492* (2013.01); *A61N 1/056* (2013.01); *A61B 2018/0016* (2013.01);
(Continued)

(58) Field of Classification Search
CPC ...... A61B 18/1492; A61B 2018/00375; A61B 2018/00613; A61B 2018/1467;
(Continued)

(56) References Cited

U.S. PATENT DOCUMENTS

| 4,200,104 A | 4/1980 | Harris |
| 4,470,407 A | 9/1984 | Hussein |

(Continued)

FOREIGN PATENT DOCUMENTS

| EP | 1042990 A1 | 10/2000 |
| EP | 1125549 | 8/2001 |

(Continued)

OTHER PUBLICATIONS

Office Action for Canadian Application No. 2,881,462, dated Mar. 19, 2019, 5 pages.
(Continued)

*Primary Examiner* — Thomas A Giuliani
(74) *Attorney, Agent, or Firm* — Cooley LLP

(57) ABSTRACT

Systems, devices, and methods for electroporation ablation therapy are disclosed, with the device including a set of splines coupled to a catheter for medical ablation therapy. Each spline of the set of splines may include a set of electrodes formed on that spline. The set of splines may be configured for translation to transition between a first configuration and a second configuration. The devices described herein may be used to form a lesion via focal ablation.

21 Claims, 59 Drawing Sheets

Related U.S. Application Data a continuation of application No. 16/375,561, filed on Apr. 4, 2019, now Pat. No. 10,660,702, which is a continuation-in-part of application No. PCT/US2019/014226, filed on Jan. 18, 2019, which is a continuation-in-part of application No. PCT/US2018/029938, filed on Apr. 27, 2018, which is a continuation-in-part of application No. 15/874,721, filed on Jan. 18, 2018, now Pat. No. 10,130,423, and a continuation-in-part of application No. 15/711,266, filed on Sep. 21, 2017, now Pat. No. 10,172,673, which is a continuation-in-part of application No. PCT/US2017/012099, filed on Jan. 4, 2017.

(60) Provisional application No. 62/769,407, filed on Nov. 19, 2018, provisional application No. 62/744,495, filed on Oct. 11, 2018, provisional application No. 62/529,268, filed on Jul. 6, 2017, provisional application No. 62/491,910, filed on Apr. 28, 2017, provisional application No. 62/274,943, filed on Jan. 5, 2016.

(51) Int. Cl.
*A61B 18/00* (2006.01)
*A61N 1/32* (2006.01)
*A61N 1/362* (2006.01)

(52) U.S. Cl.
CPC ............ *A61B 2018/0022* (2013.01); *A61B 2018/00261* (2013.01); *A61B 2018/00267* (2013.01); *A61B 2018/00357* (2013.01); *A61B 2018/00363* (2013.01); *A61B 2018/00375* (2013.01); *A61B 2018/00577* (2013.01); *A61B 2018/00613* (2013.01); *A61B 2018/00642* (2013.01); *A61B 2018/00708* (2013.01); *A61B 2018/00761* (2013.01); *A61B 2018/00839* (2013.01); *A61B 2018/1467* (2013.01); *A61N 1/327* (2013.01); *A61N 1/362* (2013.01)

(58) Field of Classification Search
CPC .. A61B 2018/0016; A61B 2018/00214; A61B 2018/00267; A61B 2018/00279; A61B 2018/00404; A61B 2018/00577; A61B 2018/1465; A61B 2018/00357; A61B 2018/00702; A61B 2018/00767; A61N 1/056
USPC ..... 606/34, 40–42, 49; 607/98, 99, 115, 116
See application file for complete search history.

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,860,974 A | 1/1999 | Abele |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 5,938,660 A | 8/1999 | Swartz et al. |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,142,993 A | 11/2000 | Whayne et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,109 B1 | 6/2001 | Hasset et al. |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,405,732 B1 | 6/2002 | Edwards et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |

(56) References Cited

U.S. PATENT DOCUMENTS

| | | |
|---|---|---|
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,613,046 B1 | 9/2003 | Jenkins et al. |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,842,031 B2 | 11/2010 | Abboud et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 8,996,091 B2 | 3/2015 | de la Rama et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,113,911 B2 | 8/2015 | Sherman |

(56) References Cited

U.S. PATENT DOCUMENTS

| | | |
|---|---|---|
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,204,916 B2 | 12/2015 | Lalonde |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,351,789 B2 | 5/2016 | Novichenok et al. |
| 9,375,268 B2 | 6/2016 | Long |
| 9,387,031 B2 | 7/2016 | Stewart et al. |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,510,888 B2 | 12/2016 | Lalonde |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,801,681 B2 | 10/2017 | Laske et al. |
| 9,808,304 B2 | 11/2017 | Lalonde |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 * | 6/2018 | Bowers ............... A61B 18/1492 |
| 9,999,465 B2 | 6/2018 | Long et al. |
| 10,010,368 B2 | 7/2018 | Laske et al. |
| 10,016,232 B1 | 7/2018 | Bowers et al. |
| 10,130,423 B1 | 11/2018 | Viswanathan et al. |
| 10,172,673 B2 * | 1/2019 | Viswanathan ......... A61N 1/056 |
| 10,194,818 B2 | 2/2019 | Williams et al. |
| 10,285,755 B2 | 5/2019 | Stewart et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 10,617,467 B2 | 4/2020 | Viswanathan et al. |
| 10,660,702 B2 | 5/2020 | Viswanathan et al. |
| 10,687,892 B2 | 6/2020 | Long et al. |
| 10,842,561 B2 | 11/2020 | Viswanathan et al. |
| 10,893,905 B2 | 1/2021 | Viswanathan et al. |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0120304 A1 | 8/2002 | Mest |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0204185 A1 | 10/2003 | Sherman et al. |
| 2003/0229379 A1 | 12/2003 | Ramsey |
| 2004/0002748 A1 | 1/2004 | Ryan et al. |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2005/0288730 A1 | 12/2005 | Deem et al. |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0083192 A1 | 4/2007 | Welch |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |

(56) References Cited

U.S. PATENT DOCUMENTS

| | | |
|---|---|---|
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0171352 A1 | 7/2009 | Sutter |
| 2009/0182287 A1 | 7/2009 | Kassab |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0204560 A1 | 8/2010 | Salahieh et al. |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0301587 A1 | 12/2011 | Deem et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0123778 A1 | 5/2013 | Richardson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1* | 7/2013 | Just .................. A61B 5/6858 600/374 |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0257130 A1 | 9/2014 | Cao et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0330266 A1 | 11/2014 | Thompson et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0141982 A1 | 5/2015 | Lee |
| 2015/0142041 A1 | 5/2015 | Kendale et al. |
| 2015/0148796 A1 | 5/2015 | Bencini |

(56) References Cited

U.S. PATENT DOCUMENTS

| | | |
|---|---|---|
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1* | 4/2016 | Maor ............... A61B 18/1492 606/41 |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0249972 A1 | 9/2016 | Klink |
| 2016/0256682 A1 | 9/2016 | Paul et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331254 A1 | 11/2016 | Tegg et al. |
| 2016/0331441 A1 | 11/2016 | Konings |
| 2016/0331459 A1 | 11/2016 | Townley et al. |
| 2016/0338770 A1 | 11/2016 | Bar-Tal et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1* | 4/2017 | Cao ................... A61N 1/325 |
| 2017/0120048 A1 | 5/2017 | He et al. |
| 2017/0146584 A1 | 5/2017 | Daw et al. |
| 2017/0151014 A1 | 6/2017 | Perfler |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0028252 A1 | 2/2018 | Lalonde |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0161093 A1 | 6/2018 | Basu et al. |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0235496 A1 | 8/2018 | Wu et al. |
| 2018/0256109 A1 | 9/2018 | Wu et al. |
| 2018/0280080 A1 | 10/2018 | Govari et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344202 A1 | 12/2018 | Bar-Tal et al. |
| 2018/0344393 A1 | 12/2018 | Gruba et al. |
| 2018/0360531 A1 | 12/2018 | Holmes et al. |
| 2018/0360534 A1 | 12/2018 | Teplitsky et al. |
| 2019/0015007 A1 | 1/2019 | Rottmann et al. |
| 2019/0015638 A1 | 1/2019 | Gruba et al. |
| 2019/0030328 A1 | 1/2019 | Stewart et al. |
| 2019/0046791 A1 | 2/2019 | Ebbers et al. |
| 2019/0069950 A1 | 3/2019 | Viswanathan et al. |
| 2019/0076179 A1 | 3/2019 | Babkin et al. |
| 2019/0125439 A1 | 5/2019 | Rohl et al. |
| 2019/0125788 A1 | 5/2019 | Gruba et al. |
| 2019/0143106 A1 | 5/2019 | Dewitt et al. |
| 2019/0151015 A1 | 5/2019 | Viswanathan et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0192223 A1 | 6/2019 | Rankin |
| 2019/0201089 A1 | 7/2019 | Waldstreicher et al. |
| 2019/0201688 A1 | 7/2019 | Olson |
| 2019/0209235 A1 | 7/2019 | Stewart et al. |
| 2019/0223948 A1 | 7/2019 | Stewart et al. |
| 2019/0231421 A1 | 8/2019 | Viswanathan et al. |
| 2019/0231425 A1 | 8/2019 | Waldstreicher et al. |
| 2019/0254735 A1 | 8/2019 | Stewart et al. |
| 2019/0269912 A1 | 9/2019 | Viswanathan et al. |
| 2019/0298442 A1 | 10/2019 | Ogata et al. |
| 2019/0307500 A1 | 10/2019 | Byrd et al. |
| 2019/0336198 A1 | 11/2019 | Viswanathan et al. |
| 2019/0336207 A1 | 11/2019 | Viswanathan |
| 2019/0350647 A1 | 11/2019 | Ramberg et al. |
| 2019/0350649 A1 | 11/2019 | Sutermeister et al. |
| 2020/0008869 A1 | 1/2020 | Byrd |
| 2020/0008870 A1 | 1/2020 | Gruba et al. |
| 2020/0009378 A1 | 1/2020 | Stewart et al. |
| 2020/0038104 A1 | 2/2020 | Mickelsen |

(56) References Cited

U.S. PATENT DOCUMENTS

| | | | |
|---|---|---|---|
| 2020/0046423 A1 | 2/2020 | Viswanathan et al. | |
| 2020/0093539 A1 | 3/2020 | Long et al. | |
| 2020/0397505 A1 | 12/2020 | Viswanathan et al. | |

FOREIGN PATENT DOCUMENTS

| | | |
|---|---|---|
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/049407 | 9/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/145073 | 10/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/201504 | 11/2017 |
| WO | WO 2017/218734 | 12/2017 |
| WO | WO 2018/005511 | 1/2018 |
| WO | WO 2018/106569 | 6/2018 |
| WO | WO 2018/200800 | 11/2018 |
| WO | WO 2019/023259 | 1/2019 |
| WO | WO 2019/023280 | 1/2019 |
| WO | WO 2019/035071 | 2/2019 |
| WO | WO 2019/133606 | 7/2019 |
| WO | WO 2019/133608 | 7/2019 |
| WO | WO 2019/136218 | 7/2019 |
| WO | WO 2019/181612 | 9/2019 |
| WO | WO 2019/234133 | 12/2019 |

OTHER PUBLICATIONS

Partial Supplementary European Search Report for European Application No. 13827672.0, dated Mar. 23, 2016, 6 pages.
Supplementary European Search Report for European Application No. 13827672.0, dated Jul. 11, 2016, 12 pages.
Office Action for European Application No. 13827672.0, dated Feb. 5, 2018, 6 pages.
Notice of Reasons for Rejection for Japanese Application No. 2015-526522, dated Mar. 6, 2017, 3 pages.
Office Action for U.S. Appl. No. 14/400,455, dated Mar. 30, 2017, 10 pages.
International Search Report and Written Opinion for International Application No. PCT/US2013/031252, dated Jul. 19, 2013, 12 pages.
Extended European Search Report for European Application No. 19182099.2, dated Dec. 13, 2019, 7 pages.
Office Action for Japanese Application No. 2018-036714, dated Jan. 16, 2019, 8 pages.
Office Action for Japanese Application No. 2018-036714, dated Nov. 27, 2019, 5 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
Office Action for U.S. Appl. No. 15/917,194, dated Apr. 29, 2019, 10 pages.
Office Action for U.S. Appl. No. 15/917,194, dated Dec. 20, 2019, 10 pages.
First Office Action for Chinese Application No. 201580006848.8, dated Jan. 29, 2018, 15 pages.
Office Action for European Application No. 15701856.5, dated Dec. 11, 2017, 6 pages.
Notice of Reasons for Rejection for Japanese Application No. 2016-544072, dated Oct. 1, 2018, 11 pages.
Office Action for U.S. Appl. No. 15/201,983, dated Apr. 3, 2019, 16 pages.
Office Action for U.S. Appl. No. 15/201,983, dated Nov. 15, 2019, 15 pages.
International Search Report and Written Opinion for International Application No. PCT/US2015/010138, dated Mar. 26, 2015, 14 pages.

(56) References Cited

OTHER PUBLICATIONS

International Preliminary Report on Patentability for International Application No. PCT/US2015/010138, dated Jul. 12, 2016, 9 pages.
Supplementary European Search Report for European Application No. 15733297.4, dated Aug. 10, 2017, 7 pages.
Office Action for U.S. Appl. No. 15/201,997, dated Apr. 3, 2017, 6 pages.
Office Action for U.S. Appl. No. 15/201,997, dated Aug. 29, 2017, 12 pages.
Office Action for U.S. Appl. No. 15/201,997, dated Jul. 12, 2018, 12 pages.
Office Action for U.S. Appl. No. 15/201,997, dated Dec. 17, 2018, 17 pages.
International Search Report and Written Opinion for International Application No. PCT/US2015/010223, dated Apr. 10, 2015, 19 pages.
International Preliminary Report on Patentability for International Application No. PCT/US2015/010223, dated Jul. 12, 2016, 12 pages.
Office Action for U.S. Appl. No. 15/341,512, dated Aug. 1, 2019, 19 pages.
Office Action for U.S. Appl. No. 15/341,512, dated Nov. 12, 2019, 18 pages.
International Search Report and Written Opinion for International Application No. PCT/US2015/029734, dated Nov. 24, 2015, 15 pages.
Extended European Search Report for European Application No. 18189811.5, dated May 14, 2019, 7 pages.
Office Action for U.S. Appl. No. 15/795,062, dated Dec. 19, 2017, 14 pages.
Office Action for U.S. Appl. No. 15/795,062, dated Apr. 9, 2018, 20 pages.
Office Action for U.S. Appl. No. 15/795,062, dated May 3, 2019, 21 pages.
Office Action for U.S. Appl. No. 15/795,062, dated Nov. 4, 2019, 23 pages.
Office Action for European Application No. 15726465.6, dated Dec. 10, 2019, 6 pages.
Office Action for U.S. Appl. No. 15/341,523, dated Jan. 29, 2019, 10 pages.
Office Action for U.S. Appl. No. 15/341,523, dated Jul. 30, 2019, 8 pages.
International Search Report and Written Opinion for International Application No. PCT/US2015/031086, dated Oct. 21, 2015, 16 pages.
Office Action for U.S. Appl. No. 15/795,075, dated Feb. 6, 2018, 9 pages.
Office Action for U.S. Appl. No. 15/795,075, dated Jun. 15, 2018, 10 pages.
Office Action for U.S. Appl. No. 15/795,075, dated Apr. 10, 2019, 11 pages.
Office Action for U.S. Appl. No. 15/795,075, dated Jul. 31, 2019, 12 pages.
Extended European Search Report for European Application No. 15849844.4, dated May 3, 2018, 8 pages.
Office Action for U.S. Appl. No. 15/484,969, dated Sep. 4, 2019, 12 pages.
International Search Report and Written Opinion for International Application No. PCT/US2015/055105, dated Mar. 1, 2016, 15 pages.
Office Action for U.S. Appl. No. 15/796,255, dated Jan. 10, 2018, 12 pages.
Extended European Search Report for European Application No. 15806855.1, dated Jan. 3, 2018, 8 pages.
Office Action for U.S. Appl. No. 15/354,475, dated May 23, 2019, 7 pages.
International Search Report and Written Opinion for International Application No. PCT/US2015/035582, dated Oct. 2, 2015, 17 pages.

Extended European Search Report for European Application No. 15806278.6, dated Feb. 9, 2018, 5 pages.
International Search Report and Written Opinion for International Application No. PCT/US2015/035592, dated Oct. 2, 2015, 13 pages.
Extended European Search Report for European Application No. 16884132.8, dated Jul. 8, 2019, 7 pages.
Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2016/057664, dated Feb. 24, 2017, 11 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
Office Action for U.S. Appl. No. 16/416,677, dated Aug. 15, 2019, 8 pages.
Extended European Search Report for European Application No. 17736218.3 dated Aug. 23, 2019, 9 pages.
International Search Report and Written Opinion for International Application No. PCT/US2017/012099, dated May 18, 2017, 17 pages.
Office Action for U.S. Appl. No. 15/711,266, dated Feb. 23, 2018, 14 pages.
International Search Report and Written Opinion for International Application No. PCT/US2018/029938, dated Aug. 29, 2018, 14 pages.
Office Action for U.S. Appl. No. 16/181,027, dated Sep. 4, 2019, 12 pages.
International Search Report and Written Opinion for International Application No. PCT/US2019/014226, dated Apr. 29, 2019, 15 pages.
Office Action for U.S. Appl. No. 16/240,066, dated May 29, 2019, 7 pages.
Office Action for U.S. Appl. No. 16/375,561, dated Oct. 17, 2019, 15 pages.
Office Action for U.S. Appl. No. 16/595,250, dated Mar. 16, 2020, 7 pages.
International Search Report and Written Opinion for International Application No. PCT/US2017/037609, dated Nov. 8, 2017, 13 pages.
Office Action for U.S. Appl. No. 15/672,916, dated Feb. 13, 2018, 16 pages.
Office Action for U.S. Appl. No. 15/672,916, dated Jul. 20, 2018, 23 pages.
Office Action for U.S. Appl. No. 15/672,916, dated Apr. 9, 2019, 31 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
Partial European Search Report for European Application No. 18170210.1, dated Feb. 14, 2019, 13 pages.
Extended European Search Report for European Application No. 18170210.1, dated May 17, 2019, 11 pages.
International Search Report and Written Opinion for International Application No. PCT/US2018/050660, dated Nov. 26, 2018, 13 pages.
Office Action for U.S. Appl. No. 15/970,404, dated Oct. 9, 2018, 21 pages.
Office Action for U.S. Appl. No. 15/970,404, dated Apr. 12, 2019, 20 pages.
Office Action for U.S. Appl. No. 15/970,404, dated Nov. 12, 2019, 19 pages.

(56) References Cited

OTHER PUBLICATIONS

International Search Report and Written Opinion for International Application No. PCT/US2019/028943, dated Sep. 17, 2019, 17 pages.
International Search Report and Written Opinion for International Application No. PCT/US2019/017322, dated May 10, 2019, 15 pages.
International Search Report and Written Opinion for International Application No. PCT/US2019/030922, dated Sep. 6, 2019, 12 pages.
International Search Report and Written Opinion for International Application No. PCT/US2019/030882, dated Sep. 10, 2019, 17 pages.
International Search Report and Written Opinion for International Application No. PCT/US2019/051998, dated Feb. 26, 2020, 11 pages.
Office Action for U.S. Appl. No. 16/573,704, dated Dec. 17, 2019, 6 pages.
Office Action for U.S. Appl. No. 16/405,515, dated Sep. 6, 2019, 9 pages.
International Search Report and Written Opinion for International Application No. PCT/US2019/031135, dated Aug. 5, 2019, 11 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
First Office Action for Chinese Application No. 201780005770.7, dated Sep. 27, 2020, 8 pages.
Notice of Reasons for Rejection for Japanese Application No. 2018-534873, dated Oct. 16, 2020, 7 pages.
Office Action for U.S. Appl. No. 16/828,593, dated Oct. 23, 2020, 28 pages.
International Search Report and Written Opinion for International Application No. PCT/US2020/026682, dated Jun. 16, 2020, 10 pages.
Office Action for U.S. Appl. No. 16/817,410, dated Jul. 16, 2020, 23 pages.
Office Action for U.S. Appl. No. 16/828,593, dated Jul. 8, 2020, 25 pages.
International Search Report and Written Opinion for International Application No. PCT/US2020/037948, dated Jul. 20, 2020, 16 pages.
Extended European Search Report for European Application No. 18790020.4, dated Feb. 2, 2021, 9 pages.

\* cited by examiner

SYSTEMS, DEVICES, AND METHODS FOR FOCAL ABLATION

CROSS-REFERENCE TO RELATED APPLICATIONS

This application is a continuation of PCT Application No. PCT/US2020/026682, filed on Apr. 3, 2020, which is a continuation of U.S. patent application Ser. No. 16/375,561, filed on Apr. 4, 2019, now issued as U.S. Pat. No. 10,660,702, which is continuation-in-part of PCT Application No. PCT/US2019/014226, filed Jan. 18, 2019. PCT Application No. PCT/US2019/014226 is a continuation-in-part of PCT Application No. PCT/US2018/029938, filed on Apr. 27, 2018, which is a continuation-in-part of U.S. patent application Ser. No. 15/874,721, filed Jan. 18, 2018, now issued as U.S. Pat. No. 10,130,423, and U.S. patent application Ser. No. 15/711,266, filed Sep. 21, 2017, now issued as U.S. Pat. No. 10,172,673. U.S. patent application Ser. No. 15/874,721 claims the benefit of U.S. Provisional Application No. 62/529,268, filed on Jul. 6, 2017. U.S. patent application Ser. No. 15/711,266 is a continuation-in-part of PCT Application No. PCT/US2017/012099, filed Jan. 4, 2017, which claims the benefit of U.S. Provisional Application No. 62/274,943, filed Jan. 5, 2016. U.S. patent application Ser. No. 15/711,266 also claims the benefit of U.S. Provisional Application No. 62/491,910, filed Apr. 28, 2017, and U.S. Provisional Application No. 62/529,268, filed Jul. 6, 2017. PCT Application No. PCT/US2019/014226 also claims the benefit of U.S. Provisional Application No. 62/744,495, filed on Oct. 11, 2018, and U.S. Provisional Application No. 62/769,407, filed on Nov. 19, 2018. The entire disclosure of each of the foregoing applications is incorporated herein by reference in its entirety.

BACKGROUND

The generation of pulsed electric fields for tissue therapeutics has moved from the laboratory to clinical applications over the past two decades, while the effects of brief pulses of high voltages and large electric fields on tissue have been investigated for the past forty years or more. Application of brief high DC voltages to tissue may generate locally high electric fields typically in the range of hundreds of volts per centimeter that disrupt cell membranes by generating pores in the cell membrane. While the precise mechanism of this electrically-driven pore generation or electroporation continues to be studied, it is thought that the application of relatively brief and large electric fields generates instabilities in the lipid bilayers in cell membranes, causing the occurrence of a distribution of local gaps or pores in the cell membrane. This electroporation may be irreversible if the applied electric field at the membrane is larger than a threshold value such that the pores do not close and remain open, thereby permitting exchange of biomolecular material across the membrane leading to necrosis and/or apoptosis (cell death). Subsequently, the surrounding tissue may heal naturally.

While pulsed DC voltages may drive electroporation under the right circumstances, there remains an unmet need for thin, flexible, atraumatic devices that effectively deliver high DC voltage electroporation ablation therapy selectively to endocardial tissue in regions of interest while minimizing damage to healthy tissue.

SUMMARY

Described here are systems, devices, and methods for ablating tissue through irreversible electroporation. In some embodiments, an apparatus may comprise a first shaft defining a longitudinal axis and a lumen, a second shaft disposed within the lumen and having a distal portion that extends from a distal end of the first shaft, a plurality of electrodes configured to generate an electric field for ablating tissue, a set of splines, each spline of the set of splines including: a set of electrodes from the plurality of electrodes formed on that spline, each set of electrodes including (1) a distal electrode such that the set of splines includes a set of distal electrodes and (2) a proximal electrode such that the set of splines includes a set of proximal electrodes. A proximal end may be coupled to the distal end of the first shaft. A distal end may be coupled to a distal end of the second shaft. The set of splines may be configured to transition into an expanded configuration in which a distal portion of each spline from the set of splines is angled greater than about 70 degrees relative to the longitudinal axis.

In some embodiments, an apparatus may comprise a first shaft defining a longitudinal axis and a lumen, a second shaft disposed within the lumen and having a distal portion that extends from a distal end of the first shaft, a plurality of electrodes configured to generate an electric field for ablating tissue, a set of splines, each spline of the set of splines including: a set of electrodes from the plurality of electrodes formed on that spline, each set of electrodes including (1) a distal electrode such that the set of splines includes a set of distal electrodes and (2) a proximal electrode such that the set of splines includes a set of proximal electrodes. A proximal end may be coupled to the distal end of the first shaft. A distal end may be coupled to a distal end of the second shaft. The set of splines may be configured to transition into an expanded configuration, the set of splines defining a space therebetween, the space being larger in the expanded configuration of the set of splines. An inflatable member may be disposed distal to the distal end of the first shaft and within the space between the set of splines. The inflatable member may be configured to be transitioned into an inflated configuration when the set of splines are in the expanded configuration.

In some embodiments, an inflatable member may be disposed distal to the distal end of the first shaft and within a space between the set of splines. The inflatable member may be configured to transition into an inflated configuration. In some embodiments, the inflatable member in the inflated configuration may substantially fill the space between the set of splines in their expanded configuration. The inflatable member may be configured to transition from a deflated configuration in which an outer surface of the inflatable member is approximately parallel to the longitudinal axis to the inflated configuration in which the outer surface of the inflatable member bows radially outward from the longitudinal axis. The set of splines may be configured to transition into the expanded configuration in response to the inflatable member transitioning into the inflated configuration.

In some embodiments, when the set of splines is in the expanded configuration, a distal portion of each spline from the set of splines may be angled at least about 70 degrees relative to the longitudinal axis. In some embodiments, the inflatable member in the inflated configuration may form an asymmetrical shape in which a distal portion of the inflatable member has an outer diameter larger than that of a proximal portion of the inflatable member. The inflatable member in the inflated configuration may form a shape with an outer diameter at a largest portion of between about 6 mm to about 24 mm. In some embodiments, when the set of splines is in the expanded configuration, at least one electrode from the set of distal electrodes may be configured to contact a tissue surface and form a focal ablation lesion on the tissue surface having a diameter between about 0.5 cm and about 2.5 cm.

In some embodiments, at least a portion of the inflatable member may be formed of an insulating material. The inflatable member may include a radiopaque portion. The first shaft may be a first inner shaft and the second shaft may be a second inner shaft. The apparatus may further comprise an outer shaft. The first inner shaft and the second inner shaft may be configured to slide relative to the outer shaft, and a proximal portion of the inflatable member may be coupled to a distal portion of the outer shaft. A distal portion of the inflatable member may be coupled to a distal portion of the first inner shaft. In some of these embodiments, the first inner shaft may be configured to couple to a fluid source such that fluid can be delivered into the inflatable member via the lumen of the first inner shaft to transition the inflatable member into the inflated configuration. The set of splines may be configured to transition into the expanded configuration in response to the second inner shaft moving relative to the first inner shaft. The inflatable member may define a lumen, and the second inner shaft may extend through the lumen of the inflatable member.

In some embodiments, the inflatable member may be configured in fluid communication with a fluid source. The fluid source may be configured to deliver a fluid to the inflatable member to transition the inflatable member into the inflated configuration. In some embodiments, when the set of splines is in the expanded configuration, the set of splines may extend outward from the distal end of the first shaft by between about 6 mm and about 24 mm. The first shaft may have an outer diameter of between about 1.5 mm and about 6.0 mm. The set of splines may be configured to transition into the expanded configuration in response to the second shaft moving relative to the first shaft along the longitudinal axis. When the set of splines is in the expanded configuration, the set of distal electrodes may be angled relative to the set of proximal electrodes between about 70 degrees and about 180 degrees.

The set of splines in the expanded configuration may form an asymmetrical shape in which a distal portion has an outer diameter larger than that of a proximal portion. The distal end of the second shaft may be separated from each distal electrode from the set of distal electrodes by at most about 6 mm. The distal end of the second shaft may have a cross-sectional diameter of between about 0.7 mm and about 5 mm. A distal portion of the apparatus may have an atraumatic shape. Each electrode from the plurality of electrodes may encircle a circumference of a respective spline from the set of splines on which that electrode is disposed.

At least one distal electrode from the set of distal electrodes may be configured to be activated with a first polarity. At least one proximal electrode from the set of proximal electrodes may be configured to be activated with a second polarity being opposite from the first polarity, to collectively generate the electric field. The set of distal electrodes may be configured to be activated with a first polarity, and the set of proximal electrodes may be configured to be activated with a second polarity being opposite from the first polarity.

Each electrode from the plurality of electrodes may have a length between about 0.5 mm and about 5 mm. Each electrode from the plurality of electrodes may be independently addressable from the other electrodes from the plurality of electrodes. Each spline from the set of splines may include a set of insulated electrical leads disposed therein. Each insulated electrical lead from the set of insulated electrical leads may be electrically coupled to at least one electrode from the set of electrodes formed on that spline and configured to sustain a voltage potential of at least about 700 V without dielectric breakdown of its corresponding insulation. Each electrode from the plurality of electrodes may have a diameter of between about 0.5 mm and about 3 mm. For each spline from the set of splines, the distal most distal electrode may be separated from the distal most proximal electrode by between about 1 mm and about 40 mm.

Each spline from the set of splines may include a plurality of proximal electrodes and at least one flexible portion disposed between adjacent proximal electrodes from the plurality of proximal electrodes for increasing spline flexibility. The set of proximal electrodes may include at least one coil electrode. The set of electrodes of each spline in the set of splines may include at least one electrode configured only for ablation and at least one electrode configured for receiving an electrocardiogram (ECG) signal. In some of these embodiments, the at least one electrode may be configured only for ablation and the at least one electrode may be configured for receiving the ECG signal are coupled to separate insulated electrical leads.

In some embodiments, a method may comprise disposing an ablation device in a cardiac chamber of a heart of a subject, the ablation device defining a longitudinal axis and including a set of splines. The set of splines may be transitioned into an expanded configuration in which a distal portion of each spline of the set of splines is angled greater than about 70 degrees relative to the longitudinal axis. An ablation pulse waveform may be delivered to a plurality of electrodes disposed on the set of splines such that the set of splines generates an electric field for ablating tissue of the cardiac chamber.

In some embodiments, a method may comprise disposing an ablation device in a cardiac chamber of a heart of a subject, the ablation device defining a longitudinal axis and including a set of splines and an inflatable member disposed in a space between the set of splines. The set of splines may transition into an expanded configuration in which a distal portion of each spline of the set of splines bows radially outward from the longitudinal axis. The inflatable member may transition into an inflated configuration. An ablation pulse waveform may be delivered to a plurality of electrodes disposed on the set of splines such that the set of splines generates an electric field for ablating tissue of the cardiac chamber.

In some embodiments, the electric field may be configured to form a focal ablation lesion on a surface of the tissue having a diameter between about 0.5 cm and about 2.5 cm. The ablation device may include a first shaft and a second shaft disposed within the first shaft and translatable relative to the first shaft. The set of splines may transition into the expanded configuration including retracting a distal portion of the second shaft relative to the first shaft. In some of these embodiments, retracting the distal portion of the second shaft relative to the first shaft includes using a handle coupled to at least one of the second shaft or the first shaft. In some embodiments, the tissue may include an endocardial surface of the cardiac chamber. In some of these embodiments, the cardiac chamber may be a ventricle.

In some embodiments, each spline from the set of splines includes a set of electrodes from the plurality of electrodes, the method further comprising configuring a first electrode from the set of electrodes of at least one spline as an anode, configuring a second electrode from the set of electrodes of the at least one spline as a cathode, and delivering the ablation pulse waveform to the first electrode and the second electrode.

In some embodiments, each spline from the set of splines may include a set of electrodes from the plurality of electrodes. At least one set of electrodes may be configured for ablation and at least one set of electrodes for receiving electrophysiology data. Electrophysiology data may be recorded from the heart using a subset of electrodes from the at least one set of electrodes. In some of these embodiments, the electrophysiology data may include intracardiac electrocardiogram (ECG) signal data of at least one pulmonary vein.

In some embodiments, a pacing device may be advanced into a right ventricle of the heart. A pacing signal for cardiac stimulation of the heart may be generated. The pacing signal may be applied to the heart using the pacing device, the ablation pulse waveform generated in synchronization with the pacing signal. In some of these embodiments, the ablation pulse waveform may include a time offset with respect to the pacing signal.

In some embodiments, a radiopaque portion of the ablation device may be fluoroscopically visualized during one or more steps. A diagnostic catheter may be advanced into the cardiac chamber and electrophysiology data may be recorded using the diagnostic catheter. In some of these embodiments, after transitioning the set of splines into the expanded configuration and transitioning the balloon into the inflated configuration, at least one spline from the set of splines may be placed in contact with the endocardium of the cardiac chamber. In some of these embodiments, the at least one spline in contact with the endocardium forms a "C" shape.

In some embodiments, the ablation device may include a shaft defining a lumen in fluid communication with the inflatable member, and transitioning the inflatable member into the inflated configuration includes delivering a fluid via the lumen of the shaft and into the inflatable member. The inflatable member may be formed of an insulating material such that the inflatable member acts as an insulator during delivery of the ablation pulse waveform. The inflatable member may include a plurality of inflatable portions, each inflatable portion from the plurality of inflatable portions independently inflatable from other inflatable portions of the plurality of inflatable portions. Transitioning the set of splines into the expanded configuration may include transitioning the set of splines such that a distal portion of each spline from the set of splines is angled greater than about 70 degrees relative to the longitudinal axis.

In some embodiments, the ablation pulse waveform includes a first level of a hierarchy of the ablation pulse waveform may include a first set of pulses, each pulse having a pulse time duration, a first time interval separating successive pulses. A second level of the hierarchy of the ablation pulse waveform may include a plurality of first sets of pulses as a second set of pulses, a second time interval separating successive first sets of pulses, the second time interval being at least three times the duration of the first time interval. A third level of the hierarchy of the ablation pulse waveform may include a plurality of second sets of pulses as a third set of pulses, a third time interval separating successive second sets of pulses, the third time interval being at least thirty times the duration of the second level time interval.

In some embodiments, transitioning of the set of splines into the expanded configuration is in response to transitioning the inflatable member into the inflated configuration.

In some embodiments, an apparatus may include a first shaft defining a longitudinal axis and a lumen, a second shaft may be disposed within the lumen and having a distal portion that extends from a distal end of the first shaft, a plurality of electrodes, and a set of splines. Each spline of the set of splines includes a set of electrodes from a plurality of electrodes formed on that spline. Each set of electrodes including (1) a distal electrode such that the set of splines includes a set of distal electrodes and (2) a proximal electrode such that the set of splines includes a set of proximal electrodes. A proximal end may be coupled to the distal end of the first shaft. A distal end may be coupled to a distal end of the second shaft.

In some embodiments, the set of splines may be transitionable into a plurality of states between and inclusive of an undeployed configuration and an expanded configuration in which a distal portion of each spline from the set of splines is set at one of a corresponding plurality of angles relative to a proximal portion of each spline from the set of splines in each of the plurality of states. A pre-selected portion of the plurality of electrodes may be activatable in each of the plurality of states to generate an electric field for ablating a tissue wall by irreversible electroporation. In some embodiments, the set of splines may be configured to ablate the tissue wall independent of an orientation of the set of splines relative to the tissue wall. In some embodiments, the pre-selected portion of the plurality of electrodes include electrodes from the plurality of electrodes orientated closer to the tissue surface.

In some embodiments, the set of splines may be transitionable into each of the plurality of states in response to the second shaft moving relative to the first shaft along the longitudinal axis. In some embodiments, when the set of splines is in the expanded configuration, at least one electrode from the set of distal electrodes may be angled relative to at least one electrode from the set of proximal electrodes by an angle between about 70 degrees and about 180 degrees. In some embodiments, the distal end of the second shaft may be separated from each distal electrode from the set of distal electrodes by at most about 6 mm.

In some embodiments, at least one distal electrode from the set of distal electrodes may be configured to be activated with a first polarity and at least one proximal electrode from the set of proximal electrodes may be configured to be activated with a second polarity being opposite from the first polarity, to collectively generate the electric field. In some embodiments, each spline from the set of splines may include a plurality of proximal electrodes and at least one flexible portion may be disposed between adjacent proximal electrodes from the plurality of proximal electrodes for increasing spline flexibility.

In some embodiments, the first shaft is a first inner shaft and the second shaft is a second inner shaft. The apparatus may include an outer shaft. The first inner shaft and the second inner shaft may be configured to slide relative to the outer shaft. In some embodiments, each distal electrode from the set of distal electrodes may be at the same distance from the distal end of the second shaft. In some embodiments, when the set of splines is in the expanded configuration. The set of splines may extend outward from the distal end of the first shaft by a radial distance between about 6 mm and about 24 mm. In some embodiments, the first shaft may have an outer diameter of between about 1.5 mm and about 6.0 mm. In some embodiments, the distal end of the second shaft may have a cross-sectional diameter of between about 0.7 mm and about 5 mm.

In some embodiments, the second shaft may further include an annular lumen and an inflatable member disposed distal to the distal end of the first shaft and within a space between the set of splines. The annular lumen of the second shaft may couple to the inflatable member and the inflatable member may be configured to transition into an inflated configuration by fluid pressure applied through the annular lumen.

In some embodiments, the set of splines may be configured to be transitionable into the plurality of states in response to the inflatable member transitioning into the inflated configuration.

In some embodiments, an apparatus may include a first shaft defining a longitudinal axis and a lumen, a second shaft disposed within the lumen and having a distal portion that extends from a distal end of the first shaft, a plurality of electrodes, and a set of splines. Each spline of the set of splines includes a set of electrodes from the plurality of electrodes formed on that spline. Each set of electrodes includes (1) a distal electrode such that the set of splines includes a set of distal electrodes and (2) a proximal electrode such that the set of splines includes a set of proximal electrodes, a proximal end coupled to the distal end of the first shaft, a distal end coupled to a distal end of the second shaft. The set of splines may be transitionable into a plurality of states between and inclusive of an undeployed configuration and an expanded configuration in which an angle between a first unit tangent vector extending through a length of a distal portion of each spline from the set of splines and a second unit tangent vector extending through a proximal portion of each spline from the set of splines varies between about 70 degrees and about 180 degrees. A pre-selected portion of the plurality of electrodes may be activatable in each of the plurality of states to generate an electric field for ablating a tissue wall by irreversible electroporation.

In some embodiments, the set of splines, when used for ventricular ablation or to ablate thicker tissue, may be transitioned into one or more states from the plurality of states in which the angle is between about 90 degrees and about 180 degrees. In some embodiments, the set of splines, when used for atrial ablation or to ablate thinner tissue, may be transitioned into one or more states from the plurality of states in which the angle is between about 70 degrees and about 120 degrees.

In some embodiments, an inflatable member may be disposed distal to the distal end of the first shaft and within a space between the set of splines. The inflatable member may be configured to transition into an inflated configuration. In some embodiments, the inflatable member may be formed of an insulating material such that the inflatable member may be configured to drive the electric field generated by the plurality of electrodes to a region outside of the space between the set of splines. In some embodiments, the set of splines may be configured to ablate the tissue wall independent of an orientation of the set of splines relative to the tissue wall. In some embodiments, the set of splines may be transitionable into the plurality of states in response to the second shaft moving relative to the first shaft along the longitudinal axis. In some embodiments, the distal end of the second shaft may be separated from each distal electrode from the set of distal electrodes by at most about 6 mm.

In some embodiments, at least one distal electrode from the set of distal electrodes may be configured to be activated with a first polarity and at least one proximal electrode from the set of proximal electrodes may be configured to be activated with a second polarity being opposite from the first polarity, to collectively generate the electric field. In some embodiments, each spline from the set of splines includes a plurality of proximal electrodes and at least one flexible portion disposed between adjacent proximal electrodes from the plurality of proximal electrodes for increasing spline flexibility.

In some embodiments, a method may include positioning an ablation device in a first location in a cardiac chamber of a heart of a subject, the ablation device defining a longitudinal axis and including a set of splines, each spline from the set of splines including a distal electrode and a proximal electrode formed on that spline. An inner shaft of the ablation device may translate relative to an outer shaft of the ablation device to transition the set of splines into a state in which a distal portion of each spline of the set of splines and a proximal portion of each spline of the set of splines is at a first angle between about 70 and about 180 degrees. Each spline from the set of splines may have a distal end coupled to the inner shaft and a proximal end coupled to the outer shaft. A first ablation pulse waveform may be delivered to a distal electrode formed on at least one spline from the set of splines and a proximal electrode formed on at least one spline from the set of splines such that the set of splines generates a first electric field for ablating a first portion of a tissue wall of the cardiac chamber. The ablation device may be positioned in a second location in the cardiac chamber. A second ablation pulse waveform may be delivered to a distal electrode formed on at least one spline from the set of splines and a proximal electrode formed on at least one spline from the set of splines such that the set of splines generates a second electric field for ablating a second portion of the tissue wall.

In some embodiments, at least one of the first electric field or the second electric field is configured to form a focal ablation lesion on a surface of the tissue having a diameter between about 0.5 cm and about 2.5 cm. In some embodiments, the ablation device further includes an inflatable member disposed in a space between the set of splines. The method may further comprise transitioning the inflatable member into an inflated configuration. At least one of the first ablation pulse waveform or the second ablation pulse waveform being delivered after the inflatable member is transitioned into the inflated configuration. In some embodiments, the first and second locations are in an atrium of the heart, and the first and second angles are between about 70 and about 120 degrees. In some embodiments, the first and second locations are in a ventricle of the heart, and the first and second angles are between about 90 and about 180 degrees.

BRIEF DESCRIPTION OF THE DRAWINGS

FIG. 8A is a side view and FIG. 8B is a front cross-sectional view.

FIG. 12A illustrates an unenergized electrode and FIG. 12B illustrates an energized electrode.

FIG. 19A is a schematic perspective view and FIG. 19B is a cross-sectional view.

FIG. 20A is a schematic perspective view and FIG. 20B is a cross-sectional view.

FIG. 27A is a side view of the ablation catheter in a second configuration. FIG. 27B is another side view of the ablation catheter in the second configuration. FIG. 27C is yet another side view of the ablation catheter in the second configuration.

FIG. 29A is a cross-sectional side view of the ablation catheter in a first configuration. FIG. 29B is a cross-sectional side view of the ablation catheter in a third configuration. FIG. 29C is another cross-sectional side view of the ablation catheter in the third configuration. FIG. 29D is yet another cross-sectional side view of the ablation catheter in the third configuration.

FIG. 31A is a perspective view of the ablation catheter in a first configuration. FIG. 31B is a perspective view of the ablation catheter in a second configuration.

FIG. 33A is a perspective view of the ablation catheter. FIG. 33B is a front view of the ablation catheter of FIG. 33A. FIG. 33C is a cut-away perspective view of a spline of the ablation catheter of FIG. 33A. FIG. 33D is a cross-sectional view of a spline of the ablation catheter of FIG. 33A. FIG. 33E is a perspective view of the ablation catheter of FIG. 33A disposed adjacent to tissue.

FIG. 34A is a side view of a spline with a unit tangent vector. FIG. 34B is a side view with two unit tangent vectors.

FIG. 36A is a side view of an ablation catheter in a second configuration. FIG. 36B is another side view of an ablation catheter in a second configuration. FIG. 36C is a side view of an ablation catheter near tissue.

FIG. 37A is a perspective view of an ablation catheter disposed in a left atrium. FIG. 37B is a perspective view of a left atrium after tissue ablation.

FIG. 38A is a perspective view of the ablation catheter according to a first configuration. FIG. 38B is another perspective view of the ablation catheter according to a second configuration. FIG. 38C is an annotated perspective view of the ablation catheter. FIG. 38D is a perspective view of the ablation catheter disposed adjacent to tissue.

FIG. 39A is a perspective view of the ablation catheter inflated configuration. FIG. 39B is another perspective view of the ablation catheter with the inflatable member in a deflated configuration. FIG. 39C is another perspective view of the ablation catheter with an inflatable member in a deflated configuration. FIG. 39D is an annotated perspective view of the ablation catheter with an inflatable member in an inflated configuration.

DETAILED DESCRIPTION

Figure 1:
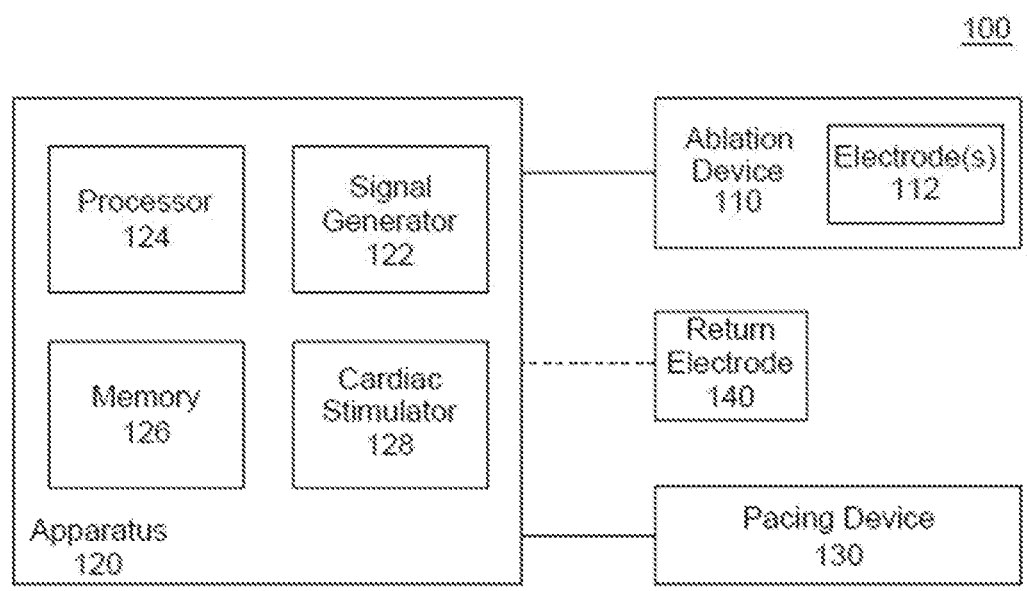
FIG. 1 is a block diagram of an electroporation system, according to embodiments.

Described herein are systems, devices, and methods for selective and rapid application of pulsed electric fields to ablate tissue by irreversible electroporation. Generally, the systems, devices, and methods described herein may be used to generate large electric field magnitudes at desired regions of interest and reduce peak electric field values elsewhere in order to reduce unintended tissue damage. An irreversible electroporation system as described herein may include a signal generator and a processor configured to apply one or more voltage pulse waveforms to a selected set of electrodes of an ablation device to deliver energy to a region of interest (e.g., ablation energy for a set of tissue in a pulmonary vein ostium). The pulse waveforms disclosed herein may aid in therapeutic treatment of a variety of cardiac arrhythmias (e.g., atrial fibrillation). In order to deliver the pulse waveforms generated by the signal generator, one or more electrodes of the ablation device may have an insulated electrical lead configured for sustaining a voltage potential of at least about 700 V without dielectric breakdown of its corresponding insulation. Subsets of electrodes may be independently addressable such that the subset may be controlled (e.g., deliver energy) independently of any other electrode of the device. In this manner, the electrodes and/or electrode subsets may deliver different energy waveforms with different timing synergistically for electroporation of tissue.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in International Application Serial No. PCT/US2016/057664, filed on Oct. 19, 2016, and titled "SYSTEMS, APPARATUSES AND METHODS FOR DELIVERY OF ABLATIVE ENERGY TO TISSUE," the contents of which are hereby incorporated by reference in its entirety.

In some embodiments, the systems may further include a cardiac stimulator used to synchronize the generation of the pulse waveform to a paced heartbeat. The cardiac stimulator may electrically pace the heart with a cardiac stimulator and ensure pacing capture to establish periodicity and predictability of the cardiac cycle. A time window within a refractory period of the periodic cardiac cycle may be selected for voltage pulse waveform delivery. Thus, voltage pulse waveforms may be delivered in the refractory period of the cardiac cycle so as to avoid disruption of the sinus rhythm of the heart. In some embodiments, an ablation device may include one or more catheters, guidewires, balloons, and electrodes. The ablation device may transform into different configurations (e.g., compact and expanded) to position the device within an endocardial space. In some embodiments, the system may optionally include one or more return electrodes.

Generally, to ablate tissue, one or more catheters may be advanced in a minimally invasive fashion through vasculature to a target location. In a cardiac application, the electrodes through which the voltage pulse waveform is delivered may be disposed on an epicardial device or on an endocardial device. The methods described here may include introducing a device into an endocardial space of the left atrium of the heart and positioning (e.g., disposing) the device in contact with a pulmonary vein ostium. A plurality of pulse waveforms may be generated and delivered to one or more electrodes of the device to ablate tissue. In some embodiments, the pulse waveform may be generated in synchronization with a pacing signal of the heart to avoid disruption of the sinus rhythm of the heart. In some embodiments, the electrodes may be configured in anode-cathode subsets. The pulse waveform may include hierarchical waveforms to aid in tissue ablation and reduce damage to healthy tissue.

Systems

Overview

Disclosed herein are systems and devices configured for tissue ablation via the selective and rapid application of voltage pulse waveforms to aid tissue ablation, resulting in irreversible electroporation. Generally, a system for ablating tissue described here may include a signal generator and an ablation device having one or more electrodes for the selective and rapid application of DC voltage to drive electroporation. As described herein, the systems and devices may be deployed epicardially and/or endocardially to treat atrial fibrillation. Voltages may be applied to a selected subset of the electrodes, with independent subset selections for anode and cathode electrode selections. A pacing signal for cardiac stimulation may be generated and used to generate the pulse waveform by the signal generator in synchronization with the pacing signal.

Generally, the systems and devices described herein include one or more catheters configured to ablate tissue in a left atrial chamber of a heart. FIG. 1 illustrates an ablation system (100) configured to deliver voltage pulse waveforms. The system (100) may include an apparatus (120) including a signal generator (122), processor (124), memory (126), and cardiac stimulator (128). The apparatus (120) may be coupled to an ablation device (110), and optionally to a pacing device (130) and/or an optional return electrode (140) (e.g., a return pad, illustrated here with dotted lines).

The signal generator (122) may be configured to generate pulse waveforms for irreversible electroporation of tissue, such as, for example, pulmonary vein ostia. For example, the signal generator (122) may be a voltage pulse waveform generator and deliver a pulse waveform to the ablation device (110). The return electrode (140) may be coupled to a patient (e.g., disposed on a patient's back) to allow current to pass from the ablation device (110) through the patient and then to the return electrode (140) to provide a safe current return path from the patient (not shown). The processor (124) may incorporate data received from memory (126), cardiac stimulator (128), and pacing device (130) to determine the parameters (e.g., amplitude, width, duty cycle, etc.) of the pulse waveform to be generated by the signal generator (122). The memory (126) may further store instructions to cause the signal generator (122) to execute modules, processes and/or functions associated with the system (100), such as pulse waveform generation and/or cardiac pacing synchronization. For example, the memory (126) may be configured to store pulse waveform and/or heart pacing data for pulse waveform generation and/or cardiac pacing, respectively.

In some embodiments, the ablation device (110) may include a catheter configured to receive and/or deliver the pulse waveforms described in more detail below. For example, the ablation device (110) may be introduced into an endocardial space of the left atrium and positioned to align one or more electrodes (112) to one or more pulmonary vein ostia, and then deliver the pulse waveforms to ablate tissue. The ablation device (110) may include one or more electrodes (112), which may, in some embodiments, be a set of independently addressable electrodes. Each electrode may include an insulated electrical lead configured to sustain a voltage potential of at least about 700 V without dielectric breakdown of its corresponding insulation. In some embodiments, the insulation on each of the electrical leads may sustain an electrical potential difference of between about 200 V to about 1,500 V across its thickness without dielectric breakdown. For example, the electrodes (112) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like.

The pacing device (130) may be suitably coupled to the patient (not shown) and configured to receive a heart pacing signal generated by the cardiac stimulator (128) of the apparatus (120) for cardiac stimulation. An indication of the pacing signal may be transmitted by the cardiac stimulator (128) to the signal generator (122). Based on the pacing signal, an indication of a voltage pulse waveform may be selected, computed, and/or otherwise identified by the processor (124) and generated by the signal generator (122). In some embodiments, the signal generator (122) is configured to generate the pulse waveform in synchronization with the indication of the pacing signal (e.g., within a common refractory window). For example, in some embodiments, the common refractory window may start substantially immediately following a ventricular pacing signal (or after a very small delay) and last for a duration of approximately 250 ms or less thereafter. In such embodiments, an entire pulse waveform may be delivered within this duration.

The processor (124) may be any suitable processing device configured to run and/or execute a set of instructions or code. The processor may be, for example, a general purpose processor, a Field Programmable Gate Array (FPGA), an Application Specific Integrated Circuit (ASIC), a Digital Signal Processor (DSP), and/or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The memory (126) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (126) may store instructions to cause the processor (124) to execute modules, processes and/or functions associated with the system (100), such as pulse waveform generation and/or cardiac pacing.

The system (100) may be in communication with other devices (not shown) via, for example, one or more networks, each of which may be any type of network. A wireless network may refer to any type of digital network that is not connected by cables of any kind. However, a wireless network may connect to a wireline network in order to interface with the Internet, other carrier voice and data networks, business networks, and personal networks. A wireline network is typically carried over copper twisted pair, coaxial cable or fiber optic cables. There are many different types of wireline networks including, wide area networks (WAN), metropolitan area networks (MAN), local area networks (LAN), campus area networks (CAN), global area networks (GAN), like the Internet, and virtual private networks (VPN). Hereinafter, network refers to any combination of combined wireless, wireline, public and private data networks that are typically interconnected through the Internet, to provide a unified networking and information access solution.

Ablation Device

Figure 2:
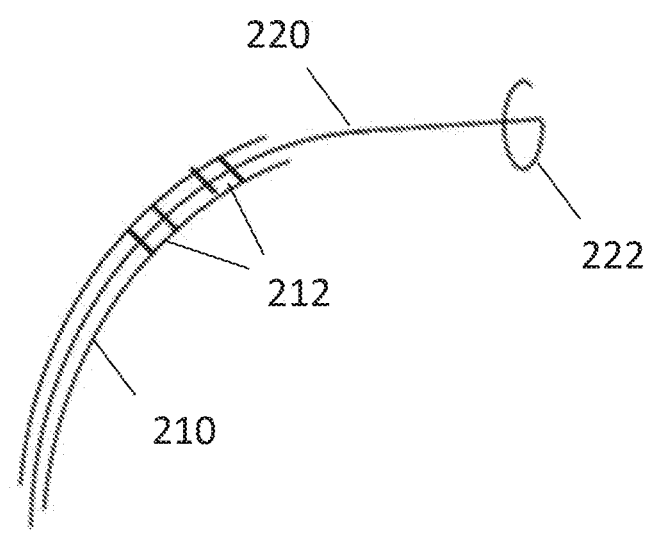
FIG. 2 is a perspective view of an ablation catheter, according to embodiments.

The systems described here may include one or more multi-electrode ablation devices configured to ablate tissue in a left atrial chamber of a heart for treating atrial fibrillation. FIG. 2 is a perspective view of an ablation device (200) (e.g., structurally and/or functionally similar to the ablation device (110)) including a catheter (210) and a guidewire (220) slidable within a lumen of the catheter (210). The guidewire (220) may include a nonlinear distal portion (222) and the catheter (210) may be configured to be disposed over the guidewire (220) during use. The distal portion (222) of the guidewire (220) may be shaped to aid placement of the catheter (210) in a lumen of the patient. For example, a shape of the distal portion (222) of the guidewire (220) may be configured for placement in a pulmonary vein ostium and/or the vicinity thereof, as described in more detail with respect to FIG. 15. The distal portion (222) of the guidewire (220) may include and/or be formed in an atraumatic shape that reduces trauma to tissue (e.g., prevents and/or reduces the possibility of tissue puncture). For example, the distal portion (222) of the guidewire (220) may include a nonlinear shape such as a circle, loop (as illustrated in FIG. 2), ellipsoid, or any other geometric shape. In some embodiments, the guidewire (220) may be configured to be resilient such that the guidewire having a nonlinear shape may conform to a lumen of the catheter (210) when disposed in the catheter (210), and re-form/otherwise regain the nonlinear shape when advanced out of the catheter (210). In other embodiments, the catheter (210) may similarly be configured to be resilient, such as for aiding advancement of the catheter (210) through a sheath (not shown). The shaped distal portion (222) of the guidewire (220) may be angled relative to the other portions of the guidewire (220) and catheter (210). The catheter (210) and guidewire (220) may be sized for advancement into an endocardial space (e.g., left atrium). A diameter of the shaped distal portion (222) of the guidewire (220) may be about the same as a diameter of a lumen in which the catheter (230) is to be disposed.

The catheter (210) may be slidably advanced over the guidewire (220) so as to be disposed over the guidewire (220) during use. The distal portion (222) of the guidewire (220) disposed in a lumen (e.g., near a pulmonary vein ostium) may serve as a backstop to advancement of a distal portion of the catheter (210). The distal portion of the catheter (210) may include a set of electrodes (212) (e.g., structurally and/or functionally similar to the electrode(s) (112)) configured to contact an inner radial surface of a lumen (e.g., pulmonary vein ostium). For example, the electrodes (212) may include an approximately circular arrangement of electrodes configured to contact a pulmonary vein ostium. As shown in FIG. 2, one or more electrodes (212) may include a series of metallic bands or rings disposed along a catheter shaft and be electrically connected together. For example, the ablation device (200) may include a single electrode having a plurality of bands, one or more electrodes each having its own band, and combinations thereof. In some embodiments, the electrodes (212) may be shaped to conform to the shape of the distal portion (222) of the guidewire (220). The catheter shaft may include flexible portions between the electrodes to enhance flexibility. In other embodiments, one or more electrodes (212) may include a helical winding to enhance flexibility.

Each of the electrodes of the ablation devices discussed herein may be connected to an insulated electrical lead (not shown) leading to a handle (not shown) coupled to a proximal portion of the catheter. The insulation on each of the electrical leads may sustain an electrical potential difference of at least 700V across its thickness without dielectric breakdown. In other embodiments, the insulation on each of the electrical leads may sustain an electrical potential difference of between about 200V to about 2000 V across its thickness without dielectric breakdown, including all values and sub-ranges in between. This allows the electrodes to effectively deliver electrical energy and to ablate tissue through irreversible electroporation. The electrodes may, for example, receive pulse waveforms generated by a signal generator (122) as discussed above with respect to FIG. 1. In other embodiments, a guidewire (220) may be separate from the ablation device (200) (e.g., the ablation device (200) includes the catheter (210) but not the guidewire (220). For example, a guidewire (220) may be advanced by itself into an endocardial space, and thereafter the catheter (210) may be advanced into the endocardial space over the guidewire (220).

Figure 3:
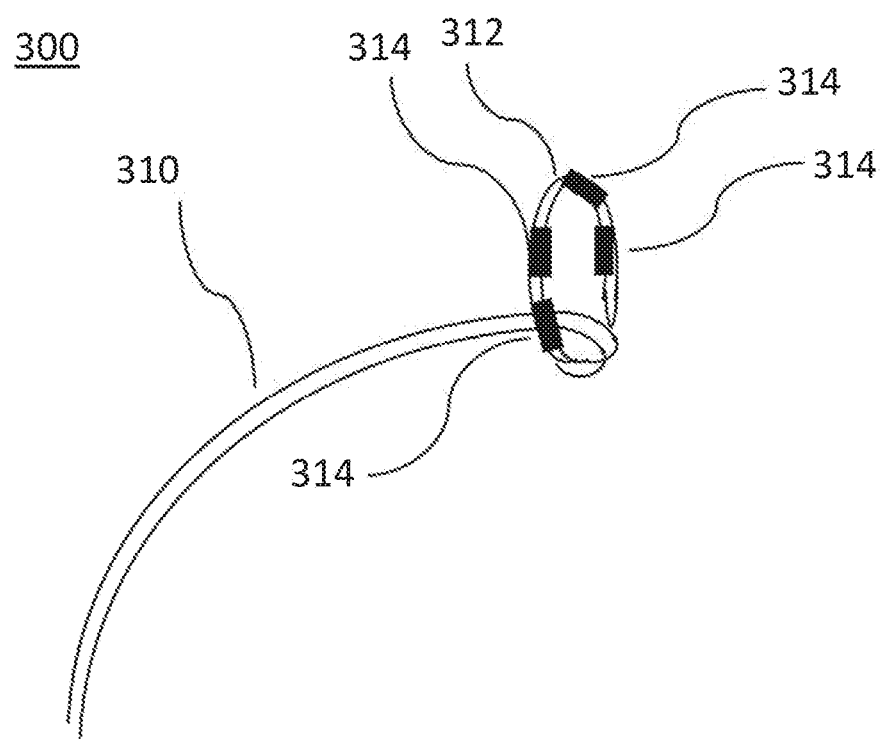
FIG. 3 is a perspective view of an ablation catheter, according to other embodiments.

FIG. 3 is a perspective view of another embodiment of an ablation device (300) (e.g., structurally and/or functionally similar to the ablation device (110)) including a catheter (310) having a set of electrodes (314) provided along a distal portion (312) of the catheter (310). The distal portion (312) of the catheter (310) may be nonlinear and form an approximately circle shape. A set of electrodes (314) may be disposed along a nonlinear distal portion (312) of the catheter (310) may form a generally circular arrangement of electrodes (314). During use, the electrodes (314) may be disposed at a pulmonary vein ostium in order to deliver a pulse waveform to ablate tissue, as described in more detail with respect to FIG. 16. The shaped distal portion (312) of the catheter (310) may be angled relative to the other portions of the catheter (310). For example, the distal portion (312) of the catheter (310) may be generally perpendicular to an adjacent portion of the catheter (310). In some embodiments, a handle (not shown) may be coupled to a proximal portion of the catheter (310) and may include a bending mechanism (e.g., one or more pull wires (not shown)) configured to modify the shape of the distal portion (312) of the catheter (310). For example, operation of a pull wire of the handle may increase or decrease a circumference of the circular shape of the distal portion (312) of the catheter (310). The diameter of the distal portion (312) of the catheter (310) may be modified to allow the electrodes (314) to be disposed near and/or in contact with a pulmonary vein ostium (e.g., in contact with an inner radial surface of the pulmonary vein). The electrodes (314) may include a series of metallic bands or rings and be independently addressable.

In some embodiments, the pulse waveform may be applied between the electrodes (314) configured in anode and cathode sets. For example, adjacent or approximately diametrically opposed electrode pairs may be activated together as an anode-cathode set. It should be appreciated that any of the pulse waveforms disclosed herein may be progressively or sequentially applied over a sequence of anode-cathode electrodes.

Figure 4:
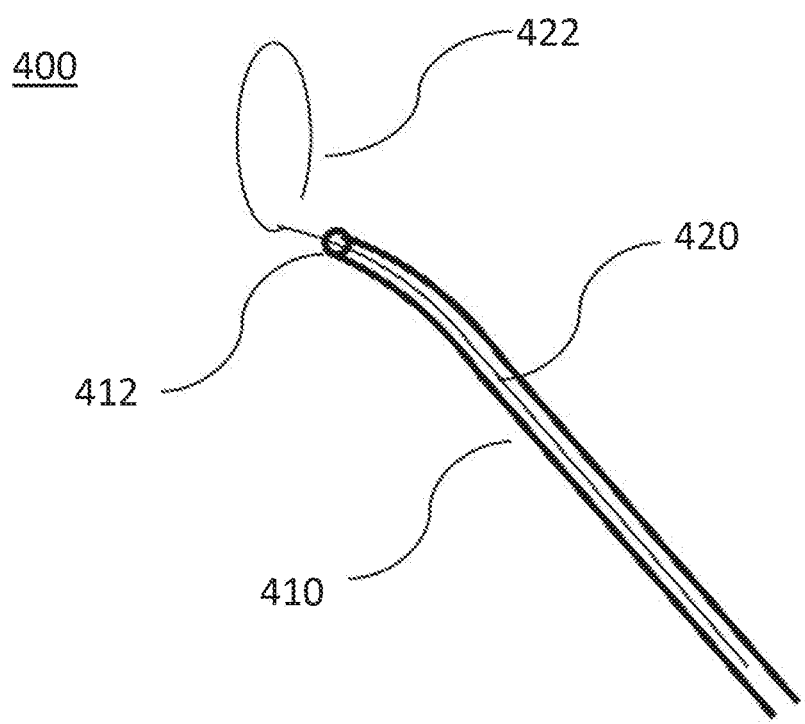
FIG. 4 is a perspective view of an ablation catheter, according to other embodiments.

FIG. 4 is a perspective view of yet another embodiment of an ablation device (400) (e.g., structurally and/or functionally similar to the ablation device (110)) including a catheter (410) and a guidewire (420) having a shaped, nonlinear distal portion (422). The guidewire (420) may be slidable within a lumen of the catheter (410). The guidewire (420) may be advanced through the lumen of the catheter (410) and a distal portion (422) of the guidewire (420) may be approximately circular shaped. The shape and/or diameter of the distal portion (422) of the guidewire (420) may be modified using a bending mechanism as described above with respect to FIG. 3. The catheter (410) may be flexible so as to be deflectable. In some embodiments, the catheter (410) and/or guidewire (420) may be configured to be resilient such that they conform to a lumen in which they are disposed and assume a secondary shape when advanced out of the lumen. By modifying a size of the guidewire (420) and manipulating the deflection of the catheter (410), the distal portion (422) of the guidewire (420) may be positioned at a target tissue site, such as, a pulmonary vein ostium. A distal end (412) of the catheter (410) may be sealed off except where the guidewire (420) extends from such that the catheter (410) may electrically insulate the portion of the guidewire (420) within the lumen of the catheter (410). For example, in some embodiments, the distal end (412) of the catheter (410) may include a seal having an opening that permits passage of the guidewire (420) upon application of force to form a compression hold (that may be fluid-tight) between the seal and the guidewire (420).

In some embodiments, the exposed distal portion (422) of the guidewire (420) may be coupled to an electrode and configured to receive a pulse waveform from a signal generator and deliver the pulse waveform to tissue during use. For example, a proximal end of the guidewire (420) may be coupled to a suitable lead and connected to the signal generator (122) of FIG. 1. The distal portion (422) of the guidewire (420) may be sized such that it may be positioned at a pulmonary vein ostium. For example, a diameter of the shaped distal portion (422) of the guidewire (420) may be about the same as a diameter of a pulmonary vein ostium. The shaped distal portion (422) of the guidewire (420) may be angled relative to the other portions of the guidewire (420) and catheter (410).

The guidewire (420) may include stainless steel, nitinol, platinum, or other suitable, biocompatible materials. In some embodiments, the distal portion (422) of the guidewire (420) may include a platinum coil physically and electrically attached to the guidewire (420). The platinum coil may be an electrode configured for delivery of a voltage pulse waveform. Platinum is radiopaque and its use may increase flexibility to aid advancement and positioning of the ablation device (400) within an endocardial space.

Figure 5:
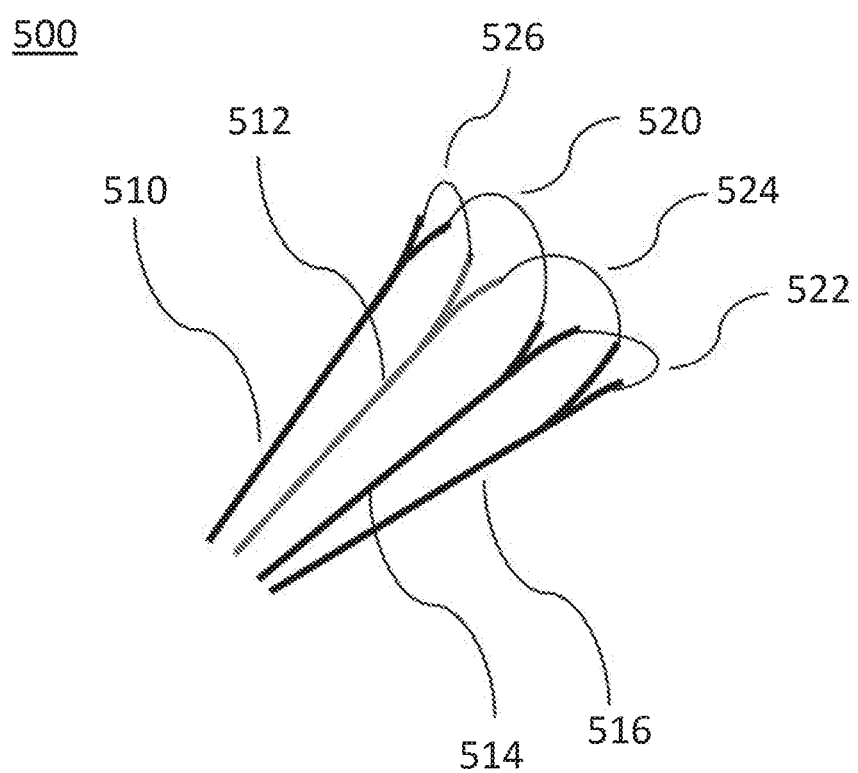
FIG. 5 is a detailed perspective view of a distal portion of an ablation catheter, according to other embodiments.

FIG. 5 is a detailed perspective view of a flower-shaped distal portion of an ablation device (500) (e.g., structurally and/or functionally similar to the ablation device (110)) including a set of electrodes (520, 522, 524, 526) each extending from a pair of insulated lead segments (510, 512, 514, 516). Each pair of adjacent insulated lead segments coupled to an uninsulated electrode (e.g., lead segments (510, 512) and electrode (526)) form a loop (FIG. 5 illustrates a set of four loops). The set of loops at the distal portion of the ablation device (500) may be configured for delivering a pulse waveform to tissue. The ablation device (500) may include a set of insulated lead segments (510, 512, 514, 516) that branch out at a distal end of the device (500) to connect to respective exposed electrodes (520, 522, 524, 526), as shown in FIG. 5. The electrodes (520, 522, 524, 526) may include an exposed portion of an electrical conductor. In some embodiments, one or more of the electrodes (520, 522, 524, 526) may include a platinum coil. The one or more segments (510, 512, 514, 516) may be coupled to a bending mechanism (e.g., strut, pull wire, etc.) controlled from a handle (not shown) to control a size and/or shape of the distal portion of the device (500).

The electrodes (520, 522, 524, 526) may be flexible and form a compact first configuration for advancement into an endocardial space, such as adjacent to a pulmonary vein ostium. Once disposed at a desired location, the electrodes (520, 522, 524, 526) may be transformed to an expanded second configuration when advanced out of a lumen, such as a sheath, to form a flower-shaped distal portion, as shown in FIG. 5. In other embodiments, the insulated lead segments (510, 512, 514, 516) and electrodes (520, 522, 524, 526) may be biased to expand outward (e.g., spring open) into the second configuration when advanced out of a lumen (e.g., sheath) carrying the device (500). The electrodes (520, 522, 524, 526) may be independently addressable and each have an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2000 V across its thickness without dielectric breakdown.

In some embodiments, the ablation device (5000) may be configured for delivering the pulse waveform to tissue during use via the set of electrodes (520, 522, 524, 526). In some embodiments, the pulse waveform may be applied between the electrodes (520, 522, 524, 526) configured in anode and cathode sets. For example, approximately diametrically opposite electrode pairs (e.g., electrodes (520, 524) and (522, 526)) may be activated together as an anode-cathode pair. In other embodiments, adjacent electrodes may be configured as an anode-cathode pair. As an example, a first electrode (520) of the set of electrodes may be configured as an anode and a second electrode (522) may be configured as a cathode.

FIGS. 6-9E, 26A-27C, and 28 illustrate additional embodiments of an ablation device (e.g., structurally and/or functionally similar to the ablation device (110)) that may be configured to deliver voltage pulse waveforms using a set of electrodes to ablate tissue and electrically isolate a pulmonary vein. In some of these embodiments, the ablation device may be transformed from a first configuration to a second configuration such that the electrodes of the ablation device expand outward to contact a lumen of tissue (e.g., pulmonary vein ostium).

Figure 6:
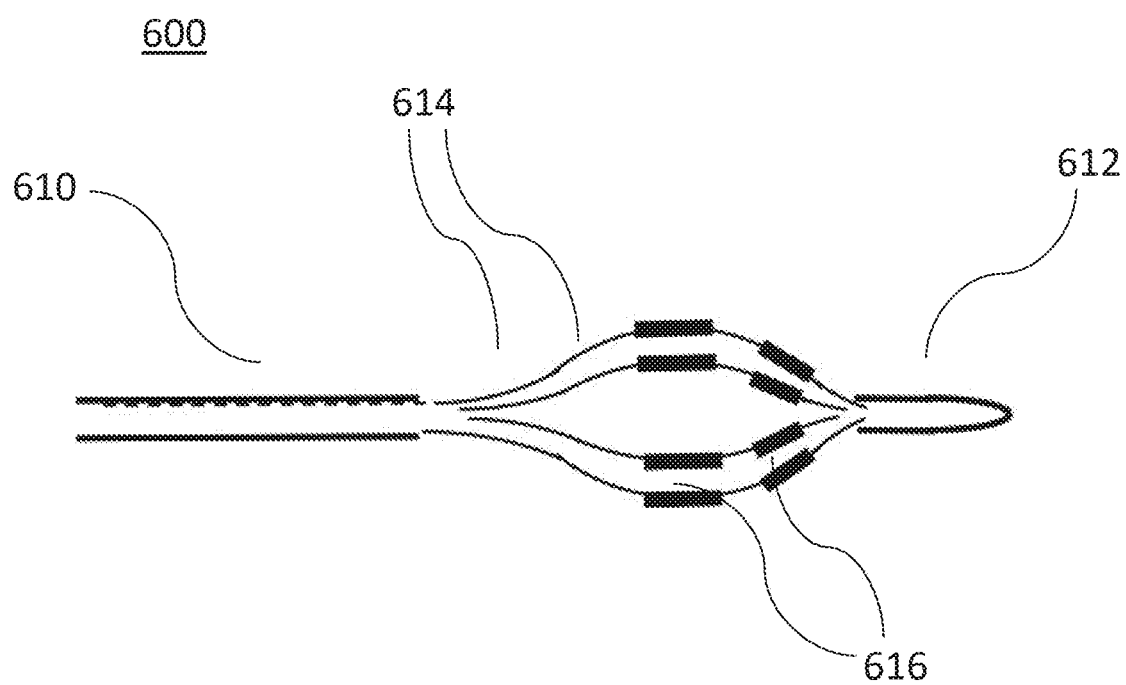
FIG. 6 is a side view of an ablation catheter, according to other embodiments.

FIG. 6 is a side view of an embodiment of an ablation device (600) including a catheter shaft (610) at a proximal end of the device (600), a distal cap (612) of the device (600), and a set of splines (614) coupled thereto. The distal cap (612) may include an atraumatic shape to reduce trauma to tissue. A proximal end of the set of splines (614) may be coupled to a distal end of the catheter shaft (610), and a distal end of the set of splines (614) may be tethered to the distal cap (612) of the device (600). The ablation device (600) may be configured for delivering a pulse waveform to tissue during use via one or more splines of the set of splines (614). As used herein, the terms "spline" and "spine" may be used interchangeably. In some embodiments, an apparatus may include a catheter defining a longitudinal axis Each spline (614) of the ablation device (600) may include one or more jointly wired, or in some cases independently addressable electrodes (616) formed on a surface of the spline (614). Each electrode (616) may include an insulated electrical lead configured to sustain a voltage potential of at least about 700 V without dielectric breakdown of its corresponding insulation. In other embodiments, the insulation on each of the electrical leads may sustain an electrical potential difference of between about 200V to about 2000 V across its thickness without dielectric breakdown. Each spline (614) may include the insulated electrical leads of each electrode (616) formed in a body of the spline (614) (e.g., within a lumen of the spline (614)). In cases where the electrodes on a single spline are wired together, a single insulated lead may carry strands connecting to different electrodes on the spline. FIG. 6 illustrates a set of splines (614) where each spline (614) includes a pair of electrodes (616) having about the same size, shape, and spacing as the electrodes (616) of an adjacent spline (614). In other embodiments, the size, shape, and spacing of the electrodes (616) may differ.

For each of the ablation devices described herein, and the ablation devices described in FIGS. 6-9E, 26A-27C, and 28 in particular, each spline of the set of splines may include a flexible curvature. The minimum radius of curvature of a spline can be in the range of about 1 cm or larger. For example, the set of splines may form a delivery assembly at a distal portion of the ablation device and be configured to transform between a first configuration where the set of splines bow radially outward from a longitudinal axis of the ablation device, and a second configuration where the set of splines are arranged generally parallel to the longitudinal axis of the ablation device. In this manner, the splines may more easily conform to the geometry of an endocardial space. In general, the "basket" of splines can have an asymmetric shape along the shaft length, so that one end (say the distal end) of the basket is more bulbous than the other end (say the proximal end) of the basket. The delivery assembly may be disposed in the first configuration in contact with the pulmonary vein ostium and transformed to the second configuration prior to delivering a pulse waveform. In some of these embodiments, a handle may be coupled to the set of splines and the handle configured for affecting transformation of the set of splines between the first configuration and the second configuration. In some embodiments, the electrical leads of at least two electrodes of the set of electrodes may be electrically coupled at or near a proximal portion of the ablation device, such as, for example, within the handle.

In one embodiment, each of the electrodes (616) on a spline (614) may be configured as an anode while each of the electrodes (616) on an adjacent spline (614) may be configured as a cathode. In another embodiment, the electrodes (616) on one spline may alternate between an anode and cathode with the electrodes of an adjacent spline having a reverse configuration (e.g., cathode and anode). The ablation device (600) may include any number of splines, for example, 3, 4, 5, 6, 7, 8, 9, 10, 12, 14, 16, 18, 20, or more splines, including all values and sub-ranges in between. In some embodiments, the ablation device (600) may include 3 to 20 splines. For example, the ablation device (600) may include 6 to 12 splines.

Figure 7:
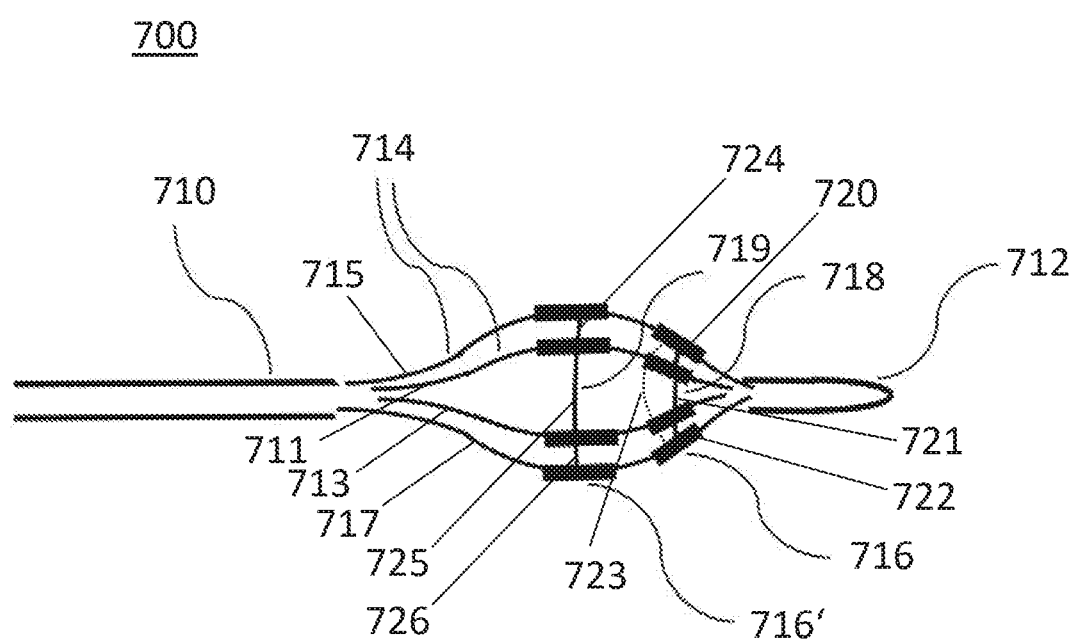
FIG. 7 is a side view of an ablation catheter, according to other embodiments.

FIG. 7 is a side view of another embodiment of an ablation device (700) including a catheter shaft (710) at a proximal end of the device (700), a distal cap (712) of the device (700), and a set of splines (714) coupled thereto. The distal cap (712) may include an atraumatic shape. A proximal end of the set of splines (714) may be coupled to a distal end of the catheter shaft (710), and a distal end of the set of splines (714) may be tethered to the distal cap (712) of the device (700). Each spline (714) of the ablation device (700) may include one or more independently addressable electrodes (716) formed on a surface of the spline (714). Each electrode (716) may include an insulated electrical lead configured to sustain a voltage potential of at least about 700 V without dielectric breakdown of its corresponding insulation. In other embodiments, the insulation on each of the electrical leads may sustain an electrical potential difference of between about 200V to about 1500 V across its thickness without dielectric breakdown. Each spline (714) may include the insulated electrical leads of each electrode (716) formed in a body of the spline (714) (e.g., within a lumen of the spline (714)). A set of spline wires (718, 719) may be electrically conductive and electrically couple adjacent electrodes (716) disposed on different splines (714) such as electrodes (716) between a pair of splines (718, 719) of the set of splines. For example, the spline wires (718, 719) may extend in a transverse direction relative to a longitudinal axis of the ablation device (700).

FIG. 7 illustrates a set of splines (714) where each spline (714) includes a pair of electrodes (716) having about the same size, shape, and spacing as the electrodes (716) of an adjacent spline (714). In other embodiments, the size, shape, and spacing of the electrodes (716) may differ. For example, the electrodes (716) electrically coupled to a first spline wire (718) may differ in size and/or shape from electrodes (716') electrically coupled to a second spline wire (719).

In some embodiments, the first spline wire (718) may include a first set of spline wires (720, 721, 722, 723), where each spline wire of the set of spline wires (720, 721, 722, 723) may couple electrodes (716) between a different pair of splines of the set of splines (714). In some of these embodiments, the set of spline wires (720, 721, 722, 723) may form a continuous loop between the electrodes (716) coupled thereto. Likewise, the second spline wire (719) may include a second set of spline wires (724, 725, 726), where each spline wire of the set of spline wires (724, 725, 726) may couple electrodes (716') across the set of splines (714). The second set of spline wires (724, 725, 726) may couple different electrodes (716') across the set of splines (714) than the first set of spline wires (720, 721, 722, 723). In some of these embodiments, the first set of spline wires (720, 721, 722, 723) may form a first continuous loop between the electrodes (716) coupled thereto and the second set of spline wires (724, 725, 726) may form a second continuous loop between the electrodes (716') coupled thereto. The first continuous loop may be electrically isolated from the second continuous loop. In some of these embodiments, the electrodes (716) coupled to the first continuous loop may be configured as anodes and the electrodes (716) coupled to the second continuous loop may be configured as cathodes. A pulse waveform may be delivered to the electrodes (716) of the first and second continuous loop. In some embodiments, the spline wires such as 721, 722, 723 etc. can be replaced by similar electrical connections in the proximal part of the device (for example, in the device handle). For example, the electrodes 716 can all be electrically wired together in the handle of the device.

In another embodiment, the first spline wire (721) of the set of spline wires (720, 721, 722, 723) may couple electrodes (716) between a first spline (711) and a second spline (713) of the set of splines (714), and a second spline wire (720) of the set of spline wires (720, 721, 722, 723) may couple electrodes (716) between the first spline (711) and a third spline (715) of the set of splines (714). The electrodes (716) coupled by the first spline wire (721) and the second spline wire (720) may be configured as an anode and cathode (or vice-versa). In yet another embodiment, the first spline wire (721) of the set of spline wires (720, 721, 722, 723) may couple the electrodes (716) between a first spline (711) and a second spline (713) of the set of splines (714), and a second spline wire (723) of the set of spline wires (720, 721, 722, 723) may couple the electrodes (716) between a third spline (715) and a fourth spline (717) of the set of splines (714). A pulse waveform may be delivered to the electrodes (716) coupled by the first spline wire (721) and the second spline wire (723). In some embodiments, instead of spline wires the electrical leads of at least two electrodes of the set of electrodes are electrically coupled at or near a proximal portion of the ablation device, such as, for example, within a handle.

In other embodiments, one or more of the spline wires (718, 719) may form a continuous loop between the electrically coupled electrodes (716). For example, a first set of spline wires (718) may form a first continuous loop between the electrodes (716) coupled thereto and a second set of spline wires (719) may form a second continuous loop between the electrodes (716) coupled thereto. In this case, the first continuous loop may be electrically isolated from the second continuous loop. In one embodiment, each of the electrodes (716) coupled to a first set of spline wires (718) may be configured as an anode while each of the electrodes (716) coupled to a second set of spline wires (719) may be configured as a cathode. Each group of electrically coupled electrodes (716) may be independently addressable. In some embodiments, instead of spline wires the electrical leads of at least two electrodes of the set of electrodes are electrically coupled at or near a proximal portion of the ablation device, such as, for example, within a handle.

In some embodiments, as discussed in further detail below with respect to FIGS. 8A-8B, a spline wire may electrically couple to a set of electrodes (e.g., 2, 3, 4, 5, etc.)

without forming a continuous loop. For example, a discontinuous loop may be formed using two spline wires. In other embodiments, the size, shape, and spacing of the electrodes (716) may differ. The ablation device (700) may include any number of splines, for example, 3, 4, 5, 6, 7, 8, 9, 10, 12, 14, 16, 18, 20, or more splines. In some embodiments, the ablation device (700) may include 3 to 20 splines. For example, in one embodiment, the ablation device (700) may include 6 to 9 splines.

Figure 8A:
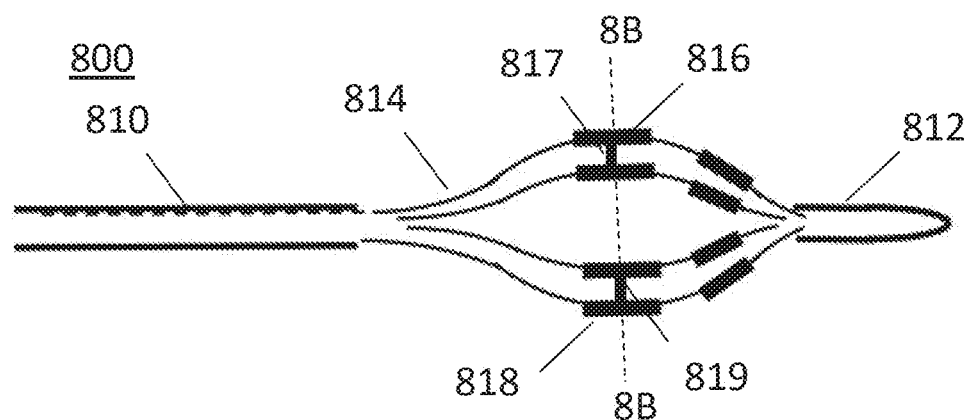
FIGS. 8A-8B are views of an ablation catheter, according to other embodiments.
Figure 8B:
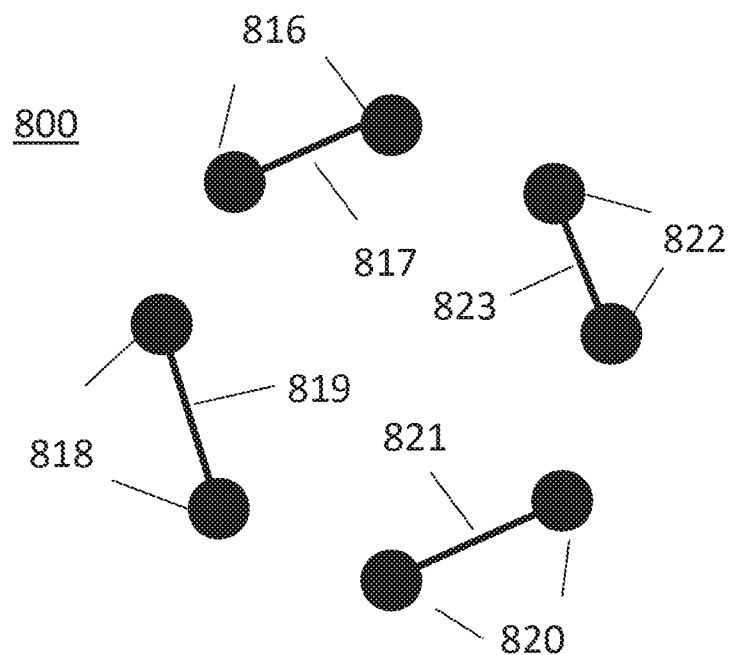

FIGS. 8A-8B are side and front cross-sectional views, respectively, of an ablation catheter (800). FIG. 8A is a side view of an embodiment of an ablation device (800) including a catheter shaft (810) at a proximal end of the device (800), a distal cap (812) of the device (800), and a set of splines (814) coupled thereto. The distal cap (812) may include an atraumatic shape. A proximal end of the set of splines (814) may be coupled to a distal end of the catheter shaft (810), and a distal end of the set of splines (14) may be tethered to the distal cap (812) of the device (800). Each spline (814) of the ablation device (800) may include one or more independently addressable electrodes (816, 818) formed on a surface of the spline (814). Each electrode (816, 818) may include an insulated electrical lead configured to sustain a voltage potential of at least about 700 V without dielectric breakdown of its corresponding insulation. In other embodiments, the insulation on each of the electrical leads may sustain an electrical potential difference of between about 200V to about 2000 V across its thickness without dielectric breakdown, including all values and subranges in between. Each spline (814) may include the insulated electrical leads of each electrode (816, 818) formed in a body of the spline (814) (e.g., within a lumen of the spline (814)). One or more spline wires (817, 819) may be electrically conductive and electrically couple adjacent electrodes (816, 818) disposed on different splines (814). For example, the spline wires (817, 819) may extend in a transverse direction relative to a longitudinal axis of the ablation device (800).

FIG. 8B is a front cross-sectional view of FIG. 8A taken along the 8B-8B line. Each spline wire (817, 819, 821, 823) electrically couples a pair of adjacent electrodes (816, 818, 820, 822) on different splines. In some embodiments, each coupled electrode pair may be electrically isolated from each other. In some embodiments, the coupled electrode pair may be configured with a common polarity. Adjacent pairs of electrodes may be configured with opposite polarities (e.g., a first electrode pair configured as an anode and an adjacent second electrode pair configured as a cathode). For example, the electrodes (816) coupled to a first set of spline wires (817) may be configured as an anode while each of the electrodes (818) coupled to a second set of spline wires (819) may be configured as a cathode. In some embodiments, each electrode formed on a spline (814) may share a common polarity (e.g., configured as an anode or cathode). Each coupled electrode pair may be independently addressable. In some embodiments, the ablation device (800) may include an even number of splines. The ablation device (800) may include any number of splines, for example, 4, 6, 8, 10, or more splines. In some embodiments, the ablation device may include 4 to 10 splines. For example, in one embodiment, the ablation device may include 6 to 8 splines. As indicated in the foregoing, in some embodiments, the spline wires such as 817, 819, etc. can be replaced by similar electrical connections in the proximal part of the device (for example, in the device handle). For example, the electrodes (816) can be electrically wired together in the handle of the device, so that these electrodes are at the same electric potential during ablation.

Figure 9A:
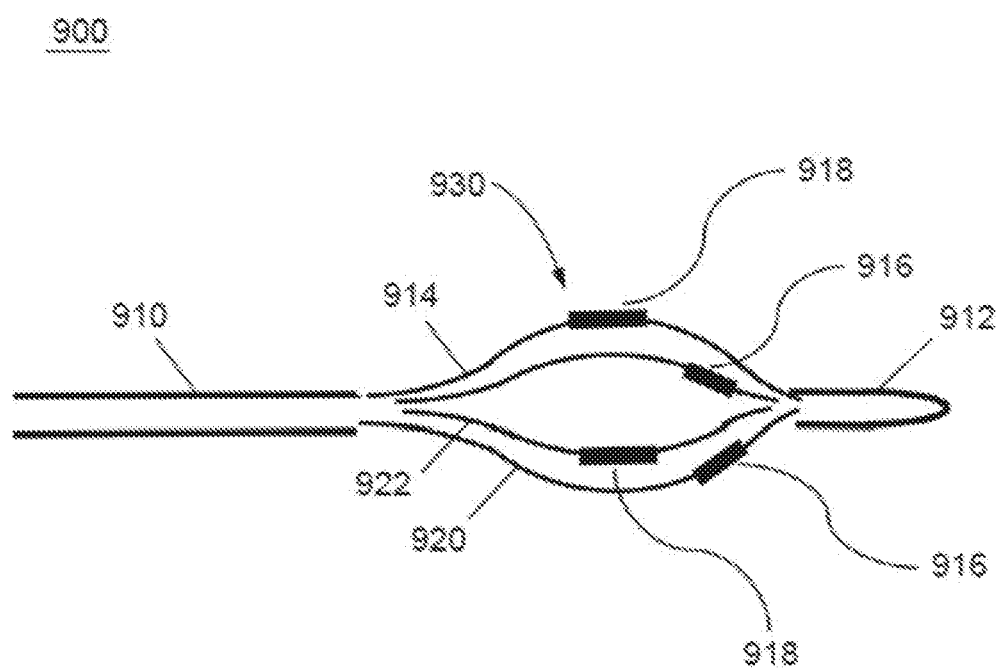
FIG. 9A is a side view of an ablation catheter in a first structure, according to other embodiments.

FIG. 9A is a side view of yet another embodiment of an ablation device (900) including a catheter shaft (910) at a proximal end of the device (900), a distal cap (912) of the device (900), and a set of splines (914) coupled thereto. The distal cap (912) may include an atraumatic shape. A proximal end of the set of splines (914) may be coupled to a distal end of the catheter shaft (910), and a distal end of the set of splines (914) may be tethered to the distal cap (912) of the device (900). Each spline (914) of the ablation device (900) may include one or more independently addressable electrodes (916, 918) formed on a surface of the spline (914). Each electrode (916, 918) may include an insulated electrical lead configured to sustain a voltage potential of at least about 700 V without dielectric breakdown of its corresponding insulation. In other embodiments, the insulation on each of the electrical leads may sustain an electrical potential difference of between about 200V to about 2000 V across its thickness without dielectric breakdown. Each spline (914) may include the insulated electrical leads of each electrode (916, 918) formed in a body of the spline (914) (e.g., within a lumen of the spline (914)). FIG. 9A illustrates a set of splines (914) where each spline (914) includes an electrode spaced apart or offset from an electrode of an adjacent spline (914). For example, the set of splines (914) including a first spline (920) and a second spline (922) adjacent to the first spline (920), wherein an electrode (916) of the first spline (920) is disposed closer to a distal end (912) of the ablation device (900) relative to an electrode (918) of the second spline (922). In other embodiments, the size and shape of the electrodes (916, 918) may differ as well.

In some embodiments, adjacent distal electrodes (916) and proximal electrodes (918) may form an anode-cathode pair. For example, the distal electrodes (916) may be configured as an anode and the proximal electrodes (918) may be configured as a cathode. In some embodiments, the ablation device (900) may include 3 to 12 splines. In FIG. 9A, one electrode (916, 918) is formed on a surface of each spline (914) such that each spline (914) includes one insulated electrical lead. A lumen of the spline (914) may therefore be reduced in diameter and allow the spline (914) to be thicker and more mechanically robust. Thus, dielectric breakdown of the insulation may be further reduced, thereby improving reliability and longevity of each spline (914) and the ablation device (900). The ablation device (900) may include any number of splines, for example, 3, 4, 5, 6, 7, 8, 9, 10, 12, 14, 16, 18, 20, or more splines. In some embodiments, the ablation device (900) may include 3 to 20 splines. For example, in one embodiment, the ablation device (900) may include 6 to 10 splines. Furthermore, in some embodiments, the shape of a bulb-like expanded structure (930) of the expanded set of splines (914) may be asymmetric, for example with its distal portion being more bulbous or rounded than its proximal portion (e.g., see FIGS. 9B-9E). Such a bulbous distal portion can aid in positioning the device at the ostium of a pulmonary vein.

Figure 9B:
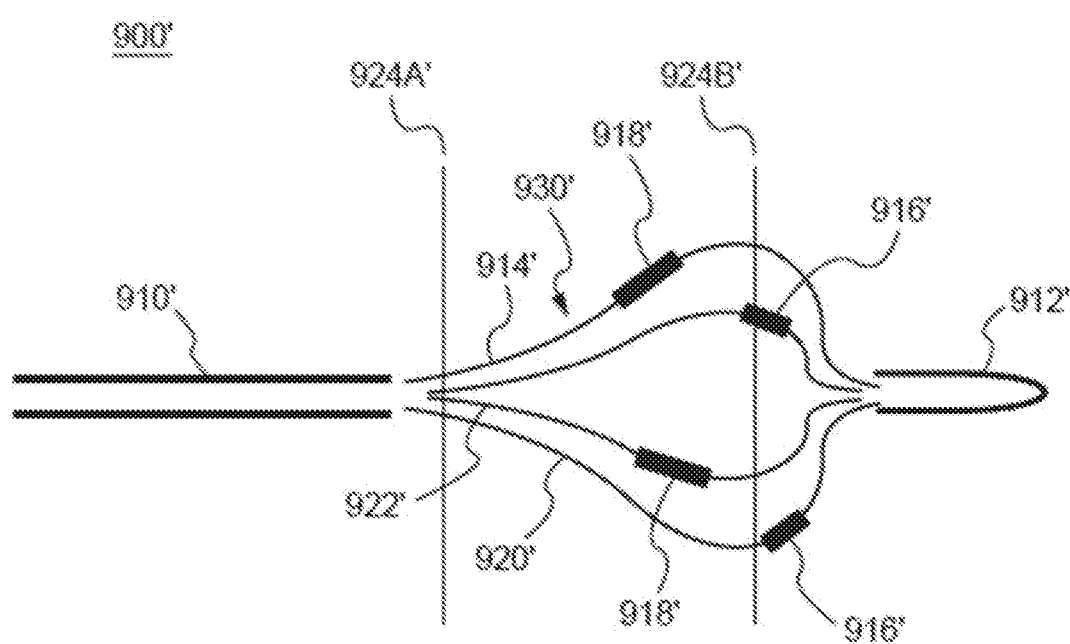
FIG. 9B is a side view of an ablation catheter in a second expanded structure, according to other embodiments.

Referring to FIGS. 9B-9E, it is understood that unless indicated otherwise, components with similar references numbers to those in FIG. 9A (e.g., the electrode (916) in FIG. 9A and the electrode (916') in FIG. 9B) may be structurally and/or functionally similar. FIG. 9B illustrates the spline wires (914', 920', 922') forming an expanded structure (930') during use such as when deployed. A first plane (924A'), also sometimes referred to as a proximal plane, of the expanded structure (930') has a cross-sectional area that is different than a cross-sectional area at a second plane (924B') of the expanded structure (930'). As illustrated in FIG. 9B, in some embodiments, the cross-sectional area of the expanded structure (930') at the second plane (924B') is greater than that at the first plane (924A'). The terms "first plane" and "second plane" as used with respect to FIG. 9B may refer to planes orthogonal to the longitudinal axis of the catheter shaft (910') that are each formed up to about 1 cm, about 2 cm, and about 3 cm or more (including all values and sub-ranges in between) from the distal end of the catheter shaft (910') and the proximal end of the distal cap (912'), respectively. Similar to FIG. 9A, the electrode (916') of the first spline (920') is disposed closer to the distal cap (912') of the ablation device (900') relative to an electrode (918') of the second spline (922').

Figure 9C:
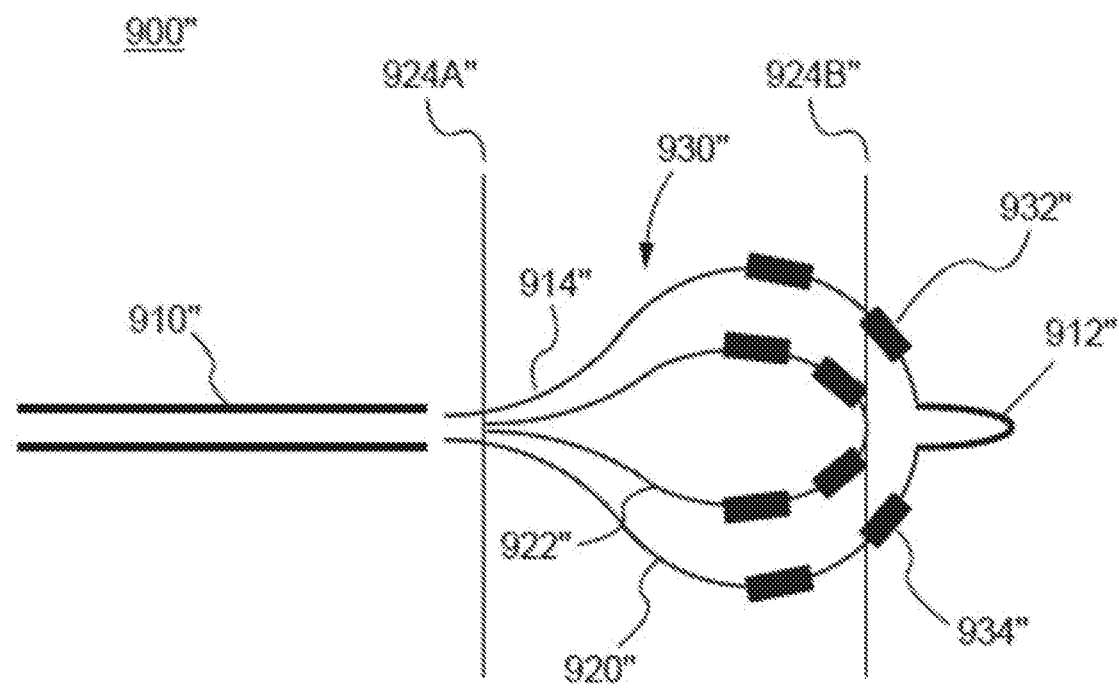
FIG. 9C is a side view of an ablation catheter in a third expanded structure, according to other embodiments.

FIG. 9C illustrates the spline wires (914", 920", 922") forming an expanded structure (930") during use such as when deployed. A first plane (924A"), also sometimes referred to as a proximal plane, of the expanded structure (930") has a cross-sectional area that is different than a cross-sectional area at a second plane (924B") of the expanded structure (930"). As illustrated in FIG. 9C, in some embodiments, the cross-sectional area of the expanded structure (930") at the second plane (924B") is greater than that at the first plane (924A"). The terms "first plane" and "second plane" as used with respect to FIG. 9C may refer to planes orthogonal to the longitudinal axis of the catheter shaft (910") that are each formed up to about 1 cm, about 2 cm, and about 3 cm or more (including all values and sub-ranges in between) from the distal end of the catheter shaft (910") and the proximal end of the distal cap (912"), respectively. Unlike FIGS. 9A-9B, multiple electrodes may be present on each spline wire, and some electrodes may be equidistant from the distal cap (912"). In this manner, relatively distal electrodes such as 932" and 934" may be apposed at or proximal/antral to a pulmonary vein ostium during use for ablation delivery to generate an ostial circumferential lesion around a pulmonary vein.

Figure 9D:
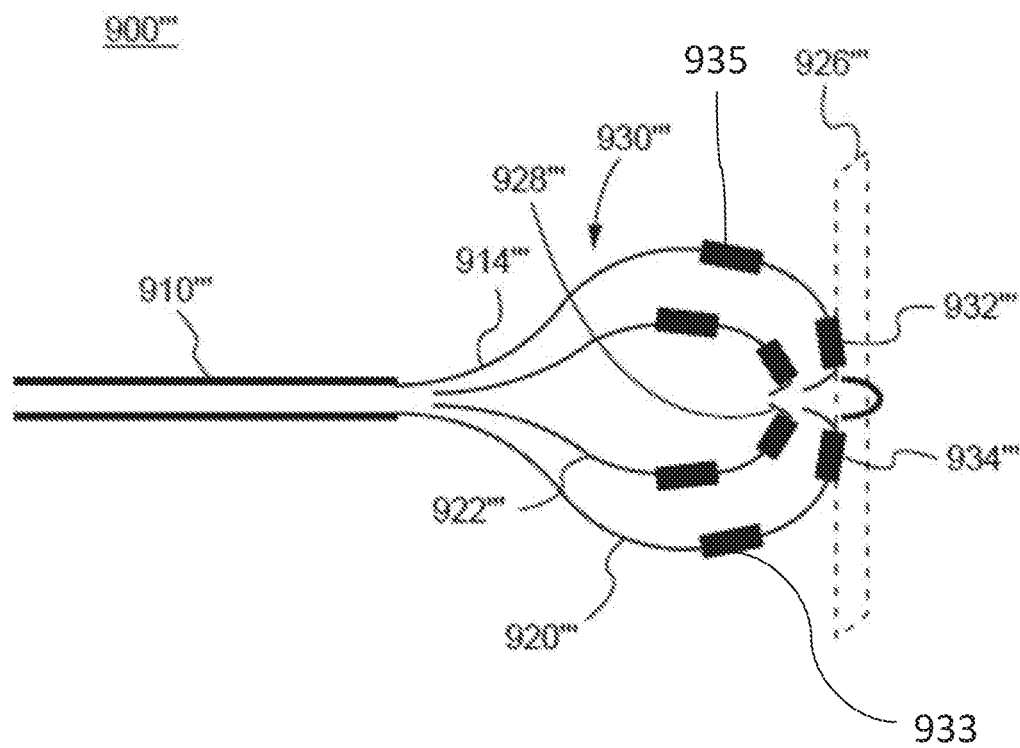
FIG. 9D is a side view of an ablation catheter in a fourth expanded structure, according to other embodiments.

FIG. 9D illustrates the spline wires (914''', 920''', 922''') forming an expanded structure (930''') during use such as when deployed. The spline wires (914''', 920''', 922''') converge at their distal ends to a point (928''') that lies inside/within the expanded structure (930'''). As illustrated in FIG. 9D, in such a configuration, at least some electrodes (932''', 934''') on the spline wires (914''', 920''', 922''') may lie in a distal end plane (926''') of the expanded structure (930'''). The term "distal end plane" as used with respect to FIG. 9D may refer to a plane orthogonal to the longitudinal axis of the catheter shaft (910''') that passes through a distal boundary of the expanded structure (930'''). In this manner, the expanded structure (930''') may be pressed against, for example, an endocardial surface such as the posterior wall of the left atrium in order to directly generate lesions thereupon by activation of appropriate electrodes in the distal end plane using any suitable combination of polarities. For example, distal electrodes (932''', 934''') may be pressed against an endocardial surface and used to form a lesion via focal ablation (e.g., a spot lesion).

Referring now to generation of focal ablation lesions using the ablation device (900'''), in some embodiments, the electrodes (933, 935) (also sometimes referred to as "proximal electrodes") and the electrodes (932''', 934''') (also sometimes referred to as "distal electrodes") may be activated with opposite polarities. Conduction between these electrodes through the blood pool results in electric field generation and application of the electric field as ablative energy to the endocardial surface present at the distal end plane (926'''), resulting in focal ablation. For example, the spline wires (914''', 920''', 922''') may form the expanded structure (930''') such that the distal electrodes (932''', 934''') lie at or within the distal end plane (926''') of an endocardial surface while the proximal electrodes (933, 935) lie outside the distal end plane (926''') and consequently do not press against or otherwise contact the endocardial surface. In some embodiments, the distal electrodes (932''', 934''') may have the same polarity while adjacent proximal electrodes (935, 933) may have the opposite polarity to the distal electrodes (932''', 934''').

In some embodiments, the electrodes of the ablation device (900''') may have a length from about 0.5 mm to about 5.0 mm and a cross-sectional dimension (e.g., a diameter) from about 0.5 mm to about 2.5 mm, including all values and subranges in between. The spline wires (914''', 920''', 922''') in the expanded structure (930''') illustrated in FIG. 9D may have a cross-sectional dimension (e.g., a diameter) from about 6.0 mm to about 30.0 mm, including all values and subranges in between. The focal ablation lesion formed in this manner may have a diameter between about 0.5 cm to about 2.5 cm, including all values and subranges in between.

In some embodiments, the distal electrodes (932''', 934''') may be configured with opposite polarities. In some embodiments, adjacent electrodes on the same spline may have the same polarity such that distal electrode (934''') may have the same polarity as proximal electrode (933) and likewise distal electrode (932''') may have the same polarity as proximal electrode (935). Electrodes (934''', 933) may have the opposite polarity as electrodes (932''', 935).

In some embodiments, adjacent distal electrodes (934''') and proximal electrodes (933) may form an anode-cathode pair. For example, the distal electrodes (934''') may be configured as an anode and the proximal electrodes (933) may be configured as a cathode. In another embodiment, the electrodes (2630) on one spline may alternate between an anode and cathode with the electrodes of an adjacent spline having a reverse configuration (e.g., cathode and anode).

Figure 9E:
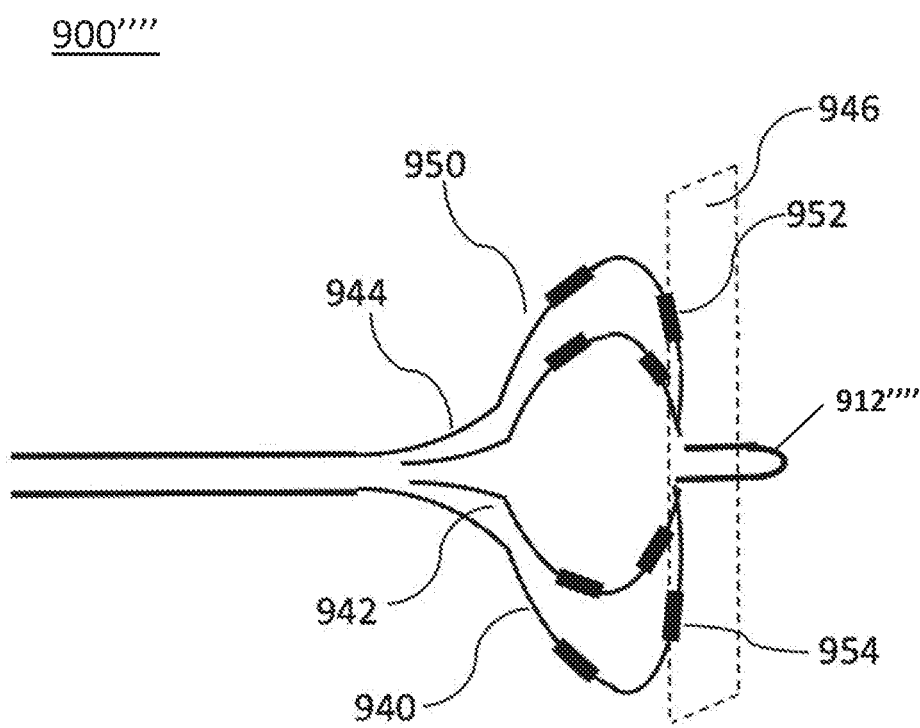
FIG. 9E is a side view of an ablation catheter in a fifth expanded structure, according to other embodiments.

FIG. 9E illustrates the spline wires (944, 940, 942) forming an expanded structure (950) during use such as when deployed. The spline wires (944, 940, 942) converge at their distal ends at a proximal end of a distal cap (912'''') inside/within the expanded structure (950). As illustrated in FIG. 9E, in such a configuration, at least some electrodes (952, 954) on the spline wires (944, 940) may lie in a distal end plane (946) of the expanded structure (950). The term "distal end plane" as used with respect to FIG. 9E may refer to a plane orthogonal to the longitudinal axis of the catheter shaft (910'''') that passes through a distal boundary of the expanded structure (950). In this manner, the expanded structure (950) may be pressed against, for example, the posterior wall of the left atrium in order to directly generate lesions thereupon by activation of appropriate electrodes in the distal end plane (946) using any suitable combination of polarities. For example, the electrodes 952 and 954 may be configured with opposite polarities. Relative to the expanded structure (930'''') in FIG. 9D, the expanded structure (950) in FIG. 9E has a more orthogonal (e.g., flattened) shape that may be pressed against, for example, the posterior wall of the left atrium for tissue ablation. In other words, the cross-sectional area of the expanded structure (930'''') at the distal end plane (926'''') is less than that the cross-sectional area of the expanded structure (950) at the distal end plane (946). As another example, distal electrodes (952, 954) may be pressed against an endocardial surface and used to form a lesion via focal ablation (e.g., a spot lesion) as generally described herein for FIG. 9D.

For each of the ablation devices described herein, each of the splines may include a polymer and define a lumen so as to form a hollow tube. The one or more electrodes of the ablation device described herein may include a diameter from about 0.2 mm to about 2.0 mm and a length from about 0.2 mm to about 5.0 mm. In some embodiments, the electrode may include a diameter of about 1 mm and a length of about 1 mm. As the electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms), as discussed in further detail below. It should be appreciated that the size, shape, and spacing of the electrodes on and between the splines may be configured to deliver contiguous/transmural energy to electrically isolate one or more pulmonary veins. In some embodiments, alternate electrodes (for example, all the distal electrodes) can be at the same electric potential, and likewise for all the other electrodes (for example, all the proximal electrodes). Thus ablation can be delivered rapidly with all electrodes activated at the same time. A variety of such electrode pairing options exist and may be implemented based on the convenience thereof.

Figure 25:
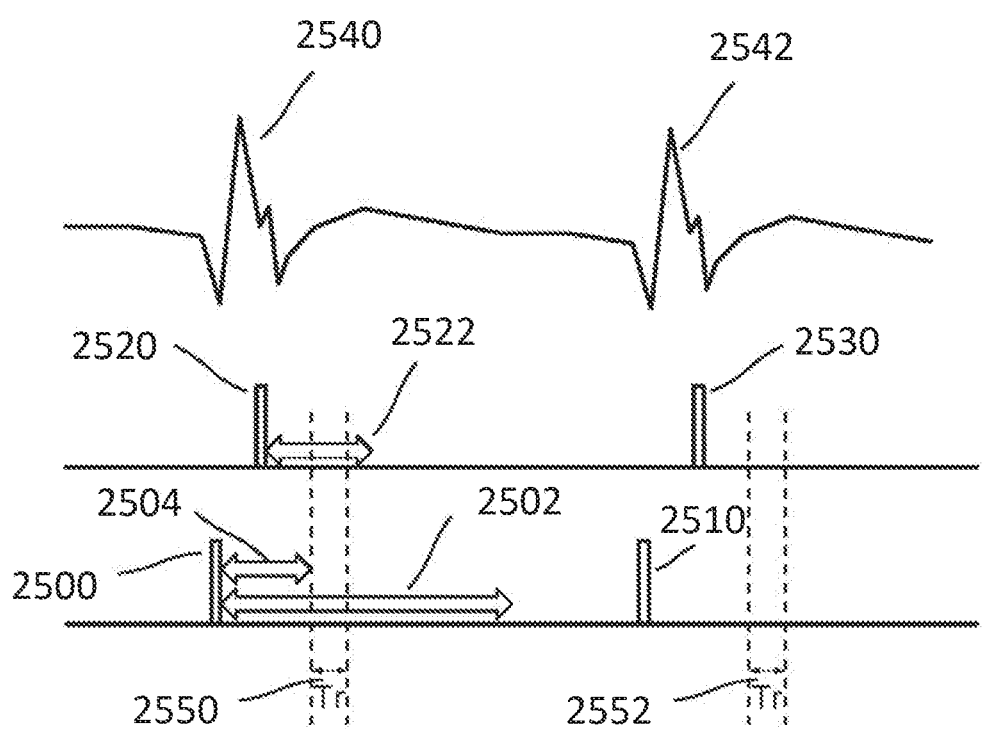
FIG. 25 illustrates schematically a time sequence of electrocardiograms and cardiac pacing signals together with atrial and ventricular refractory time periods and indicating a time window for irreversible electroporation ablation, according to embodiments.
Figure 26A:
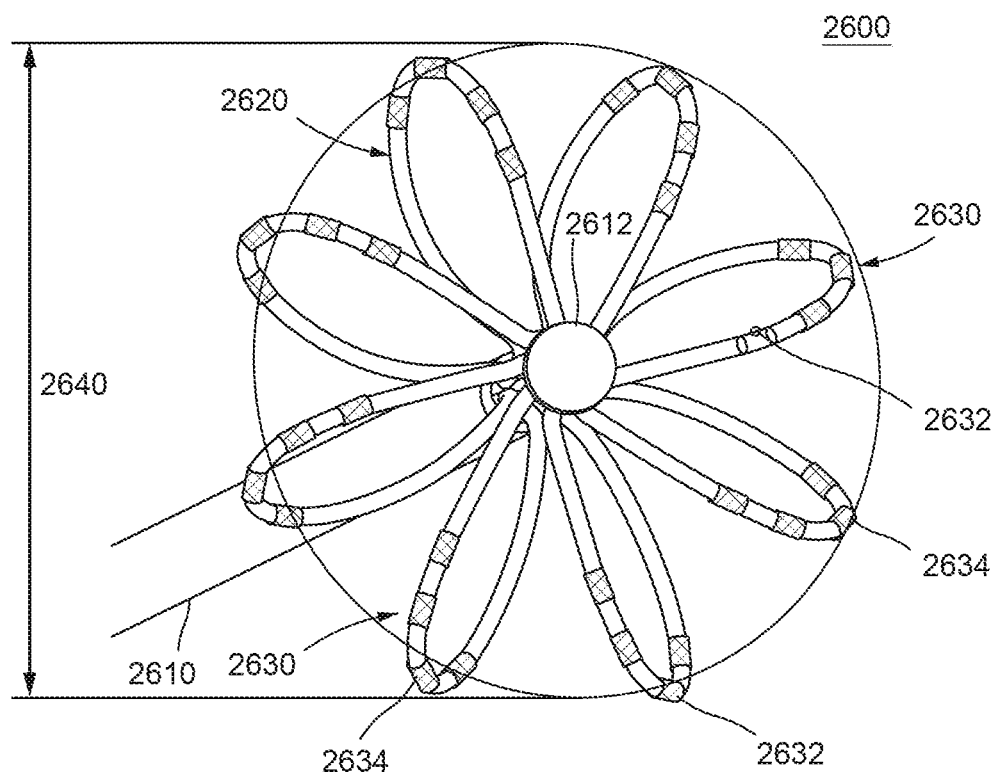
FIG. 26A is a perspective view of an ablation catheter, according to other embodiments.
Figure 26B:
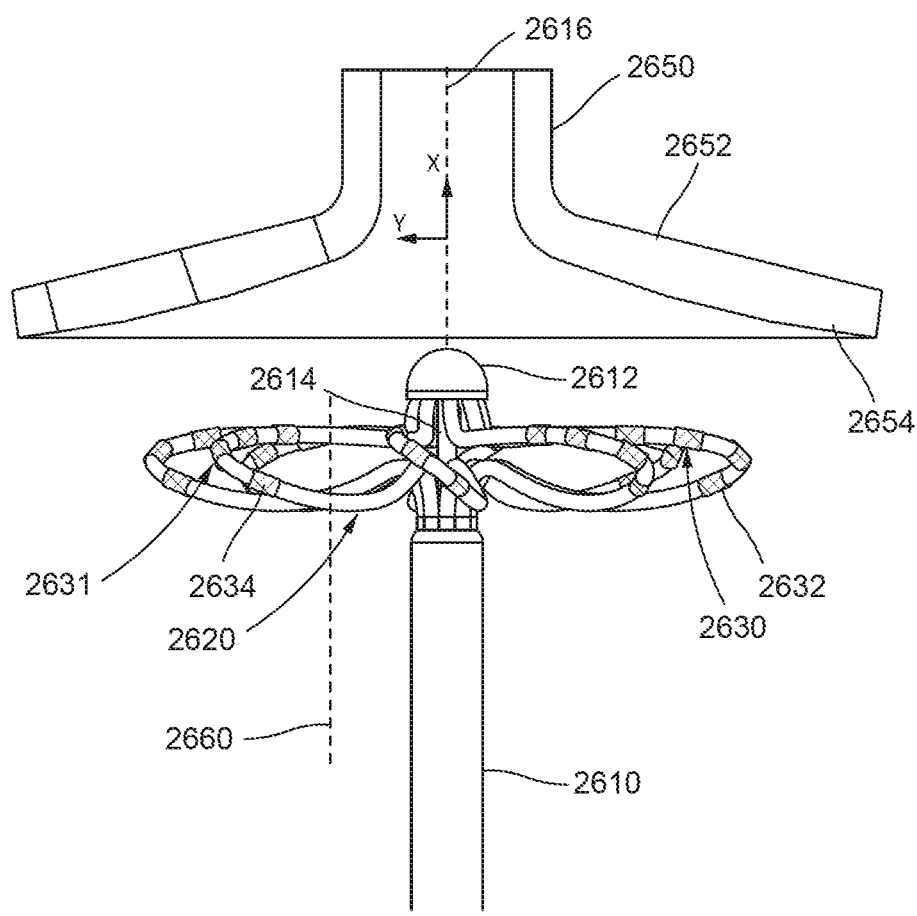
FIG. 26B is a side view of the ablation catheter depicted in FIG. 26A disposed in a left atrial chamber of a heart, adjacent to a pulmonary ostium.

FIG. 26A is a perspective view of an embodiment of an ablation device (2600) having a flower-like shape and including a catheter shaft (2610) at a proximal end of the device (2600), a distal cap (2612) of the device (2600), and a set of splines (2620) coupled thereto. As best shown in FIG. 26B, a spline shaft (2614) may be coupled at a proximal end to the proximal handle (not shown) and coupled at a distal end to the distal cap (2612). In preferred embodiments, the distance between the distal cap (2612) and the catheter shaft (2610) may be less than about 8 mm. The spline shaft (2614) and distal cap (2612) may be translatable along a longitudinal axis (2616) of the ablation device (2600). The spline shaft (2614) and distal cap (2612) may move together. The spline shaft (2614) may be configured to slide within a lumen of the catheter shaft (2610). The distal cap (2612) may include an atraumatic shape to reduce trauma to tissue. A proximal end of each spline of the set of splines (2620) may pass through a distal end of the catheter shaft (2610) and be tethered to the catheter shaft within the catheter shaft lumen, and a distal end of each spline of the set of splines (2620) may be tethered to the distal cap (2612) of the device (2600). The ablation device (2600) may be configured for delivering a pulse waveform, as disclosed for example in FIGS. 21-25, to tissue during use via one or more splines of the set of splines (2620).

Each spline (2620) of the ablation device (2600) may include one or more jointly wired electrodes (2630) formed on a surface of the spline (2620), in some embodiments. In other embodiments, one or more of the electrodes (2630) on a given spline may be independently addressable electrodes (2630). Each electrode (2630) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2000 V across its thickness without dielectric breakdown. Each spline (2620) may include the insulated electrical leads of each electrode (2630) within a body of the spline (2620) (e.g., within a lumen of the spline (2620)). FIG. 26A illustrates a set of splines (2620) where each spline includes a set of electrodes (2632 or 2634) having about the same size, shape, and spacing as the electrodes (2634 or 2632) of an adjacent spline (2620). In other embodiments, the size, shape, and spacing of the electrodes (2632, 2634) may differ. The thickness of each spline (2620) may vary based on the number of electrodes (2630) formed on each spline (2620) which may correspond to the number of insulated electrical leads in the spline (2620). The splines (2620) may have the same or different materials, thickness, and/or length.

Figure 26C:
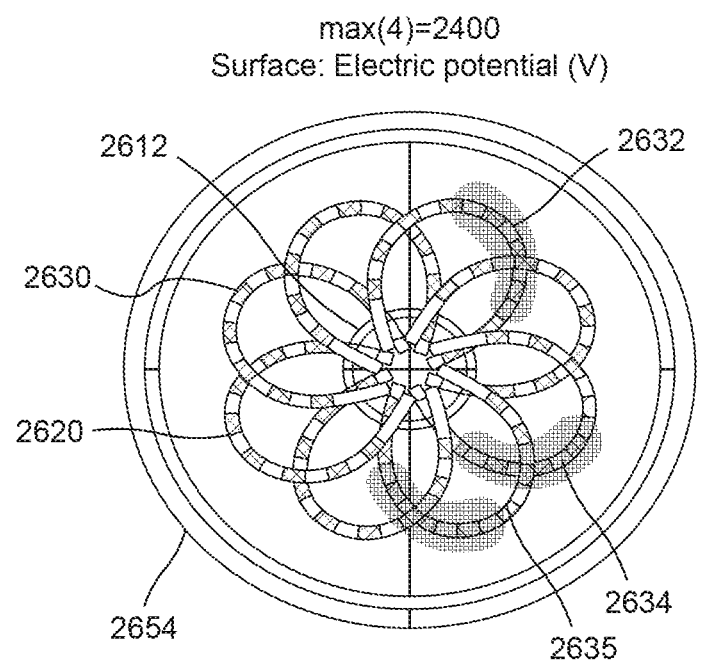
FIG. 26C is a top view of a simulation of the ablation catheter depicted in FIG. 26B, illustrating selective electrode activation according to embodiments.

Each spline of the set of splines (2620) may include a flexible curvature so as to rotate, or twist and bend and form a petal-shaped curve such as shown in FIGS. 26A-26C. The minimum radius of curvature of a spline in the petal-shaped configuration may be in the range of about 7 mm to about 25 mm. For example, the set of splines may form a delivery assembly at a distal portion of the ablation device (2600) and be configured to transform between a first configuration where the set of splines are arranged generally parallel to the longitudinal axis of the ablation device (2600), and a second configuration where the set of splines rotate around, or twist and bend, and generally bias away from the longitudinal axis of the ablation device (2600). In the first configuration, each spline of the set of splines may lie in one plane with the longitudinal axis of the ablation device. In the second configuration, each spline of the set of splines may bias away from the longitudinal axis to form a petal-like curve arranged generally perpendicular to the longitudinal axis. In this manner, the set of splines (2620) twist and bend and bias away from the longitudinal axis of the ablation device (2600), thus allowing the splines (2620) to more easily conform to the geometry of an endocardial space, and particularly adjacent to the opening of a pulmonary ostium. The second configuration may, for example, resemble the shape of a flower, when the ablation device is viewed from the front as best shown in FIG. 26C. In some embodiments, the each spline in the set of splines in the second configuration may twist and bend to form a petal-like curve that, when viewed from front, displays an angle between the proximal and distal ends of the curve of more than about 180 degrees. The set of splines may further be configured to transform from a second configuration to a third configuration where the set of splines (2620) may be impressed (e.g., in contact with) against target tissue such as tissue surrounding a pulmonary vein ostium.

In some embodiments, the spline shaft (2614) coupled to the set of splines (2620) may allow each spline of the set of splines (2620) to bend and twist relative to the catheter shaft (2610) as the spline shaft (2614) slides within a lumen of the catheter shaft (2610). For example, the set of splines (2620) may form a shape generally parallel to a longitudinal axis of the spline shaft (2614) when undeployed, be wound (e.g., helically, twisted) about an axis (2660) parallel to the longitudinal axis of the spline shaft (2620) when fully deployed, and form any intermediate shape (such as a cage or barrel) in-between as the spline shaft (2614) slides within a lumen of the catheter shaft (2610).

In some embodiments, the set of splines in the first configuration, such as the spline (2620), may be wound about an axis (2660) parallel to the longitudinal axis of the catheter shaft (2610) in some portions along its length but elsewhere may otherwise be generally parallel to the longitudinal axis of the catheter shaft (2610). The spline shaft (2614) may be retracted into the catheter shaft (2610) to transform the ablation device (2600) from the first configuration to the second configuration where the splines (2620) are generally angled or offset (e.g., perpendicular) with respect to the longitudinal axis of the catheter shaft (2610)

and twisted. As shown in the front view of FIG. 26C, each spline (2620) may form a twisting loop in this front view projection. In FIG. 26C, each spline (2620) has a set of electrodes (2630) having the same polarity. As shown in the front view of FIG. 26C, each spline of the set of splines (2620) may form a twisted loop such that each spline overlaps one or more other splines. The number and spacing of the electrodes (2630), as well as the rotated twist of the spline (2620), may be configured by suitable placement of electrodes along each spline to prevent overlap of an electrode (2630) on one spline with an electrode of an adjacent, overlapping spline (2620).

A spline having a set of anode electrodes (2632) may be activated together to deliver pulse waveforms for irreversible electroporation. Electrodes on other splines may be activated together as cathode electrodes such as electrodes (2634) and (2635) on their respective splines so at to form an anode-cathode pairing for delivery of pulse waveforms for irreversible electroporation, as shown in FIG. 26C. The anode-cathode pairing and pulse waveform delivery can be repeated sequentially over a set of such pairings.

For example, the splines (2620) may be activated sequentially in a clockwise or counter-clockwise manner. As another example, the cathode splines may be activated sequentially along with respective sequential anode spline activation until ablation is completed. In embodiments where electrodes on a given spline are wired separately, the order of activation within the electrode of each spline may be varied as well. For example, the electrodes in a spline may be activated all at once or in a predetermined sequence.

The delivery assembly may be disposed in the first configuration prior to delivering a pulse waveform and transformed to the second configuration to make contact with the pulmonary vein ostium or antrum. In some of these embodiments, a handle may be coupled to the spline shaft (2614) and the handle configured for affecting transformation of the set of splines between the first configuration and the second configuration. For example, the handle may be configured to translate the spline shaft (2614) and distal cap (2612) relative to the catheter shaft (2610), thereby actuating the set of splines (2620) coupled to the distal cap and causing them to bend and twist. The proximal ends of the splines (2620) may be fixed to the spline shaft (2614) thereby generating buckling of the splines (2620) resulting in a bending and twisting motion of the splines (2620), for example, as the distal cap (2612) and spline shaft (2614) are pulled back relative to the catheter shaft (2610) that may be held by a user. For example, a distal end of the set of splines (2620) tethered to the distal cap (2612) may be translated by up to about 60 mm along the longitudinal axis of the ablation device to actuate this change in configuration. In other words, translation of an actuating member of the handle may bend and twist the set of splines (2620). In some embodiments, actuation of a knob, wheel, or other rotational control mechanism in the device handle may result in a translation of the actuating member or spline shaft and result in bending and twisting of the splines (2620). In some embodiments, the electrical leads of at least two electrodes of the set of electrodes (2630) may be electrically coupled at or near a proximal portion of the ablation device (2600), such as, for example, within the handle.

Retraction of the spline shaft (2614) and distal cap (2612) may bring the set of splines (2620) closer together as shown in FIG. 26B where the set of splines (2620) are generally perpendicular to a longitudinal axis of the catheter shaft (2610). In some embodiments, each spline of the set of splines (2620) may be biased laterally away from the longitudinal axis of the spline shaft (2614) by up to about 3 cm. In some embodiments, the spline shaft (2614) may include a hollow lumen. In some embodiments, the cross section of a spline may be asymmetric so as to have a larger bending stiffness in one bending plane of the spline orthogonal to the plane of the cross section than in a different bending plane. Such asymmetric cross sections may be configured to present a relatively larger lateral stiffness and thereby may deploy with minimal overlap of the petal-shaped curves of each spline and its neighbors in the final or fully-deployed configuration.

In one embodiment, each of the electrodes (2632) on a spline (2620) may be configured as an anode while each of the electrodes (2634) on a different spline may be configured as a cathode. In another embodiment, the electrodes (2630) on one spline may alternate between an anode and cathode with the electrodes of another spline having a reverse configuration (e.g., cathode and anode).

In some embodiments, the spline electrodes may be electrically activated in sequential manner to deliver a pulse waveform with each anode-cathode pairing. In some embodiments, the electrodes may be electrically wired together within the spline, while in alternate embodiments they may be wired together in the handle of the device, so that these electrodes are at the same electric potential during ablation. In other embodiments, the size, shape, and spacing of the electrodes (2630) may differ as well. In some embodiments, adjacent distal electrodes and proximal electrodes may form an anode-cathode pair. For example, the distal electrodes may be configured as an anode and the proximal electrodes may be configured as a cathode.

The ablation device (2600) may include any number of splines, for example, 2, 3, 4, 5, 6, 7, 8, 9, 10, 12, 14, 16, 18, 20, or more splines, including all values and sub-ranges in between. In some embodiments, the ablation device (2600) may include 3 to 20 splines. For example, the ablation device (2600) may include from 4 to 12 splines.

Each of the splines of the set of splines (2620) may include respective electrodes (2630) having an atraumatic shape to reduce trauma to tissue. For example, the electrodes (2630) may have an atraumatic shape including a rounded, flat, curved, and/or blunted portion configured to contact endocardial tissue. In some embodiments, the electrodes (2630) may be located along any portion of the spline (2620) distal to the catheter shaft (2610). The electrodes (2630) may have the same or different sizes, shapes, and/or location along respective splines.

In this manner, the electrodes in the second configuration may be held close to or placed against a section of atrial wall of the left atrium in order to directly generate lesions thereupon by activation of appropriate electrodes using any suitable combination of polarities, as described herein. For example, the set of splines (2620) may be placed in contact against the atrial wall (2654) of atrium (2652) adjacent a pulmonary vein (2650) (e.g., ostium or antrum).

Figure 26D:
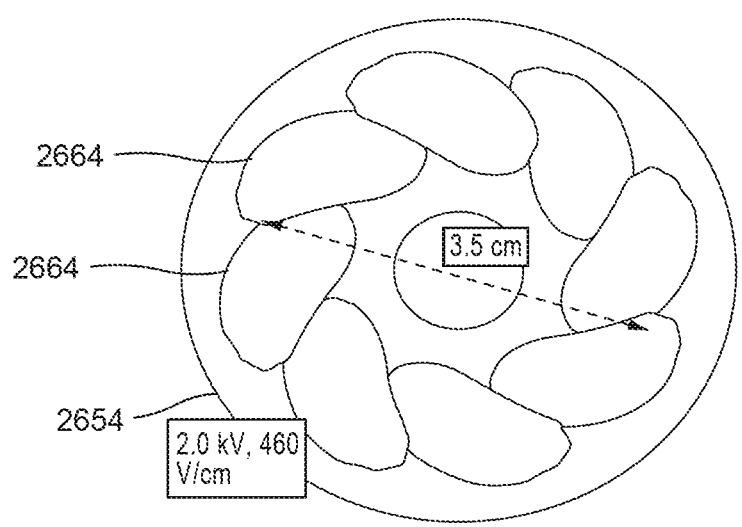
FIG. 26D is a simulated illustration of tissue ablation in a pulmonary ostium, according to embodiments.

FIG. 26D is a schematic illustration of ablation (2664) generated by the ablation device (2600) on tissue, such as the tissue surrounding a pulmonary vein ostium. For example, activation of one or more of the electrodes (2630) on one or more of the splines (2620) may generate one or more corresponding ablation areas (2664) along a wall (2654) of a pulmonary vein antrum or ostium. In some embodiments, an outline of the ablation areas (2664) in the pulmonary vein ostium may have a diameter of between about 2 cm and about 6 cm, and may be about 3.5 cm. In this manner, a contiguous, transmural lesion may be generated, resulting in electrical isolation of the pulmonary vein, which is a desired therapeutic outcome.

Alternatively, the ablation catheter with its deployed electrodes may be placed adjacent to or against a section of posterior wall of the left atrium, and by activation of suitable electrode sets, an appropriate pulse waveform may be delivered for irreversible electroporation energy delivery to ablate tissue.

In some embodiments, as the electrodes or a subset of electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms), as discussed in further detail herein. It should be appreciated that the size, shape, and spacing of the electrodes on and between the splines may be configured to deliver contiguous/transmural energy to electrically isolate one or more pulmonary veins. In some embodiments, alternate electrodes may be at the same electric potential, and likewise for all the other alternating electrodes. Thus, in some embodiments, ablation may be delivered rapidly with all electrodes activated at the same time. A variety of such electrode pairing options exists and may be implemented based on the convenience thereof.

Figure 35:
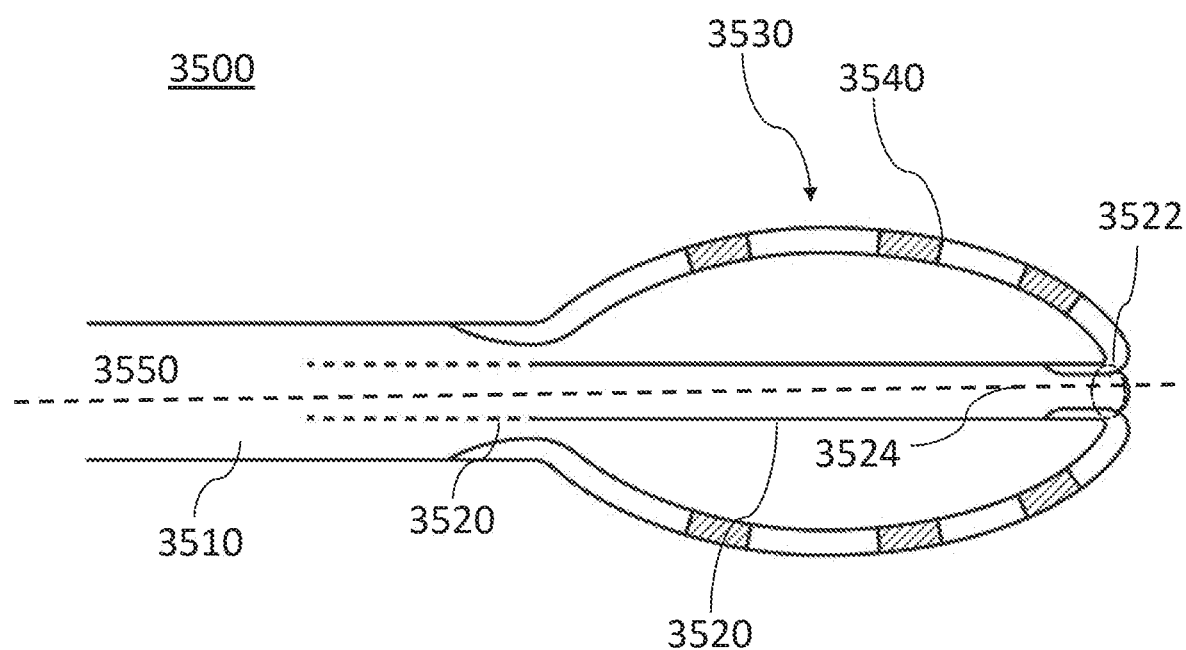
FIG. 35 is a side view of an ablation catheter in an undeployed configuration, according to other embodiments.

In some embodiments, a distal-most portion of the ablation device may include a set of splines rather than a distal cap or another element that extends a length of a catheter shaft. This may aid positioning of the set of splines against tissue and reduce contact of other elements of an ablation device to tissue that may cause trauma to tissue. For example, FIG. 35 is a side view of an embodiment of an ablation device (3500) including a first catheter (3510) (e.g., outer catheter shaft) at a proximal end of the device (3500). The first catheter (3510) may define a longitudinal axis (3550) and a lumen therethrough. A second catheter (3520) may be slidably disposed within the first catheter lumen and extend from a distal end of the first catheter lumen. The second catheter (3520) may have a diameter smaller than a diameter of the first catheter (3510). The second catheter (3520) may define a lumen therethrough. For example, the lumen may provide passage for another device such as a guidewire.

A set of splines (3530) may be coupled to the first catheter (3510) and the second catheter (3520). In particular, a proximal portion of the set of splines (3530) may be coupled to a distal end of the first catheter (3510) and a distal portion of the set of splines (3530) may be coupled to a distal end of the second catheter (3520). The second catheter (3520) may be translatable along a longitudinal axis (3550) of the ablation device (3500). A proximal end of each spline of the set of splines (3530) may pass through a distal end of the first catheter (3510) and be tethered to the first catheter (3510) within the first catheter lumen. A distal end of each spline of the set of splines (3530) may pass through a distal end of the second catheter (3520) and be tethered to the second catheter (3520) within the second catheter lumen. In some embodiments, a junction (3522) may be formed between a distal end of the second catheter (3520) and the set of splines (3530). For example, a polymer reflow process may be used to form a smooth, atraumatic junction between the second catheter (3520) and the set of splines (3530). The ablation device (3500) may be configured for delivering a pulse waveform, as disclosed for example in FIGS. 21-26, to tissue during use via the electrodes of one or more splines of the set of splines (3530).

Each spline (3530) of the ablation device (3500) may include one or more electrodes (3540) formed on a surface of the spline (3530). Each electrode (3540) may include an insulated electrical lead configured to sustain a voltage potential of at least about 700 V without dielectric breakdown of its corresponding insulation. Each spline (3530) may include the insulated electrical leads of each electrode (3540) formed in a body of the spline (3530) (e.g., within a lumen of the spline (3530)). FIG. 35 illustrates a set of splines where each spline (3530) includes a set of electrodes (3540) having about the same size, shape, and spacing as the electrodes (3540) of an adjacent spline. In other embodiments, the size, shape, and spacing of the electrodes (3540) may differ.

The ablation device (3500) may be configured for delivering a set of voltage pulse waveforms using a set of electrodes (3540) to ablate tissue. In some of these embodiments, the ablation device (3500) may be transformed from a first configuration to a second configuration such that the splines (3530) of the ablation device (3500) bow radially outward.

At least a portion of the set of splines (3530) may include a flexible curvature. For example, a proximal region (3522) and a distal region (3526) of each spline (3530). The set of splines (3530) may form a delivery assembly at a distal portion of the ablation device (3500) and may be configured to transform between a first configuration where the set of splines (3530) are arranged generally closer to the longitudinal axis (3540) of the ablation device (3500) and a second configuration where the set of splines (3530) bow radially outward from a longitudinal axis (3540) of the ablation device (3500) to form a basket-like and/or flower-like shape where each spline forms a "petal". The space curve shape of the splines in the second configuration may be described with respect to equations (1)-(3) corresponding to FIGS. 34A-34B. For example, in a fully deployed configuration, the integrated magnitude of the rotation rate of each of the splines of the set of splines (3530) along the length of each spline may be greater than $\pi$ radians.

In other embodiments, the "basket" of splines may have an asymmetric shape along the catheter length, so that one end (say the distal end) of the basket is more bulbous than the other end (say the proximal end) of the basket. The delivery assembly may be advanced through a body cavity in the first configuration and transformed to the second configuration prior to delivering a pulse waveform. In some embodiments, a handle (not shown) may be coupled to the set of splines (3530) and the handle configured for affecting transformation of the set of splines (3530) between the first configuration and the second configuration. In some embodiments, actuation of one or more knobs, wheels, sliders, pull wires, and/or other control mechanisms in the handle may result in translation of the second catheter (3520) relative to the first catheter (3510) and result in bending of the splines (3530). In some embodiments, the electrical leads of at least two electrodes of the set of electrodes (3540) may be electrically coupled at or near a proximal portion of the ablation device (3500), such as, for example, within the handle. For example, the handle may be configured to translate the second catheter (3512) relative to the first catheter (3510), thereby actuating the set of splines (3530) and causing them to bend, as shown in FIG. 35. The distal ends of the splines (3530) may be fixed to the distal end of the second catheter (3520), thereby generating buckling of the splines (3530) resulting in a bending motion of the splines (3530), for example, as the second catheter (3520) are pulled back relative to the first catheter (3510). In other words, translation of an actuating member of the handle may bend the set of splines (3530). In some embodiments, each spline of the set of splines (3530) may be biased laterally away from the longitudinal axis (3540) of the second catheter (3512) by up to about 35 mm. For example, the set of splines (3530) in the second configuration may form a shape with an effective cross-sectional diameter at its largest portion of between about 10 mm and about 35 mm. In the second configuration, the set of splines may have a length between about 15 mm and about 50 mm.

In one embodiment, each of the electrodes on a spline may be configured as an anode while each of the electrodes on a different spline may be configured as a cathode. That is, the set of electrodes on adjacent splines may have opposite polarities. In another embodiment, the electrodes on one spline may alternate between an anode and cathode with the electrodes of another spline having a reverse configuration (e.g., cathode and anode). In some embodiments, adjacent distal electrodes and proximal electrodes may form an anode-cathode pair. For example, the distal electrodes may be configured as an anode and the proximal electrodes may be configured as a cathode.

In some embodiments, the electrodes may be electrically activated in a sequential manner to deliver a pulse waveform with each anode-cathode pairing. In some embodiments, the electrodes (3540) may be electrically wired together within the spline (3530), while in alternate embodiments they may be wired together in the handle of the device (3500), so that these electrodes (3540) are at the same electric potential during ablation. In other embodiments, the size, shape, and spacing of the electrodes (3540) may differ as well. As another example, the splines (3530) may be activated sequentially in a clockwise or counter-clockwise manner. As another example, the cathode splines may be activated sequentially along with respective sequential anode spline activation until ablation is completed. In embodiments where electrodes (3540) on a given spline (3530) are wired separately, the order of activation within the electrode (3540) of each spline (3530) may be varied as well. For example, the electrodes (3540) in a spline may be activated all at once or in a predetermined sequence.

The electrodes may be energized in any sequence using any pulse waveform sufficient to ablate tissue by irreversible electroporation. It should be appreciated that the size, shape, and spacing of the electrodes on and between the splines may be configured to deliver energy to electrically isolate one or more regions of cardiac tissue. In some embodiments, alternate electrodes (for example, all the distal electrodes) can be at the same electric potential, and likewise for all the other electrodes (for example, all the proximal electrodes). Thus, ablation may be delivered rapidly with all electrodes activated at the same time. A variety of such electrode pairing options exist and may be implemented based on the convenience thereof.

Each of the splines (3530) may be composed of a polymer and define a lumen so as to form a hollow tube. The set of splines (3530) of the ablation device (3500) may have a diameter between about 1.0 mm to about 5.0 mm. The set of electrodes (3540) of the ablation device (3500) may have a diameter between about 1.0 mm to about 5.0 mm and a length between about 0.2 mm to about 5.0 mm.

The ablation device (3500) may include any number of splines, for example, 2, 3, 4, 5, 6, 7, 8, 9, 10, 12, 14, 16, or more splines, including all values and sub-ranges in between. In some embodiments, the ablation device (3500) may include 3 to 16 splines. For example, the ablation device (3500) may include from 3 to 14 splines.

Each of the splines of the set of splines (3530) may include respective electrodes (3540) having an atraumatic shape to reduce trauma to tissue. For example, the electrodes (3540) may have an atraumatic shape including a rounded, flat, curved, and/or blunted portion. In some embodiments, the electrodes (3540) may be located along any portion of the spline (3530) distal to the first catheter (3510). The electrodes (3540) may have the same or different sizes, shapes, and/or location along respective splines. The ablation device (3500) may include any number of electrodes, for example, 2, 3, 4, 5, 6, 7, 8, 9, 10, 12, or more electrodes per spline, including all values and sub-ranges in between. In some embodiments, the ablation device (3500) may include 2 to 12 electrodes per spline.

Figure 34A:
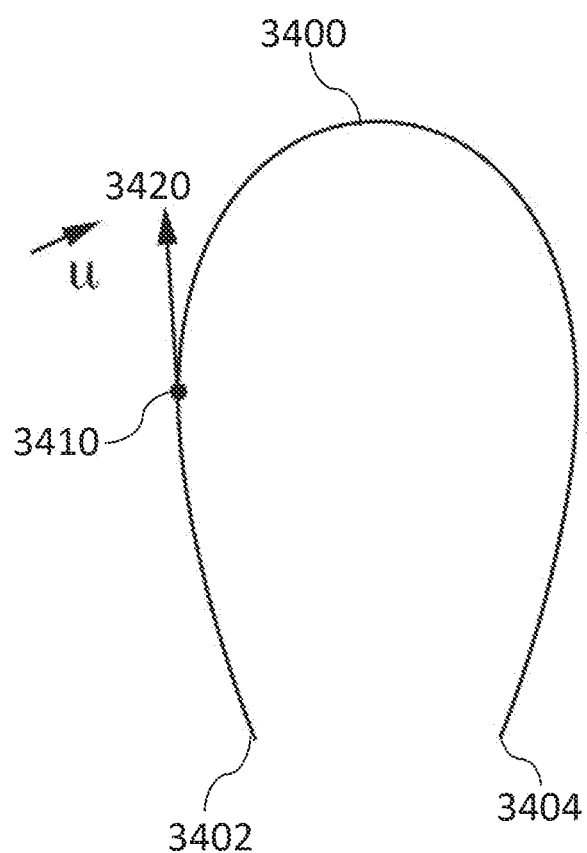
FIGS. 34A-34B are side views of a spline, according to other embodiments.
Figure 34B:
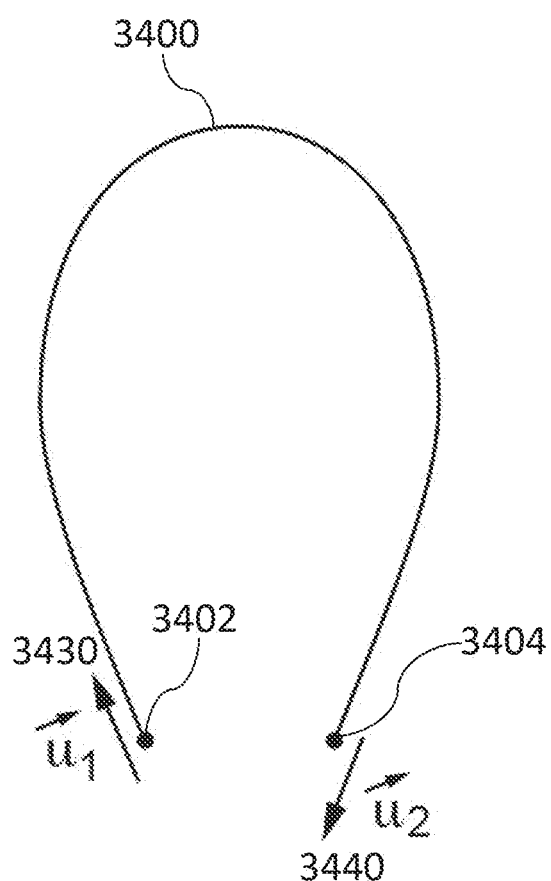
Figure 36A:
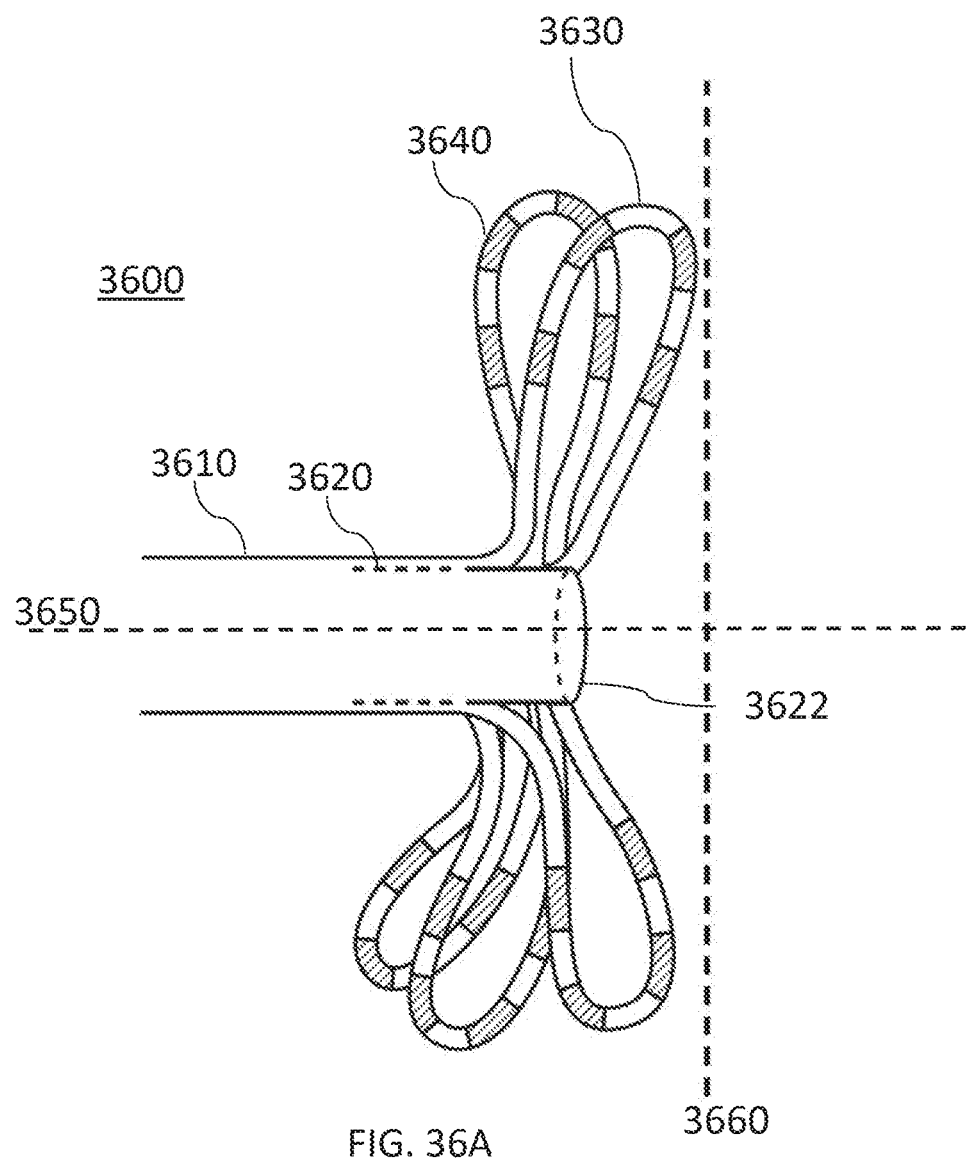
FIGS. 36A-36C are side views of an ablation catheter, according to other embodiments.
Figure 36B:
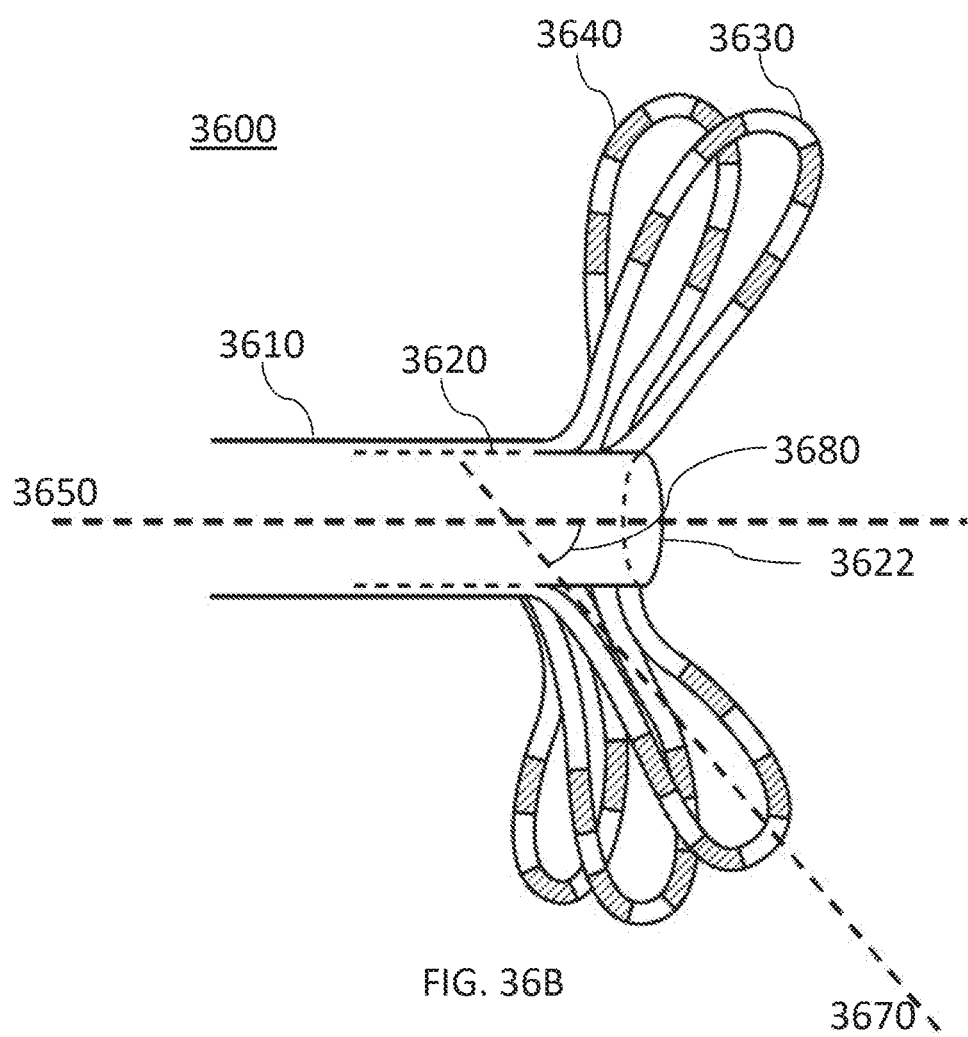
Figure 36C:
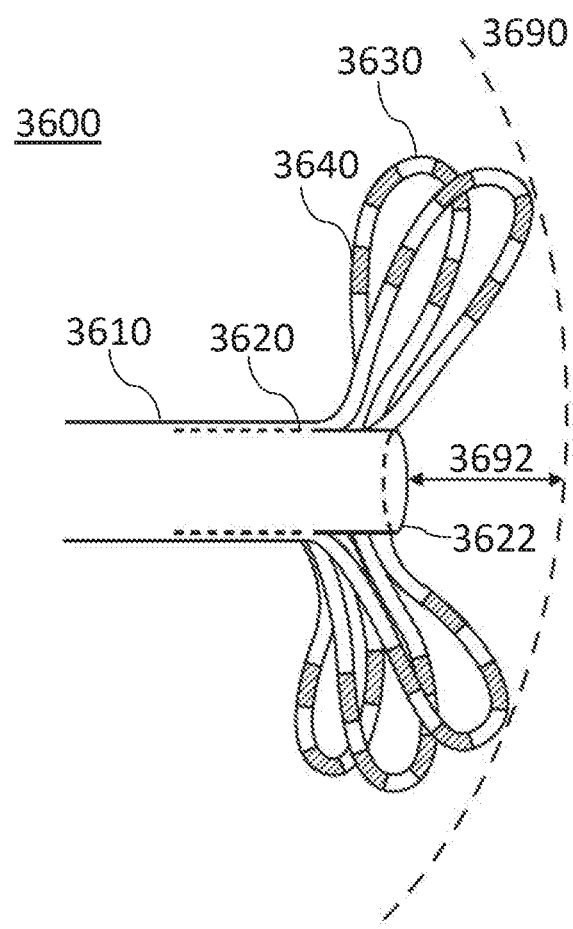

FIGS. 34A-34B are side views of a spline (3400) structurally and/or functionally similar to the splines described herein, such as the splines shown in FIGS. 36A-36C. FIG. 34A is a side view of a spline having a unit tangent vector. FIG. 34B is a side view of a spline having two unit tangent vectors. FIGS. 34A-34B depict a spline (3400) having a flower petal-like shape and may correspond to the shape of a spline in a second configuration and/or third configuration as described in detail herein. For the sake of simplicity, the spline (3400) is shown without other elements such as electrodes. The curved spline (3400) includes a proximal end (3402) and a distal end (3404). At every point (3410) along the spline (3400), a unit tangent vector u (3420) may be defined. FIG. 34B illustrates a unit tangent vector $u_1$ (3430) at the proximal end (3402) of the spline (3400) and a unit tangent vector $u_2$ (3440) at the distal end (3404) of the spline (3400).

A rate of change of a unit tangent vector along the length of spline may be governed by the equation:

$$u' = du/dl \quad (1)$$

where l is an arc length along the spline.

The rate of change of the unit tangent vector u' may be referred to as a rotation rate of the unit tangent vector along the spline. The rotation rate u' is perpendicular to the unit tangent vector u because u·u=1.

In some embodiments, the splines as described herein may be transitioned to form a petal shape may form a loop being twisted along its length such that the spline has torsion along its length. The splines as described herein have an integrated magnitude of the rotation rate governed by the inequality:

$$\int \{|u'|\} dl > \pi \quad (2)$$

That is, the integrated magnitude of the rotation rate of a spline is greater than π radians or equivalently, 180 degrees. Since u and u' are perpendicular, u·u'=0. Therefore, the vector b=u×u' is perpendicular to both u and u'.

In some embodiments, the shape of the spline is generally a space curve with torsion, so that the derivative of the rotation rate generally has a component along b at least at some locations along the length of the spline, governed by the equation:

$$\int (u'' \cdot b) dl \neq 0 \quad (3)$$

In some embodiments of the devices described herein, the deployed splines of the set of splines may satisfy both equations (2) and (3).

FIGS. 36A-36C are side views of an ablation catheter (3600) configured, when the distal splines are fully deployed, to have the deployed set of splines and a set of electrodes extending distal to the all other elements of the catheter (3600) so as to reduce trauma to tissue and aid positioning and contact between the set of electrodes and tissue. FIG. 36A is a perspective view of an embodiment of an ablation device (3600) having a flower-like shape and including a first catheter (3610) at a proximal end of the device (3600). The first catheter (3610) may define a longitudinal axis (3650) and a lumen therethrough. A second catheter (3620) may be slidably disposed within the first catheter lumen and extend from a distal end of the first catheter lumen. The first catheter and second catheter together with a catheter handle for actuation may comprise a single device. A set of splines (3630) may be coupled to the first catheter (3610) and the second catheter (3620). The second catheter (3620) may be translatable along a longitudinal axis (3650) of the ablation device (3600). A proximal end of each spline of the set of splines (3630) may pass through a distal end of the first catheter (3610) and be tethered to the first catheter (3610) within the first catheter lumen, and a distal end of each spline of the set of splines (3630) may be tethered to a distal end (3622) of the second catheter (3620), as described in detail with respect to FIG. 35. Since the ablation catheter (3600) does not include a distal cap or other protrusion extending from a distal end of a second catheter (3620), the device (3600) in a second configuration (e.g., flower shape) may engage with sensitive tissue such as a thin cardiac wall with a reduced risk of trauma from the device (3600). The ablation device (3600) may be configured for delivering a pulse waveform, as disclosed for example in FIGS. 21-26, to tissue during use via one or more electrodes on the set of splines (3630).

Each spline (3630) of the ablation device (3600) may include one or more jointly wired electrodes (3640) formed on a surface of the spline (3630), in some embodiments. In other embodiments, one or more of the electrodes (3640) on a given spline may be independently addressable electrodes (3640). Each electrode (3640) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2000 V across its thickness without dielectric breakdown. Each spline (3630) may include the insulated electrical leads of each electrode (3640) within a body of the spline (3630) (e.g., within a lumen of the spline (3630)). FIGS. 36A-36C illustrates a set of splines (3630) where each spline includes a set of electrodes (3640) having about the same size, shape, and spacing as the electrodes (3640) of an adjacent spline (3630). In other embodiments, the size, shape, and spacing of the electrodes (3640) may differ. The thickness of each spline (3630) may vary based on the number of electrodes (3640) formed on each spline (3630) which may correspond to the number of insulated electrical leads in the spline (3630). The splines (3630) may have the same or different materials, thickness, and/or length.

Each spline of the set of splines (3630) may include a flexible curvature so as to rotate, or twist and bend and form a petal-shaped curve such as shown in FIGS. 26A-26C, 34A-34B, and 36A-36C. The minimum radius of curvature of a spline in the petal-shaped configuration may be between about 7 mm to about 25 mm. For example, the set of splines may form a delivery assembly at a distal portion of the ablation device (3600) and be configured to transform between a first configuration where the set of splines are arranged generally closer to the longitudinal axis of the ablation device (3600), and a second configuration where the set of splines rotate around, or twist and bend, and generally bias away from the longitudinal axis of the ablation device (3600). In the first configuration, each spline of the set of splines may lie in one plane with the longitudinal axis of the ablation device. In the second configuration, each spline of the set of splines may bias away from the longitudinal axis to form a petal-like curve (e.g., flower shape) where the longitudinal axis of the splines is arranged generally perpendicular or has an acute angle relative to the longitudinal axis (3650). As described in detail herein, the shape (e.g., bend, curve) of the set of splines may satisfy equations (1)-(3). In this manner, the set of splines (3620) twist and bend and bias away from the longitudinal axis of the ablation device (3600), thus allowing the splines (3620) to more easily conform to the geometry of an endocardial space, such as a posterior wall and opening of a pulmonary ostium. In some embodiments, each spline in the set of splines in the second configuration may twist and bend to form a petal-like curve that, when viewed from the front, displays an angle between the proximal and distal ends of the curve of more than about 180 degrees.

In some embodiments, the second catheter (3620) coupled to the set of splines (3630) may allow each spline of the set of splines (3630) to bend and twist relative to the first catheter (3610) as the second catheter (3620) slides within a lumen of the first catheter (3610). For example, the set of splines (3630) may form a shape generally closer to a longitudinal axis of the second catheter (3620) when undeployed, and be wound (e.g., helically, twisted) about a longitudinal axis (3650) fully deployed, and form any intermediate shape (such as a cage or barrel) in-between as the second catheter (3620) slides within a lumen of the first catheter (3610).

In some embodiments, the set of splines in the first configuration, such as the spline (3630), may be wound about the longitudinal axis (3650) of the first catheter (3610) in some portions along its length but elsewhere may otherwise be generally parallel to the longitudinal axis of the first catheter (3610). The second catheter (3620) may be retracted into the first catheter (3610) to transform the ablation device (3600) from the first configuration to the second configuration where the splines (3630) twist to form a petal-like shape and are generally angled or offset (e.g., perpendicular, angled in a distal direction) with respect to the longitudinal axis (3650) of the first catheter (3610). As the second catheter (3622) is retracted further into the lumen of the first catheter (3610), the set of splines (3630) may extend further distally. As shown in FIG. 36A-36C, each spline (3630) may form a twisting loop (e.g., petal shapes where the set of splines together form a flower shape).

In the second configuration, the set of splines (3630) in the second configuration may form a flower shape and may be angled in a distal direction. FIG. 36A depicts the set of splines (3630) having at least a portion of each spline of the set of splines (3630) that extends distal to a distal end (3622) of the second catheter (3620). For example, FIG. 36A shows that a distal portion of a spline intersects a plane (3660) (perpendicular to the longitudinal axis (3650)) that is distal to a distal end (3622) of the second catheter (3620). Therefore, when the ablation device (3600) is advanced in a distal direction to contact tissue, the set of splines (3630) will make contact before the first catheter (3610) and the second catheter (3620). This may reduce trauma to tissue since tissue may contact the flexible set of splines without having to contact the relatively stiffer second catheter (3622).

FIG. 36B shows the set of splines (3630) in the second configuration forming a distal (e.g., forward) angle (3680) between a longitudinal axis (3670) of the spline (3630) and the longitudinal axis of the first catheter (3650). The longitudinal axis (3670) of the spline (3630) may be defined by a line formed between an apex of the spline (3630) and a midpoint between a proximal end and distal end of the spline (3630). In some embodiments, the distal angle may be less than about 80 degrees. For example, the distal angle may be about 60 degrees or less.

In some embodiments, each spline of the set of splines (3620) may form a twisted loop such that each spline partially overlaps one or more other splines. The number and spacing of the electrodes (3640), as well as the rotated twist of the spline (3630), may be configured by suitable placement of electrodes along each spline to prevent overlap of an electrode (3640) on one spline with an electrode of an adjacent, overlapping spline.

A spline having a set of anode electrodes may be activated together to deliver pulse waveforms for irreversible electroporation. Electrodes on other splines may be activated together as cathode electrodes such as electrodes on their respective splines so at to form an anode-cathode pairing for delivery of pulse waveforms for irreversible electroporation. The anode-cathode pairing and pulse waveform delivery can be repeated sequentially over a set of such pairings.

For example, the splines (3630) may be activated sequentially in a clockwise or counter-clockwise manner. As another example, the cathode splines may be activated sequentially along with respective sequential anode spline activation until ablation is completed. In embodiments where electrodes on a given spline are wired separately, the order of activation within the electrode of each spline may be varied as well. For example, the electrodes in a spline may be activated all at once or in a predetermined sequence.

The delivery assembly may be disposed in the first configuration prior to delivering a pulse waveform and transformed to the second configuration to make contact with the pulmonary vein ostium or antrum. For example, FIG. 36C depicts the distal-most portion of the set of splines (3630) in close proximity and/or in contact with a tissue wall (3690) such as a posterior wall of a left atrium. The set of splines (3630) in FIG. 36C are in the second configuration where at least a portion of each spline of the set of splines (3630) extend distal to a distal end (3622) of the second catheter (3620). The tissue (3690) may be a cardiac wall such as an endocardial surface of a posterior wall of a left atrium. A distal end (3622) of the second catheter (3620) may be separated from the tissue (3690) by a first distance (3692). Therefore, the ablation device (3600) in the second configuration may engage the tissue (3690) in an atraumatic manner with reduced risk of perforation or other trauma. Thus, the ablation device (3600) may be used to ablate even thin tissue structures such as a posterior wall of a left atrium.

In some of these embodiments, a handle may be coupled to the second catheter (3620) and the handle configured for affecting transformation of the set of splines between the first configuration and the second configuration. For example, the handle may be configured to translate the second catheter (3620) relative to the first catheter (3610), thereby actuating the set of splines (3630) coupled to the second catheter (3620) and causing them to bend and twist. The proximal ends of the splines (3630) may be fixed to the second catheter (3620) thereby generating buckling of the splines (3630) resulting in a bending and twisting motion of the splines (3630), for example, as the second catheter (3620) is pulled back relative to the first catheter (3610) that may be held by a user. For example, a distal end of the set of splines (3630) tethered to the second catheter (3620) may be translated by up to about 60 mm along the longitudinal axis of the ablation device to actuate this change in configuration. In other words, translation of an actuating member of the handle may bend and twist the set of splines (3630). In some embodiments, actuation of a knob, wheel, or other rotational control mechanism in the device handle may result in a translation of the actuating member or second catheter and result in bending and twisting of the splines (3630). In some embodiments, the electrical leads of at least two electrodes of the set of electrodes (3640) may be electrically coupled at or near a proximal portion of the ablation device (3600), such as, for example, within the handle.

Retraction of the second catheter (3620) relative to the first catheter (3610) may bring the set of splines (3630) closer together as shown in FIGS. 36A-36C. The set of splines (3630) are further generally perpendicular or angled distally relative to the longitudinal axis (3650) of the first catheter (3610). In some embodiments, each spline of the set of splines (3630) may be biased laterally away from the longitudinal axis (3650) by up to about 30 mm. In some embodiments, the second catheter (3620) may include a hollow lumen. In some embodiments, the cross section of a spline may be asymmetric so as to have a larger bending stiffness in one bending plane of the spline orthogonal to the plane of the cross section than in a different bending plane. Such asymmetric cross sections may be configured to present a relatively larger lateral stiffness and thereby may deploy with minimal overlap of the petal-shaped curves of each spline and its neighbors in the final or fully-deployed configuration.

In one embodiment, each of the electrodes (3640) on a spline (3630) may be configured as an anode while each of the electrodes (3640) on a different spline (3630) may be configured as a cathode. In another embodiment, the electrodes (3640) on one spline may alternate between an anode and cathode with the electrodes of another spline having a reverse configuration (e.g., cathode and anode).

In some embodiments, the spline electrodes may be electrically activated in sequential manner to deliver a pulse waveform with each anode-cathode pairing. In some embodiments, the electrodes may be electrically wired together within the spline, while in alternate embodiments they may be wired together in the handle of the device, so that these electrodes are at the same electric potential during ablation. In other embodiments, the size, shape, and spacing of the electrodes (3640) may differ as well. In some embodiments, adjacent distal electrodes and proximal electrodes may form an anode-cathode pair. For example, the distal electrodes may be configured as an anode and the proximal electrodes may be configured as a cathode.

The ablation device (3600) may include any number of splines, for example, 2, 3, 4, 5, 6, 7, 8, 9, 10, 12, 14, 16, 18, 20, or more splines, including all values and sub-ranges in between. In some embodiments, the ablation device (3600) may include 3 to 20 splines. For example, the ablation device (3600) may include from 4 to 12 splines.

Each of the splines of the set of splines (3630) may include respective electrodes (3640) having an atraumatic shape to reduce trauma to tissue. For example, the electrodes (3640) may have an atraumatic shape including a rounded, flat, curved, and/or blunted portion configured to contact endocardial tissue. In some embodiments, the electrodes (3640) may be located along any portion of the spline (3630) distal to the first catheter (3610). The electrodes (3640) may have the same or different sizes, shapes, and/or location along respective splines.

In this manner, the electrodes in the second configuration may be held close to or placed against a section of atrial wall of the left atrium in order to directly generate lesions thereupon by activation of appropriate electrodes using any suitable combination of polarities, as described herein. For example, the set of splines (3630) may be placed in contact against the atrial wall (3654) of atrium (3652) adjacent a pulmonary vein (3650) (e.g., ostium or antrum) and/or posterior wall.

Figure 37A:
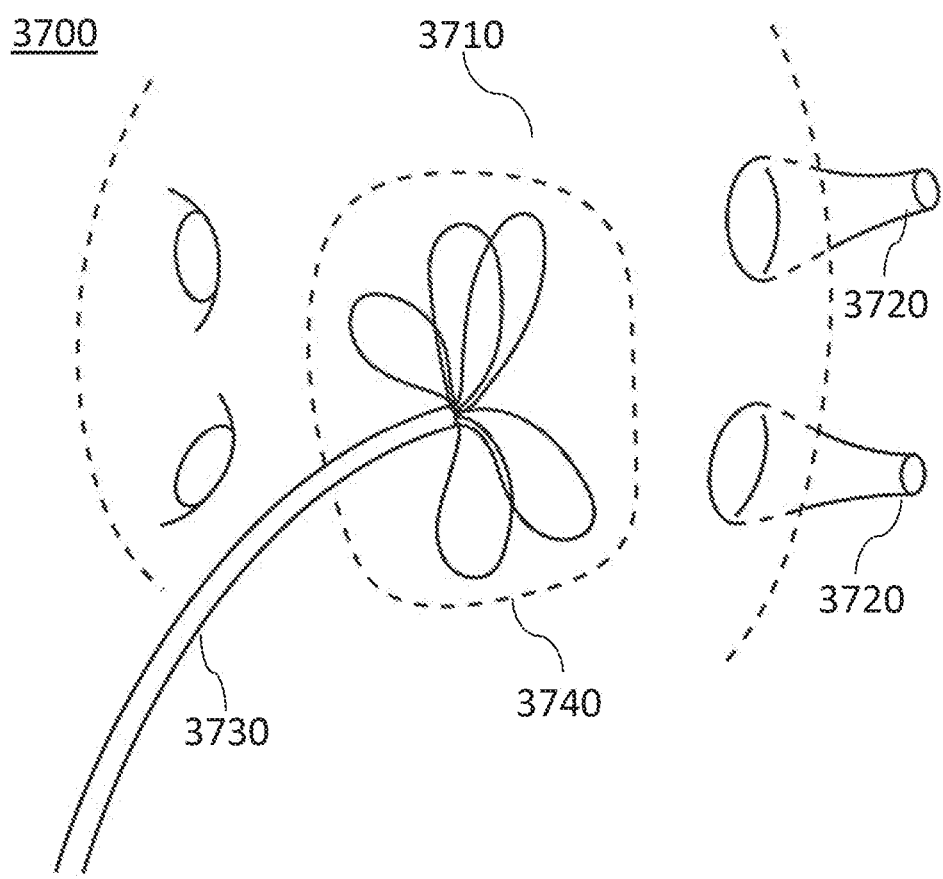
FIGS. 37A-37B are perspective views of an ablation catheter and a left atrium.
Figure 37B:
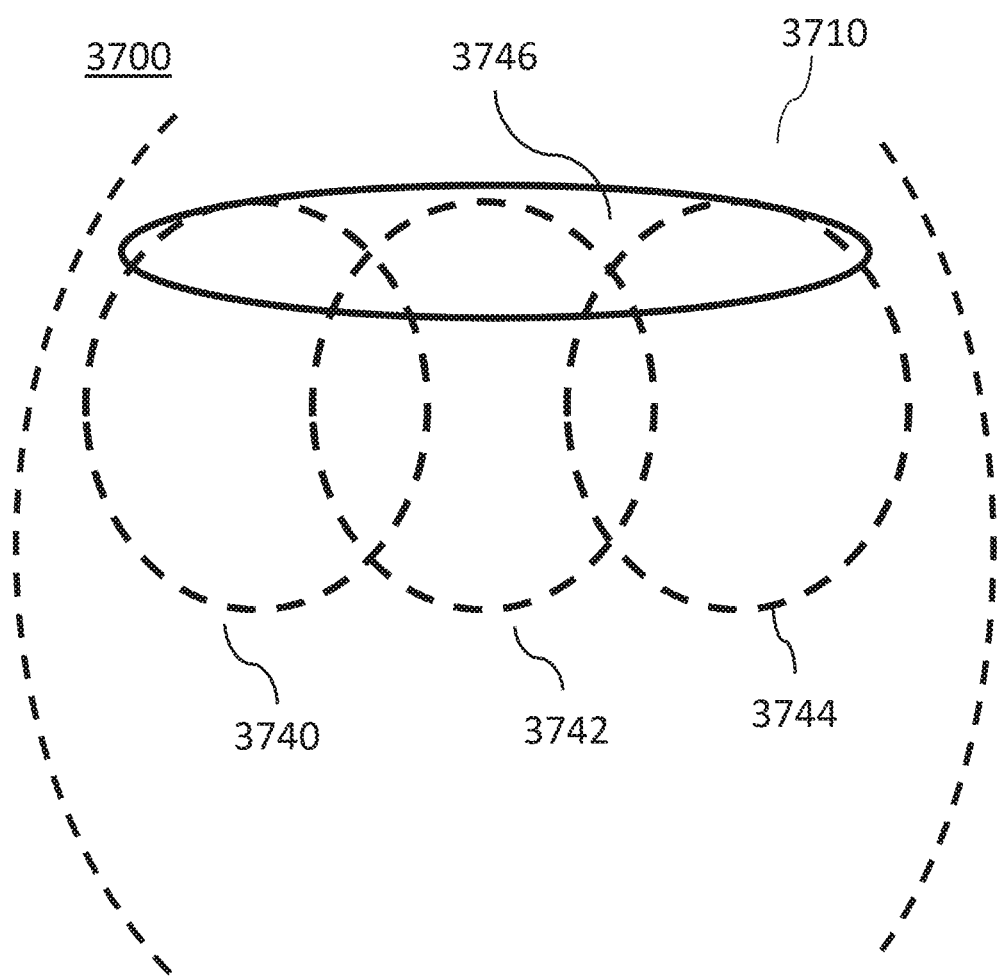

FIGS. 37A-37B are perspective views of an ablation catheter (3730) and a left atrium (3700). FIG. 37A is a perspective view of an ablation catheter (3730) disposed in a left atrium (3700). The left atrium (3700) includes a set of pulmonary veins (3720) and a posterior wall (3710). The ablation device (3730) may be structurally and/or functionally similar to the ablation devices (3500, 3600)) described herein may be advanced into the left atrium (3700) and positioned in proximity to and/or in contact with a posterior wall (3710) of the left atrium (3700) without perforating and/or causing trauma to the sensitive tissue of the posterior wall (3710). For example, the set of splines may extend distal to a distal end of a catheter coupled to the splines such that the flexible and atraumatic splines may be adjacent to or in contact with the posterior wall (3710) without any other portion of the device (3730) in contact with the posterior wall (3710). In embodiments where the distal-most portion of the device (3700) includes just the set of splines in the second configuration (e.g., having a flower shape), the deployed device may engage thin tissue structures such as a cardiac wall with minimal risk of trauma from the ablation device (3700). A set of pulse waveforms may be applied by the electrodes of the ablation device (3700) having a flower shape to ablate tissue within an ablation zone (3740).

FIG. 37B is a schematic of a perspective view of a left atrium (3700) after tissue ablation. The ablation device (3700) may be used to generate a set of ablation zones (3740, 3742, 3744) on a posterior wall (3710) of the left atrium (3700). For example, activation with one or more of the electrodes on one or more of the splines of an ablation device (3730), repeated with movement of the catheter between complete ablations, may generate the set of ablation zones (3740, 3742, 3744) along a posterior wall (3710) of a left atrium (3700). In some embodiments, the ablation zones (3740, 3742, 3744) may partially overlap with each other. These contiguous overlapping ablation zones may approximately form a thick line of ablation (3746). One or more ablation lines may connect to other ablation lines (e.g., generated around a pulmonary vein antrum or ostium) and/or ablation zones to thereby create a box lesion. For example, a set of contiguous ablation zones may be formed by the ablation device (3730) to form a box lesion around the posterior wall (3710) of the left atrium (3700) that also encircles one or more of the pulmonary veins (3720). In this manner, a contiguous, transmural lesion may be generated around all the pulmonary veins, resulting in electrical isolation of the pulmonary veins, to provide a desired therapeutic outcome. In some embodiments, each ablation zone of a set of ablation zones (3740, 3742, 3744) may have a diameter of between about 2 cm and about 6 cm. For example, an ablation zone may have a diameter of between about 2.3 cm and about 4.0 cm.

In some embodiments, as the electrodes or a subset of electrodes may be independently addressable, the electrodes may be energized in any sequence using any pulse waveform sufficient to ablate tissue by irreversible electroporation. It should be appreciated that the size, shape, and spacing of the electrodes on and between the splines may be configured to deliver sufficient energy to electrically isolate one or more pulmonary veins. In some embodiments, alternate electrodes may be at the same electric potential, and likewise for all the other alternating electrodes. Thus, in some embodiments, ablation may be delivered rapidly with all electrodes activated at the same time. A variety of such electrode pairing options exists and may be implemented based on the convenience thereof.

Figure 27A:
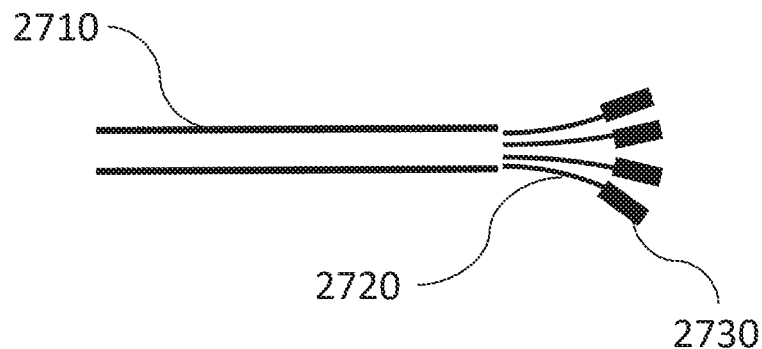
FIGS. 27A-27C are each side views of an ablation catheter, according to other embodiments.
Figure 27B:
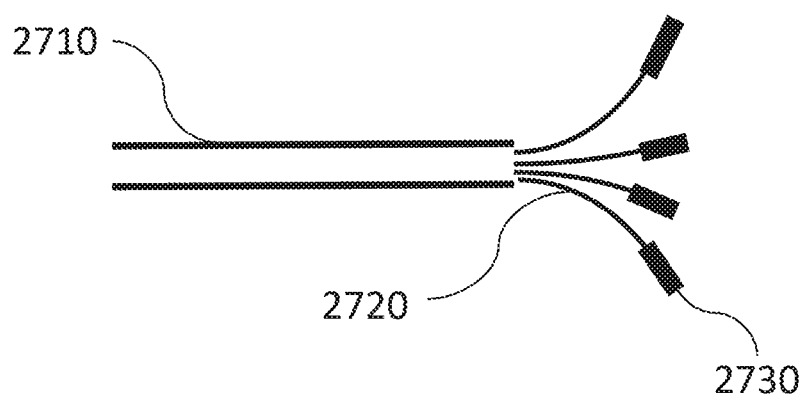

FIGS. 27A-27B are side views of an embodiment of an ablation device (2700) including a catheter shaft (2710) at a proximal end of the device (2700) and a set of splines (2720) coupled to the catheter shaft (2710) at a distal end of the device (2700). The ablation device (2700) may be configured for delivering a pulse waveform to tissue during use via one or more splines of the set of splines (2720). Each spline (2720) of the ablation device (2700) may include one or more possibly independently addressable electrodes (2730) formed on a surface (e.g., distal end) of the spline (2720). Each electrode (2730) may include an insulated electrical lead configured to sustain a voltage potential of at least about 700 V without dielectric breakdown of its corresponding insulation. In other embodiments, the insulation on each of the electrical leads may sustain an electrical potential difference of between about 200V to about 2000 V across its thickness without dielectric breakdown. Each spline of the set of splines (2720) may include the insulated electrical leads of each electrode (2730) formed in a body of the spline (2720) (e.g., within a lumen of the spline (2720)). In some embodiments, the electrodes (2730) may be formed at the distal end of their respective spline (2720).

The set of splines (2720) may form a delivery assembly at a distal portion of the ablation device (2700) and be configured to transform between a first configuration and a second configuration. The set of splines (2720) in a first configuration are generally parallel to a longitudinal axis of the ablation device (2700) and may be closely spaced together. The set of splines (2720) in a second configuration are depicted in FIGS. 27A-27B where the set of splines (2720) extend out of the distal end of the catheter shaft (2710) and bias (e.g., curve) away from the longitudinal axis of the ablation device (2700) and other splines (2720). In this manner, the splines (2720) may more easily conform to the geometry of an endocardial space. The delivery assembly may be disposed in the first configuration prior to delivering a pulse waveform and transformed to the second configuration to a section of cardiac tissue such as the posterior wall of the left atrium, or a ventricle. Such a device delivering irreversible electroporation pulse waveforms may generate large lesions for focal ablations.

A distal end of the set of splines (2720) may be configured to bias away from a longitudinal axis of the distal end of the catheter shaft (2710) and bias away from the other splines. Each spline of the set of splines (2720) may include a flexible curvature. The minimum radius of curvature of a spline (2720) may be in the range of about 1 cm or larger.

In some embodiments, a proximal end of the set of splines (2720) may be slidably coupled to a distal end of the catheter shaft (2710). Accordingly, a length of the set of splines (2720) may be varied as shown in FIGS. 27A and 27B. As the set of splines (2720) are extended further out from the catheter shaft (2710), the distal ends of the set of splines (2720) may bias further away from each other and a longitudinal axis of the catheter shaft (2710). The set of splines (2720) may be slidably advanced out of the catheter shaft (2710) independently or in one or more groups. For example, the set of splines (2720) may be disposed within the catheter shaft (2710) in the first configuration. The splines (2720) may then be advanced out of the catheter shaft (2710) and transformed into the second configuration. The splines (2720) may be advanced all together or advanced such that the set of splines (2720) corresponding to the anode electrodes (2730) are advanced separately from the set of splines (2720) corresponding to the cathode electrodes (2730). In some embodiments, the splines (2720) may be advanced independently. In the second configuration, the electrodes (2730) are biased away from the catheter shaft (2710) longitudinally and/or laterally with respect to a longitudinal axis of a distal end of the catheter shaft (2710). This may aid delivery and positioning of the electrodes (2730) against an endocardial surface. In some embodiments, each of the set of splines (2720) may extend from a distal end of the catheter shaft (2710) by up to about 5 cm.

In some embodiments, the set of splines (2720) may have a fixed length from a distal end of the catheter shaft (2710). The splines (2720) may extend from a distal end of the catheter shaft (2710) at equal or unequal lengths. For example, a spline having a greater radius of curvature than an adjacent spline may extend further from the catheter shaft (2710) than the adjacent spline. The set of splines (2720) may be constrained by a lumen of a guide sheath, such that the set of splines (2720) are substantially parallel to the longitudinal axis of the catheter shaft (2710) in the first configuration.

In some of these embodiments, a handle (not shown) may be coupled to the set of splines. The handle may be configured for affecting transformation of the set of splines between the first configuration and the second configuration. In some embodiments, the electrical leads of at least two electrodes of the set of electrodes (2730) may be electrically coupled at or near a proximal portion of the ablation device, such as, for example, within the handle. In this case the electrodes (2730) may be electrically wired together in the handle of the device (2700), so that these electrodes (2730) are at the same electric potential during ablation.

Each of the splines of the set of splines (2720) may include respective electrodes (2730) at a distal end of the set of splines (2720). The set of electrodes (2730) may include an atraumatic shape to reduce trauma to tissue. For example, the electrodes (2730) may have an atraumatic shape including a rounded, flat, curved, and/or blunted portion configured to contact endocardial tissue. In some embodiments, the electrodes (2730) may be located along any portion of the spline (2720) distal to the catheter shaft (2710). The electrodes (2730) may have the same or different sizes, shapes, and/or location along respective splines.

In one embodiment, an electrode (2730) on a spline (2720) may be configured as an anode while an electrode (2730) on an adjacent spline (2720) may be configured as a cathode. The ablation device (2700) may include any number of splines, for example, 3, 4, 5, 6, 7, 8, 9, 10, 12, 14, 16, 18, 20, or more splines, including all values and sub-ranges in between. In some embodiments, the ablation device (2700) may include 3 to 20 splines. For example, the ablation device (2700) may include 6 to 12 splines.

FIGS. 27A-27B are side views of an embodiment of an ablation device (2700) including a catheter shaft (2710) at a proximal end of the device (2700) and a set of splines (2720) coupled to the catheter shaft (2710) at a distal end of the device (2700). The ablation device (2700) may be configured for delivering a pulse waveform to tissue during use via one or more splines of the set of splines (2720). Each spline (2720) of the ablation device (2700) may include one or more possibly independently addressable electrodes (2730) formed on a surface (e.g., distal end) of the spline (2720). Each electrode (2730) may include an insulated electrical lead configured to sustain a voltage potential of at least about 700 V without dielectric breakdown of its corresponding insulation. In other embodiments, the insulation on each of the electrical leads may sustain an electrical potential difference of between about 200V to about 2000 V across its thickness without dielectric breakdown. Each spline of the set of splines (2720) may include the insulated electrical leads of each electrode (2730) formed in a body of the spline (2720) (e.g., within a lumen of the spline (2720)). In some embodiments, the electrodes (2730) may be formed at the distal end of their respective spline (2720).

The set of splines (2720) may form a delivery assembly at a distal portion of the ablation device (2700) and be configured to transform between a first configuration and a second configuration. The set of splines (2720) in a first configuration are generally parallel to a longitudinal axis of the ablation device (2700) and may be closely spaced together. The set of splines (2720) in a second configuration are depicted in FIGS. 27A-27B where the set of splines (2720) extend out of the distal end of the catheter shaft (2710) and bias (e.g., curve) away from the longitudinal axis of the ablation device (2700) and other splines (2720). In this manner, the splines (2720) may more easily conform to the geometry of an endocardial space. The delivery assembly may be disposed in the first configuration prior to delivering a pulse waveform and transformed to the second configuration to a section of cardiac tissue such as the posterior wall of the left atrium, or a ventricle. Such a device delivering irreversible electroporation pulse waveforms may generate large lesions for focal ablations.

A distal end of the set of splines (2720) may be configured to bias away from a longitudinal axis of the distal end of the catheter shaft (2710) and bias away from the other splines. Each spline of the set of splines (2720) may include a flexible curvature. The minimum radius of curvature of a spline (2720) may be in the range of about 1 cm or larger.

In some embodiments, a proximal end of the set of splines (2720) may be slidably coupled to a distal end of the catheter shaft (2710). Accordingly, a length of the set of splines (2720) may be varied as shown in FIGS. 27A and 27B. As the set of splines (2720) are extended further out from the catheter shaft (2710), the distal ends of the set of splines (2720) may bias further away from each other and a longitudinal axis of the catheter shaft (2710). The set of splines (2720) may be slidably advanced out of the catheter shaft (2710) independently or in one or more groups. For example, the set of splines (2720) may be disposed within the catheter shaft (2710) in the first configuration. The splines (2720) may then be advanced out of the catheter shaft (2710) and transformed into the second configuration. The splines (2720) may be advanced all together or advanced such that the set of splines (2720) corresponding to the anode electrodes (2730) are advanced separately from the set of splines (2720) corresponding to the cathode electrodes (2730). In some embodiments, the splines (2720) may be advanced independently. In the second configuration, the electrodes (2730) are biased away from the catheter shaft (2710) longitudinally and/or laterally with respect to a longitudinal axis of a distal end of the catheter shaft (2710). This may aid delivery and positioning of the electrodes (2730) against an endocardial surface. In some embodiments, each of the set of splines (2720) may extend from a distal end of the catheter shaft (2710) by up to about 5 cm.

In some embodiments, the set of splines (2720) may have a fixed length from a distal end of the catheter shaft (2710). The splines (2720) may extend from a distal end of the catheter shaft (2710) at equal or unequal lengths. For example, a spline having a greater radius of curvature than an adjacent spline may extend further from the catheter shaft (2710) than the adjacent spline. The set of splines (2720)

may be constrained by a lumen of a guide sheath, such that the set of splines (2720) are substantially parallel to the longitudinal axis of the catheter shaft (2710) in the first configuration.

In some of these embodiments, a handle (not shown) may be coupled to the set of splines. The handle may be configured for affecting transformation of the set of splines between the first configuration and the second configuration. In some embodiments, the electrical leads of at least two electrodes of the set of electrodes (2730) may be electrically coupled at or near a proximal portion of the ablation device, such as, for example, within the handle. In this case the electrodes (2730) may be electrically wired together in the handle of the device (2700), so that these electrodes (2730) are at the same electric potential during ablation.

Each of the splines of the set of splines (2720) may include respective electrodes (2730) at a distal end of the set of splines (2720). The set of electrodes (2730) may include an atraumatic shape to reduce trauma to tissue. For example, the electrodes (2730) may have an atraumatic shape including a rounded, flat, curved, and/or blunted portion configured to contact endocardial tissue. In some embodiments, the electrodes (2730) may be located along any portion of the spline (2720) distal to the catheter shaft (2710). The electrodes (2730) may have the same or different sizes, shapes, and/or location along respective splines.

In one embodiment, an electrode (2730) on a spline (2720) may be configured as an anode while an electrode (2730) on an adjacent spline (2720) may be configured as a cathode. The ablation device (2700) may include any number of splines, for example, 3, 4, 5, 6, 7, 8, 9, 10, 12, 14, 16, 18, 20, or more splines, including all values and sub-ranges in between. In some embodiments, the ablation device (2700) may include 3 to 20 splines. For example, the ablation device (2700) may include 6 to 12 splines.

In FIGS. 27A-27B, one electrode (2730) is formed on a surface of each spline (2720) such that each spline (2720) includes one insulated electrical lead. A lumen of the spline (2720) may therefore be reduced in diameter and allow the spline (2720) to be thicker and more mechanically robust. Thus, dielectric breakdown of the insulation may be further reduced, thereby improving reliability and longevity of each spline (2720) and the ablation device (2700). Furthermore, in some embodiments, the radius of curvature of the spline may vary over a length of the spline. For example, the radius of curvature may be monotonically increasing. Such a variable radius of curvature may aid in positioning the electrodes (2730) at some locations of endocardial tissue. The splines (2720) may have the same or different materials, thickness, and/or radius of curvature. For example, the thickness of each spline may reduce distally.

In this manner, the electrodes in the second configuration may be pressed against, for example, the posterior wall of the left atrium in order to directly generate localized or focal lesions thereupon by activation of appropriate electrodes using any suitable combination of polarities. For example, adjacent electrodes (2730) may be configured with opposite polarities.

As the electrodes or subsets of electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms), as discussed in further detail herein. It should be appreciated that the size, shape, and spacing of the electrodes on and between the splines may be configured to deliver transmural lesions over relatively wide areas of endocardial tissue. In some embodiments, alternate electrodes may be at the same electric potential, and likewise for all the other alternating electrodes. Thus, ablation may be delivered rapidly with all electrodes activated at the same time. A variety of such electrode pairing options exists and may be implemented based on the convenience thereof.

Figure 27C:
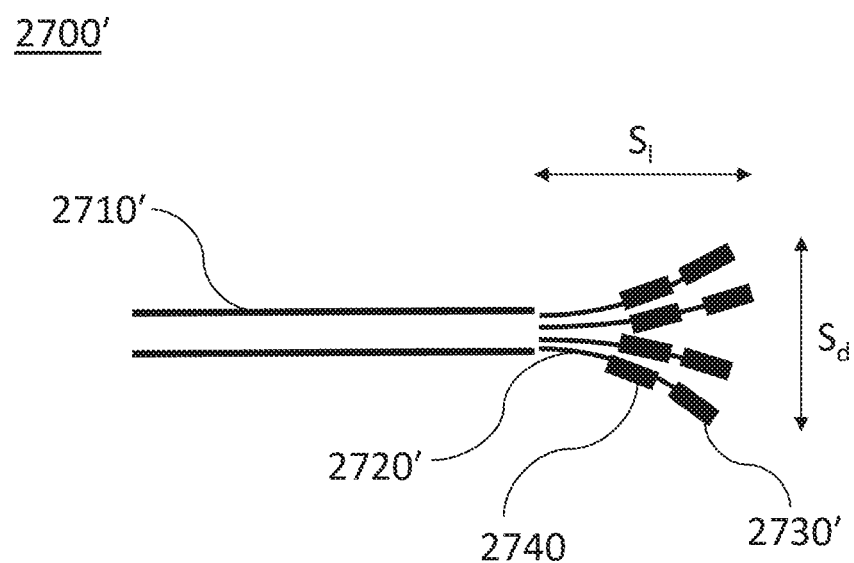

Referring to FIG. 27C, it is understood that unless indicated otherwise, components with similar references numbers to those in FIGS. 27A-27B (e.g., the electrode (2730) in FIGS. 27A-27B and the electrode (2730') in FIG. 27C) may be structurally and/or functionally similar. FIG. 27C illustrates a set of splines (2720') where each spline (2720') includes a pair of electrodes (2730', 2740).

The ablation device (2700') includes a catheter shaft (2710') at a proximal end of the device (2700') and a set of splines (2720') coupled to the catheter shaft (2710') at a distal end of the device (2700'). The ablation device (2700') may be configured for delivering a pulse waveform to tissue during use via one or more splines of the set of splines (2720'). Each spline (2720') of the ablation device (2700') may include one or more independently addressable electrodes (2730', 2740) formed on a surface of the spline (2720'). Each electrode (2730', 2740) may include an insulated electrical lead configured to sustain a voltage potential of at least about 700 V without dielectric breakdown of its corresponding insulation. In other embodiments, the insulation on each of the electrical leads may sustain an electrical potential difference of between about 200V to about 2000 V across its thickness without dielectric breakdown. Each spline of the set of splines (2720') may include the insulated electrical leads of each electrode (2730', 2740) formed in a body of the spline (2720') (e.g., within a lumen of the spline (2720')). Each electrode (2730', 2740) of a spline (2720') may have about the same size and shape. Furthermore, each electrode (2730', 2740) of a spline (2720') may have about the same size, shape, and spacing as the electrodes (2730', 2740) of an adjacent spline (2720'). In other embodiments, the size, shape, number, and spacing of the electrodes (2730', 2740) may differ.

In some embodiments, the electrodes (2730', 2740) of the ablation device (2700') may have a length from about 0.5 mm to about 5.0 mm and a cross-sectional dimension (e.g., a diameter) from about 0.5 mm to about 4.0 mm, including all values and subranges in between. The spline wires (2720') in the second configuration may splay out to an extent Sd at a distal end of the ablation device (2700') from about 5.0 mm to about 20.0 mm from each other (including all values and subranges in between), and may extend from a distal end of the catheter shaft (2710') for a length Sl from about 8.0 mm to about 20.0 mm, including all values and subranges in between. In some embodiments, the ablation device (2700') may include 4 splines, 5 splines, or 6 splines. In some embodiments, each spline may independently include 1 electrode, 2 electrodes, or 3 or more electrodes.

The set of splines (2720') may form a delivery assembly at a distal portion of the ablation device (2700') and be configured to transform between a first configuration and a second configuration. The set of splines (2720') in a first configuration are generally parallel to a longitudinal axis of the ablation device (2700) and may be closely spaced together. The set of splines (2720') in a second configuration are depicted in FIG. 27C where the set of splines (2720') extend out of the distal end of the catheter shaft (2710') and bias (e.g., curve) away from the longitudinal axis of the ablation device (2700') and other splines (2720'). In this manner, the splines (2720') may more easily conform to the geometry of an endocardial space. The delivery assembly may be disposed in the first configuration prior to delivering a pulse waveform and transformed to the second configuration to contact a region of endocardial tissue to generate large focal lesions upon delivery of pulse waveforms for irreversible electroporation as disclosed herein. In some embodiments, the electrodes (2730') (also sometimes referred to as "distal electrodes") in the second configuration depicted in FIG. 27C may be configured to contact and press against endocardial tissue while the electrodes (2740) (also sometimes referred to as "proximal electrodes") in the second configuration may not contact endocardial tissue. In this manner, an electric field generated by the electrodes due to conduction between the proximal and distal electrodes through the blood pool results in focal ablation of tissue.

In some embodiments, a proximal end of the set of splines (2720') may be slidably coupled to a distal end of the catheter shaft (2710'). As the set of splines (2720') are extended further out from the catheter shaft (2710'), the distal ends of the set of splines (2720') may bias further away from each other and a longitudinal axis of the catheter shaft (2710'). The set of splines (2720') may be slidably advanced out of the catheter shaft (2710') independently or in one or more groups. For example, the set of splines (2720') may be disposed within the catheter shaft (2710') in the first configuration. The splines (2720') may then be advanced out of the catheter shaft (2710') and transformed into the second configuration. The splines (2720') may be advanced all together or advanced such that the set of splines (2720') corresponding to the anode electrodes (2730) are advanced separately from the set of splines (2720') corresponding to the cathode electrodes (2730', 2740). In some embodiments, the splines (2710') may be advanced independently through respective lumens (e.g., sheaths) of the catheter shaft (2710'). In the second configuration, the electrodes (2730', 2740) are biased away from the catheter shaft (2710') longitudinally and/or laterally with respect to a longitudinal axis of a distal end of the catheter shaft (2710'). This may aid delivery and positioning of the electrodes (2730', 2740) against an endocardial surface. In some embodiments, each of the set of splines (2720') may extend from a distal end of the catheter shaft (2710') by up to about 5 cm.

In some embodiments, the distal electrodes (2730') may have the same polarity while adjacent proximal electrodes (2740) may have the opposite polarity as the distal electrodes (2730'). In this manner, an electric field may be generated between the distal and proximal electrodes for focal ablation.

In some of these embodiments, a handle (not shown) may be coupled to the set of splines. The handle may be configured for affecting transformation of the set of splines between the first configuration and the second configuration. In some embodiments, the electrical leads of at least two electrodes of the set of electrodes (2730', 2740) may be electrically coupled at or near a proximal portion of the ablation device, such as, for example, within the handle. In some embodiments, the electrodes (2730', 2740) may be electrically wired together in the handle of the device (2700'), so that these electrodes (2730', 2740) are at the same electric potential during ablation.

The set of electrodes (2730', 2740) may include an atraumatic shape to reduce trauma to tissue. For example, the electrodes (2730', 2740) may have an atraumatic shape including a rounded, flat, curved, and/or blunted portion configured to contact endocardial tissue. In some embodiments, the electrodes (2730', 2740) may be located along any portion of the spline (2720') distal to the catheter shaft (2710'). The electrodes (2730', 2740) may have the same or different sizes, shapes, and/or location along respective splines. One or more of the splines (2720') may include three or more electrodes.

In some embodiments, each of the electrodes (2730') on a spline (2720') may be configured as an anode while each of the electrodes (2730') on an adjacent spline (2720') may be configured as a cathode. In another embodiment, each of the electrodes (2730') on one spline may alternate between an anode and cathode with each of the electrodes of an adjacent spline having a reverse configuration (e.g., cathode and anode). In some embodiments a subset of electrodes may be electrically wired together in the handle of the device, so that these electrodes are at the same electric potential during ablation. In other embodiments, the size, shape, and spacing of the electrodes (2730) may differ as well. In some embodiments, adjacent distal electrodes (2730') and proximal electrodes (2740) may form an anode-cathode pair. For example, the distal electrodes (2730') may be configured as an anode and the proximal electrodes (2740) may be configured as a cathode.

The ablation device (2700') may include any number of splines, for example, 3, 4, 5, 6, 7, 8, 9, 10, 12, 14, 16, 18, 20, or more splines, including all values and sub-ranges in between. In some embodiments, the ablation device (2700') may include 3 to 20 splines. For example, the ablation device (2700) may include 6 to 12 splines.

In FIG. 27C, two electrodes (2730', 2740) are formed on a surface of each spline (2720') such that each spline (2720') includes two insulated electrical leads. The thickness of each spline may vary based on the number of electrodes formed on each spline (2720') which may correspond to the number of insulated electrical leads in the spline (2720'). The splines (2720') may have the same or different materials, thickness, and/or radius of curvature. For example, the thickness of each spline (2720') may reduce distally.

In this manner, the electrodes in the second configuration may be placed against, a section of endocardial tissue to directly generate lesions thereupon by activation of appropriate electrodes using any suitable combination of polarities for delivery of pulse waveforms for irreversible electroporation. For example, adjacent electrodes (2730', 2740) may be configured with opposite polarities.

As the electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms), as discussed in further detail herein. It should be appreciated that the size, shape, and spacing of the electrodes on and between the splines may be configured to deliver contiguous/transmural energy to electrically isolate one or more pulmonary veins. In some embodiments, alternate electrodes may be at the same electric potential, and likewise for all the other alternating electrodes. Thus, ablation may be delivered rapidly with all electrodes activated at the same time. A variety of such electrode pairing options exists and may be implemented based on the convenience thereof.

Figure 28:
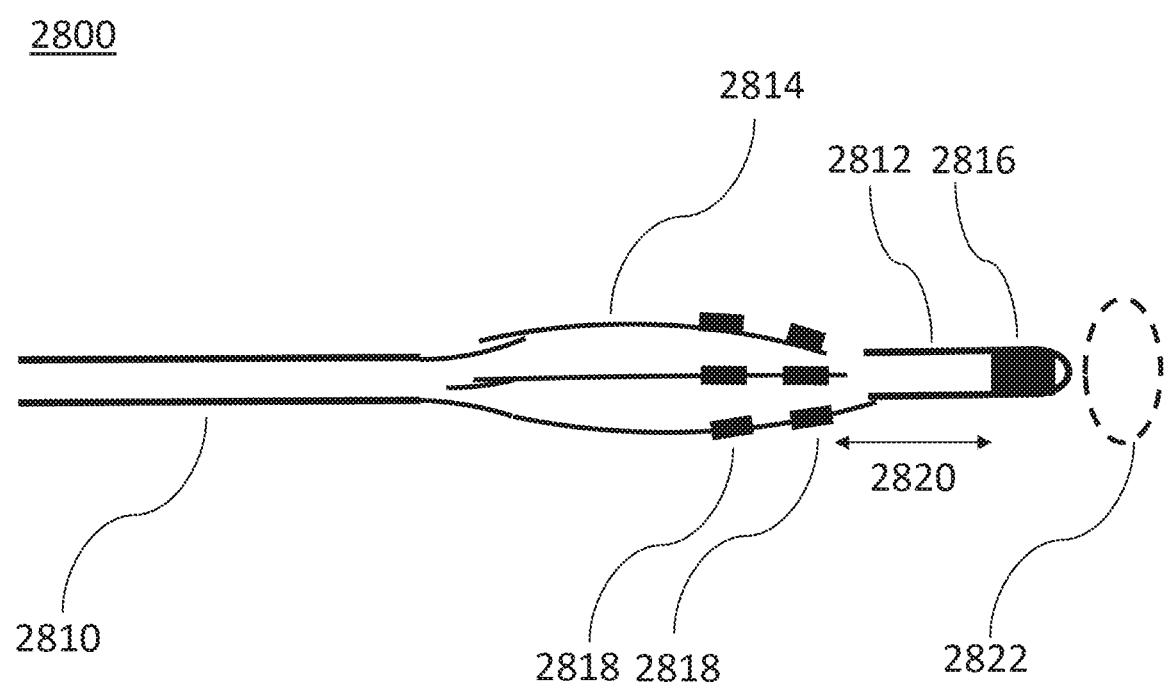
FIG. 28 is a side view of an ablation catheter, according to other embodiments.

FIG. 28 is a side view of yet another embodiment of an ablation device (2800) including a catheter shaft (2810) at a proximal end of the device (2800), a distal cap (2812) of the device (2800), and a set of splines (2814) coupled thereto. In some embodiments, the ablation device (2800) is useful for forming lesions on endocardial surfaces via focal ablation, as described herein.

The distal cap (2812) may include an atraumatic shape and one or more independently addressable electrodes (2816) (also sometimes referred to as "distal electrodes"), as described in further detail herein. A proximal end of the set of splines (2814) may be coupled to a distal end of the catheter shaft (2810), and a distal end of the set of splines (2814) may be tethered to the distal cap (2812) of the device (2800). Each spline (2814) of the ablation device (2800) may include one or more independently addressable electrodes (2818) (also sometimes referred to as "proximal electrodes") formed on a surface of the spline (2814). Each electrode (2816, 2818) may include an insulated electrical lead configured to sustain a voltage potential of at least about 700 V without dielectric breakdown of its corresponding insulation. In other embodiments, the insulation on each of the electrical leads may sustain an electrical potential difference of between about 200V to about 2000 V across its thickness without dielectric breakdown, including all values and subranges in between. Each spline (2814) may include the insulated electrical leads of each electrode (2818) formed in a body of the spline (2814) (e.g., within a lumen of the spline (2814)). One or more of the splines (2818) may further include the insulated electrical lead of the distal electrode (2816). In some embodiments, the size and/or shape of the electrodes (2816, 2818) may differ from each other.

The configuration of the set of splines (2814) and proximal electrodes (2818) may control a depth, shape, and/or diameter/size of a focal ablation lesion generated by the ablation device (2800). The ablation device (2800) may be configured to transform between a first configuration, where the set of splines (2814) are arranged generally parallel to the longitudinal axis of the ablation device (2800), and a second configuration, where the set of splines (2814) bow radially outward from a longitudinal axis of the ablation device (2800). It is understood that the set of splines (2814) may be transformed into any intermediate configuration between the first and second configurations, continuously or in discrete steps.

Activation of electrodes using a predetermined configuration may provide targeted and precise focal ablation by controlling a focal ablation spot size based on the expansion of the splines (2814). For example, in some embodiments, a distal electrode (2816) may be configured with a first polarity and one or more proximal electrodes (2818) may be configured with a second polarity opposite the first polarity. When the proximal electrodes (2818) of the ablation device (2800) are in the first configuration, a high intensity electric field having a relatively smaller/more focused diameter results in a focal ablation lesion on an endocardial surface that is relatively smaller in diameter and has greater depth. When the proximal electrodes (2818) of the ablation device (2800) are in the second configuration, a relatively more dispersed electric field is generated, resulting in a focal ablation lesion on an endocardial surface that is relatively wider and shallower than with the first configuration. In this manner, by varying the extent of expansion of the splines (2814), the depth, shape, and/or size of the lesion can be controlled without switching out the ablation device (2800). Such aspects are useful for creating multiple lesions of varying sizes and/or depths using the same ablation device.

The distal cap (2812) may be disposed to press against the endocardial tissue while the proximal electrodes (2818) in either the first or second configurations may be configured so as to not contact endocardial tissue. It should be appreciated that the distal electrode (2816) need not contact endocardial tissue. In some of these embodiments, a handle (not shown) may be coupled to the set of splines (2814) and the handle configured for affecting transformation of the set of splines (2814) between the first configuration and the second configuration. In some embodiments, the electrical leads of at least two electrodes of the set of electrodes may be electrically coupled at or near a proximal portion of the ablation device (2800), such as, for example, within the handle.

In some embodiments, the distal electrode (2816) and proximal electrodes (2818) may form anode-cathode pairs. For example, the distal electrode (2816) may be configured as an anode and each of the proximal electrodes (2818) may be configured as cathodes. In some embodiments, the ablation device (2800) may include 3 to 12 splines. The ablation device (2800) may include any number of splines, for example, 3, 4, 5, 6, 7, 8, 9, 10, 12, 14, 16, 18, 20, or more splines. In some embodiments, the ablation device (2800) may include 3 to 20 splines. For example, in one embodiment, the ablation device (2800) may include 6 to 10 splines. Furthermore, in some embodiments, the shape of the expanded set of splines (2814) may be asymmetric, for example with its distal portion being more bulbous or rounded than its proximal portion. Such a bulbous distal portion (as well as proximal electrode positioning) may aid in further controlling a size and depth of focal ablation.

A first plane (2822) depicted in FIG. 28 may refer to a plane orthogonal to the longitudinal axis of the catheter shaft (2810). The distal cap (2812) may be pressed against, for example, an endocardial surface lying within the first plane (2812), such as a lumen wall of a pulmonary vein in order to directly generate focal ablation lesions thereupon by activation of appropriate electrodes using any suitable combination of polarities. For example, distal electrode (2816) may be pressed against an endocardial surface and used to form focal ablation lesions (e.g., spot lesions). In some embodiments, one or more proximal electrodes (2818) may be configured with an opposite polarity to that of the distal electrode (2816). Conversely, one or more of the proximal electrodes (2818) may be configured with the same polarity as the distal electrodes (2816). In some embodiments, the proximal electrodes (2818) on different splines (2814) may alternate between an anode and cathode.

In some embodiments, the distal electrode (2816) of the ablation device (2800) may include a length from about 0.5 mm to about 7.0 mm and a cross-sectional dimension (e.g., a diameter) from about 0.5 mm to about 4.0 mm, including all values and subranges in between. In some embodiments, the proximal electrodes (2818) may include a length from about 0.5 mm to about 5.0 mm and a diameter from about 0.5 mm to about 2.5 mm, including all values and subranges in between. The distal electrode (2816) may be separated from the proximal electrodes (2818) by a length from about 3.0 mm to about 12.0 mm, including all values and subranges in between. The distal electrode (2816) disposed on the distal cap (2812) may be located from about 1.0 mm to about 4.0 mm away from a distal end of the distal cap (2812), including all values and subranges in between. In some embodiments, the distal end of the distal cap (2812) may include the distal electrode (2816). One or more focal ablation zones may be formed including a diameter from about 1.0 cm to about 2.0 cm, including all values and subranges in between.

Figure 29A:
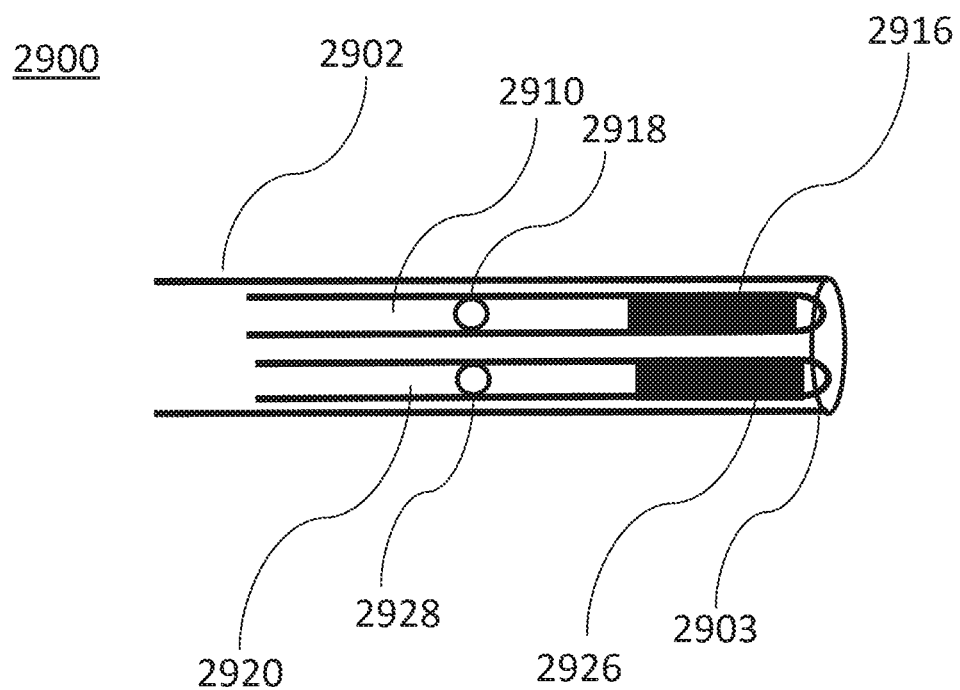
FIGS. 29A-29D are cross-sectional side views of an ablation catheter, according to other embodiments.
Figure 29B:
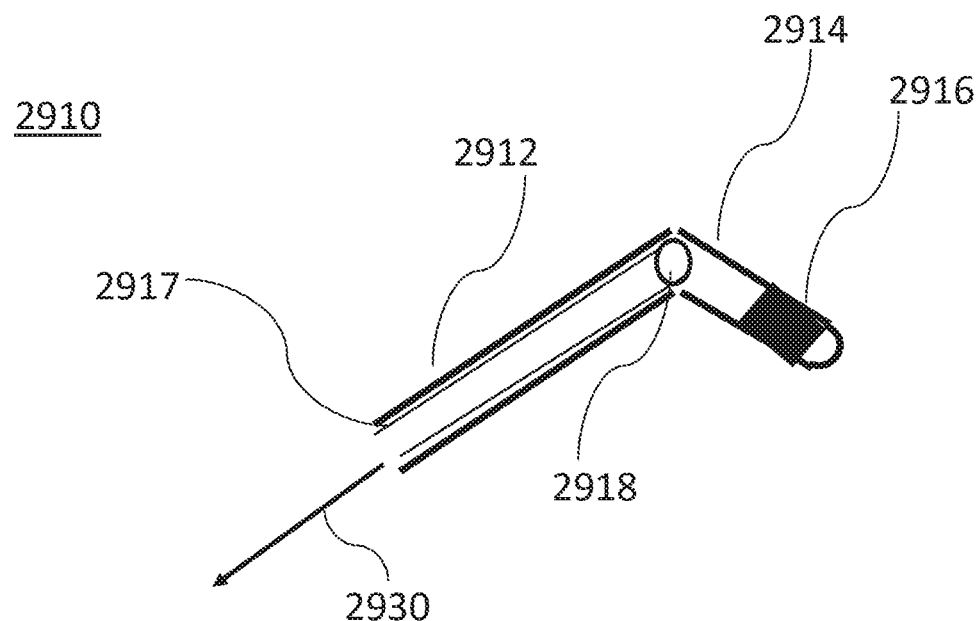
Figure 29C:
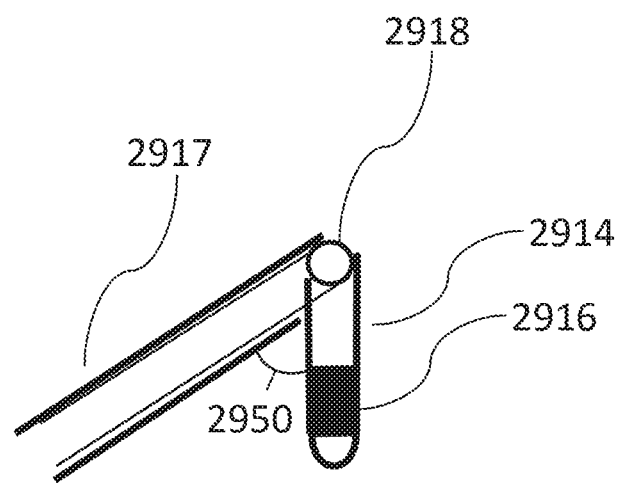
Figure 29D:
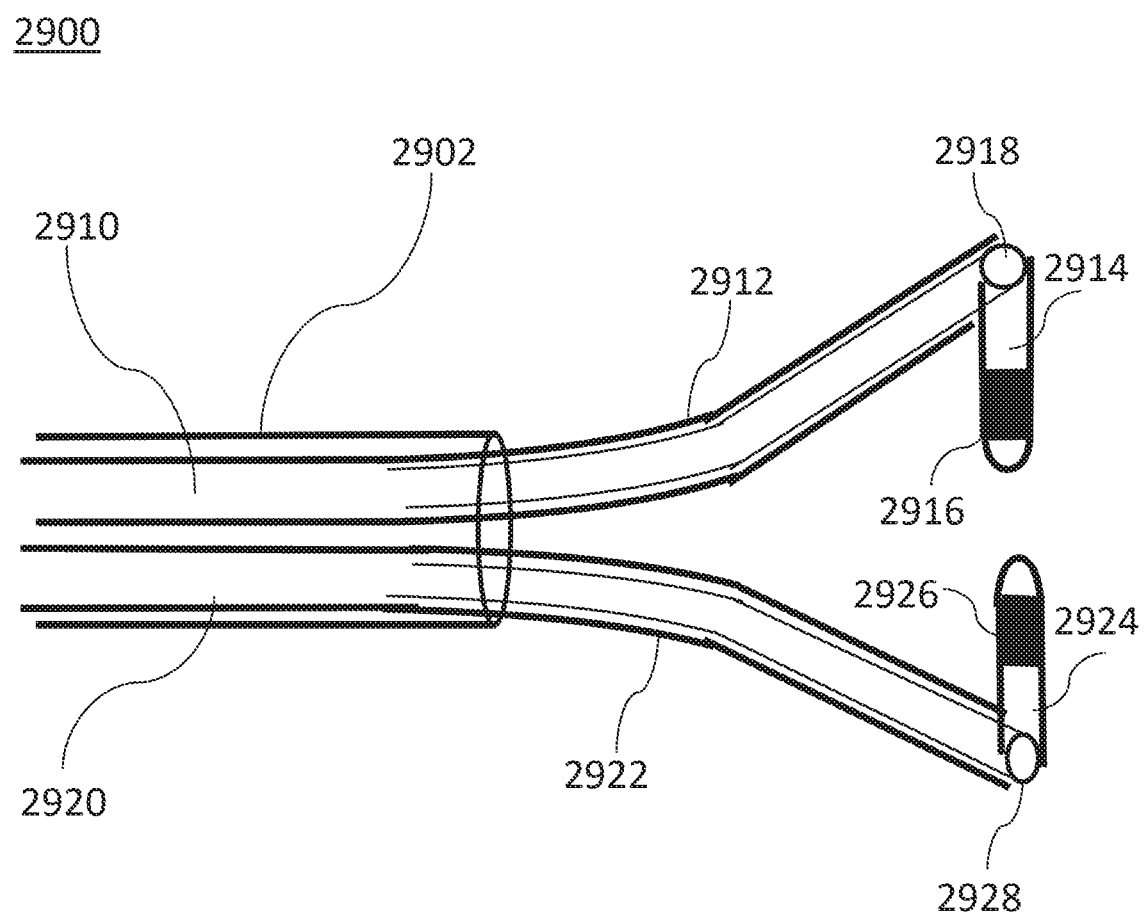

FIGS. 29A-29D are side views of yet another embodiment of an ablation device (2900) including an outer catheter or sheath (2902) and a set of inner catheters (2910, 2920) slidable within an outer catheter lumen so as to extend from a distal end of the lumen. The outer catheter may define a longitudinal axis. The inner diameter of the outer catheter (2902) may be about 0.7 mm to about 3 mm and the outer diameter of the outer catheter (2902) may be about 2 mm to about 5 mm. As best seen in FIGS. 29A, 29D, the ablation device (2900) includes a first catheter (2910) having a first proximal portion (2912), a first distal portion (2914), and a first electrode (2916) formed on the first distal portion (2914), such as on a surface of the first distal portion (2914), for example. The first proximal portion (2912) may be coupled to the first distal portion (2914) via a first hinge (2918). A second catheter (2920) includes a second proximal portion (2922), a second distal portion (2924), and a second electrode (2926) formed on the second distal portion (2924). The second proximal portion (2922) may be coupled to the second distal portion (2924) via a second hinge (2928).

In some embodiments, the ablation device (2900) is useful for forming lesions on endocardial surfaces via focal ablation, as described herein. The distal ends of the catheters (2910, 2920) and/or the electrodes (2916, 2922) may include an atraumatic shape to reduce trauma to tissue. For example, the distal end of the catheters (2910, 2920) and/or the electrodes (2916, 2922) may have an atraumatic shape including a rounded, flat, curved, and/or blunted portion configured to contact endocardial tissue.

Each electrode (2916, 2926) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2000 V across its thickness without dielectric breakdown, including all values and subranges in between. Each catheter (2910, 2920) may include the insulated electrical lead of each electrode (2916, 2926) formed in a body of the catheter (2910, 2920) (e.g., within a lumen of the catheter (2910, 2920)). Each of the electrodes (2916, 2926) may be connected to a corresponding insulated electrical lead leading to a handle (not shown) coupled to a proximal portion of the catheter (2910, 2920). In some embodiments, the size, shape, and/or location of the electrodes (2916, 2926) may differ from each other.

In some embodiments, the configuration of the catheters (2910, 2920) and electrodes (2916, 2926) may control a depth, shape, and/or diameter/size of a focal ablation lesion generated by the ablation device (2900). The first and second catheters (2910, 2920) may be configured for translation along the longitudinal axis of the outer catheter (2902). In some embodiments, the ablation device (2900) may be configured to transform between: a first configuration, where the set of catheters (2910, 2920) are arranged generally parallel to the longitudinal axis of the outer catheter (2902) and a distal portion of the catheters (2910, 2920) are disposed within the outer catheter (2902) (e.g., FIG. 29A); a second configuration, where the electrodes (2916, 2926) are advanced out of and away from the distal end (2903) of the outer catheter lumen (2902) by any suitable distance; and a third configuration, where a distal portion of each catheter (2910, 2920) may rotate, twist, or bend about its corresponding hinge (2918, 2928) relative to a proximal portion of its corresponding catheter (2910, 2920) (e.g., FIGS. 29B-29D). For example, as best illustrated in FIGS. 29B-29C, the first catheter (2910) may include a distal portion (2914) rotatable about a first hinge (2918) that may be configured to position the distal portion (2914) relative to the proximal portion (2912) at a plurality of positions. The catheters (2910, 2912) in the second and third configurations may angle away from each other so as to bias away from a longitudinal axis of the outer catheter (2902). A distal end of the proximal portions (2912, 2922) may form an angle with respect to the longitudinal axis between about 5 degrees and about 75 degrees (e.g., FIG. 29D). It is understood that the ablation device (2900) may be transformed into any intermediate configuration between the first, second, and third configurations, continuously or in discrete steps.

In some embodiments, conduction between electrodes through the blood pool and/or endocardial tissue results in electric field generation and application of the electric field as ablative energy to an endocardial surface. The electrodes may be held close to or placed in physical contact against a section of atrial wall of the left atrium in order to generate lesions thereupon by activation of one or more of the electrodes using any suitable combination of polarities. In this manner, activation of electrodes using a predetermined configuration may provide targeted and precise focal ablation by controlling a focal ablation spot size based on the position and orientation of the electrodes (2916, 2926) relative to a proximal portion (2912, 2922) of the catheters (2910, 2920). For example, in some embodiments, a first electrode (2916) may be configured with a first polarity and a second electrode (2926) may be configured with a second polarity opposite the first polarity. When the electrodes (2916, 2926) are rotated such that they are relatively close to each other (e.g., when the proximal portion (2912) and distal portion (2914) form an acute angle (2950)), a relatively higher intensity electric field that has a relatively smaller/more focused diameter results in a focal ablation lesion on an endocardial surface that is relatively smaller in diameter and has a good depth. Purely for non-limiting illustrative purposes, the acute angle formed at the articulated hinge may range between about 15 degrees and about 70 degrees. In some embodiments, the electric field intensity in the focal ablation zone may be about 200 V/cm or more. When the electrodes (2916, 2926) are rotated about their corresponding hinges (2918,2928) such that they are relatively farther from each other (e.g., when the proximal portion (2912) and distal portion (2914) form a larger angle), a relatively more dispersed and lower intensity electric field is generated, resulting in a focal ablation lesion on an endocardial surface that is relatively wider and shallower. In this manner, by varying the extent of rotation of the electrodes (2916, 2926) relative to a proximal portion (2912, 2922) of the catheters (2910, 2920), the depth, shape, and/or size of the lesion can be controlled without switching out the ablation device (2900). Such aspects are useful for creating multiple lesions of varying sizes, shapes, and/or depths using the same ablation device. For example, the lesion diameter may be from about 2 mm to about 3 cm, and the lesion depth may be between about 2 mm and about 12 mm. Although the electrodes (2916, 2926) may be disposed to touch endocardial tissue, it should be appreciated that the electrodes (2916, 2926) need not contact the endocardial tissue.

In some of these embodiments, a handle (not shown) may be coupled to the set of catheters (2910, 2920) and the handle configured for affecting transformation of the catheters (2910, 2920) between the first, second, and third configurations. In some embodiments, actuation of one or more knobs, wheels, sliders, pull wires, and/or other control mechanisms in the handle may result in translation of one or more catheters (2910, 2920) through the outer catheter (2902) and/or rotation of a distal portion (2914, 2924) of the catheter about a hinge (2918, 2928).

FIGS. 29B-29C depict a first catheter (2910) having an articulated distal portion (2914). The first catheter (2910) may include a proximal portion (2912) coupled to a distal portion (2914) via a hinge (2918). The distal portion (2914)

may include an electrode (2916) as described herein. In some embodiments, the hinge (2918) may include a rotatable wheel. In other embodiments, the hinge (2918) may include a portion of the proximal portion (2912) or distal portion (2914) having a reduced cross-sectional area relative to the first catheter (2910) that is more flexible than other portions of the catheter. In yet other embodiments, the hinge (2918) may include a joint, rotatable wheel, ball and socket joint, condyloid joint, saddle joint, pivot, track, and the like.

The rotatable wheel may be coupled to a wire (2917) (e.g., pull wire). For example, the wire (2917) may be attached around the hinge (2918) and the distal portion (2914) may be attached to a portion of the hinge (2918). Accordingly, actuation (2930) of the wire (2917) (e.g., pulling one end of the wire proximally) may in turn rotate the wheel (2918) and the distal portion (2914) such that the distal portion (2914) rotates relative to the proximal portion (2912) of the first catheter (2910). In some embodiments, the distal portion may rotate with respect to the proximal portion by an angle from about 110 degrees to about 165 degrees, and the length of the distal portion may be from about 3 mm to about 12 mm. A proximal end of the wire (2917) may in some embodiments be coupled to a handle (not shown) having a control mechanism (e.g., one or more knobs, wheels, sliders). The operator may operate the control mechanism to manipulate the wire (2917) to rotate the distal portion (2914) of the first catheter (2910) about the hinge (2918). The control mechanism of the handle may include a lock to fix a position of the distal portion (2914). FIG. 29B depicts an embodiment of the first catheter (2910) having the distal portion (2914) in between the second and third configurations. FIG. 29C depicts an embodiment of the first catheter (2910) in the third configuration. The electrodes (2916, 2926) may bias towards each other in the third configuration.

FIG. 29D depicts an embodiment of the ablation device (2900) in the third configuration, where distal portions of the first and second catheters (2910, 2920) are extended out of an outer catheter or sheath (2902) and rotated to a desired position (e.g., fully rotated, fully articulated) relative to proximal portions (2912, 2922) of the catheters (2910, 2920). In some embodiments, the wires (2912, 2922) of each of the catheters (2910, 2920) may be coupled together at the handle such that actuation of the control mechanism controls the wires (2912, 2922) together such that the distal portions (2914, 2924) of each of the catheters (2910, 2920) may be simultaneously rotated about their respective hinges (2918, 2928). In the second and third configurations, the first and second catheters (2910, 2920) may bias away from the longitudinal axis of the outer catheter (2902).

When the first and second catheters (2910, 2920) are extended out of the outer catheter (2902), one or more portions of the catheters (2910, 2920) may assume their natural (e.g., unconstrained) shape(s), such as a curved shape. The catheters (2910, 2920) may be advanced out of the outer catheter (2902) together or independently. In some embodiments, the proximal portions (2912, 2922) of the catheters (2910, 2920) may include a flexible curvature such that the distal ends of the catheters (2910, 2920) may be configured to splay away from each other. The minimum radius of curvature of the catheter (2910, 2920) may be in the range of about 1 cm or larger. For example, the proximal portions (2912, 2922) may have a radius of curvature of about 1 cm or larger. In some embodiments, the distal portions (2914, 2924) may have a radius of curvature of about 1 cm or larger.

In some embodiments, the electrodes (2916, 2926) of the ablation device (2900) may include a length from about 0.5 mm to about 7.0 mm and a cross-sectional dimension (e.g., a diameter) from about 0.5 mm to about 4.0 mm, including all values and subranges in between. The electrodes (2916, 2926) of different catheters (2910, 2920) may be separated from each other by a distance from about 3.0 mm to about 20 mm, including all values and subranges in between. The electrode (2916, 2926) may be located from about 1.0 mm to about 4.0 mm away from a distal end of its corresponding catheter (2910, 2920), including all values and subranges in between. In some embodiments, the distal end of the catheter (2910, 2920) may include the electrode (2916, 2926). One or more focal ablation lesions may be formed including a diameter from about 1.0 cm to about 2.0 cm, including all values and subranges in between.

Figure 30:
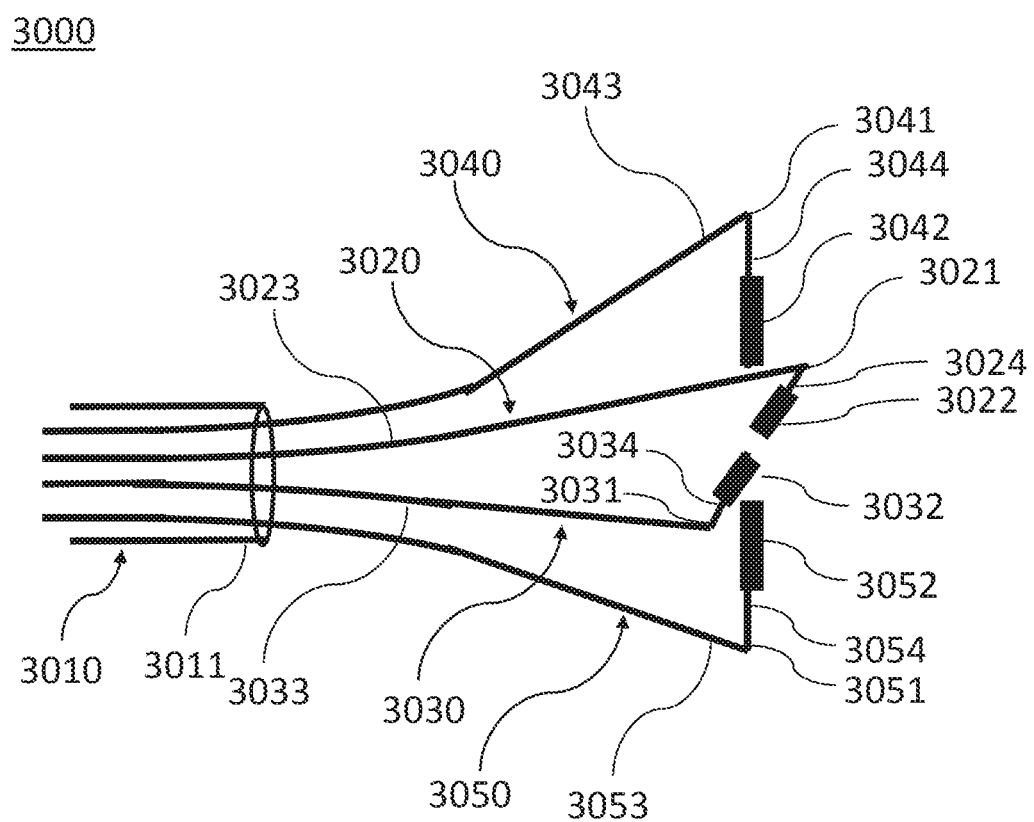
FIG. 30 is a side view of an ablation catheter, according to other embodiments.

FIG. 30 is a side view of another embodiment of an ablation device (3000) including an outer catheter or sheath (3010) defining a longitudinal axis and a set of four catheters (3020, 3030, 3040, 3050) slidable within a lumen (3010). Each of the catheters (3020, 3030, 3040, 3050) may include a proximal portion (3023, 3033, 3043, 3053), distal portion (3024, 3034, 3044, 3054), and a hinge (3021, 3031, 3041, 3051) coupling the proximal portion (3023, 3033, 3043, 3053) to the distal portion (3024, 3034, 3044, 3054). Each of the distal portions (3024, 3034, 3044, 3054) may include an electrode (3022, 3032, 3042, 3052). The distal ends of the catheters (3020, 3030, 3040, 3050) and/or the electrodes (3022, 3032, 3042, 3052) may include an atraumatic shape (e.g., rounded, flat, curved, and/or blunted portion) to reduce trauma to tissue. Each of the catheters (3020, 3030, 3040, 3050) may include a hinge (3021, 3031, 3041, 3051) as described in detail herein. It should be appreciated that the ablation device (3000) may include any number of catheters including a set of 2, 3, 4, 5, 6, or more catheters.

Each electrode (3022, 3032, 3042, 3052) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2000 V across its thickness without dielectric breakdown, including all values and subranges in between. Each catheter (3020, 3030, 3040, 3050) may include the insulated electrical lead of each electrode (3022, 3032, 3042, 3052) formed in a body of the catheter (3020, 3030, 3040, 3050) (e.g., within a lumen of the catheter (3020, 3030, 3040, 3050)). Each of the electrodes (3022, 3032, 3042, 3052) may be connected to a corresponding insulated electrical lead leading to a handle (not shown) coupled to a proximal portion of the catheter. In some embodiments, the size, shape, and/or location of the electrodes (3022, 3032, 3042, 3052) may differ from each other.

In some embodiments, the configuration of the catheters (3020, 3030, 3040, 3050) and electrodes (3022, 3032, 3042, 3052) may control a depth, shape, and/or diameter/size of a focal ablation lesion generated by the ablation device (3000). The set of catheters (3020, 3030, 3040, 3050) may be configured to translate along the longitudinal axis to transition between a first, second, and third configuration. In some embodiments, the ablation device (3000) may be configured to transform between: a first configuration, where the set of catheters (3020, 3030, 3040, 3050) are arranged generally parallel to the longitudinal axis of the outer catheter or sheath (3010) and a distal portion of the catheters (3020, 3030, 3040, 3050) are disposed within the outer catheter (3010); a second configuration, where the electrodes (3022, 3032, 3042, 3052) are advanced out of and away from a distal end (3011) of the outer catheter (3010)

lumen by any suitable distance; and a third configuration, where a distal portion of each catheter (3020, 3030, 3040, 3050) may rotate, twist, or bend about its corresponding hinge (3021, 3031, 3041, 3051) relative to a proximal portion of its corresponding catheter (3020, 3030, 3040, 3050) (e.g., FIG. 30). For example, the first catheter (3020) may include a distal portion (3024) rotatable about a first hinge (3021) that may be configured to position the distal portion (3024) relative to the proximal portion (3023) at a plurality of positions as discussed above with respect to FIGS. 29A-29D. It is understood that the ablation device (3000) may be transformed into any intermediate configuration between the first, second, and third configurations, continuously or in discrete steps. In the second configuration, the set of catheters may bias away from the longitudinal axis.

In some embodiments, one or more pulse waveforms may be applied between the electrodes (3022, 3032, 3042, 3052) configured in anode and cathode sets. For example, adjacent or approximately diametrically opposed electrode pairs may be activated together as an anode-cathode set. In FIG. 30, first electrode (3022) may be configured as an anode and paired with second electrode (3032) configured as a cathode. Third electrode (3042) may be configured as an anode and paired with fourth electrode (3052) configured as a cathode. The first and second electrode (3022, 3032) pair may apply a first pulse waveform followed sequentially by second pulse waveform using the third and fourth electrode (3042, 3052) pair. In another embodiment, a pulse waveform may be applied simultaneously to each of the electrodes where the second and third electrodes (3032, 3042) may be configured as anodes and the first and fourth electrodes (3022, 3052) may be configured as cathodes. It should be appreciated that any of the pulse waveforms disclosed herein may be progressively or sequentially applied over a sequence of anode-cathode electrodes. Some embodiments of the ablation device (3000) may have the same dimensions as described above with respect to the ablation device (2900).

In other embodiments, one or more of the electrodes (3022, 3032, 3042, 3052) may be configured with a first electrical polarity, while one or more electrodes (not shown) disposed on a surface of the outer catheter shaft (3010) (not shown) may be configured with a second electrical polarity opposite the first electrical polarity.

Figure 31A:
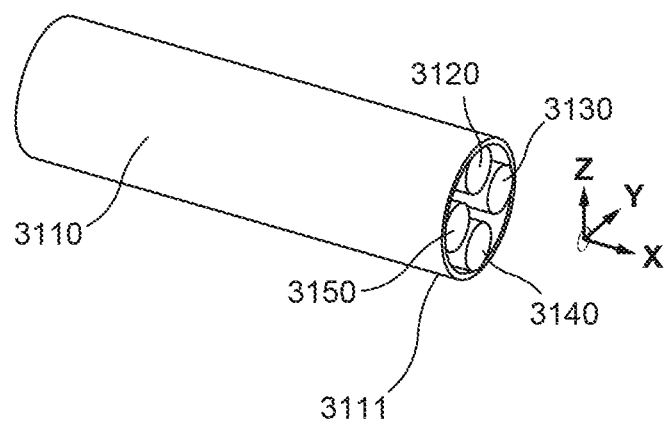
FIGS. 31A-31B are perspective views of an ablation catheter, according to other embodiments.
Figure 31B:
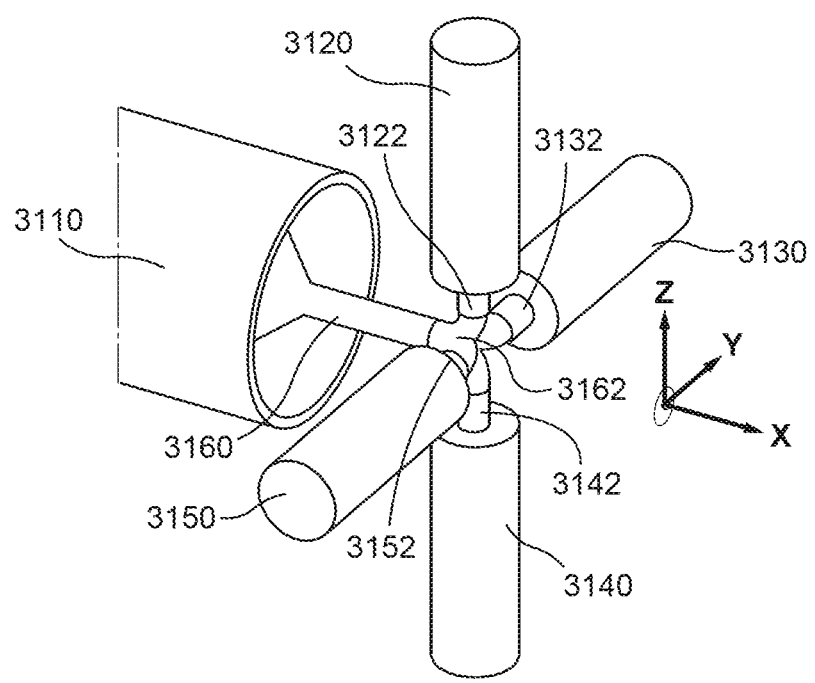

FIG. 31A-31B are perspective views of a yet another embodiment of an ablation device (3100) including an outer catheter or sheath (3110) defining a longitudinal axis and a catheter (3160) slidable within an outer catheter lumen. The catheter (3160) may extend from a distal end of the lumen. The catheter (3160) may include a proximal portion (3160), multiple distal portions (3122, 3132, 3142, 3152), and articulation (3162) coupling the proximal portion to each of the multiple distal portions. For example, articulation (3162) may include a hinge, joint, rotatable wheel, ball and socket joint, condyloid joint, saddle joint, pivot, track, and the like. The distal portions (3122, 3132, 3142, 3152) are folded back within the outer catheter (3110) and internal springs (not shown) connecting to each portion are in a stressed configuration when each distal portion (3122, 3132, 3142, 3152) is folded. When the distal portions (3122, 3132, 3142, 3152) are not constrained (i.e., when the inner catheter (3160) is deployed or pushed out far enough from the outer catheter (3110)), the springs assume their native or unstressed configurations resulting in articulation of the articulation (3162) whereupon the distal portions (3122, 3132, 3142, 3152) articulate outward and assume a configuration approximately perpendicular to the longitudinal axis of the catheter.

As shown in FIG. 31B, the distal end of the catheter (3160) may be coupled to a set of electrodes (3120, 3130, 3140, 3150) via articulation (3162). In some embodiments, the articulation (3162) may be coupled to a first distal portion (3122), a second distal portion (3132), a third distal portion (3142), and a fourth distal portion (3152). The electrodes (3120, 3130, 3140, 3150) may be disposed on a surface of respective distal portions (3122, 3132, 3142, 3152). When the catheter (3160) is advanced out of the outer catheter (3110), the distal portions (3120, 3130, 3140, 3150) may assume their natural (e.g., unconstrained) shapes so as to be approximately perpendicular to a longitudinal axis of the catheter (3160).

The electrodes (3120, 3130, 3140, 3150) may include an atraumatic shape (e.g., rounded, flat, curved, and/or blunted portion) to reduce trauma to tissue. Each electrode (3120, 3130, 3140, 3150) may include an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2000 V across its thickness without dielectric breakdown, including all values and subranges in between. The catheter (3160) may include the insulated electrical lead of each electrode (3120, 3130, 3140, 3150) formed in a body (e.g., lumen) of the catheter (3160). Each of the electrodes (3120, 3130, 3140, 3150) may be connected to a corresponding insulated electrical lead leading to a handle (not shown) coupled to a proximal portion of the catheter (3160). In some embodiments, the size, shape, and/or location of the electrodes (3120, 3130, 3140, 3150) may differ from each other.

The catheter (3160) may be configured for translation along the longitudinal axis to transition between a first, second, and third configuration. In some embodiments, the ablation device (3100) may be configured to transform between: a first configuration, where the set of electrodes (3120, 3130, 3140, 3150) are arranged generally parallel to the longitudinal axis of the outer catheter (3110) and within the outer catheter (3110) (e.g., FIG. 31A); a second configuration, where the set of electrodes (3120, 3130, 3140, 3150) are advanced out of and away from the distal end (3111) of the outer catheter lumen by any suitable distance (not shown in FIG. 31A); and a third configuration, where the electrodes (3120, 3130, 3140, 3150) may rotate, twist, or bend about its corresponding articulation (3162) relative to a proximal portion of the catheter (3160) (e.g., FIG. 31B). The transition from the first configuration to the second and third configurations may be performed by advancing the catheter (3160) and electrodes (3120, 3130, 3140, 3150) out of a distal end of the outer catheter (3110). It is understood that the ablation device (3100) may be transformed into any intermediate configuration between the first, second, and third configurations, continuously or in discrete steps.

FIG. 31B illustrates the electrodes (3120, 3130, 3140, 3150) evenly spaced apart to form a plus ("+") shape. However, an angle between adjacent electrodes (3120, 3130, 3140, 3150) may be selected based upon a desired focal ablation pattern. Similarly, the electrodes (3120, 3130, 3140, 3150) in FIG. 31B are approximately perpendicular to the longitudinal axis of the catheter (3160) but may be adjusted based upon a set of ablation parameters.

In some embodiments, one or more pulse waveforms may be applied between the electrodes (3120, 3130, 3140, 3150) configured in anode and cathode sets. For example, adjacent or approximately diametrically opposed electrode pairs may be activated together as an anode-cathode set. In FIG. 31B, first electrode (3120) may be configured as an anode and paired with third electrode (3140) configured as a cathode. Second electrode (3130) may be configured as an anode and paired with fourth electrode (3150) configured as a cathode. The first and third electrode (3120, 3140) pair may apply a first pulse waveform followed sequentially by second pulse waveform using the second and fourth electrode (3130, 3150) pair. In another embodiment, a pulse waveform may be applied simultaneously to each of the electrodes where the first and second electrodes (3120, 3130) may be configured as anodes and the third and fourth electrodes (3140, 3150) may be configured as cathodes. It should be appreciated that any of the pulse waveforms disclosed herein may be progressively or sequentially applied over a sequence of anode-cathode electrodes.

In other embodiments, one or more of the electrodes (3120, 3130, 3140, 3150) may be configured with a first electrical polarity, and one or more electrodes disposed on a surface of the outer catheter shaft (3110) may be configured with a second electrical polarity opposite the first electrical polarity.

Figure 32:
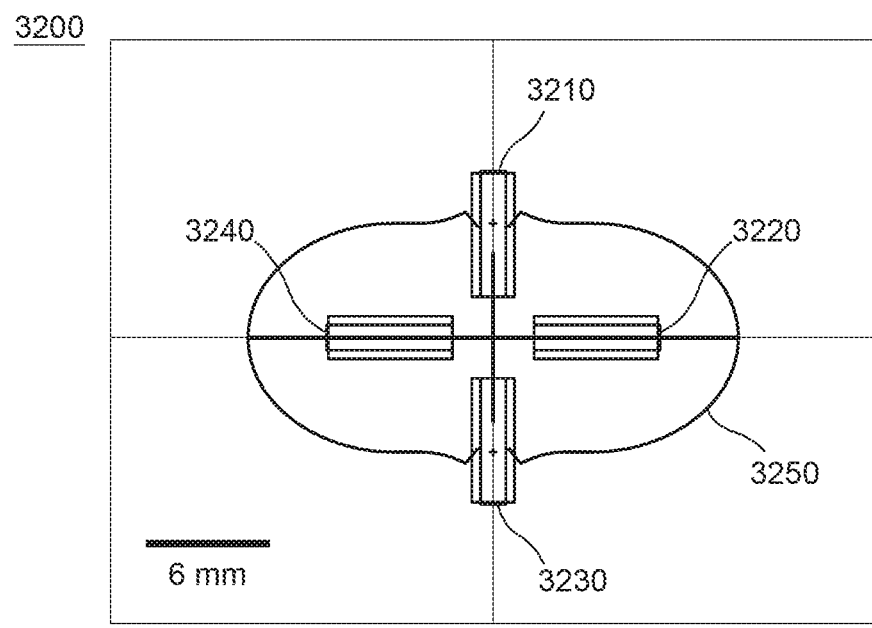
FIG. 32 is a cross-sectional schematic view of an ablation catheter, according to other embodiments.

FIG. 32 is a cross-sectional schematic view of a high intensity electric field generated by an ablation device (3200) for ablation of tissue, such as tissue in a ventricular chamber. For example, the ablation device (3200) may be disposed in the endocardial space of the left ventricle of the heart. The ablation device (3200) depicted in FIG. 32 may be similar to those ablation devices (3000, 3100) described with respect to FIGS. 30 and 31A-31B. In some embodiments, the electrodes (3210, 3220, 3230, 3240) may be apposed to a tissue wall when in the third configuration. In some embodiments, the electrodes (3210, 3220, 3230, 3240) of FIG. 32 may have a width of between about 1 mm to about 3 mm and a length of between about 3 mm and about 9 mm. For example, the electrodes (3210, 3220, 3230, 3240) may have a width of about 2 mm and a length of about 6 mm.

In some embodiments, the electrodes (3210, 3220, 3230, 3240) may form anode-cathode pairs. For example, the first electrode (3210) may be configured as an anode and the third electrode (3230) may be configured as a cathode. The first and second electrodes (3210, 3230) may have a potential difference of up to about 1500 V. Activation of one or more of the electrodes (3210, 3220, 3230, 3240) of one or more catheters may generate one or more ablation zones along a portion of the wall of a cardiac chamber. Electric field contour (3350) is an iso-magnitude line corresponding to an ablation zone (3350) having an electric field intensity threshold of about 460 V/cm when the first and third electrodes (3220, 3240) are activated. In some embodiments, the ablation zone (3350) may have a width of up to about 12 mm and a length of up to about 20 mm. Alternatively, the ablation device may be placed adjacent to or against a section of posterior wall of the left atrium, and by activation of one or more electrodes, an appropriate pulse waveform may be delivered for irreversible electroporation energy delivery to ablate tissue.

Figure 33A:
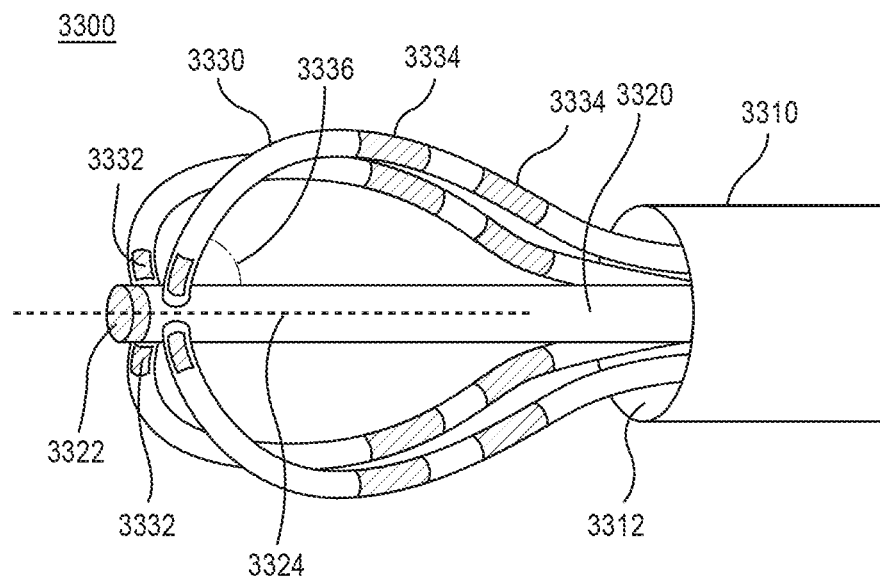
FIGS. 33A-33E are illustrative views of an ablation catheter, according to other embodiments.

FIG. 33A is a perspective view of another embodiment of an ablation device/apparatus (3300) in the form of a catheter including an outer shaft (3310) extending to a proximal end of the device (3300), an inner shaft (3320) extending from a distal end of a shaft lumen (3312) of the outer shaft (3310), and a set of splines (3330) coupled thereto. The inner shaft (3320) may be coupled at a proximal end to a handle (not shown) and disposed at a distal portion (e.g., a distal end) to a cap electrode (3322). The inner shaft (3320) and the set of splines (3330) may be translatable along a longitudinal axis (3324) of the ablation device (3300). In some embodiments, the inner shaft (3320) and the set of splines (3330) may move together or may be independently translated. The inner shaft (3320) may be configured to slide within the lumen (3312) of the outer shaft (3310). The cap electrode (3322) may include an atraumatic shape to reduce trauma to tissue. For example, the cap electrode (3322) may have a flat, circular shape and/or a rounded and blunt profile. A distal end of each spline of the set of splines (3330) may be tethered to a distal portion of the inner shaft (3320). Proximal portions of the set of splines (3330) may be attached to the outer shaft (3310). The ablation device (3300) may be configured for delivering a pulse waveform, as disclosed for example in FIGS. 21-25, to tissue during use via the electrodes (3332, 3334) on the splines (3330) and the distal cap electrode (3322).

Each spline of the set of splines (3330) may include a set of electrodes (3332, 3334) on the surface of that spline. Each set of electrodes may include a distal electrode (3332) such that the set of splines includes a set of distal electrodes (3332). Each of the distal electrodes (3332) are the nearest to the cap electrode (3322) relative to other electrodes (e.g., the set of proximal electrodes (3334)) of its corresponding set of electrodes on the same spline. Furthermore, in some embodiments, the distal electrodes (3332) may have only an outward-facing exposed portion, i.e., a portion facing away from an inner space/volume defined by the set of splines. For example, if the distal electrodes (3332) are constructed from metallic rings, a portion of each ring may be insulated such that only an outward-facing exposed portion or "window" is exposed for delivery of ablation energy. The cap electrode (3322) and each distal electrode (3332) of the set of distal electrodes may collectively have the same polarity during use. This combination of closely-placed distal electrodes having outward-facing windows and a cap electrode allows the distal end of the ablation device (3300) to generate and project a stronger electric field, and to thereby more effectively generate focal ablation lesions of tissue at a desired depth compared to any one of these electrodes alone.

Each spline (3330) of the ablation device (3300) may include at least a set of independently addressable electrodes (3332, 3334) on the surface of that spline (3330). distal cap electrode (3322) may be formed at the distal end of the catheter device (3300). Each electrode (3322, 3332, 3334) may be coupled to an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 2000 V across its thickness without dielectric breakdown. Each spline (3330) may include insulated electrical leads of each electrode (3332, 3334) within a body of the spline (3330) (e.g., within a lumen of the spline (3330)). Likewise, in some embodiments, the inner shaft (3320) may include an insulated electrical lead for the cap electrode (3322). In other embodiments, subsets of the electrodes (3322, 3332, 3334) may be jointly wired. For example, the proximal electrodes (3334) of each spline of the set of splines (3330) may be jointly wired. As another example, all the distal electrodes (3332) and the cap electrode (3322) may be jointly wired.

In some embodiments, the set of splines (3330) may be configured to transform between a first configuration, where the set of splines (3330) are arranged generally parallel to the longitudinal axis (3324) of the ablation device (3300), and a second configuration, where a distal end of each spline of the set of splines (3330) bows radially outward from the longitudinal axis (3324). In this manner, the set of distal electrodes (3332) and the cap electrode (3322) may be shaped/oriented to form the second configuration shown in FIGS. 33A, 33B, and 33E. The cap electrode (3322) may be separated from each distal electrode of the set of distal electrodes (3332) by at most about 5 mm, including all values and sub-ranges in between. For example, the cap electrode (3322) may be separated from each distal electrode of the set of distal electrodes (3332) by between about 0.5 mm and about 3 mm. In the second configuration, the distal portion of each spline of the set of splines (3330) may be angled (3336) between about 45 degrees and about 90 degrees relative to the longitudinal axis (3312), including all values and sub-ranges in between. For example, the distal portion of each spline of the set of splines (3330) in the second configuration may be angled (3336) between about 70 degrees and about 80 degrees relative to the longitudinal axis (3312). For example, in the second configuration, the cap electrode (3322) and set of distal electrodes (3332) can assume the shape of a "plus" symbol when projected onto a plane perpendicular to the longitudinal axis (3324), as can be seen in the front view in FIG. 33B.

In some embodiments, the inner shaft (3320) may be retracted into the outer catheter lumen (3312) by a predetermined amount to transform the ablation device (3300) from the first configuration to the second configuration. It is understood that the set of splines (3330) may be transformed into any intermediate configuration between the first and second configurations, continuously or in discrete steps. The set of splines (3330) may form a shape generally parallel to a longitudinal axis (3324) of the inner shaft (3320) when undeployed, and form a basket-like or bulb-like shape when a distal end of the set of splines (3330) bows radially outward from the longitudinal axis (3324).

Figure 33B:
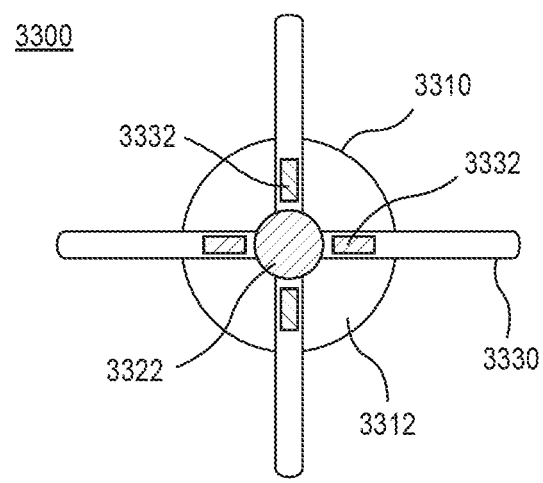
Figure 33C:
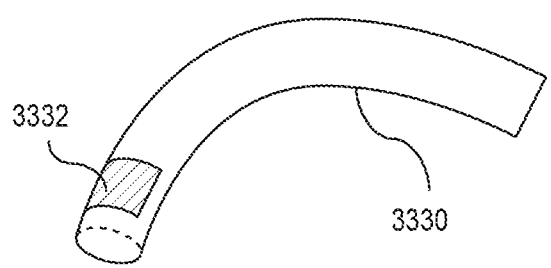
Figure 33D:
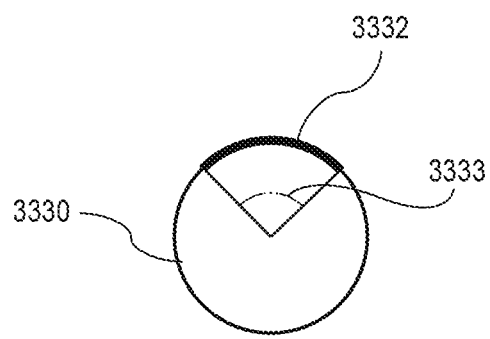
Figure 33E:
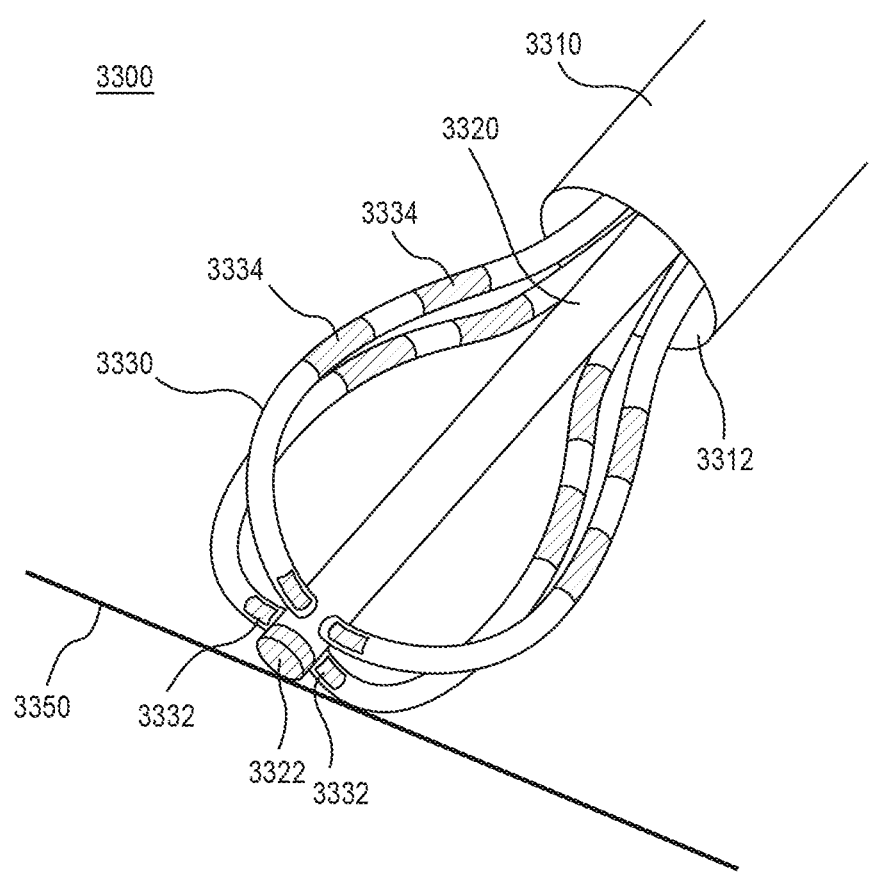

FIGS. 33A, 33B, and 33E illustrate a set of splines (3330) where each spline of the set of splines (3330) includes a distal electrode (3332) and one or more proximal electrodes (3334) that differ in one or more of size, shape, number, and spacing. For example, FIG. 33A illustrates one distal electrode (3332) and two proximal electrodes (3334) for each spline of the set of splines (3330). In some embodiments, each proximal electrode (3334) may be formed on a surface of its spline (3330) along its entire circumference, i.e., around the entire thickness of the spline. In some embodiments, each distal electrode (3332) may be formed on the surface of a portion of a circumference of its spline. That is, as shown in FIGS. 33C and 33D, the distal electrode (3332) may partially lie on the circumference of its corresponding spline and not cover the entire circumference of its spline (3330). For example, the distal electrode (3332) may encircle the circumference of its corresponding spline and be partially covered by a layer of insulation such that only a portion (e.g., window) of the distal electrode (3332) is exposed. In some embodiments, one or more electrodes may be fully covered by a thin layer of insulation for biphasic operation. In some embodiments, the set of distal electrodes (3332) of the set of splines (3330) may subtend an angle (3333) of between about 30 degrees to about 300 degrees about a center of its corresponding spline (3330), including all values and sub-ranges in between. For example, the set of distal electrodes (3332) of the set of splines (3330) may subtend an angle (3333) of between about 60 degrees to about 120 degrees about a center of its corresponding spline (3330). In this manner, a significant fraction of the electric field generated by the set of distal electrodes (3332) in the second configuration may be directed in a forward direction and projected into target tissue to aid focal ablation rather than away from the target tissue and into blood.

In this manner, the distal electrodes (3332) may be configured to face a particular direction. For example, FIGS. 33A and 33E show the set of distal electrodes (3332) and the cap electrode (3322) facing generally forward at the distal end of the device (3300) in the second configuration when a distal end of the set of splines (3330) bows radially outward from the longitudinal axis (3324). Furthermore, the distal electrodes (3332) may be disposed at a distal end of its spline such that the distal electrodes (3332) of the set of splines (3330) are disposed near to the cap electrode (3322).

In some embodiments, each spline of the set of splines (3330) may include a set of electrodes (3332, 3334) having about the same size, shape, number, and spacing as the corresponding electrodes (3332, 3334) of an adjacent spline. The thickness of each spline (3330) may vary based on the number of electrodes (3332, 3334) formed on each spline (3330) which may correspond to the number of insulated electrical leads in the spline (3330). The splines (3330) may have the same or different materials, thickness, and/or length.

In some embodiments, the cap electrode (3322) and the set of electrodes (3332, 3334) may be configured in anode-cathode sets. For example, the cap electrode (3322) and each distal electrode of the set of distal electrodes (3332) may be collectively configured as an anode, and all proximal electrodes (3334) may be collectively configured as a cathode (or vice-versa). In some embodiments, the set of distal electrodes (3332) and the set of proximal electrodes (3334) may have opposite polarities. For example, the distal electrode (3332) and the set of proximal electrodes (3334) for a given spline may have opposite polarities. The cap electrode (3322) and the set of distal electrodes (3332) may have the same polarity. As discussed herein, the set of distal electrodes (3332) and the cap electrode (3322) may be jointly wired. In some embodiments, the cap electrode and the set of electrodes (3332, 3334) of one or more splines of the set of splines (3330) may be activated together to deliver pulse waveforms for irreversible electroporation. In other embodiments, the pulse waveform delivery may be repeated sequentially over predetermined subsets of the set of electrodes (3332, 3334).

In some embodiments, the set of distal electrodes (3332) may be separated from the cap electrode (3322) by at most 3 mm from the distal end of each spline (3330). In some embodiments, the set of distal electrodes (3332) may be separated from the set of proximal electrodes (3334) by between about 1 mm and about 20 mm. In some embodiments, each electrode of the set of electrodes (3332, 3334) may include a diameter of between about 0.5 mm to about 3 mm. In some embodiments, the cap electrode (3322) may include a cross-sectional diameter of between about 1 mm and about 5 mm. In some embodiments, each electrode of the set of electrodes (3332, 3334) may have a length from about 0.5 mm to about 5 mm. In some embodiments, the set of splines (3330) in the second configuration may have an expanded cross-sectional diameter (i.e., effective diameter of the expanded or second configuration at its largest portion) of between about 6 mm and about 24 mm. In some embodiments, the set of splines (3300) may extend from the distal end (3312) of the outer shaft (3310) by between about 6 mm and about 30 mm. In some embodiments, the outer shaft (3310) may have an outer diameter of between about 1.5 mm and about 6.0 mm.

The ablation device (3300) as described herein may be disposed in the first configuration prior to delivering a pulse waveform and transformed to the second configuration to make contact with a tissue surface (e.g., an inner wall of the left atrium or ventricle, and/or the like). In some of these embodiments, a handle (not shown) may be coupled to the catheter (3300) and the set of splines (3330) and the handle configured for affecting transformation of the set of splines (3330) between the first configuration and the second configuration. For example, the handle may be configured to translate the inner shaft (3320) relative to the outer shaft (3310). For example, retracting the inner shaft (3320) into a lumen (3312) of the outer shaft (3310) may deploy the set of splines (3330) into the bulb-like shape illustrated herein. In some embodiments, actuation of a knob, wheel, or other control mechanism in the device handle may result in translation of the inner shaft (3324) and result in deployment of the set of splines (3330). In some embodiments, the electrical leads of at least two electrodes of the set of electrodes (3322, 3332, 3334) may be electrically coupled at or near a proximal portion of the ablation device (3300), such as, for example, within the handle.

Furthermore, the catheter handle (not shown) may include a mechanism for deflecting or steering the distal portion of the catheter device (3300). For example, a pull wire may extend from the catheter handle to one side of the distal portion of the device (3300) at or near the distal end of the outer shaft (3310), with tensioning of the pull wire resulting in deflection of the distal portion of the device (3300). Deflection of the device (3300) may assist positioning of the device (3300) by a user at a suitable anatomical location in a controlled manner. In some embodiments, the distal cap electrode (3322) may be electrically wired separately from the distal spline electrodes (3332). In this manner, intracardiac ECG signals may be recorded only from the distal cap electrode (3322). In some embodiments, one or more distal spline electrodes (3332) may be electrically wired separately, for monitoring of intracardiac ECG signals from each such electrode (3332). In some embodiments, some distal spline electrodes (3332) may be used for ECG monitoring while other distal spline electrodes (3332) may be used for delivery of ablation energy. It should be appreciated that any of the ablation devices described herein may be used with an electrode electrically wired separately, for monitoring of intracardiac ECG signals from each such electrode. In some embodiments, some electrodes on one or more splines of a set of splines may be used for ECG monitoring while other electrodes may be used for delivery of ablation energy.

The ablation device (3300) may include any number of splines, for example, 2, 3, 4, 5, 6, 7, 8, 9, 10, 12, 14, 16, 17, 20 or more splines, including all values and sub-ranges in between. In some embodiments, the ablation device (3300) may include 3 to 20 splines. For example, the ablation device (3300) may include from 4 to 12 splines.

Each of the splines of the set of splines (3300) may include respective electrodes (3332, 3334) having an atraumatic, generally rounded shape to reduce trauma to tissue. In this manner, the distal electrodes in the second configuration may be held close to or placed against a section of atrial wall of the left atrium in order to generate lesions thereupon by activation of appropriate electrodes using any suitable combination of polarities, as described herein. For example, the cap electrode (3322) and the distal electrodes (3332) of the set of splines (3330) may be placed in contact against or in close proximity to a tissue wall (3350), as shown in FIG. 33E, at either an approximately perpendicular or a generally oblique orientation to a tissue wall. The configuration of distal electrodes (3322, 3332) allows the generation of a focal lesion at a desired depth even when the ablation device (3300) in the deployed configuration abuts the tissue wall (3350) at an angle (e.g., obliquely).

In some embodiments, the ablation device (3300) shown in FIGS. 33A-33E may be configured for focal ablation and may include an atraumatic distal portion or cap (3322) that does not include a distal electrode.

Figure 38A:
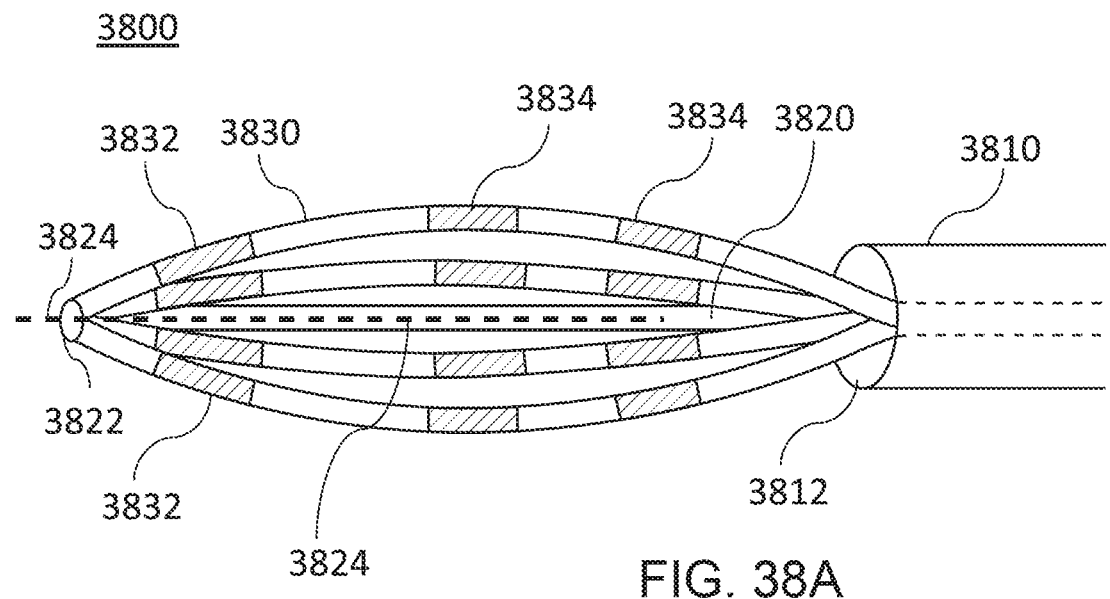
FIGS. 38A-38D are illustrative views of an ablation catheter, according to other embodiments.

FIG. 38A is a perspective view of another embodiment of an ablation device/apparatus (3800) in the form of a catheter including an outer shaft (3810) (e.g., first shaft) extending to a proximal end of the device (3800), an inner shaft (3820) (e.g., second shaft) extending from a distal end of a shaft lumen (3812) of the outer shaft (3810), and a set of splines (3830) coupled thereto. The ablation device/apparatus (3800) may include similar components and/or functionality as the ablation device/apparatus (3300), but the ablation device/apparatus (3800) does not include a cap electrode. The inner shaft (3820) may be coupled at a proximal end to a handle (not shown) and have a distal end disposed near or adjacent to a distal portion (3822) (e.g., a distal end). For example, the distal portion (3822) may be coupled to the distal end of the inner shaft (3820). A proximal end of the set of splines (3830) may be coupled to a distal end of the outer shaft (3810) and may extend from the distal end of the outer shaft (3810). The inner shaft (3820) and the set of splines (3830) may be translatable along a longitudinal axis (3824) of the ablation device (3800) (e.g., longitudinal axis of the outer shaft (3810)). In some embodiments, the inner shaft (3820) and the set of splines (3830) may move together. The splines may be flexible. The splines may transition between configurations (e.g., deployed, undeployed) as the inner shaft is translated relative to the outer shaft (3810). The inner shaft (3820) may be configured to slide within the lumen (3812) of the outer shaft (3810). The distal portion (3822) may include an atraumatic shape to reduce trauma to tissue. For example, the distal portion (3822) may have a flat, circular shape and/or a rounded and blunt profile. In some embodiments, the distal portion (3822) may comprise a cap. In FIGS. 38A-38D, the distal portion (3822) does not include an electrode. A distal end of each spline of the set of splines (3830) may be tethered to and/or coupled to a distal portion (e.g., distal end) of the inner shaft (3820). Proximal portions of the set of splines (3830) may be attached to and/or coupled to the outer shaft (3810). The ablation device (3800) may be configured for delivering a pulse waveform, as disclosed for example in FIGS. 21-25, to tissue during use via electrodes (3832, 3834) on the splines (3830).

The ablation device/apparatus may include a plurality of electrodes configured to generate an electric field for ablating tissue. Each spline of the set of splines (3830) may include a set of electrodes (3832, 3834) from the plurality of electrodes formed on the surface of that spline. Each set of electrodes may include a distal electrode (3832) such that the set of splines includes a set of distal electrodes (3832). Each of the distal electrodes (3832) are the nearest to the distal portion (3822) relative to other electrodes (e.g., the set of proximal electrodes (3834)) of its corresponding set of electrodes on the same spline. Each set of electrodes may include a proximal electrode such that the set of splines includes a set of proximal electrodes (3834). In some embodiments, the set of electrodes (3832, 3834) may each extend around a circumference of its spline. For example, the distal electrodes (3832) may be constructed from metallic rings that encircle a circumference of its spline. In some embodiments, each distal electrode (3832) of the set of distal electrodes may collectively have the same polarity during use. This combination of closely-placed distal electrodes allows the distal end of the ablation device (3800) to generate and project a stronger electric field, and to thereby more effectively generate focal ablation lesions of tissue at a desired depth compared to any one of these electrodes alone. In other embodiments, at least two distal electrodes may have the same electrical polarity for ablation delivery.

Each spline (3830) of the ablation device (3800) may include at least a set of independently addressable electrodes (3832, 3834) on the surface of that spline (3830). Each electrode (3832, 3834) may be coupled to an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 3000 V across its thickness without dielectric breakdown. Each spline (3830) may include insulated electrical leads of each electrode (3832, 3834) within a body of the spline (3830) (e.g., within a lumen of the spline (3830)). In some embodiments, the inner shaft (3820) may include an insulated electrical lead for one or more of the distal electrodes (3832). In other embodiments, subsets of the electrodes (3832, 3834) may be jointly wired. For example, the proximal electrodes (3834) of each spline of the set of splines (3830) may be jointly wired. As another example, all the distal electrodes (3832) may be jointly wired.

In some embodiments, the set of splines (3830) may be configured to transition into a plurality of states between and inclusive of an undeployed configuration and an expanded configuration in which a distal portion of each spline from the set of splines is set at one of a corresponding plurality of angles relative to a proximal portion of each spline from the set of splines in each of the plurality of states. In some embodiments, the set of splines (3830) may be configured to transition into each of the plurality of states in response to the inner shaft (3820) moving relative to the outer shaft (3810) along the longitudinal axis (3824). For example, the set of splines (3830) may be configured to transform between a first configuration (e.g., undeployed configuration) shown in FIG. 38A, where the set of splines (3830) are arranged generally parallel to the longitudinal axis (3824) of the ablation device (3800), and a second configuration (e.g., expanded configuration, basket configuration, deployed configuration) shown in FIG. 38B, where a distal portion (3804) of each spline of the set of splines (3830) bows radially outward from the longitudinal axis (3824). That is, a distal portion (3804) of the spline (3830) forms a bend with respect to a proximal portion (3802) of the spline (3830) as described in more detail with respect to FIGS. 38B and 38C. In some embodiments, the inner shaft (3820) may be pulled toward the outer shaft (3810) (e.g., moved proximally relative to the outer shaft (3810)) to deploy the device (3800) in the second configuration. The set of splines (3830) in the second configuration may define a space therebetween, the space being larger in the expanded configuration of the set of splines than in the first configuration.

Figure 38B:
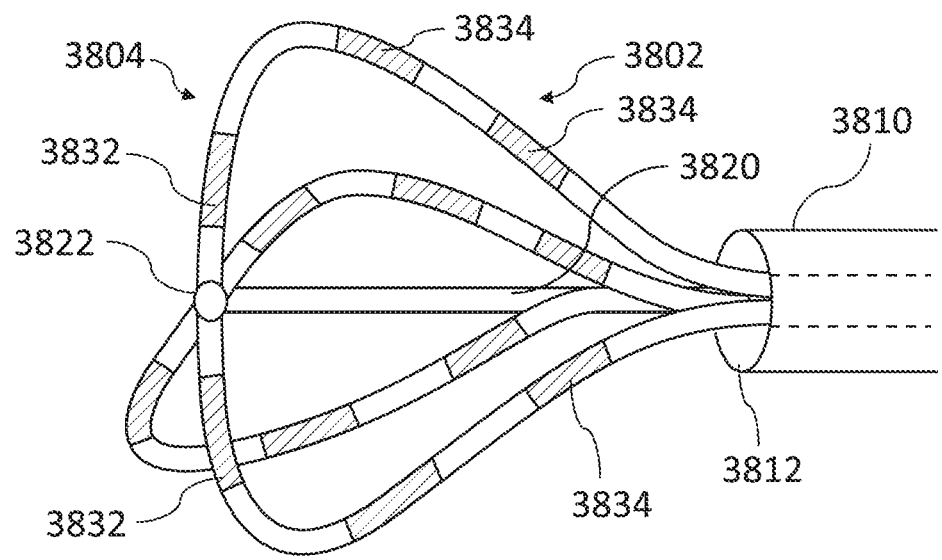
Figure 38C:
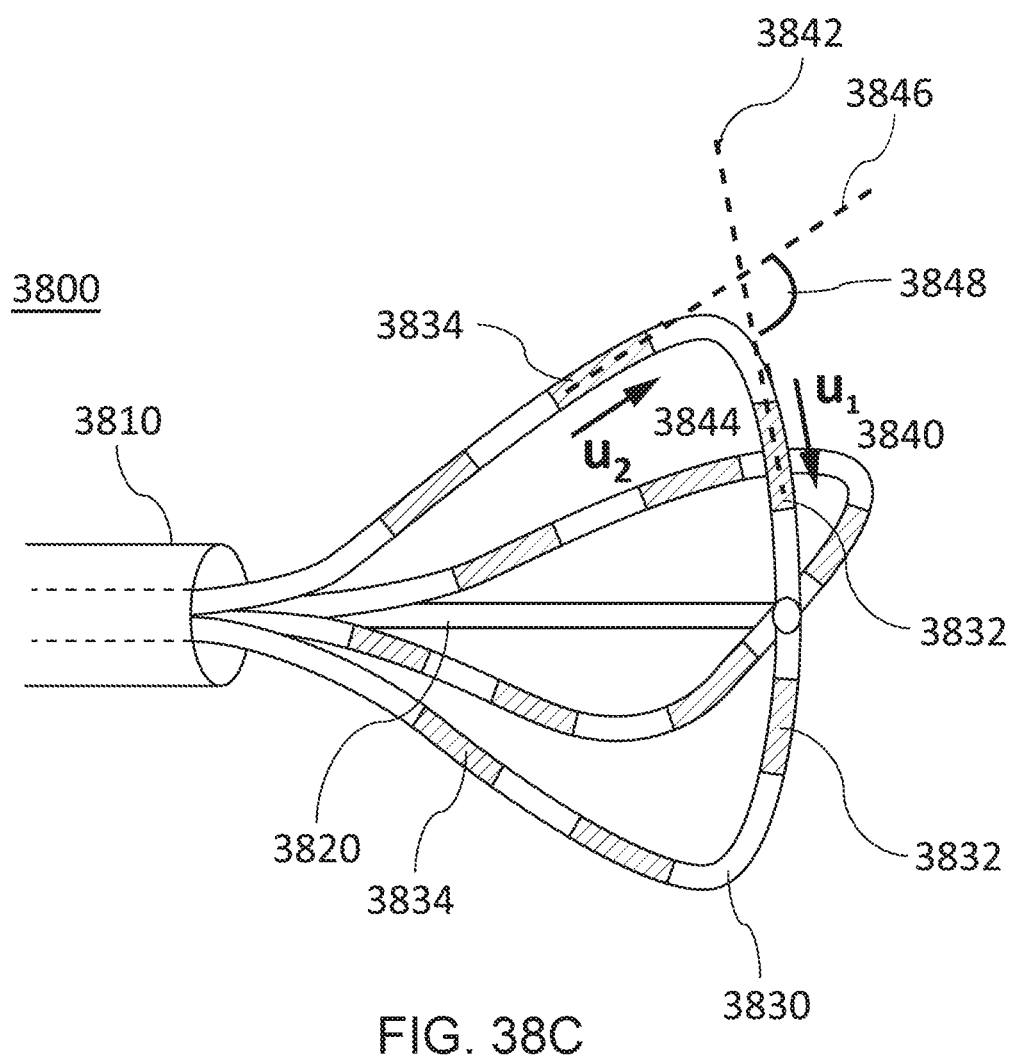

FIG. 38C is a perspective view of a spline (3830) having two unit tangent vectors. FIGS. 38A and 38B depict a set of splines (3830) having a basket or pyramid-like shape and may correspond to the shape of the splines in a second configuration. At every point along the spline (3830), a unit tangent vector u may be defined. FIG. 38C illustrates a first unit tangent vector $u_1$ (3840) at a distal portion (3804) of the spline (3830) and a second unit tangent vector $u_2$ (3844) at a proximal portion (3802) of the spline (3830). For example, unit tangent vector $u_1$ (3840) corresponds to a distal electrode (3832) and extends in a distal direction of the distal electrode (3832). Similarly, unit tangent vector $u_2$ (3844) corresponds to a proximal electrode (3832) and extends in a distal direction of the proximal electrode (3832). First line (3842) is tangent to distal electrode (3832) and second line (3846) is tangent to proximal electrode (3834). The intersection of first line (3842) and second line (3846) forms an angle (3848) as shown in FIG. 38C.

In some embodiments, the set of splines (3830) may be configured to transition into a plurality of states between and inclusive of an undeployed configuration and an expanded configuration in which an angle between a first unit tangent vector $u_1$ (3840) extending through a length of a distal portion of each spline from the set of splines (3830) and a second unit tangent vector $u_2$ (3844) extending through a proximal portion of each spline from the set of splines (3830) varies between about 70 degrees and about 180 degrees. A pre-selected portion of the plurality of electrodes (3832, 3834) may be configured to activate in each of the plurality of states to generate an electric field for ablating a tissue wall by irreversible electroporation.

The dot product of the unit vectors $u_1$ and $u_2$ is equal to the cosine of the angle (3848). In some embodiments, the dot product of respective unit tangent vectors is negative. That is, the angle (3848) between the distal electrode (3832) and the proximal electrode (3834) is between about 90 degrees and about 180 degrees.

Figure 38D:
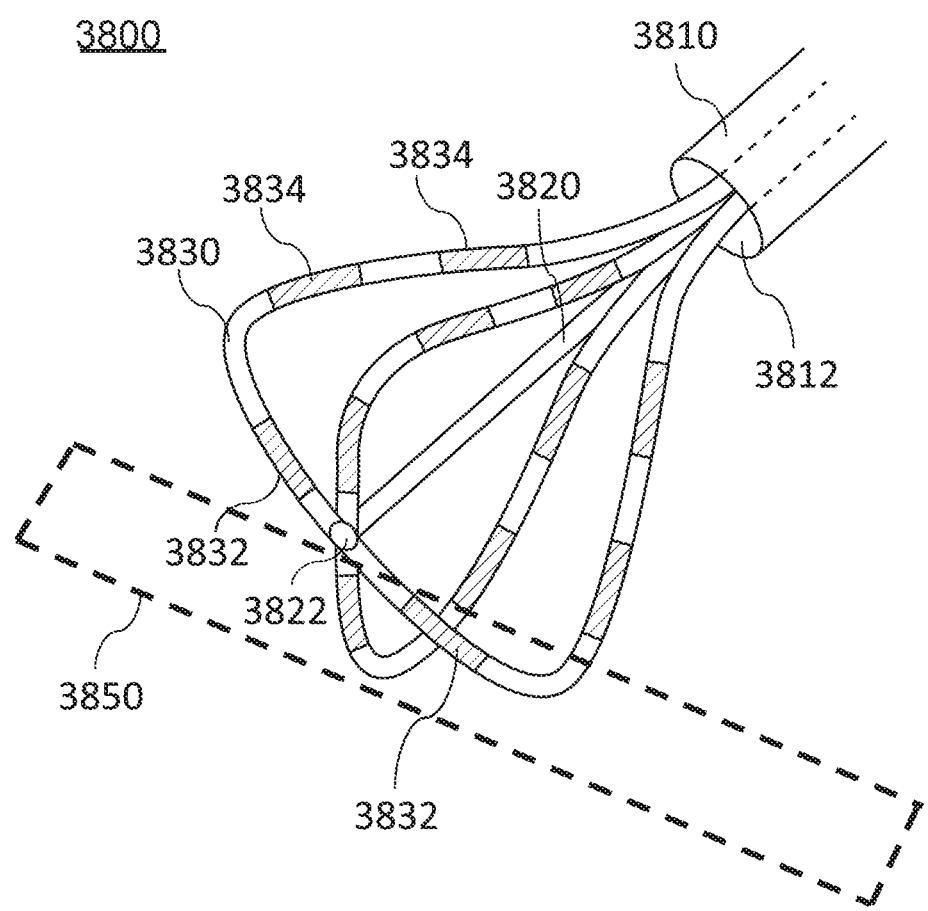
Figure 40:
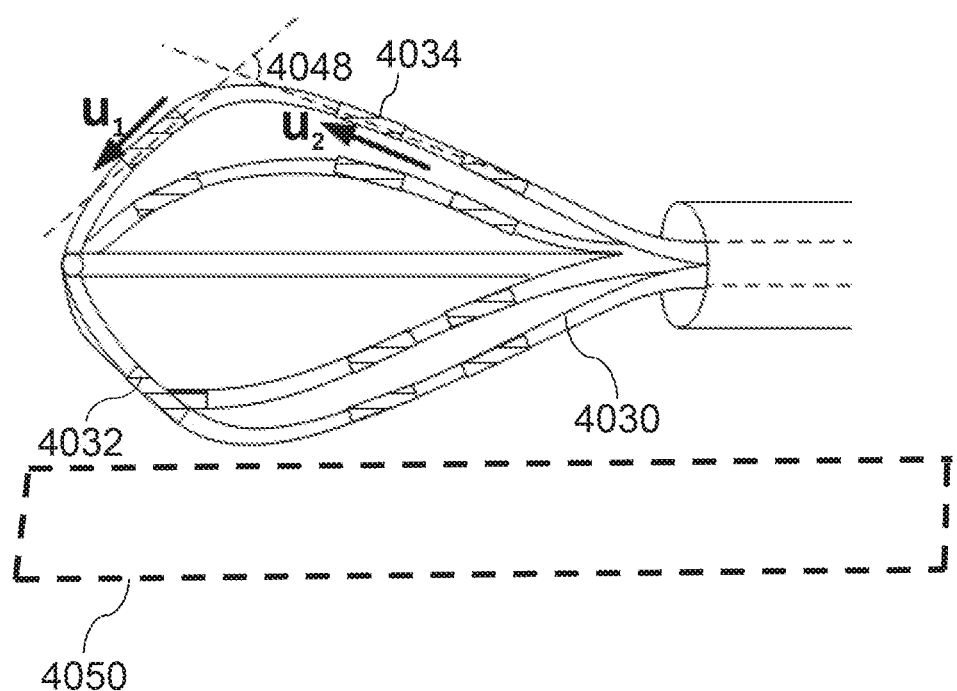
FIG. 40 is a side view of an ablation catheter disposed adjacent to tissue, according to embodiments described herein.

The distal electrode (3432) and the proximal electrode (3834) can be angled at different degrees, depending on a particular application. For example, the inner shaft (3820) can be retracted to different positions relative to the outer shaft (3810), to create a different angle between the distal electrode (3432) and the proximal electrode (3834). The adjustability of the angle between the distal electrode (3432) and the proximal electrode (3834) can be advantageous to suit different applications. For example, when performing atrial ablation, the distal electrode (3432) and the proximal electrode (3834) can be less angled relative to one another, e.g., angled at less than about 90 degrees, such that the set of splines (3830) form an expanded structure with a distal portion that is more rounded. FIG. 40, described below, provides a more detailed view of this expanded structure. In such a deployment, the angle between the unit vectors $u_1$ and $u_2$ may be about 70 degrees or more. Alternatively, when performing ventricular ablation, the distal electrode (3432) and the proximal electrode (3834) can be more angled relative to one another, e.g., angled between about 90 and about 180 degrees, such that the set of splines (3830) form an expanded structure having a more orthogonal or flattened distal end. As depicted in FIG. 38D, the more flattened distal end can enable the distal end of the ablation device (3800) to be generally closer to an endocardial surface (such that a larger number of distal electrodes are closer to a tissue surface) and used to form a lesion via focal ablation.

In this manner, the set of distal electrodes (3832) may be shaped/oriented to form the second configuration shown in FIGS. 38B, 38C, and 38D. The distal portion (3822) may be separated from each distal electrode of the set of distal electrodes (3832), e.g., by at most about 6 mm, including all values and sub-ranges in between. For example, the distal portion (3822) may be separated from each distal electrode of the set of distal electrodes (3832) by between about 0.5 mm and about 3 mm. In the second configuration, the distal portion (3804) of each spline of the set of splines (3830) may be angled (3836) between about 90 degrees and about 180 degrees relative to the proximal portion (3802), including all values and sub-ranges in between. The distal portion (3804) may be generally linear in the second configuration depending in part on the length and stiffness of the set of distal electrodes (3832). For example, in the second configuration, the distal portion (3822) and set of distal electrodes (3832)

can assume the shape of a "plus" symbol (e.g., a "X" or cross) when projected onto a plane perpendicular to the longitudinal axis (3824), in a manner similar to the front view of the device/apparatus (3300) shown in FIG. 33B.

In some embodiments, the inner shaft (3820) may be retracted into the outer catheter lumen (3812) by a predetermined amount to transform the ablation device (3800) from the first configuration to the second configuration. It is understood that the set of splines (3830) may be transformed into any intermediate configuration between the first and second configurations, continuously or in discrete steps. The set of splines (3830) may form a shape generally parallel to a longitudinal axis (3824) of the inner shaft (3820) when undeployed, and form a basket-like or pyramid-like shape when a distal portion of the set of splines (3830) bows radially outward from the longitudinal axis (3824) and forms an angle relative to a proximal portion (3802) of the splines.

FIGS. 38A, 38B, 38C, and 38D illustrate a set of splines (3830) where each spline of the set of splines (3830) includes a distal electrode (3832) and a plurality of proximal electrodes (3834). In some embodiments, a different number of proximal electrodes (3834) and/or proximal electrodes (3834) or distal electrodes (3832) that differ in one or more of size, shape, number, and spacing can be used. For example, FIG. 38A illustrates one distal electrode (3832) and two proximal electrodes (3834) for each spline of the set of splines (3830). In some embodiments, each spline of the set of splines (3830) may comprise a plurality of proximal electrodes (3834). The proximal electrodes (3834) may form a proximal electrode region of a given length, but by being divided into a set of shorter length electrode segments, the proximal electrodes (3834) enable flexibility of a proximal portion (3802) of the spline (3830). In some embodiments, each proximal electrode (3834) may be formed on a surface of its spline (3830) along its entire circumference, e.g., around the entire circumference of the spline. In some embodiments, each distal electrode (3832) may be formed on the surface of its spline (3830) along its entire circumference. That is, the distal electrode (3832) may cover (e.g., extend around, encircle) the entire circumference of its spline (3830). Additionally or alternatively, one or more proximal electrodes (3834) may comprise a coil electrode, which may enable flexibility of a proximal portion (3802) of the spline (3830). For example, in an embodiment, a plurality of proximal electrodes (3834) may be replaced with a single proximal electrode (3834) having a coiled configuration that is sufficiently flexible for enabling the device/apparatus (3800) to transition between its first configuration and second (deployed) configuration.

The set of distal electrodes (3832) may be configured to face a particular direction. For example, FIGS. 38B, 38C, and 38D show the set of distal electrodes (3832) and the distal portion (3822) facing generally forward at the distal end of the device (3800) in the second configuration when a distal portion (3822) of the set of splines (3830) bows radially outward from the longitudinal axis (3824). Furthermore, the distal electrodes (3832) may be disposed at a distal end of its spline such that the distal electrodes (3832) of the set of splines (3830) are disposed near to the distal portion (3822) of the device (3800).

In some embodiments, each spline of the set of splines (3830) may include a set of electrodes (3832, 3834) having about the same size, shape, number, and spacing as the corresponding electrodes (3832, 3834) of an adjacent spline. The thickness of each spline (3830) may vary based on the number of electrodes (3832, 3834) formed on each spline (3830) which may correspond to the number of insulated electrical leads in the spline (3830). The splines (3830) may have the same or different materials, thickness, and/or length.

In some embodiments, the set of electrodes (3832, 3834) of each spline of the set of splines (3830) can have about the same size, shape, number, and spacing as the corresponding electrodes (3832, 3834) of an adjacent spline. The thickness of each spline (3830) may vary based on the number of electrodes (3832, 3834) formed on each spline (3830) which may correspond to the number of insulated electrical leads in the spline (3830). The splines (3830) may have the same or different materials, thickness, and/or length In some embodiments, each spline of the set of splines (3830) may comprise a plurality of proximal electrodes (3834). The proximal electrodes (3834) may form a proximal electrode region of a given length, but by being divided into a set of shorter length electrode segments, the proximal electrodes (3834) enable flexibility of a proximal portion (3802) of the spline (3830). In some embodiments, at least one flexible portion is disposed between adjacent proximal electrodes from the plurality of proximal electrodes for increasing flexibility of that spline at a location of the plurality of proximal electrodes. In some embodiments, each distal electrode (3832) from the set of distal electrodes may be at the same distance from the distal end of the inner shaft (3820).

The set of electrodes (3832, 3834) may be suitably polarized to deliver high voltage pulses corresponding to Pulsed Electric Field (PEF) ablation energy that may be applied tissue to cause cell death by irreversible electroporation. In some embodiments, at least one distal electrode from the set of distal electrodes may be configured to be activated with a first polarity and at least one proximal electrode from the set of proximal electrodes may be configured to be activated with a second polarity being opposite the first polarity, to collectively generate the electric field. For example, a subset of distal electrodes (3832) may have one electrical polarity, while a subset of proximal electrodes (3834) may have the opposite electrical polarity, thus defining an electrode bipole pairing for the delivery of PEF ablation energy. In general, a sequence of similar bipoles may be defined for PEF ablation delivery. As another example, all of the distal electrodes (3832) may have one electrical polarity, while all of the proximal electrodes (3834) may have the opposite electrical polarity.

In some embodiments, the set of electrodes (3832, 3834) may be configured in anode-cathode sets. For example, each distal electrode of the set of distal electrodes (3832) may be collectively configured as an anode, and the set of proximal electrodes (3834) may be collectively configured as a cathode (or vice-versa). In some embodiments, the set of distal electrodes (3832) and the set of proximal electrodes (3834) may have opposite polarities. For example, the distal electrode (3832) and the set of proximal electrodes (3834) for a given spline may have opposite polarities. The set of distal electrodes (3832) may have the same polarity. As discussed herein, the set of distal electrodes (3832) may be jointly wired. In some embodiments, the set of electrodes (3832, 3834) of one or more splines of the set of splines (3830) may be activated together to deliver pulse waveforms for irreversible electroporation. For example, a pre-selected portion of the plurality of electrodes are activatable in each of the plurality of states to generate an electric field for ablating a tissue wall (e.g., cardiac chamber) by irreversible electroporation. In other embodiments, the pulse waveform delivery may be repeated sequentially over predetermined subsets of the set of electrodes (3832, 3834). For example, a particular activation sequence may include activating distal electrodes (3432) of half of the splines (3830) (e.g., two of the four splines (3830) depicted in FIGS. 38A-38D) and activating proximal electrodes (3834) of half of the splines (3830) (e.g., two of the four splines (3830) depicted in FIGS. 38A-38D). Depending on the direction of the electric field generated by the electrodes (3832, 3834) that is desired, the distal electrodes (3832) and the proximal electrodes (3834) that are activated may be offset from one another (e.g., the distal electrodes (3832) may be on adjacent splines (3830) from the proximal electrodes (3834), or the distal electrodes (3832) may be offset at an angle (e.g., 90 degrees) from the proximal electrodes (3834)). In some embodiments, the set of splines may be configured to ablate the tissue wall independent of an orientation of the set of splines relative to the tissue wall. In some embodiments, the pre-selected portion of the plurality of electrodes may include electrodes from the plurality of electrodes orientated close to a tissue surface.

In some embodiments, the set of distal electrodes (3832) may be separated from the distal portion (3822) by at most 6 mm from the distal end of each spline (3830). In some embodiments, the set of distal electrodes (3832) may be separated from the set of proximal electrodes (3834) by between about 1 mm and about 20 mm. In some embodiments, each electrode of the set of electrodes (3832, 3834) may include a diameter of between about 0.5 mm to about 3 mm. In some embodiments, the distal portion (3822) of the inner shaft (3820) may include a cross-sectional diameter of between about 0.7 mm and about 5 mm. In some embodiments, each electrode of the set of electrodes (3832, 3834) may have a length from about 0.5 mm to about 5 mm. In some embodiments, the set of splines (3830) in the second configuration (e.g., expanded configuration) may have an expanded cross-sectional diameter (i.e., effective diameter of the expanded or second configuration at a plane corresponding to its largest portion) of between about 6 mm and about 24 mm. In some embodiments, the set of splines (3800) may extend from the distal end (3812) of the outer shaft (3810) by between about 6 mm and about 24 mm. For example, when the set of splines (3830) is in the expanded configuration, the set of splines (3830) may extend outward from the distal end of the outer shaft (3810) by a radial distance between about 6 mm and about 24 mm. In some embodiments, the outer shaft (3810) may have an outer diameter of between about 1.5 mm and about 6.0 mm.

The ablation device (3800) as described herein may be disposed in the first configuration prior to delivering a pulse waveform and transformed to the second configuration to make contact with a tissue surface (e.g., an inner wall of the left atrium or ventricle, and/or the like). In some of these embodiments, a handle (not shown) may be coupled to the catheter (3800) and the set of splines (3830) and the handle configured for affecting transformation of the set of splines (3830) between the first configuration and the second configuration. For example, the handle may be configured to translate the inner shaft (3820) relative to the outer shaft (3810). For example, retracting the inner shaft (3820) into a lumen (3812) of the outer shaft (3810) may deploy the set of splines (3830) into basket or pyramid-like shape illustrated herein. In some embodiments, actuation of a knob, wheel, or other control mechanism in the device handle may result in translation of the inner shaft (3824) and result in deployment of the set of splines (3830). In some embodiments, the electrical leads of at least two electrodes of the set of electrodes (3832, 3834) may be electrically coupled at or near a proximal portion of the ablation device (3800), such as, for example, within the handle.

Furthermore, the catheter handle (not shown) may include a mechanism for deflecting or steering the distal portion (3804) of the catheter device (3800). For example, a pull wire may extend from the catheter handle to one side of the distal portion (3804) of the device (3800) at or near the distal end of the outer shaft (3810), with tensioning of the pull wire resulting in deflection of the distal portion (3804) of the device (3800). Deflection of the device (3800) may assist positioning of the device (3800) by a user at a suitable anatomical location in a controlled manner. In some embodiments, one or more distal spline electrodes (3832) may be electrically wired separately, for monitoring of intracardiac ECG signals from each such electrode (3832). In some embodiments, some distal spline electrodes (3832) may be used for ECG monitoring while other distal spline electrodes (3832) may be used for delivery of ablation energy. In some embodiments, some proximal spline electrodes (3834) may be wired separately for intracardiac ECG monitoring. It should be appreciated that any of the ablation devices described herein may be used with an electrode electrically wired separately, for monitoring of intracardiac ECG signals from each such electrode. In some embodiments, some electrodes on one or more splines of a set of splines may be used for ECG monitoring while other electrodes may be used for delivery of ablation energy.

The ablation device (3800) may include any number of splines, for example, 2, 3, 4, 5, 6, 7, 8, 9, 10, 12, 14, 16, 17, 20 or more splines, including all values and sub-ranges in between. In some embodiments, the ablation device (3800) may include 3 to 20 splines. For example, the ablation device (3800) may include from 4 to 12 splines.

Each of the splines of the set of splines (3800) may include respective electrodes (3832, 3834) having an atraumatic, generally rounded shape to reduce trauma to tissue. In this manner, the distal electrodes in the second configuration may be held close to or placed against a section of atrial wall of the left atrium, or more generally, any atrial or ventricular chamber in order to generate lesions thereupon by activation of appropriate electrodes using any suitable combination of polarities, as described herein. For example, the distal portion (3822) and/or the distal electrodes (3832) of the set of splines (3830) may be placed in contact against or in close proximity to a tissue wall (3850), as shown in FIG. 38D, at either an approximately perpendicular or a generally oblique orientation to a tissue wall. The configuration of distal electrodes (3832) allows the generation of a focal lesion at a desired depth even when the ablation device (3800) in the deployed configuration abuts the tissue wall (3850) at an angle (e.g., obliquely).

As noted above, in some embodiments, the angle between the distal electrode (3832) and the proximal electrode (3834) can vary based on the particular application. More specifically, the set of splines (3830) may be configured to transition into a plurality of states between and inclusive of an undeployed configuration and an expanded configuration in which an angle between a first unit tangent vector $u_1$ (3840) extending through a length of a distal portion of each spline from the set of splines (3830) and a second unit tangent vector $u_2$ (3844) extending through a proximal portion of each spline from the set of splines (3830) varies between about 70 degrees and about 180 degrees. For example, when using the device for ventricular ablation and/or to penetrate thicker tissue, the angle between the distal electrode (3832) and the proximal electrode (2834) can be between about 90 and about 180 degrees, such that the expanded structure of the splines (3830) has a flatter distal end suitable for being positioned generally closer to the tissue and providing a larger surface area for forming deeper focal lesions. Alternatively, when the device is being used for atrial ablation and/or to ablate thinner tissue, the set of splines may be transitioned into one or more states from the plurality of states in which the angle is between about 70 degrees and about 90 degrees or between about 70 and about 120 degrees, including all sub-ranges and values in-between. For example, the angle between the distal electrode (3832) and the proximal electrode (2834) can be lower (e.g., between about 70 and about 90 degrees, between about 70 and about 120 degrees including all sub-ranges and values in-between). Such a shape enables the splines (3830) to be placed at different orientations relative to a tissue surface. For example, as depicted in FIG. 40, an ablation device (4000) including a set of splines (4030) can be placed such that the splines (4030) are laterally orientated relative to a tissue wall (4050). Each spline (4030) can have at least one distal electrode (4032) and at least one proximal electrode (4034). As depicted, the distal electrode (4032) can be angled relative to the proximal electrode (4034) at an angle (4048) of less than about 90 degrees, i.e., a unit tangent vector $u_1$ extending through the distal electrode (4032) can be angled relative to a unit tangent vector $u_2$ extending through a proximal electrode (4034) at an angle (4048) of less than about 90 degrees. In an embodiment, the angle (4048) can be about 70 degrees. A pre-selected set of electrodes (4032, 4034) on the splines (4030) can then be activated to ablate the tissue. The same set of electrodes (4032, 4034) can be activated to ablate tissue regardless of the orientation of the splines (4030) relative to the tissue wall (4050). Alternatively, different sets of electrodes can be activated to ablate the tissue, depending on which splines (4030) are oriented closer to a tissue surface.

Figure 39A:
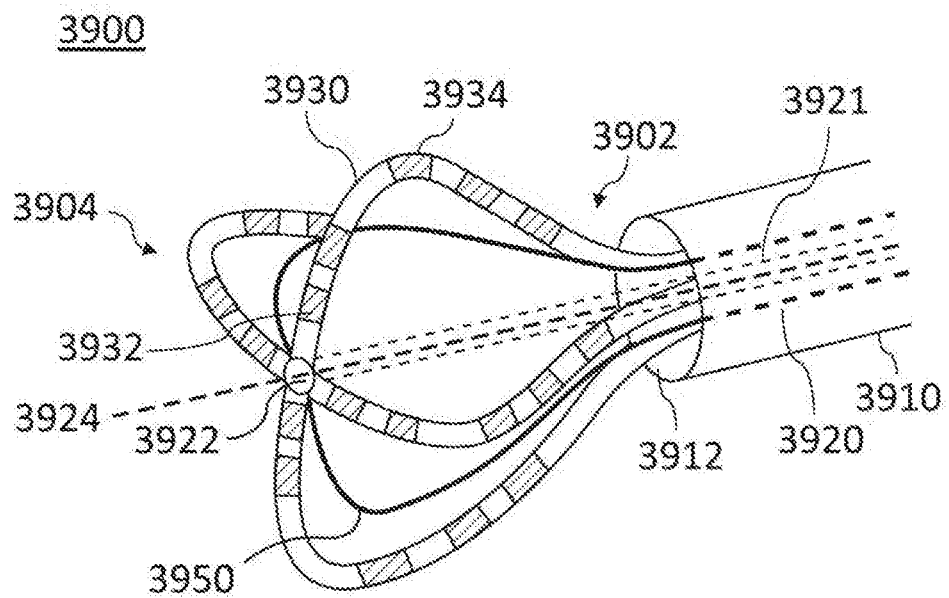
FIGS. 39A-39D are illustrative views of an ablation catheter, according to other embodiments.

FIG. 39A is a perspective view of another embodiment of an ablation device/apparatus (3900) in the form of a catheter including an outer shaft (3910) extending to a proximal end of the device (3900), a first inner shaft (3920) and a second inner shaft (3921) extending from a distal end of a shaft lumen (3912) of the outer shaft (3910), a set of splines (3930), and an inflatable member (3950). The ablation device (3900) can have components that are functionally and/or structurally similar to other ablation devices described herein, e.g., ablation device (3800). The second inner shaft (3921) may extend from a distal end of the first inner shaft (3920) and couple to the set of splines (3930). The ablation device/apparatus (3900) may include similar components and/or functionality as the ablation device/apparatus (3300, 3800). In some embodiments, the ablation device/apparatus (3900) does not include a cap electrode formed on a distal portion (3922). The first inner shaft (3920), the second inner shaft (3921), and the outer shaft (3910) may be coupled at respective proximal ends to a catheter handle (not shown). A distal end of the second inner shaft (3921) may be coupled to the distal portion (3922). A proximal portion of the inflatable member (3950) (e.g., expandable member, balloon) may be coupled to a distal portion of the first inner shaft (3920). For example, the inflatable member (3950) may be disposed distal to the distal end of the outer shaft (3910) and within a space between the set of splines (3930).

Optionally, a distal portion of the inflatable member (3950) may be coupled to one or more of the distal portion (3922) and a distal portion of the second inner shaft (3921). A proximal portion of each spline of the set of splines (3930) may be coupled to a distal portion of the outer shaft (3910).

A distal portion of each spline of the set of splines (3930) may be coupled to one or more of the distal portion (3922) and a distal portion of the second inner shaft (3921). The inflatable member (3950) may be disposed in a space between the set of splines (3930) so as to be surrounded by the set of splines (3930). In some embodiments, the inflatable member (3950) can be translatable separately from the set of splines (3930), e.g., the inflatable member (3950) can be movable relative to the set of splines (3930). In such embodiments, the inflatable member (3950) can be moved into specific, predetermined positions relative to the set of splines (3930). In some embodiments, the inflatable member (3950) can be coupled to a shaft or other structure different from the first inner shaft (3920), the second inner shaft (3921), and/or the distal portion (3922). For example, the inflatable member (3950) can be coupled to a third inner shaft (not depicted). In some embodiments, the inflatable member defines a lumen and the second inner shaft (3921) may extend through the lumen of the inflatable member.

The first inner shaft (3920), the second inner shaft (3921), and the set of splines (3930) may be translatable along a longitudinal axis (3924) of the ablation device (3900). In some embodiments, the set of splines may be configured to transition into the plurality of states in response to the inflatable member transitioning into the inflated configuration. For example, the set of splines (3930) may be configured to transition into the expanded configuration in response to the second inner shaft (3921) moving relative to the first inner shaft (3920). As another example, the set of splines (3930) may be configured to transition into the expanded configuration in response to the second inner shaft (3921) moving relative to the longitudinal axis (3924). In some embodiments, the first inner shaft (3920), the second inner shaft (3921), and the set of splines (3930) may move together. The splines (3930) may be flexible. The splines may transition between configurations (e.g., deployed, undeployed) as the first and second inner shafts (3920, 3921) are translated relative to the outer shaft (3910). The first inner shaft (3920) and second inner shaft (3921) may be configured to slide within the lumen (3912) of the outer shaft (3910). The set of splines (3930) may be translated by moving the second inner shaft (3921) relative to the outer shaft (3910) using, for example, an actuation mechanism of the handle.

The distal portion (3922) may include an atraumatic shape to reduce trauma to tissue. For example, the distal portion (3922) may have a flat, circular shape and/or a rounded and blunt profile. In some embodiments, the distal portion (3922) may comprise a cap. In FIGS. 39A-39D, the distal portion (3922) does not include an electrode. This may allow the shape, profile, and size of the distal portion (3922) to be configurable and/or reduced. A distal end of each spline of the set of splines (3930) may be tethered to and/or coupled to a distal portion of the second inner shaft (3921). Proximal portions of the set of splines (3930) may be attached to and/or coupled to the outer shaft (3910). The ablation device (3900) may be configured for delivering a pulse waveform, as disclosed for example in FIGS. 21-25, to tissue during use via electrodes (3932, 3934) on the splines (3930).

The ablation device/apparatus may include a plurality of electrodes configured to generate an electric field for ablating tissue. Each spline of the set of splines (3930) may include a set of electrodes (3932, 3934) from the plurality of electrodes formed on the surface of that spline. Each set of electrodes may include a distal electrode (3932) such that the set of splines includes a set of distal electrodes (3932). Each of the distal electrodes (3932) are nearest to the distal portion (3922) relative to other electrodes (e.g., the set of proximal electrodes (3934)) of its corresponding set of electrodes on the same spline. Each set of electrodes may include a proximal electrode such that the set of splines includes a set of proximal electrodes (3934). In some embodiments, the set of electrodes (3932, 3934) may each extend around a circumference of its spline. For example, the distal electrodes (3932) may be constructed from metallic rings that encircle a circumference of its spline. In some embodiments, each distal electrode (3932) of the set of distal electrodes may collectively have the same polarity during use. This combination of closely-placed distal electrodes allows the distal end of the ablation device (3900) to generate and project a stronger electric field, and to thereby more effectively generate focal ablation lesions of tissue at a desired depth compared to any one of these electrodes alone. In other embodiments, at least two distal electrodes may have the same electrical polarity for ablation delivery.

Each spline (3930) of the ablation device (3900) may include at least a set of independently addressable electrodes (3932, 3934) on the surface of that spline (3930). Each electrode (3932, 3934) may be coupled to an insulated electrical lead configured to sustain a voltage potential of at least about 700 V without dielectric breakdown of its corresponding insulation. In other embodiments, the insulation on each of the electrical leads may sustain an electrical potential difference of between about 200 V to about 3000 V across its thickness without dielectric breakdown. Each spline (3930) may include insulated electrical leads of each electrode (3932, 3934) within a body of the spline (3930) (e.g., within a lumen of the spline (3930)). In some embodiments, the inner shaft (3920) may include an insulated electrical lead for one or more of the distal electrodes (3932). In other embodiments, subsets of the electrodes (3932, 3934) may be jointly wired. For example, the proximal electrodes (3934) of each spline of the set of splines (3930) may be jointly wired. As another example, all the distal electrodes (3932) may be jointly wired.

Figure 39B:
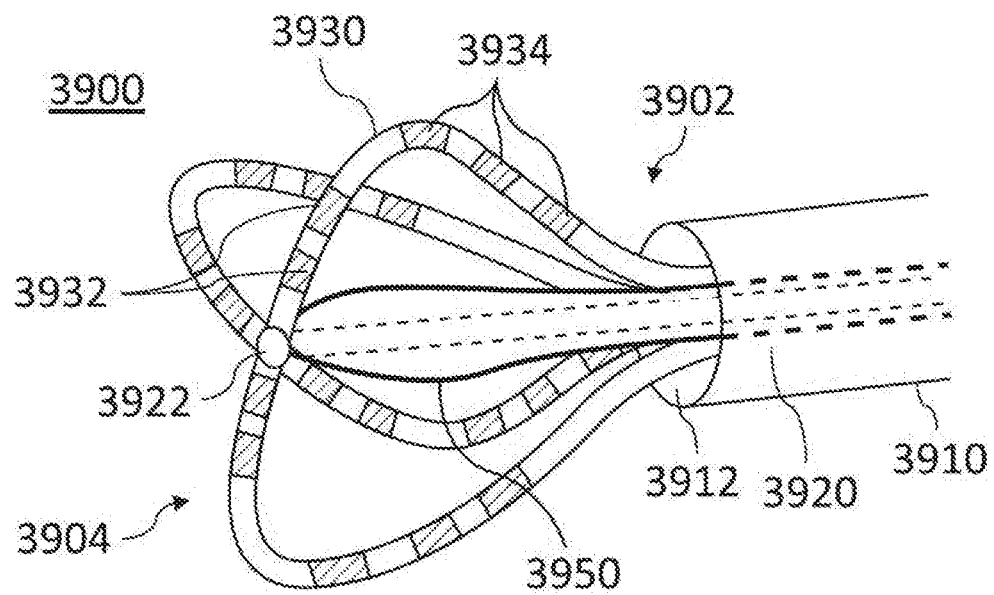
Figure 39C:
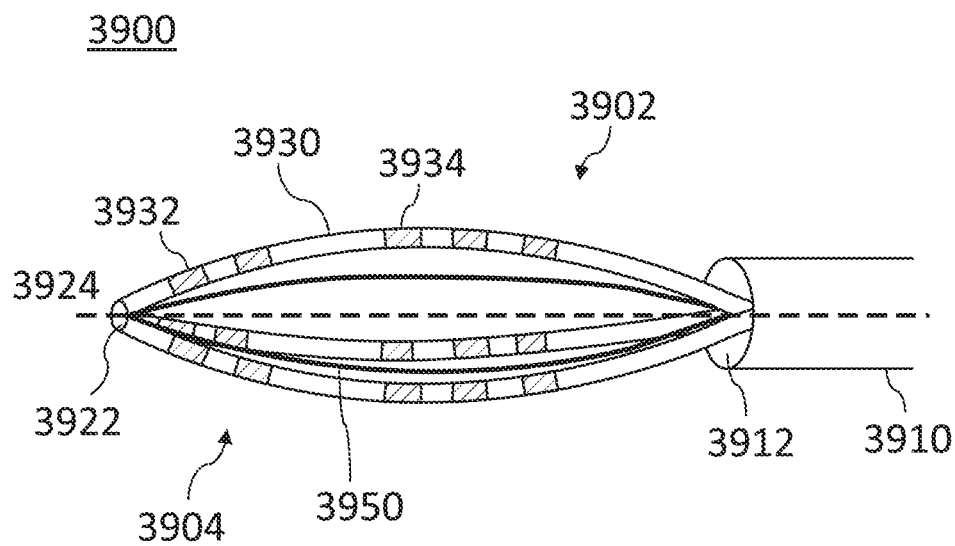

In some embodiments, the set of splines (3930) may be configured to transition into a plurality of states between and inclusive of an undeployed configuration and an expanded configuration in which a distal portion of each spline from the set of splines is set at one of a corresponding plurality of angles relative to a proximal portion of each spline from the set of splines in each of the plurality of states. In some embodiments, the set of splines (3930) may be configured to transition into one or more of the plurality of states in response to the inner shaft (3920) moving relative to the outer shaft (3910) along the longitudinal axis (3924). For example, the set of splines (3930) may be configured to transform between a first configuration shown in FIG. 39C, where the set of splines (3930) are arranged generally parallel to the longitudinal axis (3924) of the ablation device (3900), and a second configuration (e.g., expanded configuration, basket configuration, deployed configuration) shown in FIGS. 39A, 39B, and 39D, where a distal portion (3904) of each spline of the set of splines (3930) bows radially outward from the longitudinal axis (3924). That is, a distal portion (3904) of the spline (3930) forms a bend with respect to a proximal portion (3902) of the spline (3930) as described in more detail with respect to FIG. 39D. In some embodiments, the first and second inner shaft (3920, 3921) may be pulled toward the outer shaft (3910) (e.g., moved proximally relative to the outer shaft (3910)) to deploy the device (3900) in the second configuration. The set of splines (3930) in the second configuration may have a basket or pyramid-like shape. As shown in FIG. 39C, when the set of splines (3930) are in the first configuration, the inflatable member (3950) is in the deflated configuration. The set of splines (3930) in the second configuration may define a space therebetween, the space being larger in the expanded configuration of the set of splines than in the first configuration.

Figure 39D:
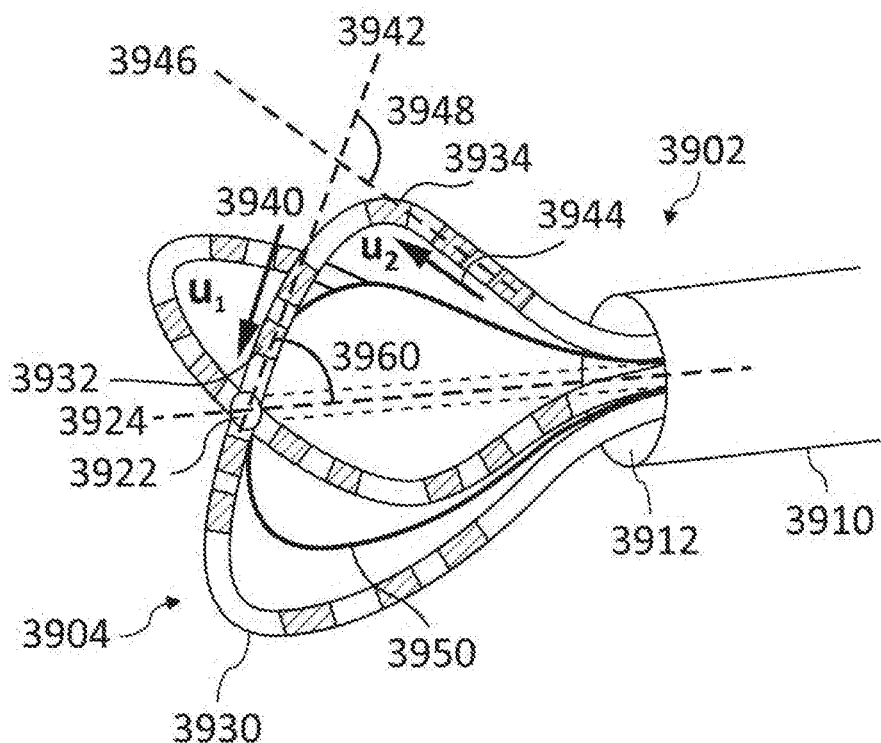

FIG. 39D is a perspective view of a spline (3930) having two unit tangent vectors. FIGS. 39A and 39B depict a set of splines (3930) having a basket or pyramid-like shape and may correspond to the shape of the splines in a second configuration. At every point along the spline (3930), a unit tangent vector u may be defined. FIG. 39D illustrates a unit tangent vector $u_1$ (3940) at a distal portion (3904) of the spline (3930) and a unit tangent vector $u_2$ (3944) at a proximal portion (3902) of the spline (3930). For example, unit tangent vector $u_1$ (3940) corresponds to a distal electrode (3932) and extends in a distal direction of the distal electrode (3932). Similarly, unit tangent vector $u_2$ (3944) corresponds to a proximal electrode (3934) and extends in a distal direction of the proximal electrode (3932). First line (3942) is tangent to distal electrode (3932) and second line (3946) is tangent to proximal electrode (3934). The intersection of first line (3942) and second line (3946) forms a first angle (3948) as shown in FIG. 39D. Similarly, the intersection of first line (3942) and the longitudinal axis (3924) forms a second angle (3960).

In some embodiments, the dot product of the unit vectors $u_1$ and $u_2$ is equal to the cosine of the angle (3948). In some embodiments, the dot product of respective unit tangent vectors is negative. That is, the first angle (3948) between the distal electrode (3932) and the proximal electrode (3934) is between about 90 degrees and about 180 degrees. In the second configuration (e.g., expanded configuration), the second angle (3960) between a distal portion of the each spline (e.g., distal electrode (3932)) and the longitudinal axis (3924) is at least about 70 degrees, as shown in FIG. 39D.

In this manner, the set of distal electrodes (3932) may be shaped/oriented to form the second configuration shown in FIGS. 39A, 39B, and 39D. The distal portion (3922) may be separated from each distal electrode of the set of distal electrodes (3932), by at most about 6 mm, including all values and sub-ranges in between. For example, the distal portion (3922) may be separated from each distal electrode of the set of distal electrodes (3932) by between about 0.5 mm and about 3 mm. In the second configuration, the distal portion (3904) of each spline of the set of splines (3930) may be angled between about 90 degrees and about 180 degrees relative to the proximal portion (3902), including all values and sub-ranges in between.

The distal portion (3904) may be generally linear in the second configuration depending in part on the length and stiffness of the set of distal electrodes (3932). For example, in the second configuration, the distal portion (3922) and set of distal electrodes (3932) can assume the shape of a "plus" symbol (e.g., a "X" or cross) when projected onto a plane perpendicular to the longitudinal axis (3924), in a manner similar to the front view of the device/apparatus (3300) shown in FIG. 33B.

In some embodiments, the second inner shaft (3921) may be retracted into the outer catheter lumen (3912) by a predetermined amount to transform the ablation device (3900) from the first configuration to the second configuration. It is understood that the set of splines (3930) may be transformed into any intermediate configuration between the first and second configurations, continuously or in discrete steps. The set of splines (3930) may form a shape generally parallel to the longitudinal axis (3924) when undeployed, and form a basket-like or pyramid-like shape when a distal portion of the set of splines (3930) bows radially outward from the longitudinal axis (3924) and forms an angle relative to a proximal portion (3902) of the splines.

In some embodiments, the inflatable member (3950) may be configured to transform between deflated configuration shown in FIGS. 39B and 39C, where an outer surface of the inflatable member (3950) is arranged approximately parallel to the longitudinal axis (3924) of the ablation device (3900), and an inflated configuration shown in FIGS. 39A and 39D, where an outer surface of the inflatable member (3950) bows radially outward from the longitudinal axis (3924) when the set of splines are in the expanded configuration. In some embodiments, the set of splines (3930) are configured to transition into the expanded configuration in response to the inflatable member transitioning into the inflated configuration. In the inflated configuration where the inflatable member (3950) is disposed distal to the distal end of the outer shaft (3910) and within a space between the set of splines (3930), the inflatable member (3950) is configured to drive the electric field generated by the plurality of electrodes out from the space between the set of splines such that the electric field can form a larger lesion in the tissue. In some embodiments, the inflatable member (3950) in the inflated configuration substantially fills the space between the set of splines in their expanded configuration. The set of splines (3930) may be in the first configuration (FIG. 39C) or the second configuration (FIG. 39B) when the inflatable member (3950) is in the deflated configuration.

In some embodiments, the inflatable member in the inflated configuration may form an asymmetrical shape (e.g., FIGS. 39A, 39D) in which a distal portion of the inflatable member has an outer diameter larger than that of a proximal portion of the inflatable member.

In some embodiments, the first and second inner shaft (3920, 3921) may be pulled toward the outer shaft (3910) (e.g., moved proximally relative to the outer shaft (3910)) to deploy the set of splines (3930) in the second configuration and/or to transform the inflatable member (3950) into the inflated, expanded configuration. In some embodiments, a fluid source in fluid communication with the inflatable member (3950) can be used to transform the inflatable member (3950) from its deflated configuration to its inflated configuration. For example, the first inner shaft (3920) may be configured to couple (e.g., be in fluid communication) to a fluid source (not shown) such that fluid can be delivered into the inflatable member (3950) via the lumen of the first inner shaft (3920) to transition the inflatable member (3950) into the inflated configuration. In some embodiments, the inflated member (3950) in the inflated configuration may conform to a shape formed by the set of splines (3930) in the second configuration. That is, the inflated or expanded inflatable member (3950) may form a bulbous, basket, or pyramid-like shape. In some embodiments, the inflatable member (3950) can expand such that an outer surface of the inflatable member (3950) engages with regions of the set of splines (3930). It is understood that the inflatable member (3950) may be transformed into any intermediate configuration between the deflated and inflated configurations, continuously or in discrete steps. In some embodiments, transitioning the inflatable member (3950) from the deflated configuration to the inflated configuration applies a force to the set of splines (3930) that transitions the set of splines from the first configuration to the second configuration. For example, the inflatable member (3950) can inflate to engage with regions of the set of splines (3930) to apply an outward force to the set of splines (3930) such that the set of splines (3930) change configuration from its first configuration (i.e., undeployed configuration shown in FIG. 39C) to its second configuration (i.e., deployed configuration shown in FIG. 39D).

In some embodiments, the inflatable member as described herein may have an expandable structure and may be composed of any of a variety of insulating or dielectric materials including, but not limited to polyvinyl chloride (PVC), polyethylene (PE), cross-linked polyethylene, polyolefins, polyolefin copolymer (POC), polyethylene terephthalate (PET), polyester, nylon, polymer blends, polyester, polyimide, polyamides, polyurethane, silicone, polydimethylsiloxane (PDMS), PEBAX, and the like. Preferred embodiments can be composed of polyurethane or silicone. In some embodiments, one or more portions of the inflatable member may comprise a radiopaque portion. In some embodiments, fluid may inflate the inflatable member (3950), e.g., through a lumen of the first inner shaft (3920), or another shaft or structure coupled to the inflatable member (3950). For example, the inflatable member (3950) may be inflated through a fluid port attached to the catheter handle wherein fluid such as distilled or deionized water can be infused under pressure.

Together with the use of a fluid (e.g., distilled or deionized water, saline, air, or other liquid, and/or gas) to inflate the inflatable member, the inflatable member serves as an effective insulator during delivery of a pulsed electric field waveform and drive the electric field to the region outside the inflatable member or balloon and surrounding the balloon. This combination of an inflatable member and a set of splines allows the distal end of the ablation device (3900) to project or deliver a stronger electric field at distances further from the ablation device (3900), and to thereby more effectively generate focal ablation lesions of tissue at a desired depth compared to the set of splines alone. Accordingly, the device (3900) in the second and inflated configurations (FIGS. 39A and 39D) may efficiently form lesions in tissue with less power by redirecting the electric fields generated by the set of electrodes (3932, 3934) away from the inflatable member (3950) and the second inner shaft (3921), and towards tissue to be ablated. In some embodiments, when the set of splines (3930) is in the expanded configuration, at least one electrode from the set of distal electrodes (3932) is configured to contact a tissue surface and form a focal ablation lesion on the tissue surface having a diameter between about 0.5 cm and about 2.5 cm.

In some embodiments, a different number of proximal electrodes (3934) and/or proximal electrodes (3934) or distal electrodes (3932) that differ in one or more of size, shape, number, and spacing can be used. For example, FIG. 39A illustrates two distal electrode (3932) and three proximal electrodes (3934) for each spline of the set of splines (3930). In some embodiments, each spline of the set of splines (3930) may comprise a plurality of proximal electrodes (3934). The proximal electrodes (3934) may form a proximal electrode region of a given length, but by being divided into a set of shorter length electrode segments, the proximal electrodes (3934) enable flexibility of a proximal portion (3902) of the spline (3930). In some embodiments, at least one flexible portion is disposed between adjacent proximal electrodes from the plurality of proximal electrodes for increasing flexibility of that spline at a location of the plurality of proximal electrodes. Each proximal electrode (3934) may be formed on a surface of its spline (3930) along its entire circumference (e.g., around the entire circumference of the spline), and/or around a portion of its entire circumference. Each distal electrode (3932) may be formed on the surface of its spline (3930) along its entire circumference and/or around a portion of its entire circumference. When the proximal and distal electrodes (3932, 3934) extend along the entire circumference, the proximal and distal electrodes (3932, 3934) may cover (e.g., extend around, encircle) the entire circumference of its spline (3930). Additionally or alternatively, one or more proximal electrodes (3934) may comprise at least one coil electrode, which may enable flexibility of a proximal portion (3902) of the spline (3930). For example, in an embodiment, a plurality of proximal electrodes (3934) may be replaced with a single proximal electrode (3934) having a coiled configuration that is sufficiently flexible for enabling the device/apparatus (3900) to transition between its first configuration and second (deployed) configuration.

The set of distal electrodes (3932) may be configured to face a particular direction. For example, FIGS. 39B, 39C, and 39D show the set of distal electrodes (3932) and the distal portion (3922) facing generally forward at the distal end of the device (3900) in the second configuration when a distal portion (3904) of the set of splines (3930) bows radially outward from the longitudinal axis (3924). Furthermore, the distal electrodes (3932) may be disposed at a distal end of its spline such that the distal electrodes (3932) of the set of splines (3930) are disposed near to the distal portion (3922) of the device (3900).

In some embodiments, the set of electrodes (3932, 3934) of each spline of the set of splines (3930) can have about the same size, shape, number, and spacing as the corresponding electrodes (3932, 3934) of an adjacent spline. The thickness of each spline (3930) may vary based on the number of electrodes (3932, 3934) formed on each spline (3930) which may correspond to the number of insulated electrical leads in the spline (3930). The splines (3930) may have the same or different materials, thickness, and/or length.

The set of electrodes (3932, 3934) may be suitably polarized to deliver high voltage pulses corresponding to Pulsed Electric Field (PEF) ablation energy that may be applied tissue to cause cell death by irreversible electroporation. In some embodiments, at least one distal electrode from the set of distal electrodes may be configured to be activated with a first polarity and at least one proximal electrode from the set of proximal electrodes may be configured to be activated with a second polarity being opposite the first polarity, to collectively generate the electric field. For example, a subset of distal electrodes (3932) may have one electrical polarity, while a subset of proximal electrodes (3934) may have the opposite electrical polarity, thus defining an electrode bipole pairing for the delivery of PEF ablation energy. In general, a sequence of similar bipoles may be defined for PEF ablation delivery. As another example, all of the distal electrodes (3932) may have one electrical polarity, while all of the proximal electrodes (3934) may have the opposite electrical polarity.

In some embodiments, the set of electrodes (3932, 3934) may be configured in anode-cathode sets. For example, each distal electrode of the set of distal electrodes (3932) may be collectively configured as an anode, and the set of proximal electrodes (3934) may be collectively configured as a cathode (or vice-versa). In some embodiments, the set of distal electrodes (3932) and the set of proximal electrodes (3934) may have opposite polarities. For example, the distal electrode (3932) and the set of proximal electrodes (3934) for a given spline may have opposite polarities. The set of distal electrodes (3932) may have the same polarity. As discussed herein, the set of distal electrodes (3932) may be jointly wired. In some embodiments, the set of electrodes (3932, 3934) of one or more splines of the set of splines (3930) may be activated together to deliver pulse waveforms for irreversible electroporation. For example, a pre-selected portion of the plurality of electrodes are activatable in each of the plurality of states to generate an electric field for ablating a tissue wall (e.g., cardiac chamber) by irreversible electroporation. In other embodiments, the pulse waveform delivery may be repeated sequentially over predetermined subsets of the set of electrodes (3932, 3934). For example, a particular activation sequence may include activating distal electrodes (3932) of half of the splines (3930) (e.g., two of the four splines (3930) depicted in FIGS. 39A-39D) and activating proximal electrodes (3934) of half of the splines (3930) (e.g., two of the four splines (3930) depicted in FIGS. 39A-39D). Depending on the electric field generated by the electrodes (3932, 3934) that is desired, the distal electrodes (3932) and the proximal electrodes (3934) that are activated may be offset from one another (e.g., the distal electrodes (3932) may be on adjacent splines (3930) from the proximal electrodes (3934), or the distal electrodes (3932) may be offset at an angle (e.g., about 90 degrees) from the proximal electrodes (3934)). In some embodiments, the set of splines may be configured to ablate the tissue wall independent of an orientation of the set of splines relative to the tissue wall. In some embodiments, the pre-selected portion of the plurality of electrodes may include electrodes from the plurality of electrodes orientated close to a tissue surface.

In some embodiments, the set of distal electrodes (3932) may be separated from the distal portion (3922) by at most 6 mm from the distal end of each spline (3930). In some embodiments, the set of distal electrodes (3932) may be separated from the set of proximal electrodes (3934) by between about 1 mm and about 20 mm. In some embodiments, each electrode of the set of electrodes (3932, 3934) may include a diameter of between about 0.5 mm to about 3 mm. In some embodiments, the distal portion (3922) and/or distal end of the second inner shaft (3921) may include a cross-sectional diameter of between about 0.7 mm and about 5 mm. In some embodiments, each electrode of the set of electrodes (3932, 3934) may have a length from about 0.5 mm to about 5 mm. In some embodiments, the set of splines (3930) in the second configuration may have an expanded cross-sectional diameter (i.e., effective diameter of the expanded or second configuration at a plane corresponding to its largest portion) of between about 6 mm and about 24 mm. In some embodiments, in the undeployed configuration, the set of splines (3900) may extend from the distal end (3912) of the outer shaft (3910) by between about 6 mm and about 30 mm. In some embodiments, the outer shaft (3910) may have an outer diameter of between about 1.5 mm and about 6.0 mm.

The ablation device (3900) as described herein may be disposed in the first configuration prior to delivering a pulse waveform and transformed to the second configuration to make contact with a tissue surface (e.g., an inner wall of the left atrium or ventricle, and/or the like). In some of these embodiments, the handle (not shown) may be coupled to the catheter (3900) and the set of splines (3930) and the handle configured for affecting transformation of the set of splines (3930) between the first configuration and the second configuration. For example, the handle may be configured to translate the first inner shaft (3920) and second inner shaft (3921) relative to the outer shaft (3910). For example, retracting the first and second inner shaft (3920, 3921) into a lumen (3912) of the outer shaft (3910) may deploy the set of splines (3930) into basket or pyramid-like shape illustrated herein. In some embodiments, actuation of a knob, wheel, or other control mechanism in the device handle may result in translation of the first and second inner shafts (3920, 3921) and result in deployment of the set of splines (3930). In some embodiments, the electrical leads of at least two electrodes of the set of electrodes (3932, 3934) may be electrically coupled at or near a proximal portion of the ablation device (3900), such as, for example, within the handle.

Furthermore, the catheter handle (not shown) may include a mechanism for deflecting or steering the distal portion (3904) of the catheter device (3900). For example, a pull wire may extend from the catheter handle to one side of the distal portion (3904) of the device (3900) at or near the distal end of the outer shaft (3910), with tensioning of the pull wire resulting in deflection of the device (3900). Deflection of the device (3900) may assist positioning of the device (3900) by a user at a suitable anatomical location in a controlled manner. For example, the device (3900) may be slidably disposed within a steerable sheath (not shown) used to deliver the device (3900) to a desired location such as a cardiac chamber. Once in the chamber, the device (3900) may be further deflected or steered to access a desired site to deliver ablation energy.

In some embodiments, one or more distal spline electrodes (3932) may be electrically wired separately, for receiving and/or monitoring of intracardiac electrocardiogram (ECG) signals from each such electrode (3932). For example, an electrode configured for ablation and another electrode configured for receiving the ECG signal may be coupled to separate insulated electrical leads. In some embodiments, some distal spline electrodes (3932) may be used for ECG monitoring while other distal spline electrodes (3932) may be used for delivery of ablation energy. In some embodiments, some proximal spline electrodes (3934) may be wired separately for intracardiac ECG monitoring. It should be appreciated that any of the ablation devices described herein may be used with an electrode electrically wired separately, for monitoring of intracardiac ECG signals from each such electrode. In some embodiments, some electrodes on one or more splines of a set of splines may be used for ECG monitoring while other electrodes may be used for delivery of ablation energy, while in other embodiments only some electrodes may be used for ECG monitoring while all electrodes may be used for delivery of ablation energy.

An illustrative method of using the ablation device (3900) including the inflatable member (3950) may include the steps of positioning (e.g., disposing) the ablation device (3900) in a first location in a cardiac chamber of a heart of a subject. The set of splines (3930) may be transitioned into an expanded configuration in which a distal portion of each spline of the set of splines bows radially outward from the longitudinal axis (3924). Transitioning the set of splines (3930) into the expanded configuration includes retracting a distal portion of the second shaft relative to the first shaft. Retracting the distal portion of the second shaft relative to the first shaft may include using a handle coupled to at least one of the second shaft or the first shaft. Translating the inner shaft of the ablation device relative to an outer shaft of the ablation device may transition the set of splines into a state in which a distal portion of each spline of the set of splines and a proximal portion of each spline of the set of splines is at a first angle between about 70 and about 180 degrees.

The inflatable member (3950) may be transitioned into an inflated configuration. An ablation pulse waveform may be delivered to a plurality of electrodes (3932, 3934) disposed on the set of splines (3930) such that the set of splines (3930) generates an electric field for ablating tissue of the cardiac chamber, the inflatable member (3950) directing the electric field toward the tissue.

In some embodiments, a first ablation pulse waveform may be delivered to a distal electrode formed on at least one spline from the set of splines and a proximal electrode formed on at least one spline from the set of splines such that the set of splines generates a first electric field for ablating a first portion of a tissue wall of the cardiac chamber. The ablation device may be positioned in a second location in the cardiac chamber. A second ablation pulse waveform may be delivered to a distal electrode formed on at least one spline from the set of splines and a proximal electrode formed on at least one spline from the set of splines such that the set of splines generates a second electric field for ablating a second portion of the tissue wall.

In some embodiments, the first and second locations are in an atrium of the heart, and the first and second angles are between about 70 and about 90 degrees or between about 70 and about 120 degrees including all sub-ranges and values in-between. In some embodiments, the first and second locations are in a ventricle of the heart, and the first and second angles are between about 90 and about 180 degrees.

In some embodiments, at least one of the first and second electric field is configured to form a focal ablation lesion on a surface of the tissue having a diameter between about 0.5 cm and about 2.5 cm. A first electrode from the set of electrodes of at least one spline may be configured as an anode. A second electrode from the set of electrodes of the at least one spline may be configured as a cathode. The ablation pulse waveform may be delivered to the first electrode and the second electrode.

At least one set of electrodes may be configured for ablation and at least one set of electrodes may be configured for receiving electrophysiology data. Electrophysiology data may be recorded from the heart using the at least one set of electrodes. The electrophysiology data may include intracardiac electrocardiogram (ECG) signal data of at least one pulmonary vein.

The tissue includes an endocardial surface of the cardiac chamber. In some applications the cardiac chamber is a ventricle and in others it may be an atrium. In some embodiments, a pacing device may be advanced into a right ventricle of the heart or other cardiac region. A pacing signal may be generated for cardiac stimulation of the heart. The pacing signal may be applied to the heart using the pacing device with the ablation pulse waveform generated in synchronization with the pacing signal. The ablation pulse waveform may include a time offset with respect to the pacing signal. A radiopaque portion of the ablation device may be fluoroscopically visualized during one or more steps.

In some embodiments, the catheter may be advanced into a cardiac chamber of the heart and electrophysiology data may be recorded using the recording electrodes. After transitioning the set of splines into the expanded configuration and transitioning the balloon into the inflated configuration, at least one spline from the set of splines may be placed in contact with an endocardial surface. At least one spline in contact with the endocardium may form a "C" shape. As described herein, the ablation device (3900) may include a shaft defining a lumen in fluid communication with the inflatable member (3950). The inflatable member transitioning into the inflated configuration includes delivering a fluid, via the lumen of the shaft, into the inflatable member. The inflatable member may be formed of an insulating material such that the inflatable member acts as an insulator during delivery of the ablation pulse waveform.

The inflatable member may include a plurality of inflatable portions. Each inflatable portion from the plurality of inflatable portions may be independently inflatable from other inflatable portions of the plurality of inflatable portions.

In some embodiments, transitioning the set of splines into the expanded configuration may include transitioning the set of splines such that a distal portion of each spline from the set of splines is angled greater than about 70 degrees relative to the longitudinal axis. In some embodiments, transitioning of the set of splines into the expanded configuration is in response to transitioning the inflatable member into the inflated configuration.

The ablation device (3900) may include any number of splines, for example, 2, 3, 4, 5, 6, 7, 8, 9, 10, 12, 14, 16, 17, 20 or more splines, including all values and sub-ranges in between. In some embodiments, the ablation device (3900) may include 3 to 20 splines. For example, the ablation device (3900) may include from 4 to 12 splines.

Each of the splines of the set of splines (3900) may include respective electrodes (3932, 3934) having an atraumatic, generally rounded shape to reduce trauma to tissue. In this manner, the distal electrodes (3932) in the second configuration may be held close to or placed against a section of atrial wall of the left ventricle, or more generally, any atrial or ventricular chamber in order to generate lesions thereupon by activation of appropriate electrodes using any suitable combination of polarities, as described herein. For example, the distal portion (3922) and/or the distal electrodes (3932) of the set of splines (3930) may be placed in contact with or in close proximity to a tissue wall (3950), similar to as shown in FIG. 38D, at either an approximately perpendicular or a generally oblique orientation to a tissue wall. The configuration of distal electrodes (3932) allows the generation of a focal lesion at a desired depth even when the ablation device (3900) in the deployed configuration abuts the tissue wall (3950) at an angle (e.g., obliquely).

In some embodiments, as the electrodes or a subset of electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms), as discussed in further detail herein. It should be appreciated that the size, shape, and spacing of the electrodes on and between the splines may be configured to deliver contiguous/transmural energy to electrically isolate one or more pulmonary veins. In some embodiments, alternate electrodes may be at the same electric potential, and likewise for all the other alternating electrodes. Thus, in some embodiments, ablation may be delivered rapidly with all electrodes activated at the same time. A variety of such electrode pairing options exists and may be implemented based on the convenience thereof.

In some embodiments, the ablation device (e.g., 2900, 3000, 3100, 3200) may include 2 to 6 catheters. The ablation device (e.g., 2900, 3000, 3100, 3200) may include any number of catheters, for example, 2, 3, 4, 5, 6 or more catheters. For example, in some embodiments, the ablation device (e.g., 2900, 3000, 3100, 3200) may include 3 to 6 catheters. In some embodiments, a catheter of an ablation device (e.g., 2900, 3000, 3100, 3200) may include 2 to 6 distal portions. The catheter may include any number of distal portions, for example, 2, 3, 4, 5, 6 or more distal portions. For example, in some embodiments, the catheter may include 2 to 4 distal portions. Furthermore, in some embodiments, the shape (e.g., curvature, length, size) of the catheters may be asymmetric to aid in controlling a depth, shape, and/or size of focal ablation.

In some embodiments, the electrodes may form anode-cathode pairs. For example, the first electrode may be configured as an anode and the second electrode may be configured as a cathode. In some embodiments, a subset of the electrodes may be independently addressable and the electrodes may be energized in any sequence using any pulse waveform sufficient to ablate tissue by irreversible electroporation. For example, different sets of electrodes may deliver different sets of pulses (e.g., hierarchical pulse waveforms).

In all the embodiments described in the foregoing and without limitation, the ablation catheter itself may be a steerable device with pull wires for controlling deflection through a suitable mechanism in the catheter handle, as is known to those skilled in the art.

Balloon

Figure 10:
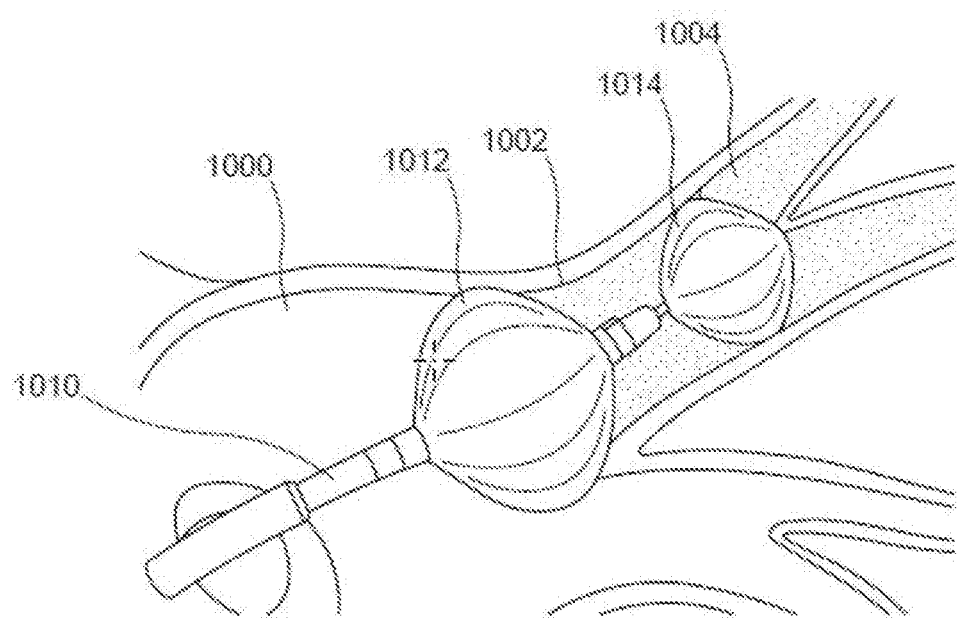
FIG. 10 is a perspective view of a balloon ablation catheter disposed in a left atrial chamber of a heart, according to other embodiments.

In some embodiments, an ablation device may include one or more balloons for delivering energy to ablate tissue by irreversible electroporation. FIG. 10 depicts an embodiment of a balloon ablation device (1010) (e.g., structurally and/or functionally similar to the ablation device (110)) disposed in a left atrial chamber (1000) of a heart. The ablation device (1010) may include a first balloon (1012) and a second balloon (1014) which may be configured to be disposed in an ostium (1002) of a pulmonary vein (1004). The first balloon (1012) in an expanded (e.g., inflated) configuration may have a larger diameter than the second balloon (1014) in an expanded configuration. This allows the second balloon (1014) to be advanced and disposed further into the pulmonary vein (1014) while the first balloon (1012) may be disposed near and/or at an ostium (1002) of the pulmonary vein (1004). The inflated second balloon serves to stabilize the positioning of the first balloon at the ostium of the pulmonary vein. In some embodiments, the first balloon (1012) and the second balloon (1014) may be filled with any suitable conducting fluid such as, for example, saline. The first balloon (1012) and the second balloon (1014) may be electrically isolated from each other. For example, each balloon (1012, 1014) may include an insulated electrical lead associated therewith, with each lead having sufficient electrical insulation to sustain an electrical potential difference of at least 700V across its thickness without dielectric breakdown. In other embodiments, the insulation on each of the electrical leads may sustain an electrical potential difference of between about 200 V to about 2500 V across its thickness without dielectric breakdown, including all values and sub-ranges in between. For example, a lead of the second balloon (1014) may be insulated as it extends through the first balloon (1012).

In some embodiments, the first and second balloons (1012, 1014) may form an anode-cathode pair. For example, in one embodiment, the first and second balloons may carry electrically separate bodies of saline fluid, and the first balloon (1012) may be configured as a cathode and the second balloon (1014) may be configured as an anode, or vice versa, where electrical energy may be capacitively coupled across the balloon or saline-filled electrodes. The device (1010) may receive a pulse waveform to be delivered to tissue (1002). For example, one or more of a biphasic signal may be applied such that tissue may be ablated between the first balloon (1012) and the second balloon (1014) at a desired location in the pulmonary vein (1004). The first and second balloons (1012, 1014) may confine the electric field substantially between the first and second balloons (1012, 1014) so as to reduce the electric field and damage to tissue away from the ostium (1002) of the pulmonary vein (1004). In another embodiment, one or both of electrodes (1018) and (1019) disposed respectively proximal to and distal to the first balloon may be used as an electrode of one polarity, while the fluid in the first balloon may act as an electrode of the opposite polarity. A biphasic pulse waveform may then be delivered between these electrodes of opposed polarities by capacitive coupling across the balloon, resulting in a zone of irreversible electroporation ablation in the region around the first balloon. In some embodiments, one or more of the balloons (1012, 1014) may include a wire mesh.

Figure 11:
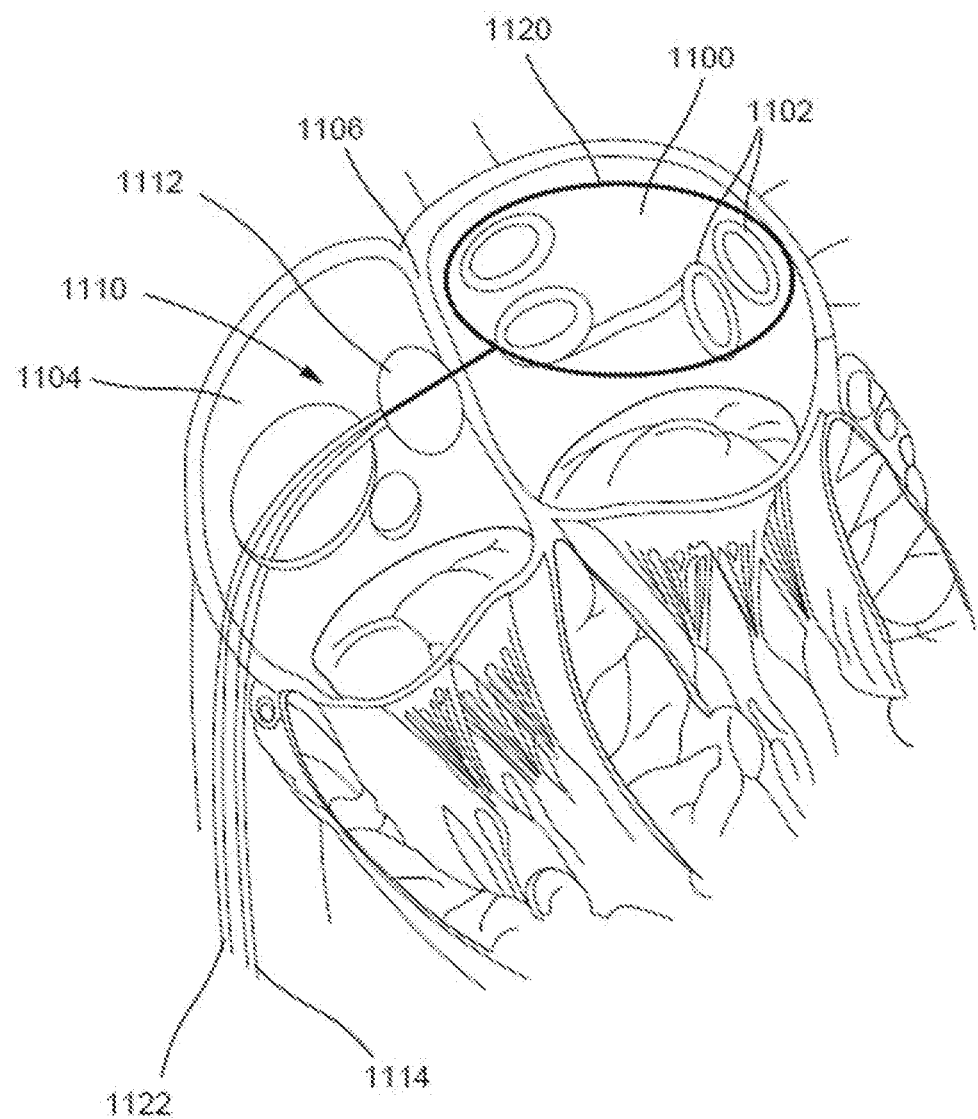
FIG. 11 is a cross-sectional view of a balloon ablation catheter disposed in a left atrial chamber of a heart, according to other embodiments.

FIG. 11 is a cross-sectional view of another embodiment of a balloon ablation device (1110) (e.g., structurally and/or functionally similar to the ablation device (1010)) disposed in a left atrial chamber (1100) and a right atrial chamber (1104) of a heart. The ablation device (1110) may include a balloon (1112) which may be configured to be advanced into and disposed in the right atrial chamber (1104). For example, the balloon (1112) may be disposed in contact with a septum (1106) of the heart. The balloon (1112) may be filled with saline. The device (1110) may further include an electrode (1120) that may be advanced from the right atrial chamber (1104) through the balloon (1112) and the septum (1106) and into the left atrial chamber (1100). For example, the electrode (1120) may extend from the balloon (1112) and puncture through the septum (1106) and be advanced into the left atrial chamber (1100). Once the electrode (1120) is advanced into the left atrial chamber (1100), a distal portion of the electrode (1120) may be modified to form a predetermined shape. For example, a distal portion of the electrode (1120) may include a nonlinear shape such as a circle, ellipsoid, or any other geometric shape. In FIG. 11, the distal portion of the electrode (1120) forms a loop that may surround a single ostium or two or more ostia of the pulmonary veins (1102) in the left atrial chamber (1100). In other embodiments, the distal portion of the electrode (1120) may have about the same diameter as an ostium of the pulmonary vein (1102).

The balloon (1112) and the electrode (1120) may be electrically isolated from each other. For example, the balloon (1112) and the electrode (1120) may each include an insulated electrical lead (1114, 1122) respectively, with each lead (1114, 1122) having sufficient electrical insulation to sustain an electrical potential difference of at least 700V across its thickness without dielectric breakdown. In other embodiments, the insulation on each of the electrical leads may sustain an electrical potential difference of between about 200 V to about 2,000 V across its thickness without dielectric breakdown, including all values and sub-ranges in between. The lead (1122) of the electrode (1120) may be insulated through the balloon (1112). In some embodiments, the saline in the balloon (1112) and the electrode (1120) may form an anode-cathode pair. For example, the balloon (1112) may be configured as a cathode and the electrode (1120) may be configured as an anode. The device (1110) may receive a pulse waveform to be delivered to the ostium of the pulmonary veins (1102). For example a biphasic waveform may be applied to ablate tissue. The pulse waveform may create an intense electric field around the electrode (1120) while the current is applied via capacitive coupling to the balloon (1112) to complete the circuit. In some embodiments, the electrode (1120) may include a fine gauge wire and the balloon (1112) may include a wire mesh.

In another embodiment, the electrode (1120) may be advanced through the pulmonary veins (1102) and disposed in one or more of the pulmonary vein ostia without being advanced through the balloon (1112) and/or the septum (1106). The balloon (1112) and electrode (1120) may be configured as a cathode-anode pair and receive a pulse waveform in the same manner as discussed above.

Return Electrode

Figure 12A:
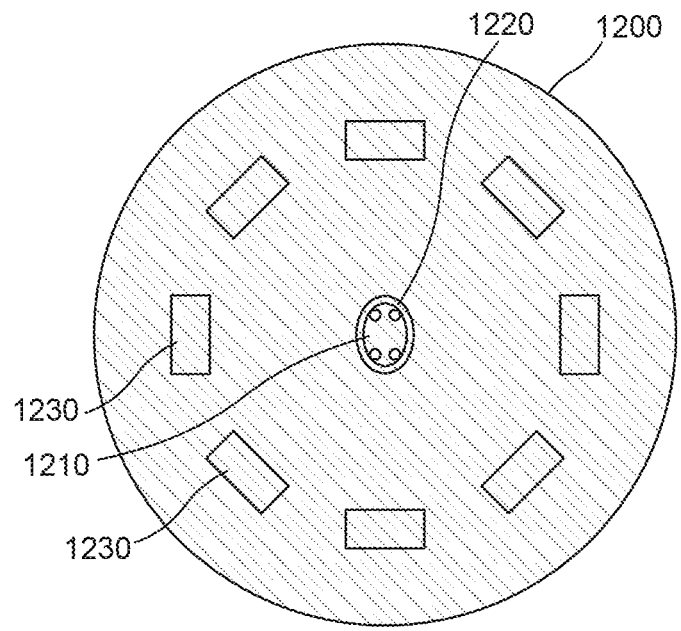
FIGS. 12A-12B are schematic views of a return electrode of an ablation system, according to embodiments.
Figure 12B:
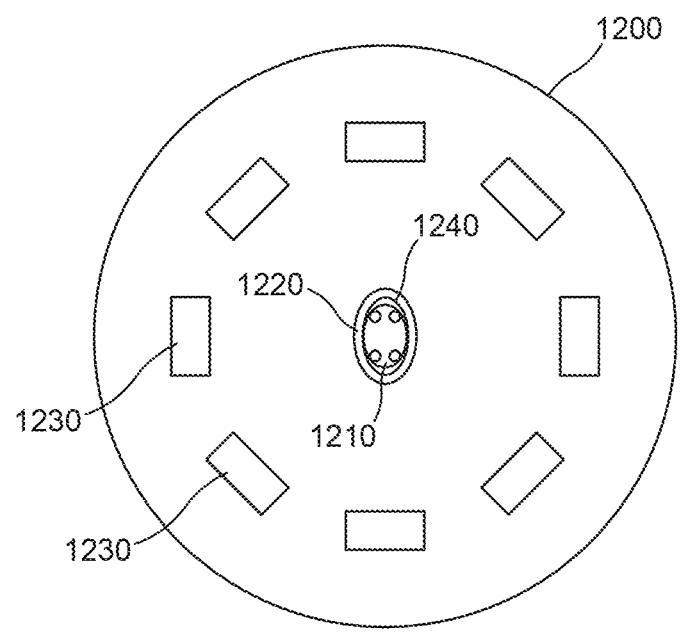

Some embodiments of an ablation system as described herein may further include a return electrode or a distributed set of return electrodes coupled to a patient to reduce the risk of unintended damage to healthy tissue. FIGS. 12A-12B are schematic views of a set of return electrodes (1230) (e.g., return pad) of an ablation system disposed on a patient (1200). A set of four ostia of the pulmonary veins (1210) of the left atrium are illustrated in FIGS. 12A-12B. An electrode (1220) of an ablation device may be positioned around one or more of the ostia of the pulmonary veins (1210). In some embodiments, a set of return electrodes (1230) may be disposed on a back of a patient (1200) to allow current to pass from the electrode (1220) through the patient (1200) and then to the return electrode (1230).

For example, one or more return electrodes may be disposed on a skin of a patient (1200). In one embodiment, eight return electrodes (1230) may be positioned on the back of the patient so as to surround the pulmonary vein ostia (1210). A conductive gel may be applied between the return electrodes (1230) and the skin to improve contact. It should be appreciated that any of the ablation devices described herein may be used with the one or more return electrodes (1230). In FIGS. 12A-12B, the electrode (1220) is disposed around four ostia (1210).

FIG. 12B illustrates the energized electrode (1220) forming an electric field (1240) around the ostia (1210) of the pulmonary veins. The return electrode (1230) may in turn receive a pulsed monophasic and/or biphasic waveform delivered by the electrode (1220). In some embodiments, the number of return electrodes (1230) may be approximately inversely proportional to the surface area of the return electrodes (1230).

For each of the ablation devices discussed herein, the electrodes (e.g., ablation electrode, return electrode) may include biocompatible metals such as titanium, palladium, silver, platinum or a platinum alloy. For example, the electrode may preferably include platinum or a platinum alloy. Each electrode may include an electrical lead having sufficient electrical insulation to sustain an electrical potential difference of at least 700V across its thickness without dielectric breakdown. In other embodiments, the insulation on each of the electrical leads may sustain an electrical potential difference of between about 200V to about 2500 V across its thickness without dielectric breakdown, including all values and sub-ranges in between. The insulated electrical leads may run to the proximal handle portion of the catheter from where they may be connected to a suitable electrical connector. The catheter shaft may be made of a flexible polymeric material such as Teflon, Nylon, Pebax, etc.

Methods

Also described here are methods for ablating tissue in a heart chamber using the systems and devices described above. The heart chamber may be the left atrial chamber and include its associated pulmonary veins. Generally, the methods described here include introducing and disposing a device in contact with one or more pulmonary vein ostial or antral regions. A pulse waveform may be delivered by one or more electrodes of the device to ablate tissue. In some embodiments, a cardiac pacing signal may synchronize the delivered pulse waveforms with the cardiac cycle. Additionally or alternatively, the pulse waveforms may include a plurality of levels of a hierarchy to reduce total energy delivery. The tissue ablation thus performed may be delivered in synchrony with paced heartbeats and with less energy delivery to reduce damage to healthy tissue. It should be appreciated that any of the ablation devices described herein may be used to ablate tissue using the methods discussed below as appropriate.

In some embodiments, the ablation devices described herein may be used for focal ablation of cardiac features/structures identified to cause arrhythmia. For example, a cardiac electrophysiology diagnostic catheter (e.g., mapping catheter) may be used to map cardiac structures such as rotors that may be subsequently ablated through focal ablation using any of the ablation devices described herein. Focal ablation may, for example, create a spot lesion that neutralizes a rotor while sparing surrounding tissue. In some embodiments, one or more focal ablation lesions may be formed in combination with one or more box or line lesions to treat cardiac arrhythmia. As a non-limiting example, in some embodiments, a system can include one or more mapping catheters, one or more ablation catheters (e.g., an ablation device as illustrated in FIGS. 9D, 9E, 27A-27C, 28, 29, 30, 31, 32) useful for creating lesions via focal ablation, and one or more catheters (e.g., an ablation device as illustrated in FIGS. 3-8, 9A-9C, 10-12, 26A-26B) useful for creating box and/or line lesions.

Figure 13:
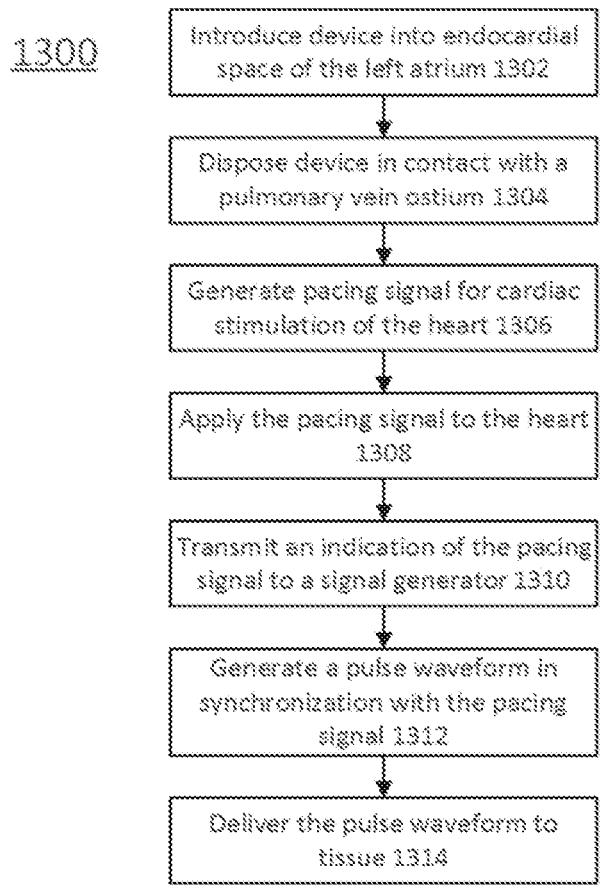
FIG. 13 illustrates a method for tissue ablation, according to embodiments.

FIG. 13 is a method (1300) for one embodiment of a tissue ablation process. In some embodiments, the voltage pulse waveforms described herein may be applied during a refractory period of the cardiac cycle so as to avoid disruption of the sinus rhythm of the heart. The method (1300) includes introduction of a device (e.g., ablation device, such as the ablation device (110), and/or any of the ablation devices (200, 300, 400, 500, 600, 700, 800, 900, 1010, 1110, 2900, 3000, 3100) into an endocardial space of a left atrium at step (1302). The device may be advanced to be disposed in contact with a pulmonary vein ostium (1304). For example, electrodes of an ablation device may form an approximately circular arrangement of electrodes disposed in contact with an inner radial surface at a pulmonary vein ostium. In some embodiments, a pacing signal may be generated for cardiac stimulation of the heart (1306). The pacing signal may then be applied to the heart (1308). For example, the heart may be electrically paced with a cardiac stimulator to ensure pacing capture to establish periodicity and predictability of the cardiac cycle. One or more of atrial and ventricular pacing may be applied. An indication of the pacing signal may be transmitted to a signal generator (1310). A time window within the refractory period of the cardiac cycle may then be defined within which one or more voltage pulse waveforms may be delivered. In some embodiments, a refractory time window may follow a pacing signal. For example, a common refractory time window may lie between both atrial and ventricular refractory time windows.

A pulse waveform may be generated in synchronization with the pacing signal (1312). For example, a voltage pulse waveform may be applied in the common refractory time window. In some embodiments, the pulse waveform may be generated with a time offset with respect to the indication of the pacing signal. For example, the start of a refractory time window may be offset from the pacing signal by a time offset. The voltage pulse waveform(s) may be applied over a series of heartbeats over corresponding common refractory time windows. The generated pulse waveform may be delivered to tissue (1314). In some embodiments, the pulse waveform may be delivered to pulmonary vein ostium of a heart of a patient via one or more splines of a set of splines of an ablation device. In other embodiments, voltage pulse waveforms as described herein may be selectively delivered to electrode subsets such as anode-cathode subsets for ablation and isolation of the pulmonary vein. For example, a first electrode of a group of electrodes may be configured as an anode and a second electrode of the group of electrodes may be configured as a cathode. These steps may be repeated for a desired number of pulmonary vein ostial or antral regions to have been ablated (e.g., 1, 2, 3, or 4 ostia).

Figure 14:
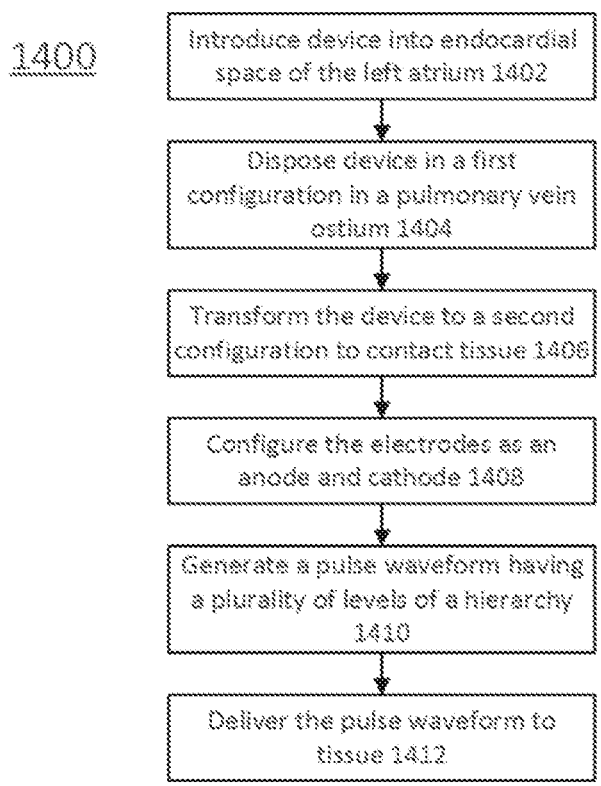
FIG. 14 illustrates a method for tissue ablation, according to other embodiments.

In some embodiments, hierarchical voltage pulse waveforms having a nested structure and a hierarchy of time intervals as described herein may be useful for irreversible electroporation, providing control and selectivity in different tissue types. FIG. 14 is a flowchart (1400) of another embodiment of a tissue ablation process. The method (1400) includes the introduction of a device (e.g., ablation device, such as any of the ablation devices (200, 300, 400, 500, 600, 700, 800, 900, 1010, 1110, 2900, 3000, 3100) into an endocardial space of a left atrium (1402). The device may be advanced to be disposed in a pulmonary vein ostium (1404). In embodiments where the device may include a first and second configuration (e.g., compact and expanded), the device may be introduced in the first configuration and transformed to a second configuration to contact tissue at or near the pulmonary vein antrum or ostium (1406). The device may include electrodes and may be configured in anode-cathode subsets (1408) as discussed in detail above. For example, a subset of electrodes of the devices may be selected as anodes, while another subset of electrodes of the device may be selected as cathodes, with the voltage pulse waveform applied between the anodes and cathodes.

A pulse waveform may be generated by a signal generator (e.g., the signal generator 122) and may include a plurality of levels in a hierarchy (1410). A variety of hierarchical waveforms may be generated with a signal generator as disclosed herein. For example, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval.

It is understood that while the examples herein identify separate monophasic and biphasic waveforms, it should be appreciated that combination waveforms, where some portions of the waveform hierarchy are monophasic while other portions are biphasic, may also be generated. A voltage pulse waveform having a hierarchical structure may be applied across different anode-cathode subsets (optionally with a time delay). As discussed above, one or more of the waveforms applied across the anode-cathode subsets may be applied during the refractory period of a cardiac cycle. The pulse waveform may be delivered to tissue (1412). It should be appreciated that the steps described in FIGS. 13 and 14 may be combined and modified as appropriate.

Figure 15:
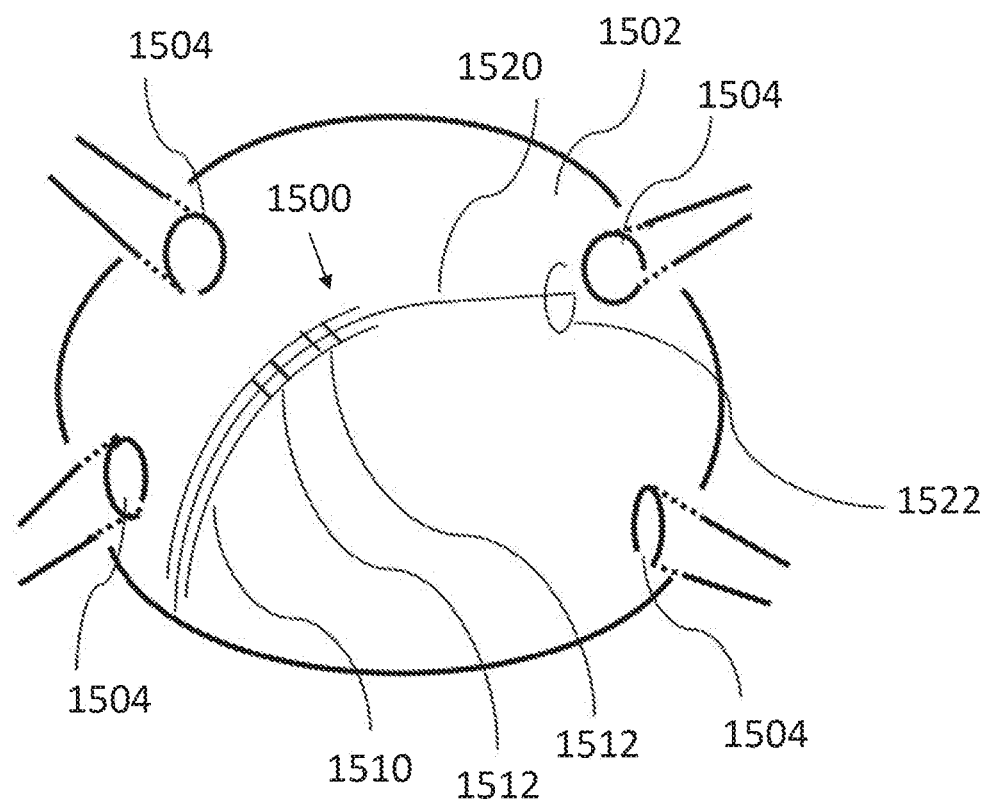
FIG. 15 is an illustration of the ablation catheter depicted in FIG. 2 disposed in a left atrial chamber of a heart.

FIGS. 15-18 depict embodiments of the methods for ablating tissue in a left atrial chamber of the heart as described above using the ablation devices described herein (e.g., FIGS. 2-5). FIG. 15 is a cross-sectional view of an embodiment of a method to ablate tissue disposed in a left atrial chamber of a heart using an ablation device (1500) corresponding to the ablation device (210) depicted in FIG. 2. The left atrial chamber (1502) is depicted having four pulmonary veins (1504) and the ablation device (1500) may be used to ablate tissue sequentially to electrically isolate one or more of the pulmonary veins (1504). As shown in FIG. 15, the ablation device (1500) may be introduced into an endocardial space such as the left atrial chamber (1502) using a trans-septal approach (e.g., extending from a right atrial chamber through the septum and into the left atrial chamber (1502)). The ablation device (1500) may include a catheter (1510) and a guidewire (1520) slidable within a lumen of the catheter (1510). A distal portion of the catheter (1510) may include a set of electrodes (1512). A distal portion (1522) of the guidewire (1520) may be advanced into the left atrial chamber (1502) so as to be disposed near an ostium of a pulmonary vein (1504). The catheter (1510) may then be advanced over the guidewire (1520) to dispose the electrodes (1512) near the ostium of the pulmonary vein (1504). Once the electrodes (1512) are in contact with the ostium of the pulmonary vein (1504), the electrodes (1512) may be configured in anode-cathode subsets. A voltage pulse waveform generated by a signal generator (not shown) may be delivered to tissue using the electrodes (1512) in synchrony with paced heartbeats and/or include a waveform hierarchy. After completion of tissue ablation in one of the pulmonary veins (1504), the catheter (1510) and guidewire (1520) may be repositioned at another pulmonary vein (1504) to ablate tissue in one or more of the remaining pulmonary veins (1504).

Figure 16:
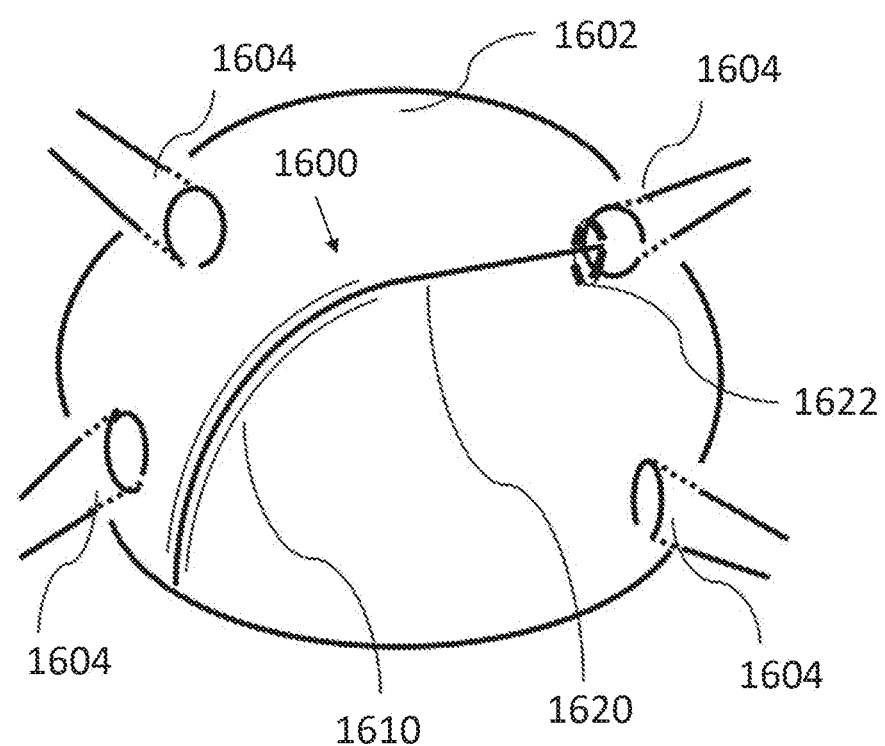
FIG. 16 is an illustration of the ablation catheter depicted in FIG. 3 disposed in a left atrial chamber of a heart.

FIG. 16 is a cross-sectional view of an embodiment of a method to ablate tissue disposed in a left atrial chamber of a heart using an ablation device (1600) corresponding to the ablation device (310) depicted in FIG. 3. The left atrial chamber (1602) is depicted having four pulmonary veins (1604) and the ablation device (1600) may be used to ablate tissue sequentially to electrically isolate one or more of the pulmonary veins (1604). As shown in FIG. 16, the ablation device (1600) may be introduced into an endocardial space such as the left atrial chamber (1602) using a trans-septal approach. The ablation device (1600) may include a sheath (1610) and a catheter (1620) slidable within a lumen of the sheath (1610). A distal portion (1622) of the catheter (1620) may include a set of electrodes. A distal portion (1622) of the catheter (1620) may be advanced into the left atrial chamber (1602) to dispose the electrodes near an ostium of a pulmonary vein (1604). Once the electrodes are in contact with the ostium of the pulmonary vein (1604), the electrodes may be configured in anode-cathode subsets. A voltage pulse waveform generated by a signal generator (not shown) may be delivered to tissue using the electrodes in synchrony with paced heartbeats and/or include a waveform hierarchy. After completion of tissue ablation in the pulmonary vein (1604), the catheter (1620) may be repositioned at another pulmonary vein (1604) to ablate tissue in one or more of the remaining pulmonary veins (1604).

Figure 17:
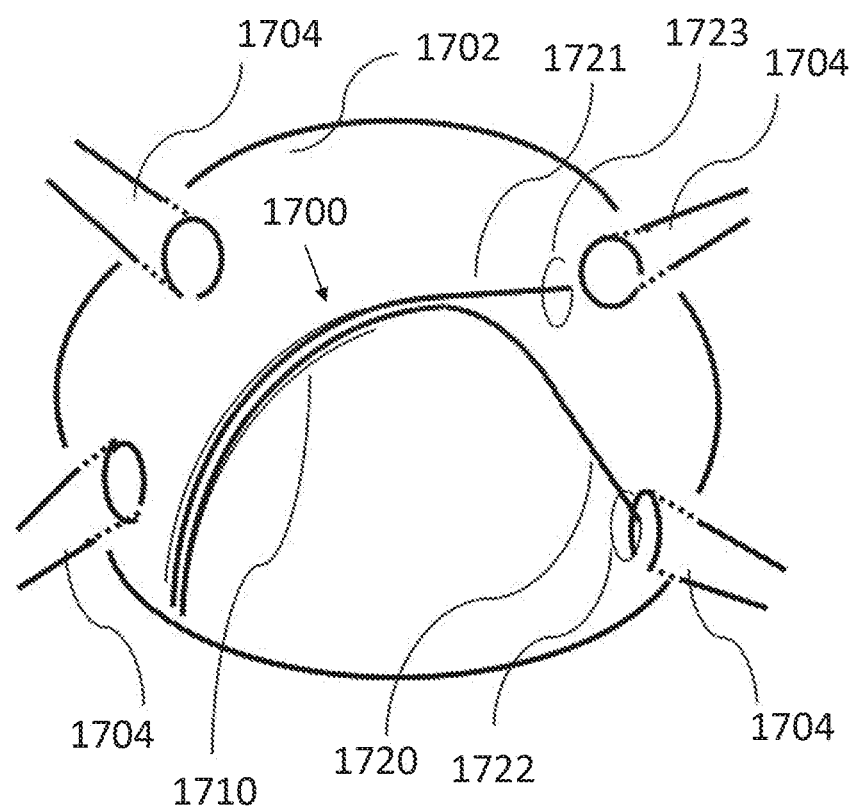
FIG. 17 is an illustration of two of the ablation catheters depicted in FIG. 4 disposed in a left atrial chamber of a heart.

FIG. 17 is a cross-sectional view of an embodiment of a method to ablate tissue disposed in a left atrial chamber of a heart using an ablation device corresponding to the ablation device (410) depicted in FIG. 4. The left atrial chamber (1702) is depicted having four pulmonary veins (1704) and the ablation device (1700) may be used to ablate tissue to electrically isolate one or more of the pulmonary veins (1704). As shown in FIG. 17, the ablation device (1700) may be introduced into an endocardial space such as the left atrial chamber (1702) using a trans-septal approach. The ablation device (1700) may include a sheath (1710) and a plurality of catheters (1720, 1721) slidable within a lumen of the sheath (1710). Each of the catheters (1720, 1721) may include a respective guidewire (1722, 1723) slidable within the catheter (1720, 1721). A distal portion of the guidewire (1722, 1723) may include an electrode configured to deliver a voltage pulse waveform. Each of the catheters (1720, 1721) and corresponding guidewires (1722, 1723) may be advanced into the left atrial chamber (1702) so as to be disposed near respective ostia of the pulmonary veins (1704). Once the guidewire electrodes (1722, 1723) are in contact with the ostium of the pulmonary vein (1704), the electrodes may be configured in anode-cathode subsets. For example, a first guidewire (1722) may be configured as an anode while a second guidewire (1723) may be configured as a cathode. In this configuration, voltage pulse waveforms generated by a signal generator (not shown) may be delivered for ablation and simultaneous isolation of the pair of pulmonary veins (1704). Additionally or alternatively, a voltage pulse waveform may be delivered to tissue using the electrodes in synchrony with paced heartbeats and/or include a waveform hierarchy. After completion of tissue ablation in two of the pulmonary veins (1704), the catheters (1720, 1721) may be repositioned to ablate tissue at the two remaining pulmonary veins (1704). In some embodiments, the sheath (1710) may include three or four catheters to be disposed in the pulmonary veins (1704).

Figure 18:
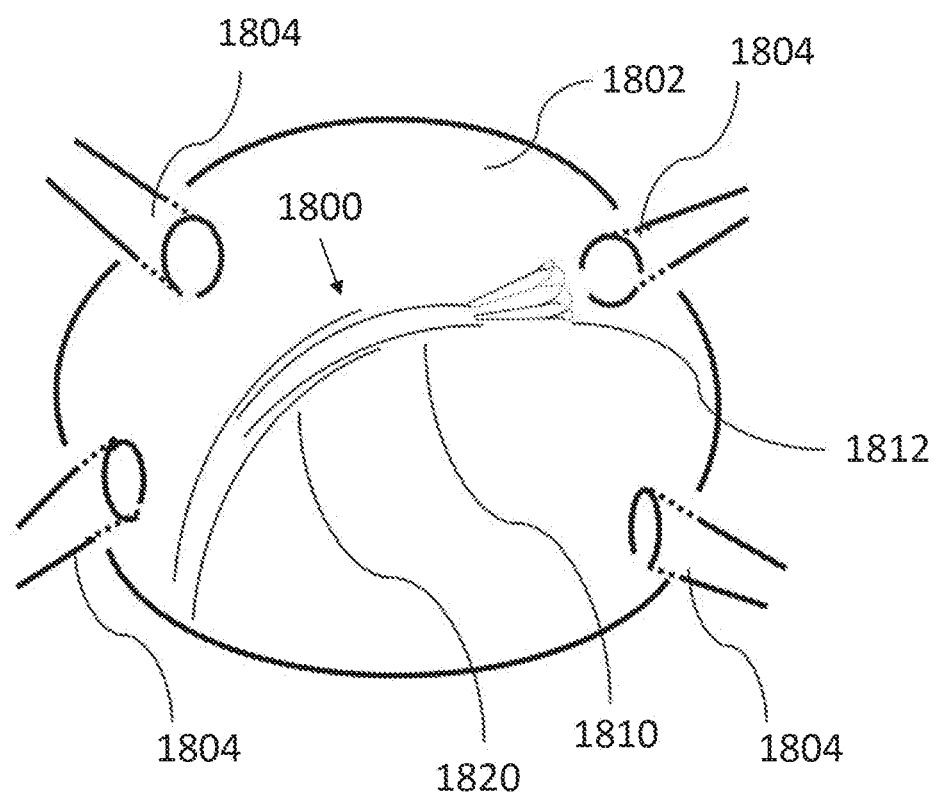
FIG. 18 is an illustration of the ablation catheter depicted in FIG. 5 disposed in a left atrial chamber of a heart.

FIG. 18 is a cross-sectional view of an embodiment of a method to ablate tissue disposed in a left atrial chamber of a heart using an ablation device (1800) corresponding to the ablation device (500) depicted in FIG. 5. The left atrial chamber (1802) is depicted having four pulmonary veins (1804) and the ablation device (1800) may be used to ablate tissue sequentially to electrically isolate one or more of the pulmonary veins (1804). As shown in FIG. 18, the ablation device may be introduced into an endocardial space such as the left atrial chamber (1802) using a trans-septal approach. The ablation device may include a sheath (1820) and a catheter (1810) slidable within a lumen of the sheath (1820). A distal portion (1812) of the catheter (1810) may be flower-shaped as discussed in detail with respect to FIG. 5. A distal portion (1812) of the catheter (1810) may be advanced into the left atrial chamber (1802) in a compact first configuration and disposed near an ostium of a pulmonary vein (1804). The distal portion (1812) of the catheter (1810) may then be transformed to an expanded second configuration to form a flower-shaped distal portion, as shown in FIG. 18, such that the distal portion (1812) of the catheter (1810) is disposed near the ostium of the pulmonary vein (1804). Once the electrodes are in contact with the ostium of the pulmonary vein (1804), the electrodes may be configured in anode-cathode subsets. A voltage pulse waveform generated by a signal generator (not shown) may be delivered to tissue using the electrodes in synchrony with paced heartbeats and/or include a waveform hierarchy. After completion of tissue ablation in the pulmonary vein (1804), the catheter (1810) may be repositioned at another pulmonary vein (1804) to ablate tissue in one or more of the remaining pulmonary veins (1804).

It should be appreciated that any of the methods described herein (e.g., FIGS. 13-18) may further include coupling a return electrode (e.g., one or more return electrodes (1230) depicted in FIGS. 12A-12B) to a patient's back and configured to safely remove current from the patient during application of a voltage pulse waveform.

Figure 19A:
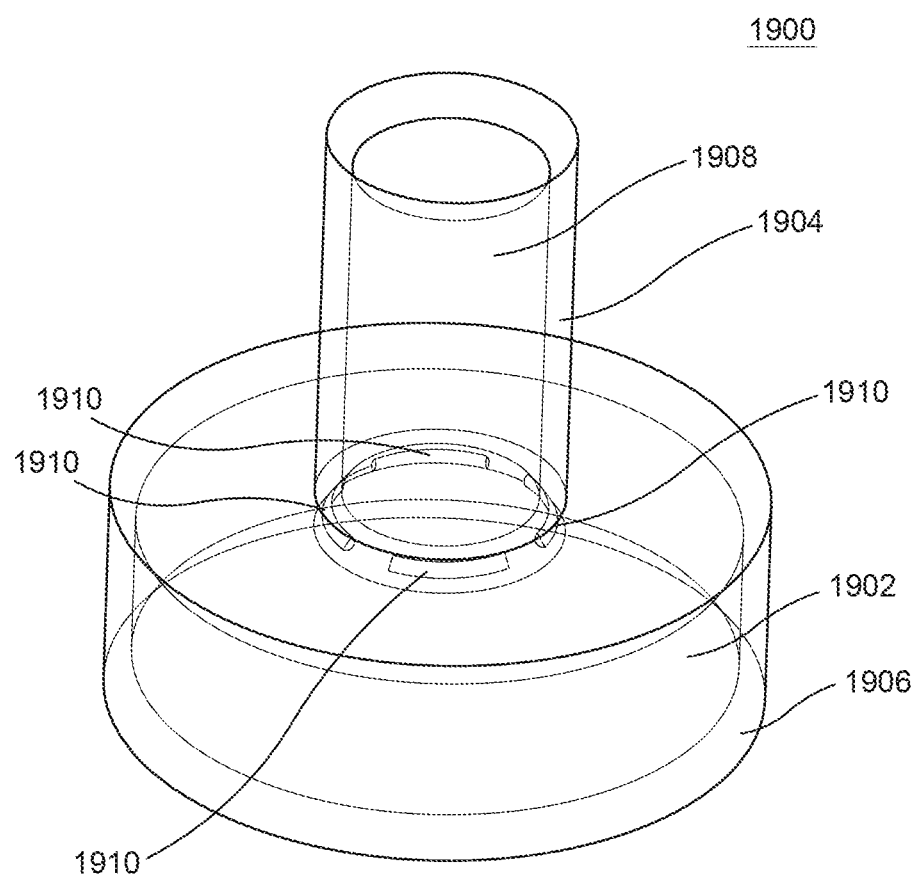
FIGS. 19A-19B are illustrative views of a set of electrodes disposed in a pulmonary vein ostium, according to other embodiments.

FIGS. 19A-20B depict embodiments of electrodes disposed in contact around an ostium of a pulmonary vein and electric fields generated therefrom. FIG. 19A is a schematic representation (1900) of an embodiment of a set of electrodes (1910) disposed in an ostium of a pulmonary vein (1904). A left atrial chamber (1902) may include a blood pool (1906) and the pulmonary vein (1904) may include a blood pool (1908). The left atrial chamber (1902) and pulmonary vein (1904) may each have a wall thickness of up to about 4 mm.

Figure 19B:
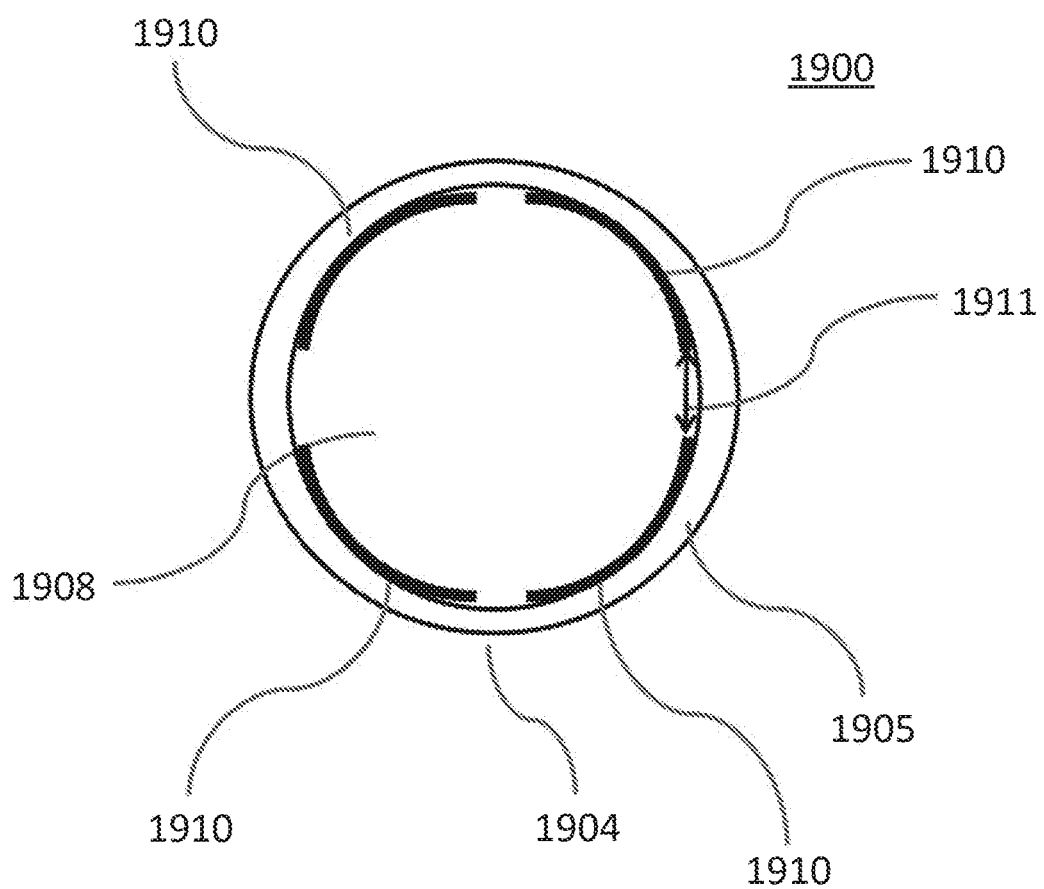

FIG. 19B is another schematic representation (1900) of the set of electrodes (1910) disposed radially along an interior surface of a pulmonary vein (1904). The pulmonary vein (1904) may include an arterial wall (1905) containing a blood pool (1908). Adjacent electrodes (1910) may be separated by a predetermined distance (1911). In some embodiments, the pulmonary vein (1904) may have an inner diameter of about 16 mm. In FIGS. 19A-19B, the electrodes (1910) may have a length of about 10 mm and be spaced apart about 4 mm from each other. It should be appreciated that the electrodes (1910) may in other embodiments be any of the electrodes disclosed herein. For example, the electrodes (1910) may include the electrodes of the flower-shaped distal portion of FIG. 5 and/or the generally circular arrangement of electrodes depicted in FIG. 3.

Figure 20A:
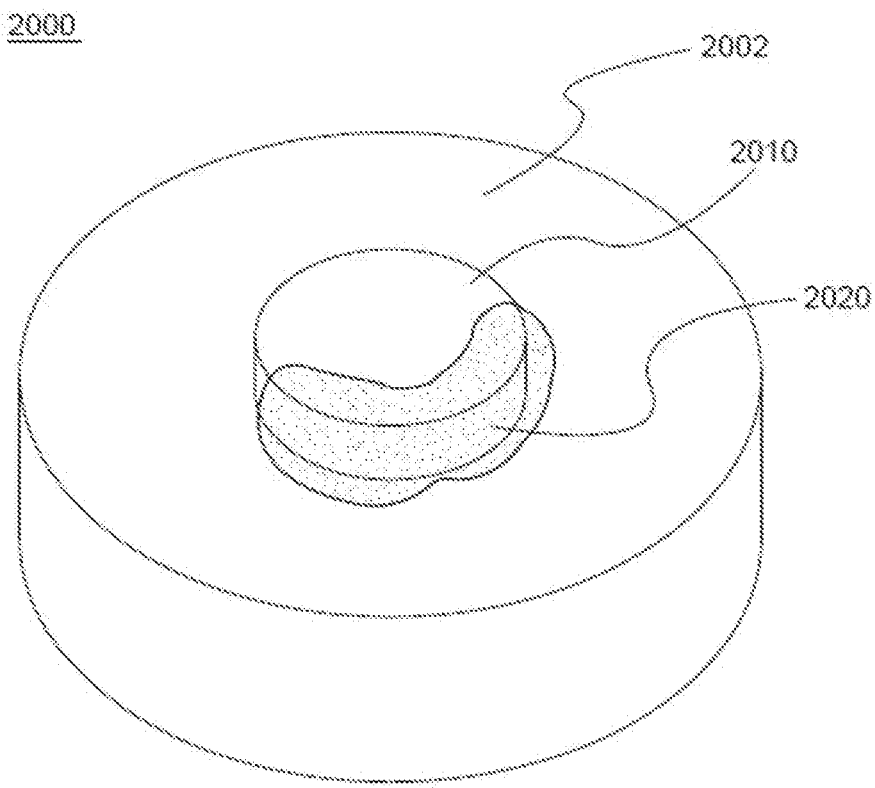
FIGS. 20A-20B are illustrative views of an electric field generated by electrodes disposed in a pulmonary vein ostium, according to other embodiments.
Figure 20B:
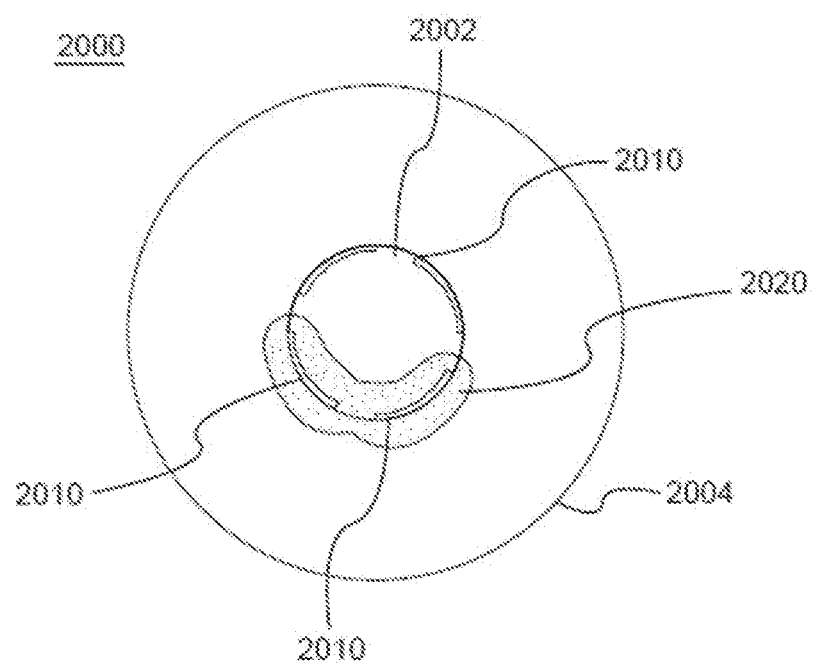

FIGS. 20A-20B are schematic representations (2000) of an embodiment of an electric field (2020) generated by a set of electrodes (2010) disposed in an ostium of a pulmonary vein (2002). FIG. 20A is a perspective view while FIG. 20B is a cross-sectional view of the pulmonary vein (2002) and outer wall of the left atrial chamber (2004). The shaded electric field (2020) illustrates where the electric field (2020) exceeds a threshold value when adjacent electrodes (2010) deliver energy (e.g., voltage pulse waveform) to ablate tissue. For example, the electric field (2020) represents a potential difference of 1500 V applied between adjacent electrodes (2010). Under this applied voltage, the electric field (2020) magnitude is at least above a threshold value of 500 V/cm within the shaded volumetric electric field (2020) and may be sufficient to generate irreversible ablation in cardiac tissue. By sequencing pulse waveforms over adjacent pairs of electrodes (2010) as described above in detail, a pulmonary vein (2002) ostium may be ablated to electrically isolate the pulmonary vein (2002) from the left atrial chamber (2004).

Pulse Waveform

Disclosed herein are methods, systems and apparatuses for the selective and rapid application of pulsed electric fields/waveforms to effect tissue ablation with irreversible electroporation. The pulse waveform(s) as disclosed herein are usable with any of the systems (100), devices (e.g., 200, 300, 400, 500, 600, 700, 800, 900, 1010, 1110, 1230, 1500, 1600, 1700, 1800, 1910, 2010, 2900, 3000, 3100), and methods (e.g., 1300, 1400) described herein. Some embodiments are directed to pulsed high voltage waveforms together with a sequenced delivery scheme for delivering energy to tissue via sets of electrodes. In some embodiments, peak electric field values can be reduced and/or minimized while at the same time sufficiently large electric field magnitudes can be maintained in regions where tissue ablation is desired. This also reduces the likelihood of excessive tissue damage or the generation of electrical arcing, and locally high temperature increases. In some embodiments, a system useful for irreversible electroporation includes a signal generator and a processor capable of being configured to apply pulsed voltage waveforms to a selected plurality or a subset of electrodes of an ablation device. In some embodiments, the processor is configured to control inputs whereby selected pairs of anode-cathode subsets of electrodes can be sequentially triggered based on a pre-determined sequence, and in one embodiment the sequenced delivery can be triggered from a cardiac stimulator and/or pacing device. In some embodiments, the ablation pulse waveforms are applied in a refractory period of the cardiac cycle so as to avoid disruption of the sinus rhythm of the heart. One example method of enforcing this is to electrically pace the heart with a cardiac stimulator and ensure pacing capture to establish periodicity and predictability of the cardiac cycle, and then to define a time window well within the refractory period of this periodic cycle within which the ablation waveform is delivered.

In some embodiments, the pulsed voltage waveforms disclosed herein are hierarchical in organization and have a nested structure. In some embodiments, the pulsed waveform includes hierarchical groupings of pulses with a variety of associated timescales. Furthermore, the associated timescales and pulse widths, and the numbers of pulses and hierarchical groupings, can be selected so as to satisfy one or more of a set of Diophantine inequalities involving the frequency of cardiac pacing.

Pulsed waveforms for electroporation energy delivery as disclosed herein may enhance the safety, efficiency and effectiveness of the energy delivery by reducing the electric field threshold associated with irreversible electroporation, yielding more effective ablative lesions with reduced total energy delivered. This in turn can broaden the areas of clinical application of electroporation including therapeutic treatment of a variety of cardiac arrhythmias.

Figure 21:
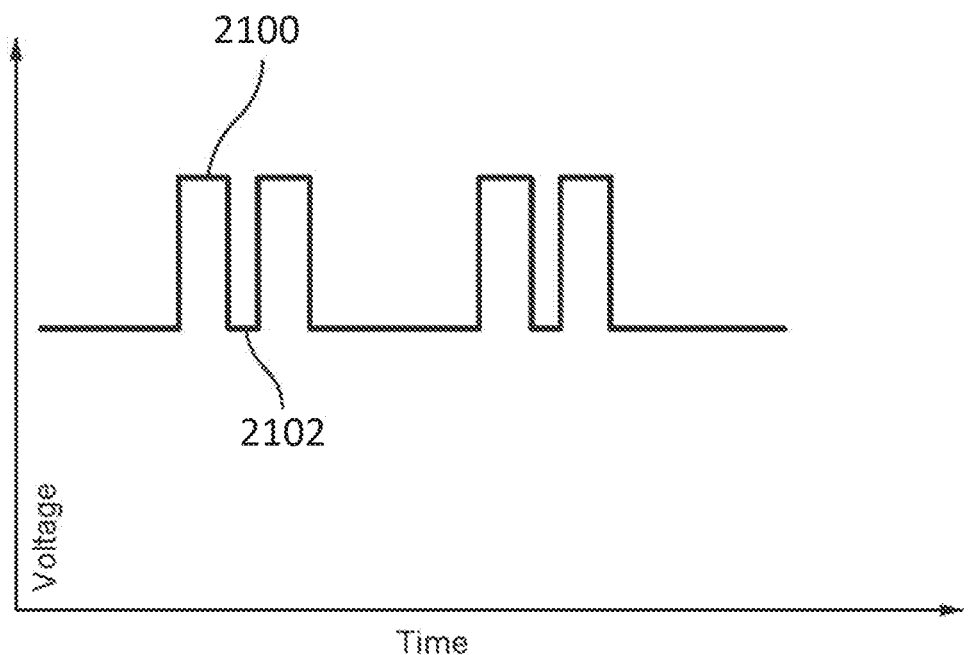
FIG. 21 is an example waveform showing a sequence of voltage pulses with a pulse width defined for each pulse, according to embodiments.

FIG. 21 illustrates a pulsed voltage waveform in the form of a sequence of rectangular double pulses, with each pulse, such as the pulse (2100) being associated with a pulse width or duration. The pulse width/duration can be about 0.5 microseconds, about 1 microsecond, about 5 microseconds, about 10 microseconds, about 25 microseconds, about 50 microseconds, about 100 microseconds, about 125 microseconds, about 140 microseconds, about 150 microseconds, including all values and sub-ranges in between. The pulsed waveform of FIG. 21 illustrates a set of monophasic pulses where the polarities of all the pulses are the same (all positive in FIG. 21, as measured from a zero baseline). In some embodiments, such as for irreversible electroporation applications, the height of each pulse (2100) or the voltage amplitude of the pulse (2100) can be in the range from about 400 volts, about 1,000 volts, about 5,000 volts, about 10,000 volts, about 15,000 volts, including all values and sub ranges in between. As illustrated in FIG. 21, the pulse (2100) is separated from a neighboring pulse by a time interval (2102), also sometimes referred to as a first time interval. The first time interval can be about 10 microseconds, about 50 microseconds, about 100 microseconds, about 200 microseconds, about 500 microseconds, about 800 microseconds, about 1 millisecond including all values and sub ranges in between, in order to generate irreversible electroporation.

Figure 22:
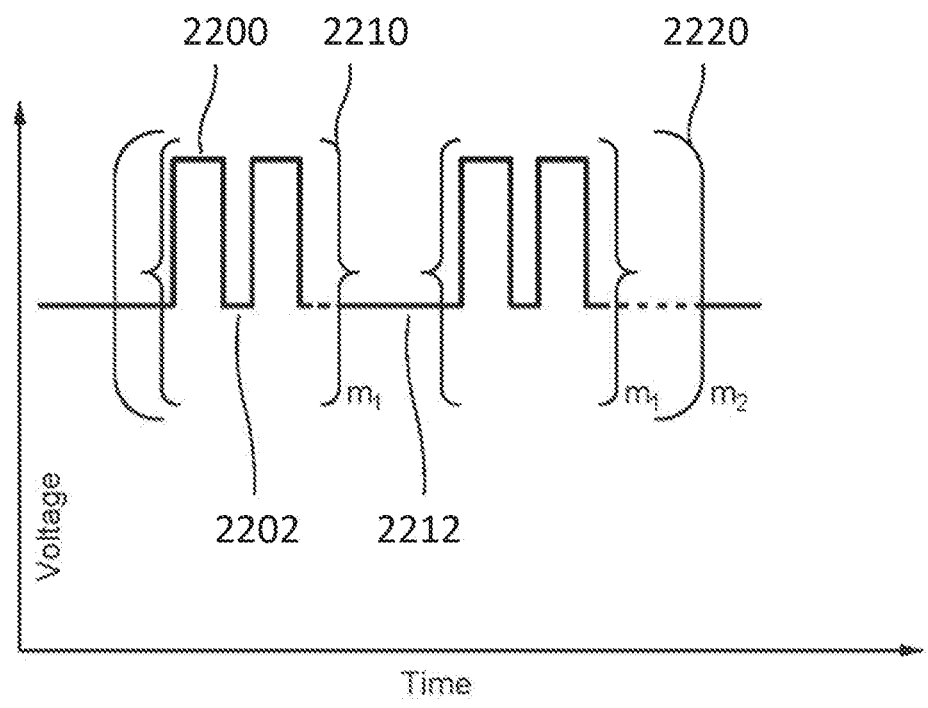
FIG. 22 schematically illustrates a hierarchy of pulses showing pulse widths, intervals between pulses, and groupings of pulses, according to embodiments.

FIG. 22 introduces a pulse waveform with the structure of a hierarchy of nested pulses. FIG. 22 shows a series of monophasic pulses such as pulse (2200) with pulse width/pulse time duration w, separated by a time interval (also sometimes referred to as a first time interval) such as (2202)

of duration t1 between successive pulses, a number m1 of which are arranged to form a group of pulses (2210) (also sometimes referred to as a first set of pulses). Furthermore, the waveform has a number m2 of such groups of pulses (also sometimes referred to as a second set of pulses) separated by a time interval (2212) (also sometimes referred to as a second time interval) of duration t2 between successive groups. The collection of m2 such pulse groups, marked by (2220) in FIG. 22, constitutes the next level of the hierarchy, which can be referred to as a packet and/or as a third set of pulses. The pulse width and the time interval t1 between pulses can both be in the range of microseconds to hundreds of microseconds, including all values and sub ranges in between. In some embodiments, the time interval t2 can be at least three times larger than the time interval t1. In some embodiments, the ratio t2/t1 can be in the range between about 3 and about 300, including all values and sub-ranges in between.

Figure 23:
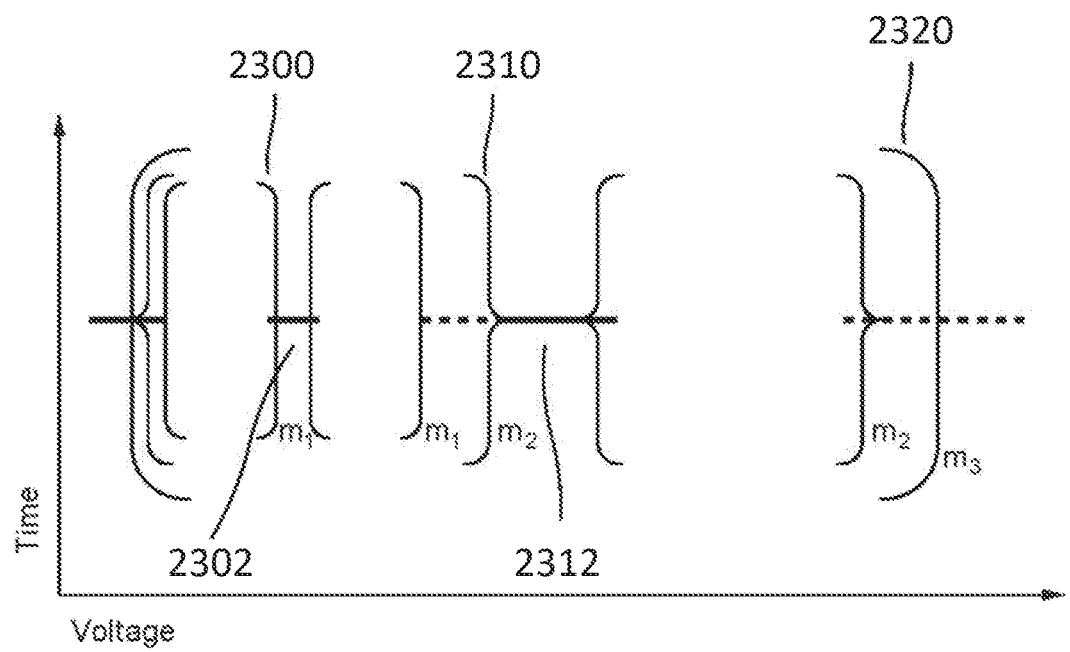
FIG. 23 provides a schematic illustration of a nested hierarchy of monophasic pulses displaying different levels of nested hierarchy, according to embodiments.

FIG. 23 further elaborates the structure of a nested pulse hierarchy waveform. In this figure, a series of m1 pulses (individual pulses not shown) form a group of pulses (2300) (e.g., a first set of pulses). A series of m2 such groups separated by an inter-group time interval (2310) of duration t2 (e.g., a second time interval) between one group and the next form a packet 132 (e.g., a second set of pulses). A series of m3 such packets separated by time intervals (2312) of duration t3 (e.g., a third time interval) between one packet and the next form the next level in the hierarchy, a super-packet labeled (2320) (e.g., a third set of pulses) in the figure. In some embodiments, the time interval t3 can be at least about thirty times larger than the time interval t2. In some embodiments, the time interval t3 can be at least fifty times larger than the time interval t2. In some embodiments, the ratio t3/t2 can be in the range between about 30 and about 800, including all values and sub-ranges in between. The amplitude of the individual voltage pulses in the pulse hierarchy can be anywhere in the range from 500 volts to 7,000 volts or higher, including all values and sub ranges in between.

Figure 24:
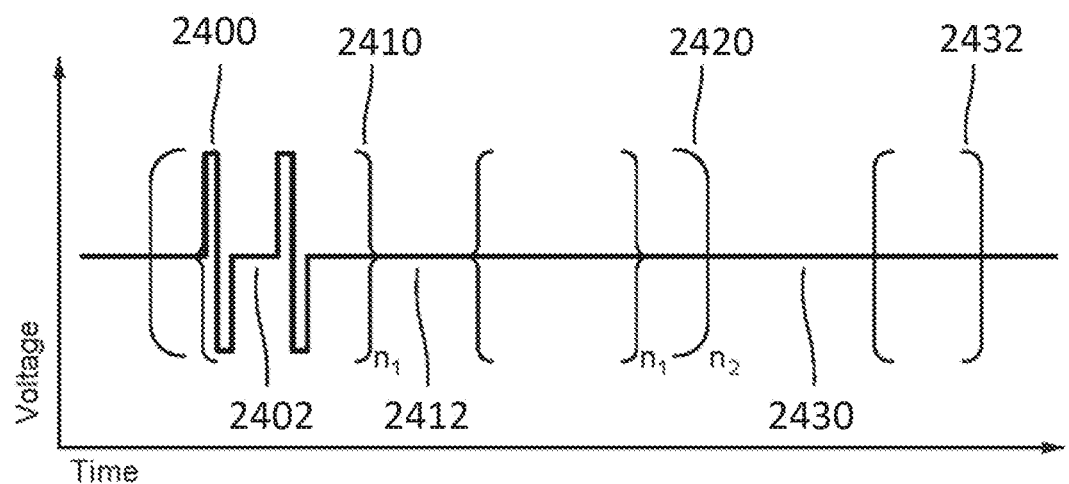
FIG. 24 is a schematic illustration of a nested hierarchy of biphasic pulses displaying different levels of nested hierarchy, according to embodiments.

FIG. 24 provides an example of a biphasic waveform sequence with a hierarchical structure. In the example shown in the figure, biphasic pulses such as (2400) have a positive voltage portion as well as a negative voltage portion to complete one cycle of the pulse. There is a time delay (2402) (e.g., a first time interval) between adjacent cycles of duration t1, and n1 such cycles form a group of pulses (2410) (e.g., a first set of pulses). A series of n2 such groups separated by an inter-group time interval (2412) (e.g., a second time interval) of duration t2 between one group and the next form a packet (2420) (e.g., a second set of pulses). The figure also shows a second packet (2430), with a time delay (2432) (e.g., a third time interval) of duration t3 between the packets. Just as for monophasic pulses, higher levels of the hierarchical structure can be formed as well. The amplitude of each pulse or the voltage amplitude of the biphasic pulse can be anywhere in the range from 500 volts to 7,000 volts or higher, including all values and sub ranges in between. The pulse width/pulse time duration can be in the range from nanoseconds or even sub-nanoseconds to tens of microseconds, while the delays t1 can be in the range from zero to several microseconds. The inter-group time interval t2 can be at least ten times larger than the pulse width. In some embodiments, the time interval t3 can be at least about twenty times larger than the time interval t2. In some embodiments, the time interval t3 can be at least fifty times larger than the time interval t2.

Embodiments disclosed herein include waveforms structured as hierarchical waveforms that include waveform elements/pulses at various levels of the hierarchy. The individual pulses such as (2200) in FIG. 22 includes the first level of the hierarchy, and have an associated pulse time duration and a first time interval between successive pulses. A set of pulses, or elements of the first level structure, form a second level of the hierarchy such as the group of pulses/second set of pulses (2210) in FIG. 22. Among other parameters, associated with the waveform are parameters such as a total time duration of the second set of pulses (not shown), a total number of first level elements/first set of pulses, and second time intervals between successive first level elements that describe the second level structure/second set of pulses. In some embodiments, the total time duration of the second set of pulses can be between about 20 microseconds and about 10 milliseconds, including all values and subranges in between. A set of groups, second set of pulses, or elements of the second level structure, form a third level of the hierarchy such as the packet of groups/third set of pulses (2220) in FIG. 22. Among other parameters, there is a total time duration of the third set of pulses (not shown), a total number of second level elements/second set of pulses, and third time intervals between successive second level elements that describe the third level structure/third set of pulses. In some embodiments, the total time duration of the third set of pulses can be between about 60 microseconds and about 200 milliseconds, including all values and sub ranges in between. The generally iterative or nested structure of the waveforms can continue to a higher plurality of levels, such as ten levels of structure, or more.

In some embodiments, hierarchical waveforms with a nested structure and hierarchy of time intervals as described herein are useful for irreversible electroporation ablation energy delivery, providing a good degree of control and selectivity for applications in different tissue types. A variety of hierarchical waveforms can be generated with a suitable pulse generator. It is understood that while the examples herein identify separate monophasic and biphasic waveforms for clarity, it should be noted that combination waveforms, where some portions of the waveform hierarchy are monophasic while other portions are biphasic, can also be generated/implemented.

In some embodiments, the ablation pulse waveforms described herein are applied during the refractory period of the cardiac cycle so as to avoid disruption of the sinus rhythm of the heart. In some embodiments, a method of treatment includes electrically pacing the heart with a cardiac stimulator to ensure pacing capture to establish periodicity and predictability of the cardiac cycle, and then defining a time window within the refractory period of the cardiac cycle within which one or more pulsed ablation waveforms can be delivered. FIG. 25 illustrates an example where both atrial and ventricular pacing is applied (for instance, with pacing leads or catheters situated in the right atrium and right ventricle respectively). With time represented on the horizontal axis, FIG. 25 illustrates a series of ventricular pacing signals such as (2500) and (2510), and a series of atrial pacing signals (2520, 2530), along with a series of ECG waveforms (2540, 2542) that are driven by the pacing signals. As indicated in FIG. 25 by the thick arrows, there is an atrial refractory time window (2522) and a ventricular refractory time window (2502) that respectively follow the atrial pacing signal (2522) and the ventricular pacing signal (2500). As shown in FIG. 25, a common refractory time window (2550) of duration Tr can be defined that lies within both atrial and ventricular refractory time windows (2522, 2502). In some embodiments, the electroporation ablation waveform(s) can be applied in this common refractory time window (2550). The start of this refractory time window (2522) is offset from the pacing signal (2500) by a time offset (2504) as indicated in FIG. 25. The time offset (2504) can be smaller than about 25 milliseconds, in some embodiments. At the next heartbeat, a similarly defined common refractory time window (2552) is the next time window available for application of the ablation waveform(s). In this manner, the ablation waveform(s) may be applied over a series of heartbeats, at each heartbeat remaining within the common refractory time window. In one embodiment, each packet of pulses as defined above in the pulse waveform hierarchy can be applied over a heartbeat, so that a series of packets is applied over a series of heartbeats, for a given electrode set.

It should be understood that the examples and illustrations in this disclosure serve exemplary purposes and departures and variations such as numbers of splines, number of electrodes, and so on can be built and deployed according to the teachings herein without departing from the scope of this invention.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention, which is limited only by the attached claims.

We claim:

1. A method of ablating via irreversible electroporation, the method comprising: configuring a first electrode formed on each spline from a first subset of splines from a set of splines of an ablation device as an anode, the ablation device disposable in a cardiac chamber of a heart of a subject, the ablation device including a catheter defining a longitudinal axis; configuring a second electrode formed on each spline from a second subset of splines from the set of splines as a cathode; transitioning the set of splines from an undeployed state in which the set of splines is approximately parallel to the longitudinal axis to a first deployed state in which the set of splines bows radially outward from the longitudinal axis to form an asymmetric shape with asymmetry along the longitudinal axis of the catheter where a distal portion of the asymmetric shape has a larger diameter than a proximal portion of the asymmetric shape; generating a voltage pulse waveform using a signal generator; delivering, with the set of splines in the first deployed state and via a set of insulated electrical leads coupled to the first and second electrodes, the voltage pulse waveform to each first and second electrode such that the first and second electrodes collectively generate an electric field having an electric field intensity of at least about 200 V/cm to form a first lesion in tissue via irreversible electroporation, the first lesion extending a first depth into tissue, each insulated electrical lead from the set of insulated electrical leads configured to sustain a voltage potential of at least about 700 V without dielectric breakdown; transitioning the set of splines into a second deployed state in which an angle between tangent vectors at distal and proximal portions of each spline from the set of splines is less than an angle between the tangent vectors when the set of splines is in the first deployed state; and delivering, with the set of splines in the second deployed state, the voltage pulse waveform to form a second lesion that extends a second depth into tissue, the second depth being less than the first depth.

2. The method of claim 1, wherein each spline from the set of splines includes a tubular body that houses the insulated electrical leads associated with the first and second electrodes formed on that spline, each spline from the set of splines coupled at an end to a shaft of the catheter, each spline from the set of splines bowing outwardly from the shaft in the first deployed state spaced from adjacent splines such that central portions of the tubular bodies of the set of splines are spaced from one another.

3. The method of claim 2, wherein the first and second electrodes formed on each spline from the set of splines are metallic rings disposed about the tubular body of that spline.

4. The method of claim 1, wherein the first electrode is formed on the distal portion of each spline from the first subset of splines, and the second electrode is formed on the proximal portion of each spline from the second subset of splines, the distal and proximal portions of each spline from the plurality of splines being set such that the angle between the tangent vectors at the distal and proximal portions of each spline is between about 70 and about 180 degrees when the set of splines is in the first deployed state.

5. The method of claim 4, wherein the ablation device includes a shaft that is slidably disposed within the catheter and extends distally from a distal end of the catheter,
the distal portion of each spline from the set of splines being coupled to the shaft, each first electrode being disposed the same distance from a distal end of the shaft, the distance being less than about 6 mm.

6. The method of claim 4, wherein, when the voltage pulse waveform is delivered to the first and second electrodes to form the first lesion, the angle between the tangent vectors at the distal and proximal portions of each spline from the plurality of splines in the first deployed state is between about 90 degrees and about 180 degrees.

7. The method of claim 1, wherein the voltage pulse waveform is delivered to the first and second electrodes such that the first and second electrodes collectively generate the electric field to form the first lesion having a diameter between about 0.5 cm and about 2.5 cm.

8. The method of claim 1, wherein:
each spline from the set of splines has a distal end coupled to a shaft of the ablation device and a proximal end coupled to the catheter, the shaft being slidably disposed within the catheter and extending distally from a distal end of the catheter,
the transitioning the set of splines from the undeployed state to the first deployed state including translating the shaft relative to the catheter.

9. The method of claim 1, wherein each spline from the set of splines includes a tubular body, the first and second electrodes formed on each spline from the first and second subsets of splines are metallic rings disposed about the tubular body of that spline.

10. The method of claim 1, wherein, when the set of splines is in the second deployed state, the first and second electrodes are configured to form the second lesion independent of an orientation of the set of splines relative to tissue.

11. The method of claim 1, wherein the voltage pulse waveform is delivered to the first and second electrodes such that the first and second electrodes collectively generate the electric field to form the first lesion in a portion of tissue disposed distal to distal ends of the set of splines.

12. The method of claim 1, wherein the voltage pulse waveform is delivered to the first and second electrodes such that the first and second electrodes collectively generate the electric field to form the first lesion having a depth of up to about 12 mm.

13. A method of ablating via irreversible electroporation, the method comprising: configuring a first electrode formed on a linear distal portion of each spline from a first subset of splines from a set of splines of an ablation device as an anode, the ablation device disposable in a cardiac chamber of a heart of a subject, the ablation device including a catheter defining a longitudinal axis; configuring a second electrode formed on a linear proximal portion of each spline from a second subset of splines from the set of splines as a cathode, each spline from the set of splines including a tubular body housing a set of insulated electrical leads, the first and second electrodes formed on each spline from the first and second subsets of splines coupled to a different insulated electrical lead from the set of insulated electrical leads of that spline and transitioning the set of splines from an undeployed state in which the set of splines is approximately parallel to the longitudinal axis to a first deployed state in which the linear distal portion and the linear proximal portion of each spline from the set of splines is separated by a bend such that central portions of the tubular bodies of the set of splines are spaced from one another; generating a voltage pulse waveform using a signal generator; delivering, with the set of splines in the first deployed state and via the set of insulated electrical leads of each spline from the set of splines, the voltage pulse waveform to each first and second electrode such that the first and second electrodes collectively generate an electric field having an electric field intensity of at least about 200 V/cm to form a first lesion in tissue via irreversible electroporation, the first lesion extending a first depth into tissue; transitioning the set of splines into a second deployed state in which an angle between tangent vectors at the linear distal and linear proximal portions of each spline from the set of splines is less than an angle between the tangent vectors when the set of splines is in the first deployed state; and delivering, with the set of splines in the second deployed state, the voltage pulse waveform to form a second lesion that extends a second depth into tissue, the second depth being less than the first depth.

14. The method of claim 13, wherein the first and second electrodes formed on each spline from the first and second subsets of splines are metallic rings disposed about the tubular body of that spline.

15. The method of claim 13, wherein: the linear distal and linear proximal portions of each spline from the plurality of splines are set such that the angle between the tangent vectors at the linear distal and linear proximal portions of each spline is between about 70 and about 180 degrees when the set of splines is in the first deployed state.

16. The method of claim 15, wherein, when the voltage pulse waveform is delivered to the first and second electrodes to form the first lesion, the angle between the tangent vectors at the linear distal and linear proximal portions of each spline from the plurality of splines in the first deployed state is between about 90 degrees and about 180 degrees.

17. The method of claim 13, wherein the voltage pulse waveform is delivered to the first and second electrodes such that the first and second electrodes collectively generate the electric field to form the first lesion having a diameter between about 0.5 cm and about 2.5 cm.

18. The method of claim 13, wherein, when the set of splines is in the second deployed state, the first and second electrodes are configured to form the second lesion independent of an orientation of the set of splines relative to tissue.

19. The method of claim 13, wherein the voltage pulse waveform is delivered to the first and second electrodes such that the first and second electrodes collectively generate the electric field to form the first lesion in a portion of tissue disposed distal to distal ends of the set of splines.

20. The method of claim 13, wherein the voltage pulse waveform is delivered to the first and second electrodes such that the first and second electrodes collectively generate the electric field to form the first lesion having a depth between about 1 mm and about 12 mm.

21. A method of ablating via irreversible electroporation, the method comprising: configuring a first electrode formed on each spline from a first subset of splines from a set of splines of an ablation device as an anode, the ablation device disposable in a cardiac chamber of a heart of a subject, the ablation device including a catheter defining a longitudinal axis; configuring a second electrode formed on each spline from a second subset of splines from the set of splines as a cathode; transitioning the set of splines from an undeployed state to a first deployed state, the set of splines in the undeployed state being approximately parallel to the longitudinal axis, the set of splines in the first deployed state having (1) an angle between a tangent vector at a distal portion of each spline and a tangent vector at a proximal portion of each spline be between about 70 and about 180 degrees and (2) an angle between the distal portions of each spline and the longitudinal axis of the catheter be between about 45 and about 90 degrees; generating a voltage pulse waveform using a signal generator; delivering, with the set of splines in the first deployed state and via a set of insulated electrical leads coupled to the first and second electrodes, the voltage pulse waveform to each first and second electrode such that the first and second electrodes collectively generate an electric field having an electric field intensity of at least about 200 V/cm to form a first lesion in tissue via irreversible electroporation, the first lesion extending a first depth into tissue; transitioning the set of splines into a second deployed state in which the angle between the tangent vectors at the distal and proximal portions of each spline from the set of splines is less than the angle between the tangent vectors when the set of splines is in the first deployed state; and delivering, with the set of splines in the second deployed state, the voltage pulse waveform to form a second lesion that extends a second depth into the tissue, the second depth being less than the first depth.

* * * * *